United States Patent
Ding et al.

(10) Patent No.: US 9,969,719 B2
(45) Date of Patent: May 15, 2018

(54) SUBSTITUTED 2-HYDROGEN-PYRAZOLE DERIVATIVE SERVING AS ANTICANCER DRUG

(71) Applicants: CHIA TAI TIANQING PHARMACEUTICAL GROUP CO., LTD., Lianyungang (CN); MEDSHINE DISCOVERY INC., Nanjing (CN)

(72) Inventors: Charles Z. Ding, Shanghai (CN); Shuhui Chen, Shenghai (CN); Baoping Zhao, Shanghai (CN); Zhaobing Xu, Shanghai (CN); Yingchun Liu, Shanghai (CN); Ruibin Lin, Shanghai (CN); Fei Wang, Shanghai (CN); Jian Li, Shanghai (CN)

(73) Assignees: CHIA TAI TIANQING PHARMACEUTICAL GROUP CO., LTD., Jiangsu (CN); MEDSHINE DISCOVERY INC., Jiangsu (CN)

( * ) Notice: Subject to any disclaimer, the term of this patent is extended or adjusted under 35 U.S.C. 154(b) by 0 days. days.

(21) Appl. No.: 15/557,210

(22) PCT Filed: Mar. 10, 2016

(86) PCT No.: PCT/CN2016/076041
§ 371 (c)(1),
(2) Date: Sep. 11, 2017

(87) PCT Pub. No.: WO2016/141881
PCT Pub. Date: Sep. 15, 2016

(65) Prior Publication Data
US 2018/0072707 A1 Mar. 15, 2018

(30) Foreign Application Priority Data

Mar. 11, 2015 (CN) .......................... 2015 1 0107436
Jan. 12, 2016 (CN) .......................... 2016 1 0019047

(51) Int. Cl.
| | |
|---|---|
| C07D 403/14 | (2006.01) |
| C07D 401/14 | (2006.01) |
| C07D 471/04 | (2006.01) |
| C07D 487/10 | (2006.01) |
| C07D 498/04 | (2006.01) |
| C07D 487/08 | (2006.01) |

(52) U.S. Cl.
CPC ......... *C07D 403/14* (2013.01); *C07D 401/14* (2013.01); *C07D 471/04* (2013.01); *C07D 487/08* (2013.01); *C07D 487/10* (2013.01); *C07D 498/04* (2013.01)

(58) Field of Classification Search
CPC .. C07D 401/14; C07D 403/14; C07D 487/08; C07D 487/10; C07D 498/04; C07D 471/04
USPC ........ 540/575; 544/105, 238, 295, 331, 364; 514/218, 230.5, 252.14, 253.01, 253.09
See application file for complete search history.

(56) References Cited

U.S. PATENT DOCUMENTS

| | | | |
|---|---|---|---|
| 7,781,583 B2 | 8/2010 | Erdman et al. | |
| 7,855,211 B2 | 12/2010 | Coates et al. | |
| 8,623,885 B2 | 1/2014 | Chen et al. | |
| 8,957,074 B2 | 2/2015 | Brain et al. | |
| 9,309,252 B2 | 4/2016 | Brain et al. | |
| 2008/0125588 A1 | 5/2008 | Erdman et al. | |
| 2010/0160340 A1 | 6/2010 | Coates et al. | |
| 2012/0244110 A1 | 9/2012 | Chen et al. | |
| 2013/0035336 A1 | 2/2013 | Borland et al. | |
| 2013/0150342 A1 | 6/2013 | Brain et al. | |
| 2014/0163052 A1 | 6/2014 | Chen et al. | |
| 2016/0008367 A1 | 1/2016 | Borland et al. | |

FOREIGN PATENT DOCUMENTS

| | | |
|---|---|---|
| CN | 101511829 A | 8/2009 |
| CN | 102264725 A | 11/2011 |
| CN | 102869358 A | 1/2013 |
| CN | 102918043 A | 2/2013 |
| CN | 103703000 A | 4/2014 |
| WO | 2008003766 A3 | 2/2008 |

OTHER PUBLICATIONS

International Search Report dated Jun. 22, 2016 in corresponding International application No. PCT/CN2016/076041, with English-language translation (8 pages).

*Primary Examiner* — Deepak R Rao
(74) *Attorney, Agent, or Firm* — Fish & Richardson P.C.

(57) ABSTRACT

Disclosed is a substituted 2H-pyrazole derivative serving as a selective CDK4/6 inhibitor. Specifically, disclosed is a compound of formula (I) or a pharmaceutically acceptable salt thereof which serves as a selective CDK4/6 inhibitor.

(I)

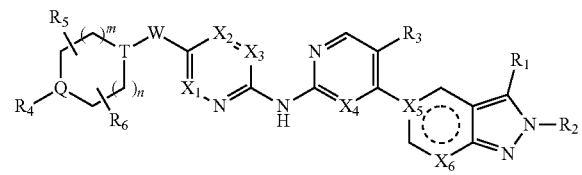

15 Claims, No Drawings

SUBSTITUTED 2-HYDROGEN-PYRAZOLE DERIVATIVE SERVING AS ANTICANCER DRUG

TECHNICAL FIELD

The present invention relates to a substituted 2H-pyrazole derivative serving as a selective CDK4/6 inhibitor. Specifically, the present invention relates to a compound of formula (I) or a pharmaceutically acceptable salt thereof which serves as a selective CDK4/6 inhibitor.

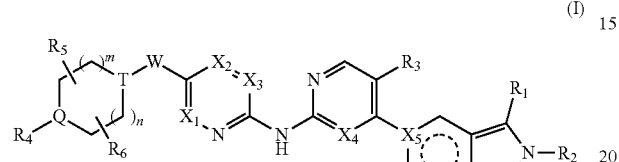

(I)

BACKGROUND OF THE INVENTION

The regulation of the cell cycle is mainly influenced by a family of serine/threonine kinases, such serine/threonine kinases are also known as cyclin-dependent kinases (CDKs). They promote the progression of the cell cycle, the transcription of the genetic information, and the normal division and proliferation of cells by binding to the corresponding cyclins which regulate the subunits. CDK4/6 is the critical regulatory factor of the cell cycle and is capable of triggering the transition of the cell cycle from the growth phase (G1 phase) to the DNA replication phase (S1 phase). During the cell proliferation, the complex formed by cyclin D and CDK4/6 can phosphorylate the retinoblastoma protein (Rb). Upon the phosphorylation of the tumor suppressor protein Rb, the transcription factor E2F which has been tightly bound to the unphosphorylated Rb can be released. The activation of E2F further transcribe, which promotes the cell cycle to pass the restriction point (R point) and proceed from the G1 phase to the S phase, leading to the cycle of cell proliferation. Hence, inhibiting CDK4/6 from forming Cyclin D-CDK4/6 complex can prevent the progression of the cell cycle from G1 phase to S phase and thereby realizing the purpose of inhibiting the tumor proliferation. In estrogen receptor positive (ER+) breast cancer (BC), overactivity of CDK4/6 is rather frequent while CDK4/6 is a critical downstream target of the estrogen receptor (ER) signaling. Preclinical data suggests that the dual inhibition of CDK4/6 and the ER signaling produces a synergistic effect and is capable of inhibiting the growth of estrogen receptor positive (ER+) breast cancer (BC) cells in the G1 phase.

CDK4/6 as a target has been a development area with fierce competition. In 2010, Pietzsch summarized the development in this field (Mini-Rev. Med. Chem. 2010, 10, 527-539). In 2014, Malorni also summarized the latest achievements of CDK4/6 inhibitors in the preclinical and clinical research on breast cancer (Curr. Opin. Oncol. 2014, 26, 568-575). Extensive research on CDK4/6 promoted the development of a series of CDK inhibitors with different selectivity and also led to the discovery of a few CDK4/6 inhibitors with efficacy and high selectivity. Palbociclib (PD0332991) is one of these CDK4/6 inhibitors with efficacy and high selectivity, it has entered the human clinical trials and has been applied to the treatment of women with estrogen receptor positive (ER+) and human epidermal growth factor receptor 2 negative (HER2-) advanced or metastatic breast cancer. On the basis of the mid-term data of PALOMA-1, Pfizer has filed a New Drug Application (NDA) of palbociclib to the United States Food and Drug Administration (FDA) in August 2014. In February 2015, the FDA approved the request of launching palbociclib. Abemaciclib (LY2835219) and LEE-011, two other CDK4/6 inhibitors, have begun to recruit patients for their phase 3 clinical trials. These small-molecule heterocyclic compounds are applicable for the treatment of a variety of other cancers in addition to breast cancer. These patents include WO2012018540, WO2012129344, WO2011101409, WO2011130232, WO2010075074, WO2009126584, WO2008032157 and WO2003062236.

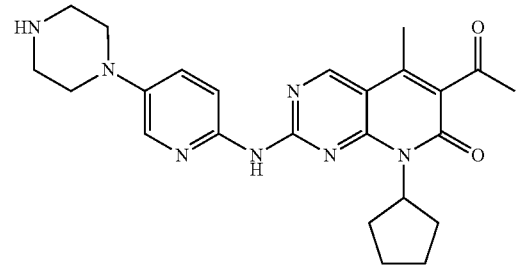

Palbociclib

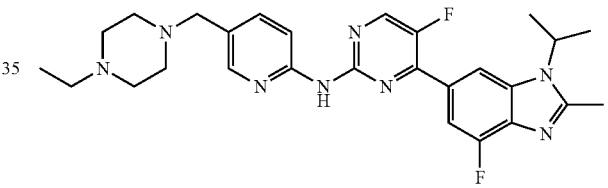

LY-2835219

We hope to develop a new generation of CDK4/6 inhibitors with high selectivity, higher safety and higher efficacy to better meet the market's demands and achieve better therapeutic efficacy of tumor. The present invention provides a selective CDK4/6 inhibitor with a novel structure, and the compounds with the structure are found to show excellent anticancer effect.

SUMMARY

The objective of the present invention is to provide a compound of formula (I) or a pharmaceutically acceptable salt thereof,

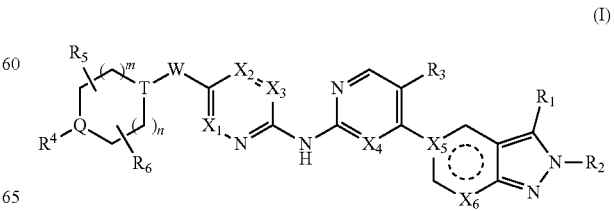

(I)

wherein

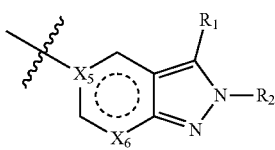

is selected from a group consisting of

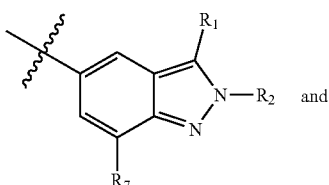 and

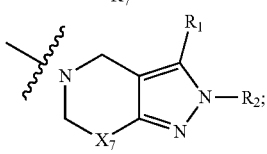

$R_1$ is selected from a group consisting of H, halogen, OH, $NH_2$, $C_{1-8}$ alkyl, $C_{2-8}$ alkenyl, $C_{2-8}$ alkenylalkyl and $C_{3-7}$ cycloalkyl;

$R_2$ is selected from a group consisting of H, halogen, $C_{1-8}$ alkyl, $C_{3-7}$ cycloalkyl, aryl group and heteroaryl group;

$R_3$ is selected from a group consisting of H, halogen, $-OR_8$, $-SR_8$, $-N(R_8)(R_9)$ and $C_{1-3}$ alkyl;

$R_4$, $R_5$ and $R_6$ are each independently selected from a group consisting of H, halogen, OH, $NH_2$, CN, $NO_2$ and $=O$, or selected from a group consisting of $C_{1-8}$ alkyl, $C_{1-8}$ alkylamino, N,N-di($C_{1-8}$ alkyl)amino, $C_{1-8}$ alkoxyl-$C_{1-8}$ alkyl-, $C_{1-8}$ hydroxyalkyl, $C_{2-8}$ alkenyl, $C_{2-8}$ alkynyl, $C_{3-7}$ cycloalkyl and a 3- to 7-membered heterocycloalkyl group, each of which is optionally substituted with 1, 2 or 3 R;

optionally, any two of $R_4$, $R_5$ and $R_6$ can form a 3- to 7-membered ring together;

$R_7$ is selected from a group consisting of H, halogen, $-OR_8$, $-SR_8$, $-N(R_8)(R_9)$ and $C_{3-7}$ cycloalkyl;

$X_1$, $X_2$, $X_3$ and $X_4$ are each independently selected from a group consisting of N and $C(R_{10})$;

$X_7$ is selected from a group consisting of carbonyl and $C(R_{11})(R_{12})$;

W is selected from a group consisting of O, S and a single bond;

T is selected from a group consisting of N and $C(R_{10})$, and T is not N when W is O or S;

Q is selected from a group consisting of N and $C(R_{10})$;

m and n are each independently selected from a group consisting of 0, 1 and 2;

$R_8$ and $R_9$ are each independently selected from a group consisting of H, $C_{1-8}$ alkyl and $C_{3-7}$ cycloalkyl;

R is selected from a group consisting of F, Cl, Br, I, $NH_2$, CN, OH, $CF_3$, $CHF_2$, $CH_2F$, $NHCH_3$ and $N(CH_3)_2$;

optionally, $R_8$ and $R_9$ are linked to the same one atom and form a 3- to 7-membered ring with 1-4 heteroatoms;

the term "hetero" or "heteroatom" represents O, S, $S(=O)$, $S(=O)_2$ or N;

$R_{10}$ is selected from a group consisting of H, halogen, OH, $NH_2$, CN, $C_{1-6}$ alkyl, $C_{1-6}$ alkoxyl, $C_{3-5}$ cycloalkyl, CN, $-OR_8$, $-SR_8$, $-N(R_8)(R_9)$, $-C(=O)R_8$, $-C(=O)OR_8$, $-C(=O)N(R_8)(R_9)$, $-S(=O)R_8$, $-S(=O)_2R_8$, $-S(=O)N(R_8)(R_9)$ and $-S(=O)_2N(R_8)(R_9)$;

$R_{11}$ and $R_{12}$ are each independently selected from a group consisting of H, OH, halogen, $C_{1-8}$ alkyl and $C_{3-7}$ cycloalkyl;

optionally, $R_4$ and $R_{10}$ are linked to the same one atom and form a 3- to 7-membered ring; and optionally, the structural unit

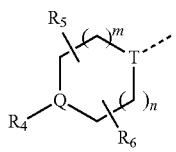

can be substituted by the structural unit

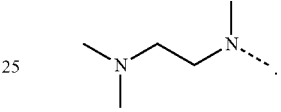

In some embodiments of the present invention, aforementioned $R_1$ is selected from a group consisting of isopropyl, 2-propenyl and allyl.

In some embodiments of the present invention, aforementioned $R_2$ is selected from a group consisting of methyl and phenyl.

In some embodiments of the present invention, aforementioned $R_3$ is F.

In some embodiments of the present invention, aforementioned $R_4$, $R_5$ and $R_6$ are each independently selected from a group consisting of H, halogen, OH, $NH_2$,

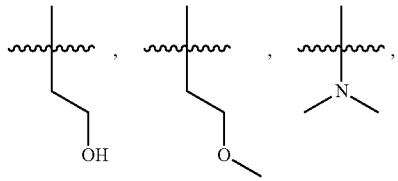

Me, Et, CN, $NO_2$,

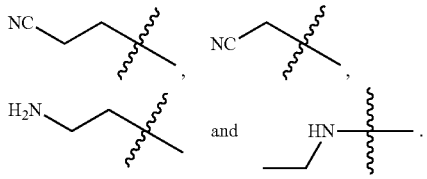

In some embodiments of the present invention, aforementioned $R_7$ is selected from a group consisting of H, F and Cl.

In some embodiments of the present invention, the structural unit

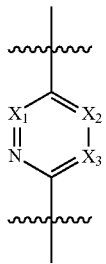

is selected from a group consisting of

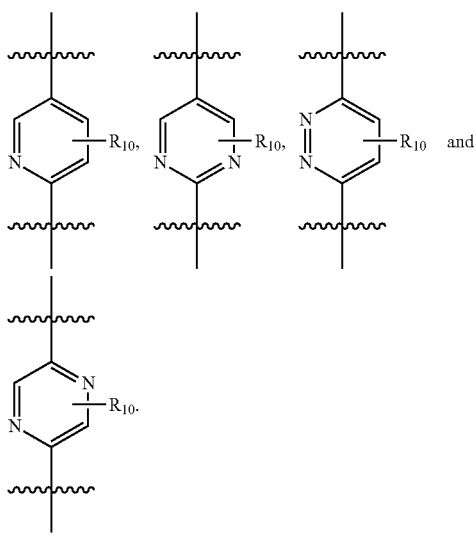

In some embodiments of the present invention, aforementioned $R_{10}$ is selected from a group consisting of H, OH, $NH_2$, F, Cl, CN,

and Me.

In some embodiments of the present invention, aforementioned $X_4$ is selected from a group consisting of N and CH.

In some embodiments of the present invention, the aforementioned structural unit

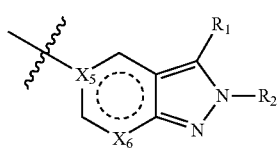

is selected from a group consisting of

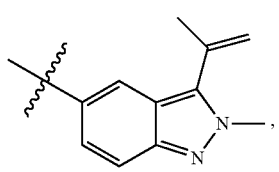

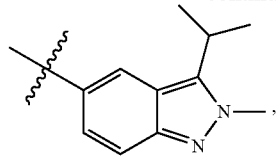

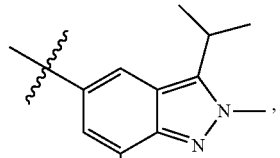

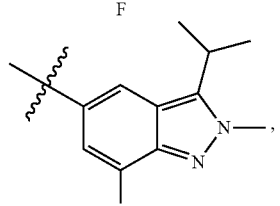

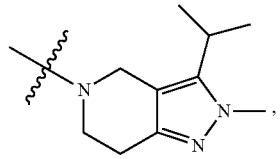

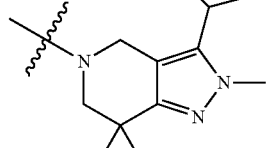

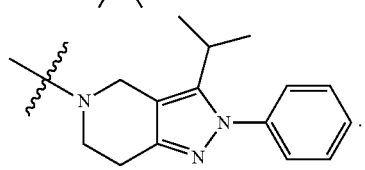

In some embodiments of the present invention, the aforementioned structural unit

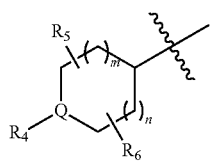

is selected from a group consisting of

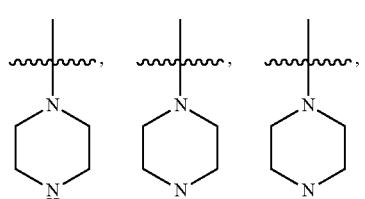

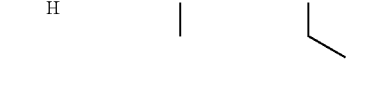

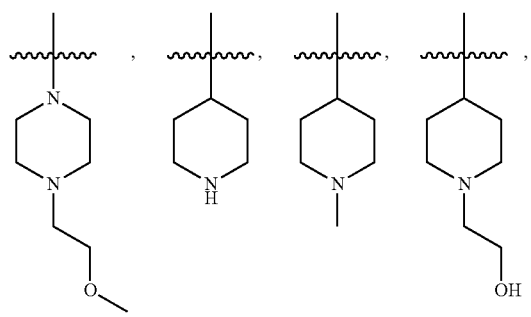
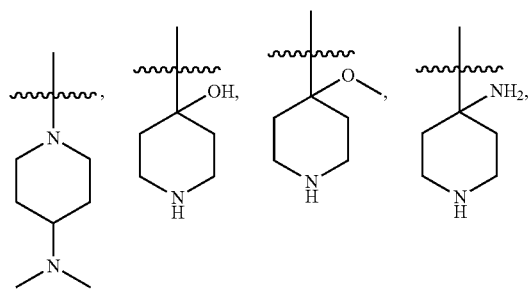
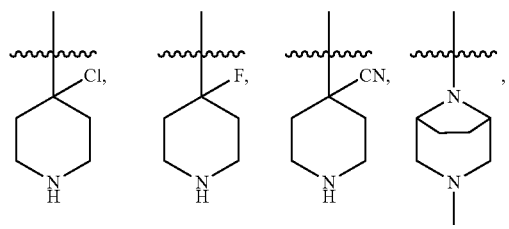
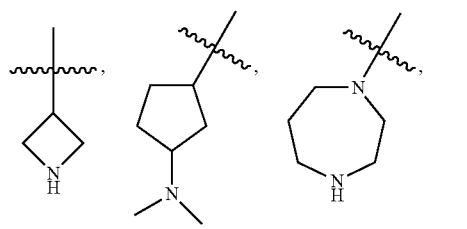
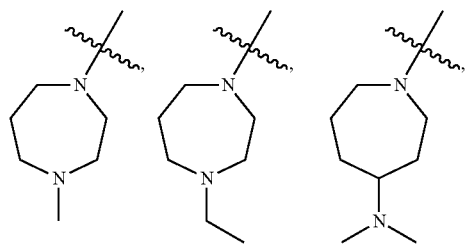
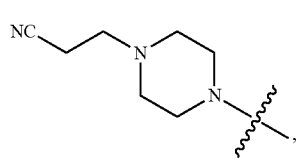
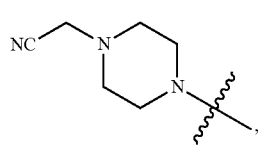
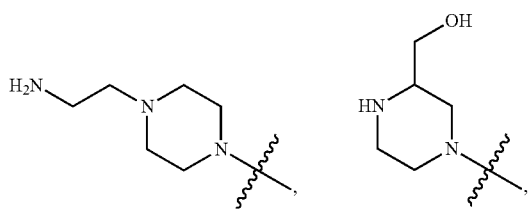
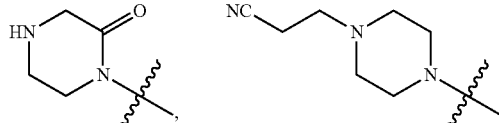
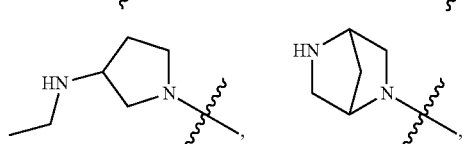
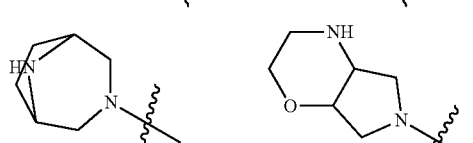
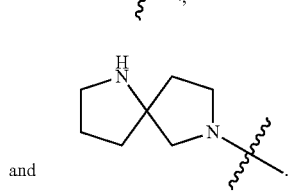
and
The compound of the present invention is selected from a group consisting of
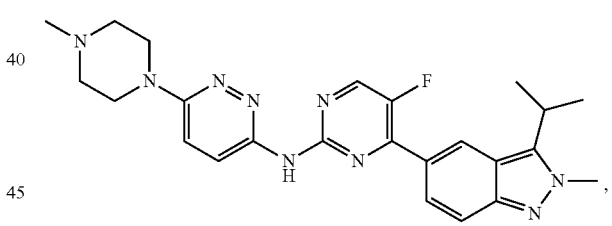
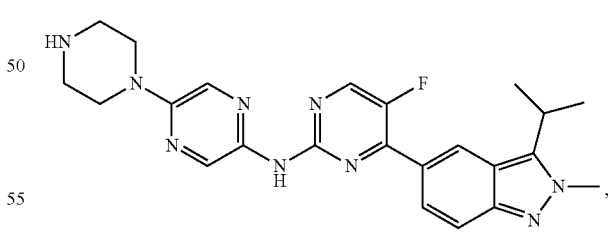
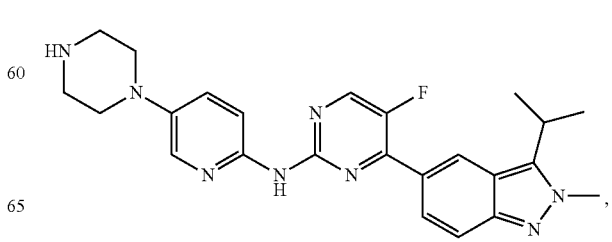

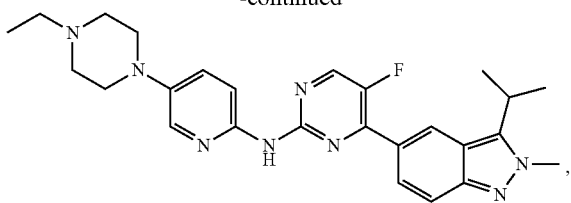
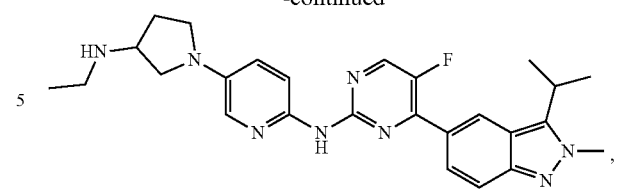
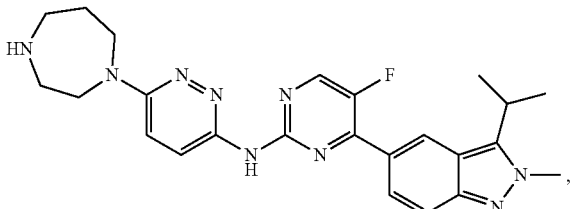
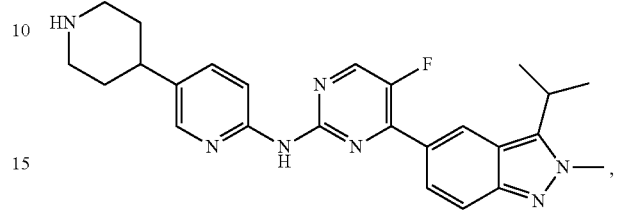
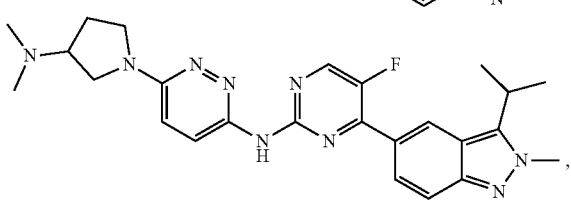
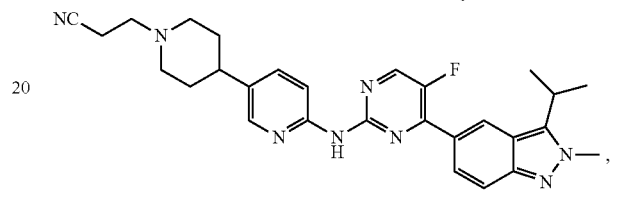
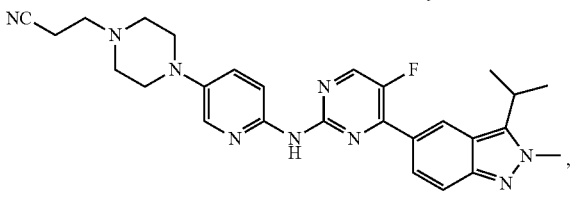
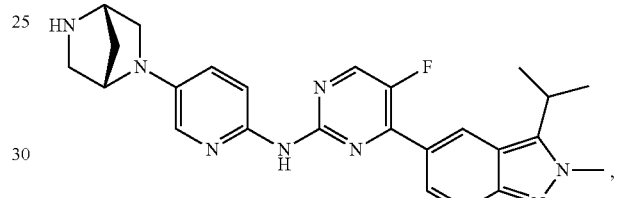
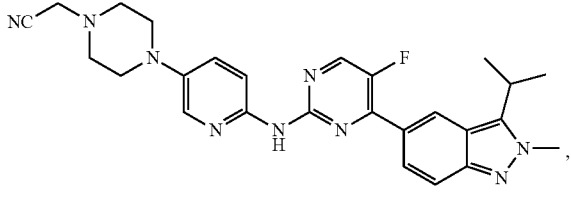
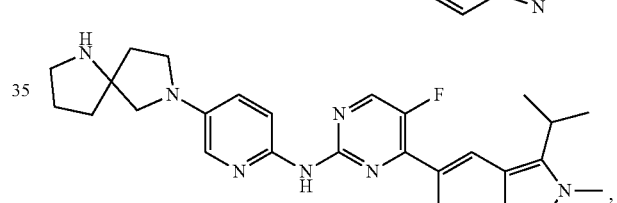
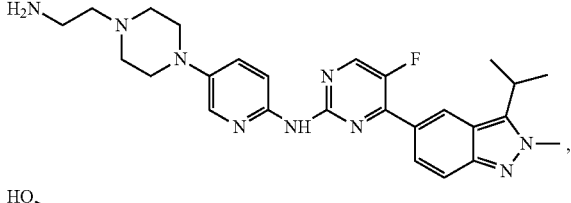
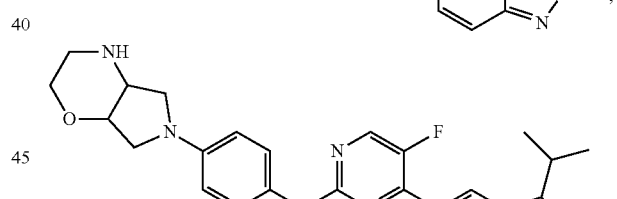
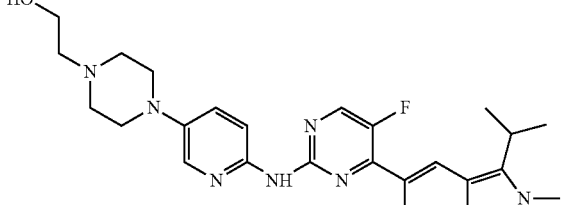
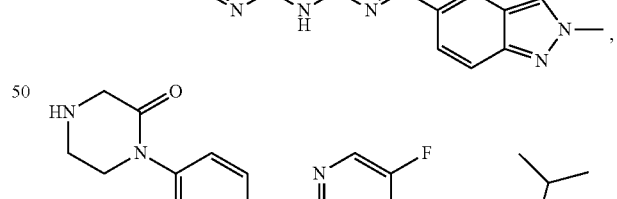
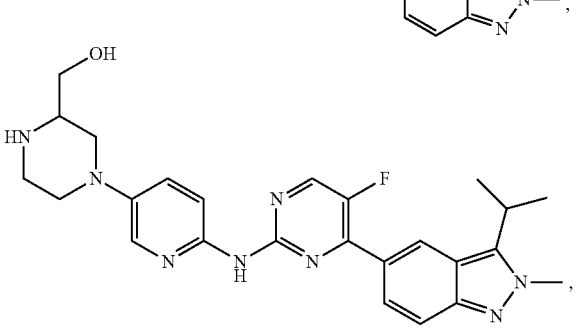
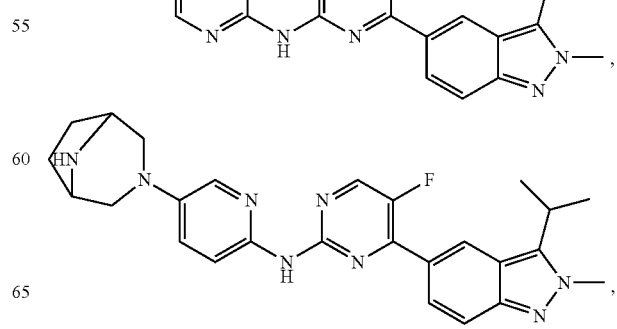

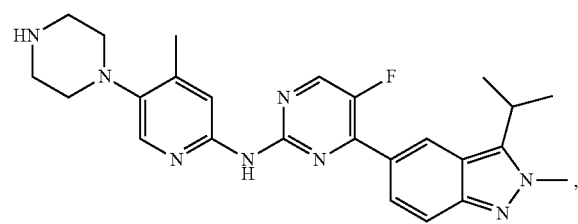
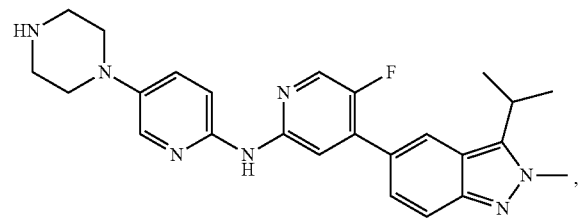
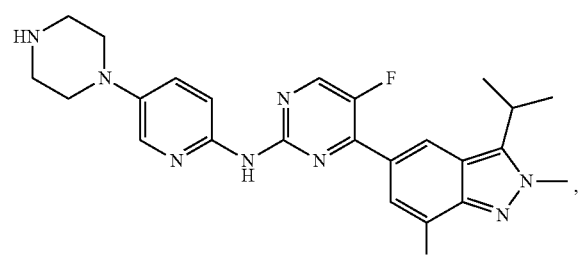
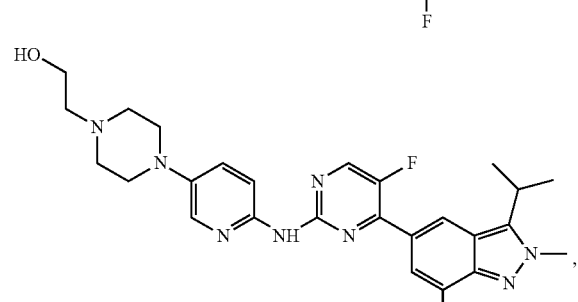
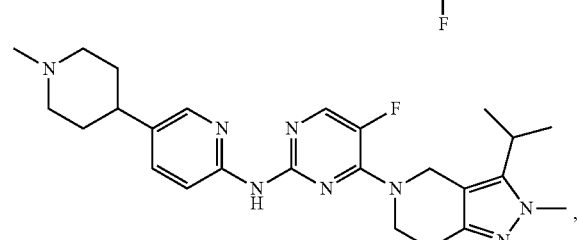
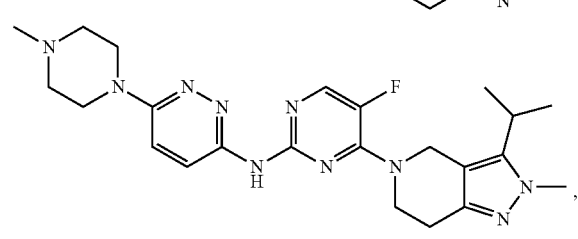
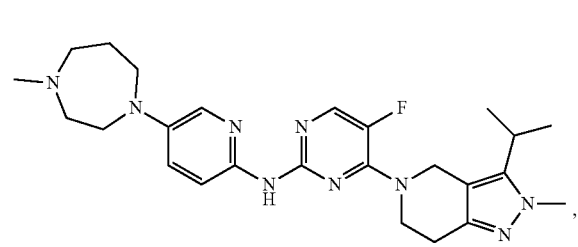
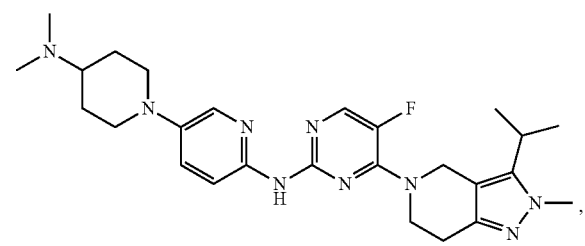
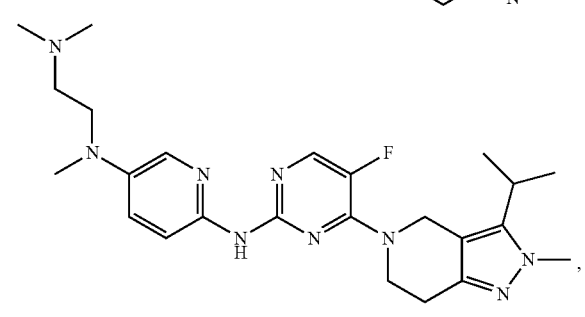
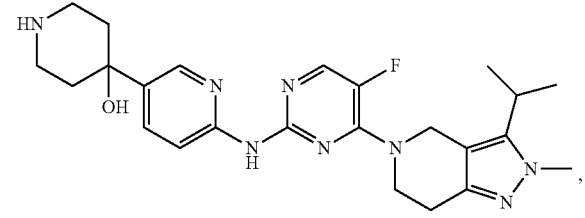
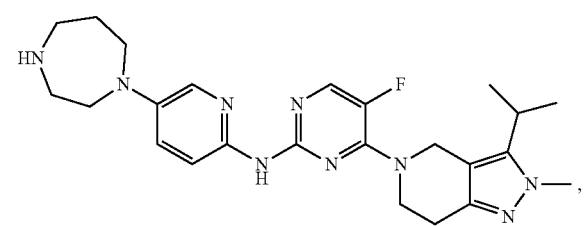
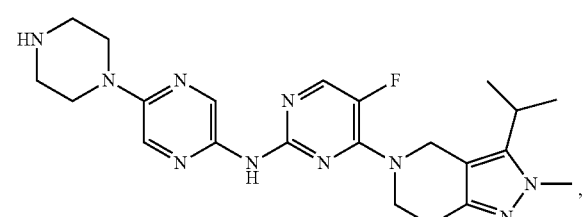
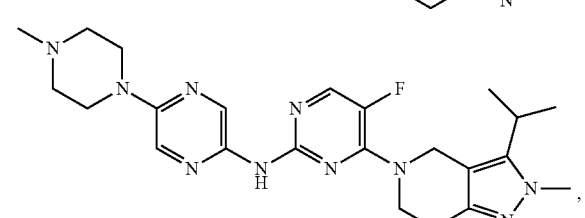
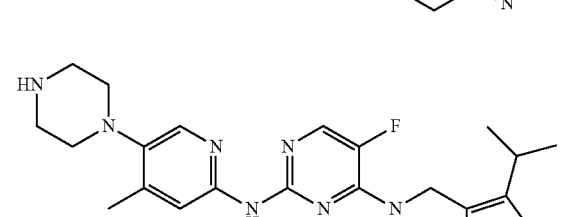

-continued

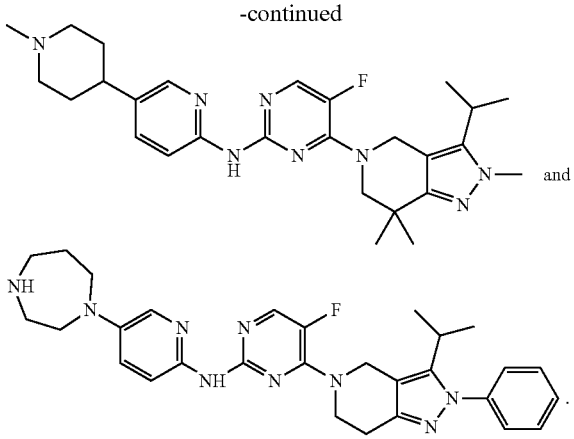

and

Definitions and Explanations

Herein the following terms and phrases are intended to have meanings as follows unless otherwise specified. A specific term or phrase should not be considered as being indefinite or unclear if it is not particularly defined, but rather should be understood as its ordinary meaning. When a trade name appears herein, it is intended to refer to the corresponding product or the active component thereof.

$C_{1-8}$ represents the number of carbon atoms contained in a hydrocarbon group. For instance, $C_1$ represents that only one carbon atom is contained, $C_2$ represents that two carbon atoms are contained, and so on.

In the compound of formula (I), the term "$C_{1-8}$ alkyl" represents a straight or branched hydrocarbon group having 1-8 carbon atoms, including, for example, methyl, ethyl, n-propyl, isopropyl, n-butyl, sec-butyl, isobutyl, t-butyl, n-pentyl, 2,2-dimethylpropyl, n-hexyl, n-heptyl, n-octyl, and the like.

The term "$C_{2-8}$ alkenyl" represents a straight or branched hydrocarbon group having 2-8 carbon atoms and one double bond, including ethenyl, 1-propenyl, 2-propenyl, 1-butenyl, 2-butenyl, and the like.

The term "$C_{2-8}$ alkynyl" represents a straight or branched hydrocarbon group having 2-8 carbon atoms and one triple bond, including ethynyl, propynyl, 1-butynyl, 2-butynyl, and the like.

The term "$C_{3-7}$ cycloalkyl" represents a monocyclic or dicyclic hydrocarbon group having 3-7 carbon atoms, including cyclopropyl, cyclobutyl, cyclopentyl, cyclohexyl, cycloheptyl, and the like.

Herein the term "pharmaceutically acceptable" means, for compounds, materials, compositions and/or dosage forms, being suitable for using in contact with human and animal tissues within a range of reliable medical judgment, without excessive toxicity, irritation, anaphylaxis, other problems or complications, and commensurate with a reasonable benefit/risk ratio.

The term "pharmaceutically acceptable salt" refers to the salts of the compounds of the present invention that are prepared using the compounds of the present invention which have specific substituents, and relatively non-toxic acids or alkalis. When a compound of the present invention contains relatively acid functional groups, its alkali addition salt can be obtained by contacting an adequate amount of alkali with the neutral form of the compound in a pure solution or a suitable inert solvent. Pharmaceutically accept- able alkali addition salts include sodium, potassium, calcium, ammonium, organic amine, magnesium salts, or the like. When a compound of the present invention contains relatively alkaline functional groups, its acid addition salt can be obtained by contacting an adequate amount of acid with the neutral form of the compound in a pure solution or a suitable inert solvent. Examples of pharmaceutically acceptable acid addition salts include the salts of inorganic acids and the salts of organic acids. Said inorganic acids include, for example, hydrochloric acid, hydrobromic acid, nitric acid, carbonic acid, bicarbonate ion, phosphoric acid, monohydrogenphosphate ion, dihydrogenphosphate ion, sulfuric acid, hydrosulfate ion, hydriodic acid, phosphorous acid, and the like. Said organic acids include, for example, acetic acid, propionic acid, isobutyric acid, maleic acid, malonic acid, benzoic acid, succinic acid, suberic acid, fumaric acid, lactic acid, mandelic acid, phthalic acid, benzene sulfonic acid, p-toluene sulfonic acid, citric acid, tartaric acid, methane sulfonic acid, and the like. The pharmaceutically acceptable acid addition salts also include the salts of amino acids (e.g., arginine, etc.) and the salts of organic acids such as glucuronic acid (see Berge et al., "Pharmaceutical Salts", Journal of Pharmaceutical Science 66: 1-19 (1977)). Some certain compounds of the present invention have alkaline or acid functional groups, therefore, they can be converted into any alkali or acid addition salts.

Preferably, the neutral form of a compound is regenerated by contacting a salt with an alkali or acid in conventional manner and then separating the parent compound. The parent form of a compound differs from its various salt forms in some physical properties, e.g., the different solubilities in polar solvents.

"A pharmaceutically acceptable salt" herein belongs to the derivatives of the compounds of the present invention, wherein said parent compound is modified by reacting with an acid or alkali to form a salt. Examples of pharmaceutically acceptable salts include, but are not limited to, the inorganic or organic acid salts of an alkali such as an amine, and the alkali metal or organic salts of an acid such as a carboxylic acid. Pharmaceutically acceptable salts include the conventional non-toxic salts or the quaternary ammonium salts of the parent compounds, such as salts formed by non-toxic inorganic or organic acids. The conventional non-toxic salts include, but are not limited to, those salts derived from inorganic or organic acids. Said inorganic or organic acids are selected from a group consisting of 2-acetoxybenzoic acid, 2-hydroxyethanesulfonic acid, acetic acid, ascorbic acid, benzene sulfonic acid, benzoic acid, bicarbonate, carbonic acid, citric acid, edetic acid, ethane disulfonic acid, ethane sulfonic acid, fumaric acid, glucoheptose, gluconic acid, glutamic acid, glycolic acid, hydrobromic acid, hydrochloric acid, hydriodic acid, hydroxy naphthalene, isethionic acid, lactic acid, lactose, dodecylsulfonic acid, maleic acid, malic acid, mandelic acid, methane sulfonic acid, nitric acid, oxalic acid, pamoic acid, pantothenic acid, phenylacetic acid, phosphoric acid, polygalactaldehyde acid, propionic acid, salicylic acid, stearic acid, folinate, succinic acid, sulfamic acid, p-aminobenzenesulfonic acid, sulfuric acid, tannin, tartaric acid and p-toluenesulfonic acid.

Pharmaceutically acceptable salts of the present invention may be synthesized using the parent compounds containing acid or alkaline groups by a conventional chemical process. Generally, the preparation method of such salts is as follows: reacting these parent compounds in their free acid or alkali form with a stoichiometric amount of a suitable alkali or acid in water, an organic solvent or a mixture thereof. In general, a non-aqueous medium such as ether, ethyl acetate, ethanol, isopropanol, acetonitrile or the like is preferred.

In addition to the salt form, a compound provided by the present invention may also be present in the form of a prodrug. Prodrugs of the compounds described herein readily undergo chemical changes under physiological conditions, thereby being converted to the compounds of the present invention. In addition, prodrugs can be converted to the compounds of the present invention by chemical or biochemical methods in an in vivo environment.

Some compounds of the present invention may exist in unsolvated forms or solvated forms including hydrates. Generally, the solvated forms are equivalent to the unsolvated forms, which both fall within the scope of the present invention.

Some compounds of the present invention may comprise asymmetric carbon atoms (optical centers) or double bonds. Racemates, diastereomers, geometrical isomers and individual isomers all fall within the scope of the present invention.

Herein, racemates, ambiscalemic and scalemic, or enantiomerically pure compounds are graphically represented using the method from Maehr., J. Chem. Ed., 1985, 62:114-120. Wedged bonds and dashed bonds are used to indicate the absolute configuration of a stereogenic center unless otherwise specified. When the compounds described herein contain ethylenically double bonds or other geometrically asymmetric centers, they include the E- and Z-geometrical isomers unless otherwise specified. Similarly, all the tautometric forms fall within the scope of the present invention.

The compounds of the present invention may exist in particular geometric or stereoisomeric forms. The compounds of the present invention in any conceivable form including trans- and cis-isomers, (−)- and (+)-enantiomers, (R)- and (S)-enantiomers, diastereomers, (D)-enantiomers and (L)-enantiomers, the racemates thereof and other mixture such as a mixture rich in enantiomers or diastereomers all fall within the scope of the present invention. Other asymmetric carbon atoms may exist in substituents such as alkyl groups. All these isomers and a mixture thereof also fall within the scope of the present invention.

The optically active (R)- and (S)-enantiomers and (D)- and (L)-enantiomers can be prepared by chiral synthesis, using chiral reagents, or by other conventional techniques. An enantiomer of a compound of the present invention can be prepared by asymmetric synthesis or the derivation with chiral auxiliary, wherein the diastereomeric mixture is separated and the auxiliary group is cleaved to provide the desired pure enantiomer. Alternatively, when there is an alkaline group (e.g., an amine group) or an acid group (e.g., a carboxyl group) in the molecule, the salts of diastereoisomers can be formed with suitable optically active acids or alkalis. Then, the diastereomers are resolved using a method known in this field, and the pure enantiomers are recovered. In addition, the separation of enantiomers and diastereomers are usually accomplished using a chromatographic method. Said chromatographic method employs chiral stationary phase and is optionally combined with chemical derivatization (e.g., deriving a carbamate from an amine).

The compounds of the present invention may contain unnatural ratios of isotopes at one or more atoms which constitute the compounds. For example, radioactive isotopes such as tritium ($^3$H), iodine-125 ($^{125}$I) or carbon-14 ($^{14}$C) may be used to label the compounds. All isotopic variations of the compounds of the present invention, whether radioactive or not, fall within the scope of the present invention.

The term "pharmaceutically acceptable carrier" refers to any formulation or carrier medium that is capable of delivering an effective amount of an active agent of the present invention, does not interfere with the bioactivity of the active agent, and has no toxic side effects to the hosts or patients. Representative carriers include water, oil, vegetables and minerals, cream base, lotion base, ointment base, etc. These base materials include suspending agents, viscosifiers, transdermal enhancers and the like. Their preparations are those known to a person skilled in the field of cosmetics or topical remedies. See Remington: The Science and Practice of Pharmacy, 21st Ed., Lippincott, Williams & Wilkins (2005) for more details of carriers. The document is herein incorporated by reference in its entirety.

The term "excipient" refers to the carriers, diluents and/or medium needed in formulating effective pharmaceutical compositions.

For drugs or pharmacologically active agents, the term "an effective amount" or "a therapeutically effective amount" refers to an adequate amount of the drug that is non-toxic but capable of achieving the expected effect. For the oral dosage form in the present invention, "an effective amount" of an active agent in the composition refers to the amount of the active agent that is needed to achieve the expected effect when used in combination with another active agent in the composition. The determination of the effective amount varies from person to person and depends on the age and the general condition of the subjects. It also depends on the specific active agent. The suitable effective amount for individuals can be determined by those skilled in the art through routine experimentation.

The term "active component", "therapeutic agent", "active material" or "active agent" refers to a chemical entity which is capable of treating the targeted disorders, diseases or conditions effectively.

The term "substituted" refers to the substitution of one or more hydrogen atoms (including variants of hydrogen and deuterium) on a specific atom by substituents, provided that the valence of the specific atom keeps normal and the substituted compound is stable. When the substituent is an acetone group (i.e., =O), it means that two hydrogen atoms are substituted. The substitution of an acetone group will never occur on an aryl group. The term "optionally substituted" means that the substitution may take place or not. Unless otherwise specified, the substituents may be of any chemically achievable type and number.

When any variable (e.g., R) appears in the composition or the structure of a compound more than one time, the variable varies in its definition from one situation to another. Therefore, for instance, if a group is substituted with 0 to 2 Rs, then said group can be optionally substituted with at most two Rs and R has independent options under each situation. Additionally, the combination of the substituents and/or its varients is permissible only when such combination results in stable compounds.

When the bonds of a substituent may be crosslinked to two atoms of a ring, such substituent may be bonded to any atom of the ring. When no atom of the listed substituent is specified to be linked to the compound which is included in the general formula but not so specified, such substituent may be bonded via any of its atoms. The combination of the substituents and/or its varients is permissible only when such combination results in stable compounds. For example, the structural unit

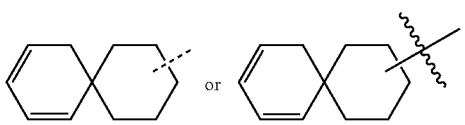

or indicates that the substitution may take place at any site of the cyclohexyl or cyclohexadiene. A substituent of an alkyl or heteroalkyl group is generally referred to as "an alkyl substituent", which can be selected from, but not limited to, one or more of the following groups: —R', —OR', =O, =NR', =N—OR', —NR'R", —SR', halogen, —SiR'R"R''', OC(O)R', —C(O)R', —CO$_2$R', —CONR'R", —OC(O)NR'R", —NR"C(O)R', NR'C(O)NR"R''', —NR"C(O)$_2$R', —NR''''—C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro-(C$_1$-C$_4$)alkyl. The number of the substituents ranges from 0 to 2m'+1, wherein m' is the total number of the carbon atoms in such atomic group. R', R", R''', R'''' and R''''' are each independently preferred to be hydrogen, a substituted or unsubstituted heteroalkyl group, a substituted or unsubstituted aryl group (e.g., an aryl substituted with 1 to 3 halogen atoms), a substituted or unsubstituted alkyl group, an alkoxyl group, a thioalkoxy group or an aralkyl group. When a compound of the present invention contains one or more R, for example, each R is independently selected, as in the case with one or more R', R", R''', R'''' and R'''''. When R' and R" are attached to the same one nitrogen atom, they may be combined with the nitrogen atom and form a 5-, 6- or 7-membered ring. For example, —NR'R" is intended to include, but not to be limited to, 1-pyrrolidinyl and 4-morpholinyl. Based on the above discussion about substituents, it can be understood by those skilled in the art that the term "alkyl" is intended to include a group whose carbon atoms are bonded to groups other than hydrogen atoms, such as a haloalkyl group (e.g., —CF$_3$, —CH$_2$CF$_3$) and an acyl group (e.g., —C(O)CH$_3$, —C(O)CF$_3$, —C(O)CH$_2$OCH$_3$, etc.).

Similar to said substituents of an alkyl atomic group, a substituent of an aryl or heteroaryl group is generally referred to as "an aryl substituent", which is selected from, for example, R', —OR', —NR'R", —SR', halogen, —SiR'R"R''', —OC(O)R', —C(O)R', —CO$_2$R', —CONR'R", —OC(O)NR'R", —NR"C(O)R', —NR'C(O)NR"R''', —NR"C(O)$_2$R', —NR''''—C(NR'R"R''')=NR'''', NR''''C(NR'R")=NR''', —S(O)R', —S(O)$_2$R', —S(O)$_2$NR'R", —NR"SO$_2$R', —CN, —N$_{O2}$, —N$_3$, —CH(Ph)$_2$, fluoro-(C$_1$-C$_4$)alkoxyl and fluoro-(C$_1$-C$_4$)alkyl. The number of the substituents ranges from 0 to the total number of the open valency on the aryl ring, wherein R', R", R''', R'''' and R''''' are independently preferred to be selected from hydrogen, a substituted or unsubstituted alkyl group, a substituted or unsubstituted heteroalkyl group, a substituted or unsubstituted aryl group, and a substituted or unsubstituted heteroaryl group. When a compound of the present invention contains one or more R, each R is independently selected, as in the case with one or more R', R", R''', R'''' or R'''''.

Two substituents on adjacent atoms of an aryl group or a heteroaryl ring may be optionally substituted by a substituent which general formula is -T-C(O)—(CRR')q-U—, wherein T and U are independently selected from —NR—, —O—, CRR'— or a single bond, and q is an integer between 0 and 3. Alternatively, two substituents on a adjacent atoms of an aryl group or a heteroaryl ring may be optionally substituted by a substituent which general formula is -A(CH$_2$)rB—, wherein A and B are independently selected from —CRR'—, —O—, —NR—, —S—, —S(O)—, S(O)$_2$—, —S(O)$_2$NR'— or a single bond, and r is an integer between 1 and 4. Optionally, a single bond on the new ring thus formed may be replaced by a double bond. Alternatively, two substituents on adjacent atoms of an aryl group or a heteroaryl ring may be optionally substituted by a substituent which general formula is -A(CH$_2$)rB—, wherein s and d are independently selected from an integer between 0 and 3, respectively. X is —O—, —NR', —S—, —S(O)—, S(O)$_2$— or S(O)$_2$NR'—. The substituents R, R', R" and R''' are independently preferred to be selected from hydrogen and a substituted or unsubstituted (C$_1$-C$_6$) alkyl group, respectively.

The term "halo" or "halogen", itself or as part of another substituent, represents fluorine, chlorine, bromine or iodine unless otherwise specified. In addition, the term "haloalkyl" is intended to include monohaloalkyl and polyhaloalkyl. For instance, the term "(C$_1$-C$_4$) haloalkyl" is intended to include, but not to be limited to, trifluoromethyl, 2,2,2-trifluoroethyl, 4-chlorobutyl, 3-bromopropyl and the like.

Examples of haloalkyl groups include, but are not limited to, trifluoromethyl, trichloromethyl, pentafluoroethyl, and pentachloroethyl. An "alkoxyl" represents the aforementioned alkyl groups that have a specific number of carbon atoms and are linked via an oxygen bridge. C$_{1-6}$ alkoxyl group includes C$_1$ alkoxyl, C$_2$ alkoxyl, C$_3$ alkoxyl, C$_4$ alkoxyl, C$_5$ alkoxyl and C$_6$ alkoxyl. Examples of alkoxyl include, but are not limited to, methoxyl, ethoxyl, n-propoxyl, isopropoxyl, n-butoxyl, sec-butoxyl, tert-butoxyl, n-pentyloxyl and s-pentyloxyl. A "cycloalkyl" includes a saturated cyclic group such as cyclopropyl, cyclobutyl or cyclopentyl. C$_{3-7}$ cycloalkyl includes C$_3$ cycloalkyl, C$_4$ cycloalkyl, C$_5$ cycloalkyl, C$_6$ cycloalkyl and C$_7$ cycloalkyl. An "alkenyl" includes a straight-chain or branched hydrocarbon group, wherein one or more carbon-carbon double bonds (such as ethenyl and propenyl) exist at any stable site on the chain.

The term "halo" or "halogen" refers to fluorine, chlorine, bromine and iodine.

The term "hetero" represents heteroatoms or heteroatomic groups (i.e., atomic groups containing hetroatom(s)), including atoms other than carbon atom (C) and hydrogen atom (H), for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

The term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called rings include a single ring, a linked ring, a spiral ring, a combined ring or a bridge ring. The number of atoms on a ring is usually defined as the number of the ring members. For example, a "5- to 7-membered ring" refers to the fact that 5 to 7 atoms form a ring. Unless otherwise specified, the ring optionally contains 1 to 3 heteroatoms. Thus, a "5- to 7-membered ring" includes, for example, phenylpyridine and piperidinyl. On the other hand, the term "5- to 7-membered heterocycloalkyl ring" includes pyridyl and piperidinyl, and it does not include phenyl. The term "ring" also includes the ring system containing at least one ring, wherein each "ring" is in accordance with the above definition independently.

Unless otherwise specified, the term "heterocycle" or "heterocyclic" means a stable monocyclic, bicyclic or tricyclic ring that contains heteroatom(s) or heteroatomic group(s). It can be saturated, partially unsaturated or unsaturated (aromatic) and contains carbon atoms and 1, 2, 3 or 4 cyclic heteroatoms independently selected from N, O and S, wherein any of the above heterocyclic ring may be fused to a benzene ring to form a bicyclic ring. The nitrogen and sulfur heteroatoms may be optionally oxidized (i.e., NO and $S(O)_p$). The nitrogen atom may be substituted or unsubstituted (i.e., N or NR, wherein R is H or other substituent that has been defined herein). The heterocycle may be attached to the side groups of any heteroatom or carbon atom to form a stable structure. If the resulting compound is stable, the heterocycle described herein may be substituted on carbon-position or nitrogen-position. The nitrogen atom(s) in the heterocycle(s) are optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5-, 6- or 7-membered monocyclic or bicyclic ring, or a 7-, 8-, 9- or 10-membered bicyclic heterocyclic aromatic ring which comprises carbon atoms and 1, 2, 3 or 4 cyclic heteroatoms independently selected from N, O and S. The nitrogen atom may be substituted or unsubstituted (i.e., N or NR, wherein R is H or other substituent that has been defined herein). The nitrogen and sulfur heteroatoms may optionally be oxidized (i.e., NO and $S(O)_p$). It is worth noting that the total number of S and O atoms on the aromatic heterocyclic ring does not exceed 1. The bridge ring is also included in the definition of the heterocycle. When one or more atoms (i.e., C, O, N, or S) connect two nonadjacent carbon atoms or nitrogen atoms to form a bridge ring, the preferred bridged ring includes, but is not limited to, one carbon atom, two carbon atoms, one nitrogen atom, two nitrogen atoms and a carbon-nitrogen group. It is worth noting that a bridge always converts a single ring into a tricyclic ring. In the bridge ring, the substituents on the ring may also appear on the bridge.

Examples of heterocyclic compounds include, but are not limited to, acridinyl, azocinyl, benzimidazolyl, benzofuranyl, benzothiofuranyl, benzothiophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyldecahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indolyl, indolenyl, dihydroindolyl, indenyl, indolyl, 3H-indolyl, isatinoyl, isobenzofuranyl, pyran, isoindolyl, isoindolyl, isodihydroindolyl, isoindolyl, indolyl, isoquinolyl, isothiazolyl, isoisoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindolyl, pyrimidinyl, phenanthridyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridoxazole, pyridimidazole, pyridothiazole, pyridyl, pyrimidinyl, pyrrolidinyl, pyrrolinyl, 2H-pyrrolyl, pyrrolyl, pyrazolyl, quinazolinyl, quinolinyl, 4H-quinolizinyl, quinoxalinyl, quinuclidinyl, tetrahydrofuryl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thienyloxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthene. Also included are fused-ring and spiral compounds.

Unless otherwise specified, the term "hydrocarbon group" or its specific term (e.g., alkyl, alkenyl, alkynyl, phenyl, etc.), itself or as part of another substituent, represents a straight-chain, branched or cyclic hydrocarbon atomic group, or a combination thereof, which may be fully saturated, monounsaturated or polyunsaturated, may be mono-substituted, disubstituted or polysubstituted, and may be monovalent (e.g., methyl), divalent (e.g., methylene) or polyvalent (e.g., methenyl). It may include divalent or polyvalent atomic groups and have a specified number of carbon atoms (e.g., $C_1$-$C_{10}$ represents 1 to 10 carbon atoms). A "hydrocarbon group" includes, but is not limited to, aliphatic and aromatic hydrocarbon groups. Said aliphatic hydrocarbon groups include aliphatic and cyclic hydrocarbon groups, specifically including, but not limited to, alkyl, alkenyl and alkynyl. Said aromatic hydrocarbon groups include, but are not limited to, 6- to 12-membered aromatic hydrocarbon groups such as phenyl, naphthyl and the like. In some embodiments, the term "alkyl" means a straight-chain or branched atomic group or a combination thereof, which may be fully saturated, monounsaturated or polyunsaturated, and may include divalent and multivalent atomic groups. Examples of saturated hydrocarbon atomic groups include, but are not limited to, methyl, ethyl, n-propyl, isopropyl, n-butyl, t-butyl, iso-butyl, sec-butyl, cyclohexyl, (cyclohexyl)methyl, cyclopropylmethyl, and the homologues or isomers of atomic groups such as n-pentyl, n-hexyl, n-heptyl, n-octyl and the like. A unsaturated alkyl has one or more double or triple bonds, the examples of which include, but are not limited to, vinyl, 2-propenyl, butenyl, crotonyl, 2-isopentenyl, 2-(butadienyl), 2,4-pentadienyl, 3-(1,4-pentadienyl), ethynyl, 1- and 3-propinyl, 3-butynyl, and higher homologues and isomers.

Unless otherwise specified, the term "heterohydrocarbon group" or its specific term (e.g., heteroalkyl, heteroalkenyl, heteroalkynyl, heteroaryl, etc.), alone or in combination with another term, indicates a stable straight-chain, branched or cyclic hydrocarbon atomic group or a combination thereof, having certain number of carbon atoms and at least one heteroatom. In some embodiments, the term "heteroalkyl", itself or in combination with another term, indicates a stable straight-chain or branched hydrocarbon atomic group or a combination thereof, having certain number of carbon atoms and at least one heteroatom. In a typical embodiment, the heteroatoms are selected from B, O, N and S, wherein the nitrogen and sulfur atoms are optionally oxidized and the nitrogen heteroatoms are optionally quaternized. The heteroatoms B, O, N and S may be located at any internal position (including the position of the remainder of the molecule where the hydrocarbon group was attached to) of the heterohydrocarbon group. Examples include but are not limited to —$CH_2$—$CH_2$—O—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$, —$S(O)$—$CH_3$, —$CH_2$—$CH_2$—$S(O)_2$—$CH_3$, —CH=CH—O—$CH_3$, —$CH_2$—CH=N—$OCH_3$ and —CH=CH—$N(CH_3)$—$CH_3$. At most two heteroatoms may be continuous, e.g., —$CH_2$—NH—$OCH_3$.

The terms "alkoxy", "alkylamino" and "alkylthio" (or thioalkoxy) are idiomatic and refer to those alkyl groups which are linked to the remainder of the molecule by an oxygen atom, an amino group or a sulfur atom, respectively.

Unless otherwise specified, the terms "cyclic hydrocarbon group", "heterocyclc hydrocarbon group" or their specific term (such as aryl, heteroaryl, cycloalkyl, heterocycloalkyl, cycloalkenyl, heterocycloalkenyl, cycloalkynyl, heterocycloalkynyl, etc.), themselves or in combination with other terms, respectively represent cyclic "hydrocarbon group" or "heterohydrocarbon group". In addition, for heterohydrocarbon groups or heterocyclohydrocarbon groups (such as heteroalkyl, heterocycloalkyl), heteroatoms may occupy the position of the remainder of the molecule where the heterocycle is attached to. Examples of cycloalkyl include, but are not limited to, cyclopentyl, cyclohexyl, 1-cyclohexenyl, 3-cyclohexenyl, cycloheptyl and the like. Non-limiting examples of heterocyclic groups include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindole-3-yl, tetrahydrothiophen-2-yl, tetrahydrothiophen-3-yl, 1-piperazinyl and 2-piperazinyl.

Unless otherwise specified, the term "aryl" refers to a polyunsaturated aromatic hydrocarbon substituent, which may be monosubstituted, disubstituted or polysubstituted, may be monovalent, divalent or polyvalent, and may be monocyclic or polycyclic (e.g., 1 to 3 rings, at least one of which is aromatic). And the rings are fused together or covalently linked. The term "heteroaryl" refers to an aryl group (or ring) containing one to four heteroatoms. In one exemplary embodiment, the heteroatoms are selected from B, N, O and S, wherein the nitrogen and sulfur atoms are optionally oxidized and the nitrogen atom is optionally quaternized. The heteroaryl group may be attached to the remainder of the molecule by a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl and 6-quinolinyl. The substituents of any one of the above aryl and heteroaryl ring systems are selected from the acceptable substituents described below.

For the sake of simplicity, aryl groups, when used in combination with other terms (e.g., aryloxyl, arylthiol, aralkyl), include aryl and heteroaryl rings as defined above. Thus, the term "aralkyl" is intended to include those atomic groups (e.g., benzyl, phenethyl, pyridylmethyl, etc.) in which an aryl group is attached to an alkyl group, including those in which a carbon atom (such as methylene) has been replaced by an oxygen atom, such as phenoxymethyl, 2-pyridyloxymethyl, 3-(1-naphthyloxy)propyl, and the like.

The term "leaving group" refers to a functional group or atom that may be substituted by another functional group or atom through substitution reaction (e.g., nucleophilic substitution reaction). For example, the representative leaving groups include trifluoromethanesulfonate; chlorine, bromine, iodine; sulfonate groups such as methanesulfonate, tosylate, p-bromobenzenesulfonate, p-toluenesulfonate, etc.; acyloxy groups such as acetoxy, trifluoroacetoxy and the like.

The term "protecting group" includes, but is not limited to, "amino protecting group", "hydroxy protecting group" or "mercapto protecting group". The term "amino protecting group" refers to the protecting groups suitable for preventing the side reactions on the amino nitrogen. The representative amino protecting groups include, but are not limited to, formyl; acyl such as alkanoyl (such as acetyl, trichloroacetyl or trifluoroacetyl); alkoxycarbonyl such as t-butoxycarbonyl (Boc); arylmethyloxycarbonyl such as benzyloxycarbonyl (Cbz) and 9-fluorenylmethoxycarbonyl (Fmoc); arylmethyl such as benzyl (Bn), trityl (Tr), 1,1-bis(4'-methoxyphenyl) methyl; silyl such as trimethylsilyl (TMS) and t-butyldimethylsilyl (TBS) and the like. The term "hydroxy protecting group" refers to the protecting groups suitable for preventing the side reactions of hydroxyl. The representative hydroxy protecting groups include, but are not limited to, alkyl such as methyl, ethyl and t-butyl; acyl such as alkanoyl (e.g., acetyl); arylmethyl such as benzyl (Bn), p-methoxybenzyl (PMB), 9-fluorenylmethyl (Fm) and diphenylmethyl (benzhydryl, DPM); silyl such as trimethylsilyl (TMS) and t-butyldimethylsilyl (TBS), and the like The compounds of the present invention can be prepared by a variety of synthesis methods well known to those skilled in the art, including the specific embodiments listed below, the embodiments formed by combining the listed embodiments with other chemical synthesis methods, and the alternative equivalents well known to those skilled in the art. Preferred embodiments include, but are not limited to, the examples of the present invention.

The solvents used in the present invention are commercially available. The reaction is generally carried out in an anhydrous solvent in inert nitrogen atmosphere. The proton nuclear magnetic resonance data was recorded on a Bruker Avance III 400 (400 MHz) spectrometer with the chemical shifts represented by ppm relative to downfield from tetramethylsilane. The mass spectrum was measured on the Agilent 1200 Series plus 6110 (& 1956A). LC/MS or Shimadzu MS contains a DAD: SPD-M20A (LC) and a Shimadzu Micromass 2020 detector. The mass spectrometer is equipped with an electrospray ion source (ESI) operating in positive or negative mode.

High performance liquid chromatography (HPLC) was performed on a Shimadzu LC20AB system equipped with a Shimadzu SIL-20A autosampler and a Japanese Shimadzu DAD: SPD-M20A detector, a Xtimate C18 (3 μm filler, 2.1×300 mm) column was adopted. A 0-60AB_6 min method was as follows: during the first 4.2 minutes, a linear gradient elution began with 100% A (A is 0.0675% TFA in water) and ended with 60% B (B is 0.0625% TFA in MeCN), then the elution proceeded with 60% B for 1 minute. The column was then equilibrated for 0.8 minutes to achieve 100:0. The total running time was 6 minutes. A 10-80AB_6 min method was as follows: during the first 4.2 minutes, a linear gradient elution began with 90% A (A is 0.0675% TFA in water) and ended with 80% B (B is 0.0625% TFA in acetonitrile), then the elution proceeded with 80% B for 1 minute. The column was then equilibrated for 0.8 minutes to achieve 90:10. The total running time was 6 minutes. The column temperature was 50° C. and the flow rate was 0.8 mL/min. The scanning wavelength of the diode array detector was 200-400 nm.

Thin layer chromatography (TLC) was carried out on a silica gel GF254 of Sanpont-group. Spots were usually detected by UV irradiation. In some cases, spots were also examined by other methods. In these cases, iodine (obtained by adding about 1 g of iodine to 10 g of silica gel and mixing thoroughly), vanillin (obtained by dissolving about 1 g of vanillin in 100 mL of 10% $H_2SO_4$), ninhydrin (available from Aldrich) or a special developer (obtained by thoroughly mixing $(NH_4)_6Mo_7O_{24} \cdot 4H_2O$, 5 g of $(NH_4)_2Ce(IV)(NO_3)_6$, 450 mL of $H_2O$ and 50 mL of concentrated $H_2SO_4$) were used to develop the thin layer plate so that the compounds could be examined. Flash column chromatography was performed on the Silicycle 40-63 μm (230-400 mesh) silica gel column using a method similar to the technique disclosed in Still, W. C.; Kahn, M.; and Mitra, M.

Journal of Organic Chemistry, 1978, 43, 2923-2925. Solvents commonly used in flash column chromatography or thin layer chromatography include a dichloromethane/methanol mixture, an ethyl acetate/methanol mixture and a hexane/ethyl acetate mixture.

The preparative chromatographic analysis was carried out using a Gilson UV/VIS-156 detector on a Gilson-281 Prep LC 322 system. The adopted column was Agella Venusil ASB Prep C18, 5 μm, 150×21.2 mm; Phenomenex Gemini C18, 5 μm, 150×30 mm; Boston Symmetrix C18, 5 μm, 150×30 mm; or Phenomenex Synergi C18, 4 μm, 150×30 mm. At a flow rate of about 25 mL/min, the compounds were eluted with low gradient acetonitrile/water containing 0.05% HCl, 0.25% HCOOH or 0.5% $NH_3 \cdot H_2O$ in water, the total running time was 8-15 minutes.

The selective CDK4/6 inhibitors reported in the present application can be used in the treatment of a series of cancers including breast cancer, non-small cell lung cancer, esophageal cancer, rectal cancer and acute myeloid leukemia. Selective CDK4/6 inhibitors can be used as a single agent or in combination with other chemotherapeutic agents.

The present application uses the following abbreviations: MW represents microwave; r.t. represents room temperature; aq represents aqueous solution; DCM represents methylene chloride; THF represents tetrahydrofuran; DMF represents N,N-dimethylformamide; DMSO represents dimethyl sulfoxide; EtOAc represents ethyl acetate; EtOH represents ethanol; MeOH represents methanol; BOC represents tert-butoxycarbonyl, which is an amine protecting group; $Boc_2O$ represents di-tert-butyl dicarbonate; HOAc represents acetic acid; TEA represents trifluoroethylamine; DIPEA represents diisopropylethylamine; TEA or $Et_3N$ represents triethylamine; $BnNH_2$ represents benzylamine; $PMBNH_2$ represents p-methoxybenzylamine; $MnO_2$ represents manganese dioxide; HATU represents O-(7-azabenzotriazol-1-yl)-N,N,N',N'-tetramethyluronium hexafluorophosphate; $POCl_3$ represents phosphorus oxychloride; NaH represents sodium hydrogen; $LiAlH_4$ represents lithium aluminum hydride; $Pd_2(dba)_3$ represents tris(dibenzylideneacetone)dipalladium; $Pd(dppf)Cl_2$ represents [1,1'-bis(diphenylphosphino)ferrocene]palladium dichloride; $Pd(OAc)_2$ represents palladium acetate; $Pd(PPh_3)_4$ represents (triphenylphosphin)-palladium; $PPh_3$ represents triphenylphosphine; Xantphos represents 4,5-bis(diphenylphosphino)-9,9-dimethylxanthene; Xphos represents 2-dicyclohexylphosphino-2',4',6'-triisopropylbiphenyl; BINAP represents (±)-2,2'-bis(diphenylphosphino)-1,1'-binaphthyl; Xphos-PD-G2 represents chloro(2-dicyclohexylphosphino-2',4',6'-triisopropyl-1,1'-biphenyl)[2-(2'-amino-1,1'-biphenyl)]palladium(II); NIS represents N-iodosuccinimide; NBS represents N-bromosuccinimide; NCS represents N-chlorosuccinimide; t-BuOK represents potassium tert-butoxide; t-BuONa represents sodium tert-butoxide; $Cs_2CO_3$ represents cesium carbonate; $K_2CO_3$ represents potassium carbonate; $NaBH(OAc)_3$ represents sodium triacetoxyborohydride; $NaBH_3CN$ represents sodium cyanoborohydride; $NaHCO_3$ represents sodium bicarbonate; $Na_2SO_4$ represents sodium sulfate; KOAc represents potassium acetate; Xantphos represents 4,5-bis(diphenylphosphino)-9,9-dimethylxanthene.

The compounds of the present invention can be prepared by a variety of synthesis methods well known to those skilled in the art, including the specific embodiments listed below, the embodiments formed by combining the listed embodiments with other chemical synthesis methods, and alternative equivalents well known to those skilled in the art. Preferred embodiments include, but are not limited to, the examples of the present invention.

The compounds of the present invention can be prepared by a series of synthetic steps, wherein $R_1$, $R_2$, $R_3$, $R_4$, $R_5$, $R_6$, $R_7$, $X_1$, $X_2$, $X_3$, $X_4$, $X_5$, $X_6$, $X_7$, m, n, Q, T and W are the same as defined above.

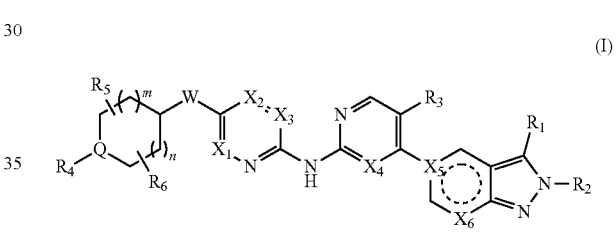

(I)

Preparation of the Compound of Formula I by Reaction Scheme 1

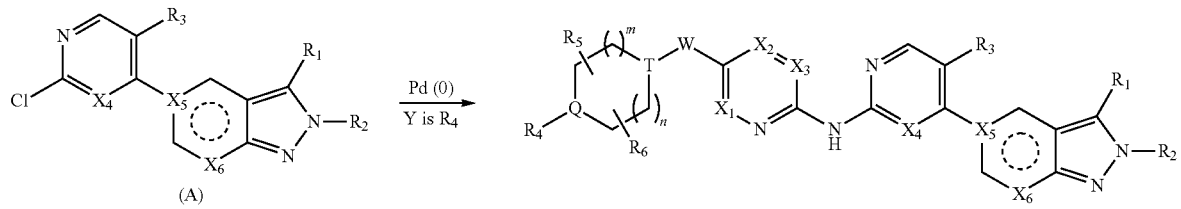

Formula 1

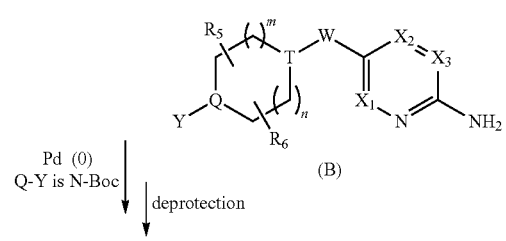

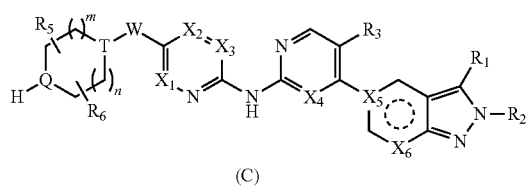
(C)

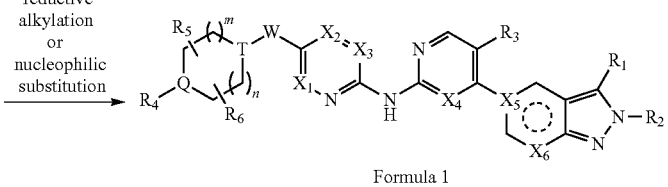
Formula 1

When Y=R₄, the compound represented by formula I is prepared by reacting 2H-pyrazole derivative (A) with 2-arylamine (B) in the above reaction shown in Reaction Scheme 1 to give the compound of formula I. The reaction requires a suitable catalyst (e.g., $Pd_2(dba)_3$), a suitable ligand (e.g., Xantphos), a suitable alkali (e.g., $Cs_2CO_3$), and a suitable solvent (e.g., 1,4-dioxane). According to Reaction Scheme 1, the reaction is more likely to occur at elevated temperatures.

When Q-Y is N-Boc, the compound represented by formula I can still be prepared by reacting 2H-pyrazole derivative (A) with 2-arylamine (B) in the below reaction shown in Reaction Scheme 1. However, the Boc group needs to be removed in a strong acid (e.g., TFA) to give amine (C), and finally amine (C) undergoes an alkylation reaction under reductive amination or nucleophilic substitution conditions (such as $NaBH_3CN$ or haloalkane) to give the compound of formula I.

Preparation of 2H-Pyrazole Derivative (A) by Reaction Scheme 2

Wherein

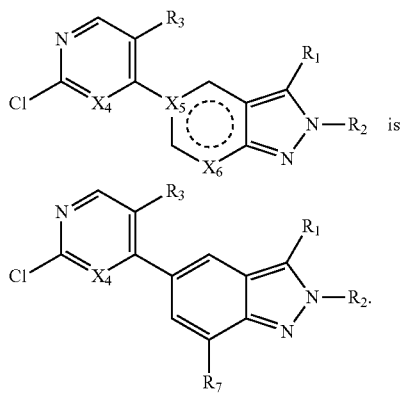

is

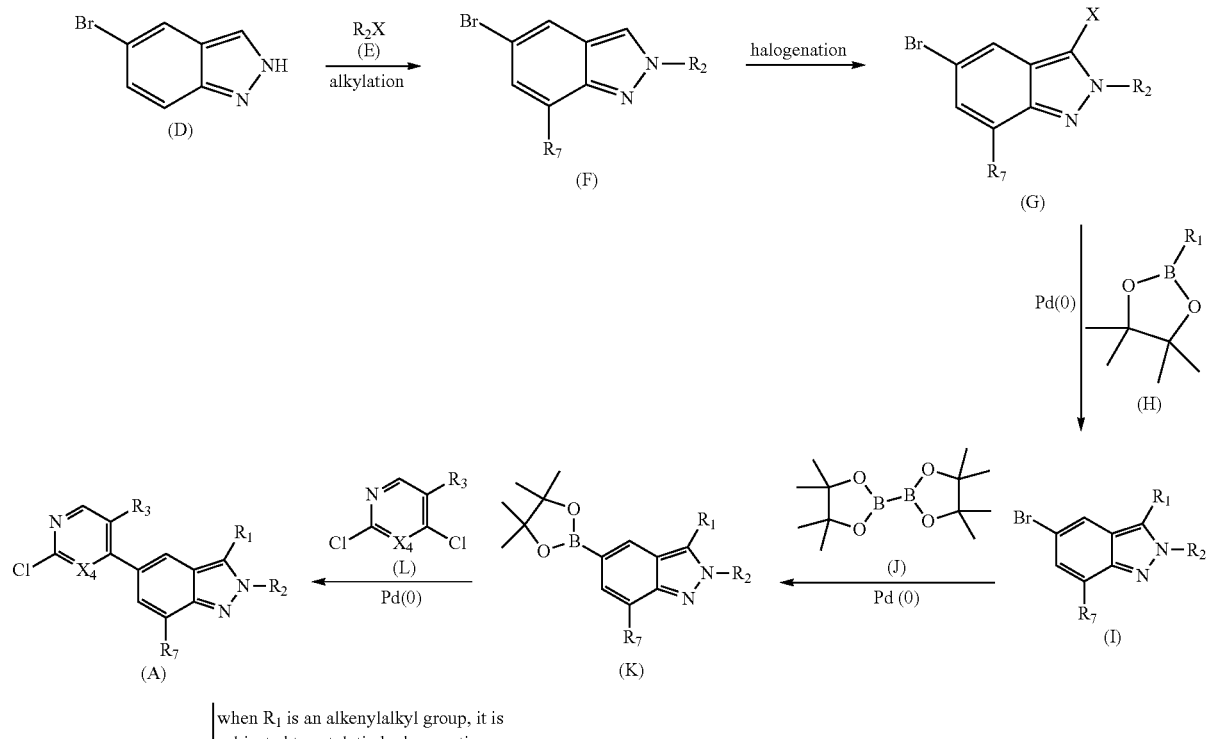

when R₁ is an alkenylalkyl group, it is subjected to catalytic hydrogenation

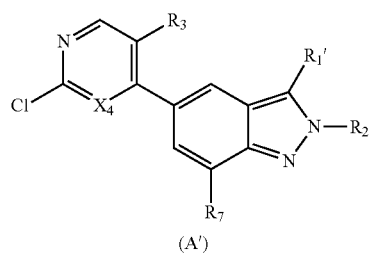

(A')

In the reaction shown in Reaction Scheme 2, 5-bromo-2H-indazole (F) can be prepared by reacting 5-bromo-2H-indazole (D) with haloalkane $R_2X$ (E). The reaction requires a suitable alkali (e.g., NaH or MeONa) and a suitable solvent (e.g., THF). 5-bromo-2H-indazole (G) can be prepared by the halogenation of 5-bromo-2H-indazole (F), the reaction requires a suitable halogenating agent (e.g., $Br_2$, NBS or NIS), a suitable solvent (e.g., DMF or MeCN). 5-bromo-2H-indazole (I) can be prepared by the palladium-catalyzed coupling of borate (H), the reaction requires a suitable catalyst (e.g., Pd(dppf)$Cl_2$), a suitable alkali (e.g., $K_2CO_3$), a suitable solvent (e.g., dioxane and water). 5-bromo-2H-indazole (K) can be prepared by the palladium-catalyzed coupling of bis(pinacolato)diboron (J), the reaction requires a suitable catalyst (e.g., Pd(dppf)$Cl_2$), a suitable alkali (e.g., KOAc), and a suitable solvent (e.g., dioxane). 2H-pyrazole derivative (A) can be prepared by the palladium-catalyzed coupling of compound (L), the reaction requires a suitable catalyst (e.g., Pd(dppf)$Cl_2$), a suitable alkali (e.g., $K_2CO_3$), and a suitable solvent (e.g., dioxane). According to Reaction Scheme 2, the reaction is more likely to occur at elevated temperatures. 2H-pyrazole derivative (A') can be prepared by the hydrogenation of the compound (A) under rhodium catalysis, the reaction requires a suitable catalyst (e.g., Rh(PPh$_3$)$_3$Cl), and a suitable solvent (e.g., tetrahydrofuran) $R_1'$ is the alkyl group after the reduction of $R_1$.

Preparation of 2H-Pyrazole Derivative (A) by Reaction Scheme 3

Wherein

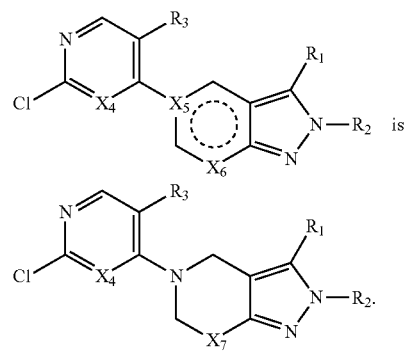

is

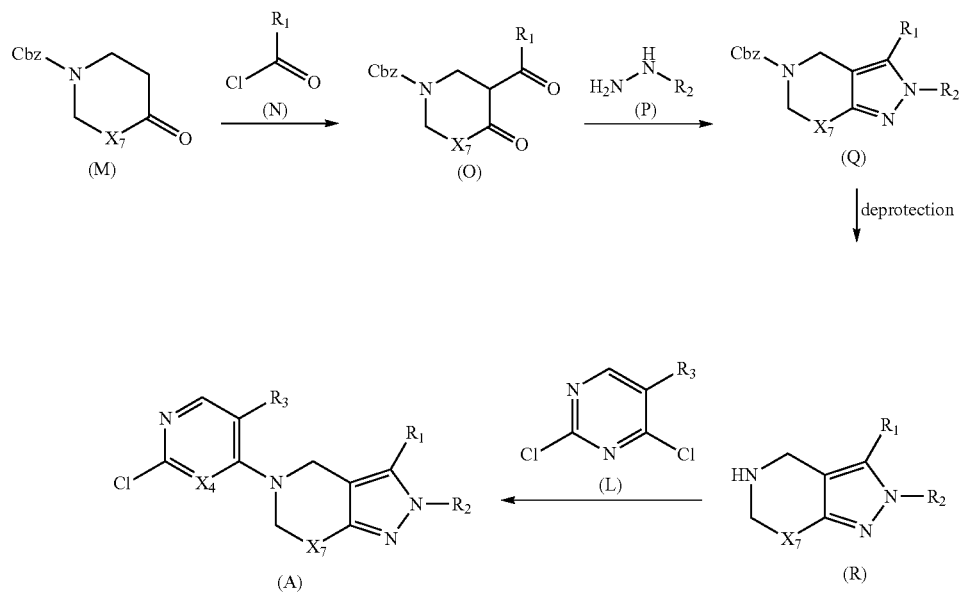

In the reaction shown in Reaction Scheme 3, compound (O) can be prepared by reacting compound (J) with acyl chloride (N). The reaction requires a suitable alkali (e.g., LiHMDS), and a suitable solvent (e.g., THF). Compound (O) may undergo cyclization to produce 2H-pyrazole (Q), the reaction requires a suitable alkyl hydrazine (P), and a suitable solvent (e.g., EtOH). 2H-pyrazole (R) can be prepared by catalytic hydrogenation, which requires a suitable catalyst (e.g., Pd/C), and a suitable solvent (e.g., MeOH). 2-H-pyrazole derivative (A) can be prepared using compound (L), the reaction requires a suitable alkali (e.g., Et₃N), and a suitable solvent (e.g., THF). According to Reaction Scheme 3, the reaction is more likely to occur at elevated temperatures.

Preparation of 2-Arylamine (B) by Reaction Scheme 4 (in which W is S or O, and T is C)

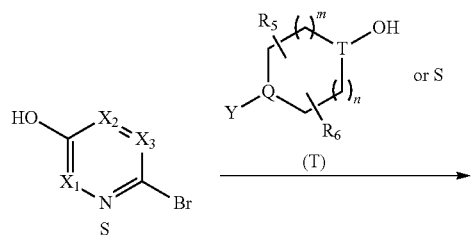

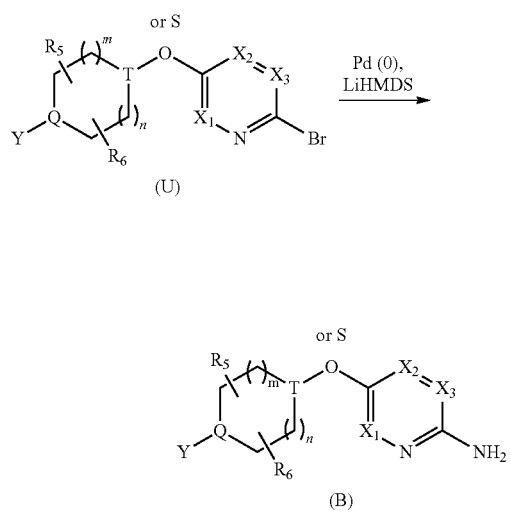

In the reaction shown in Reaction Scheme 4, pyridine bromide (U) can be prepared by reacting 2-bromo-5-hydroxy-pyridine (S) with a commercially available thiol or alcohol (T) through Mitsunobu reaction. Pyridine bromide (U) can then be converted to 2-arylamine (B) under palladium-catalyzed conditions, which requires a suitable catalyst (e.g., Pd₂(dba)₃), a suitable alkali (e.g., LiHMDS), and a suitable solvent (e.g., toluene). According to Reaction Scheme 4, the reaction is more likely to occur at elevated temperatures.

Preparation of 2-Arylamine (B) by Reaction Scheme 5 (in which W is a Directly Linked Single Bond)

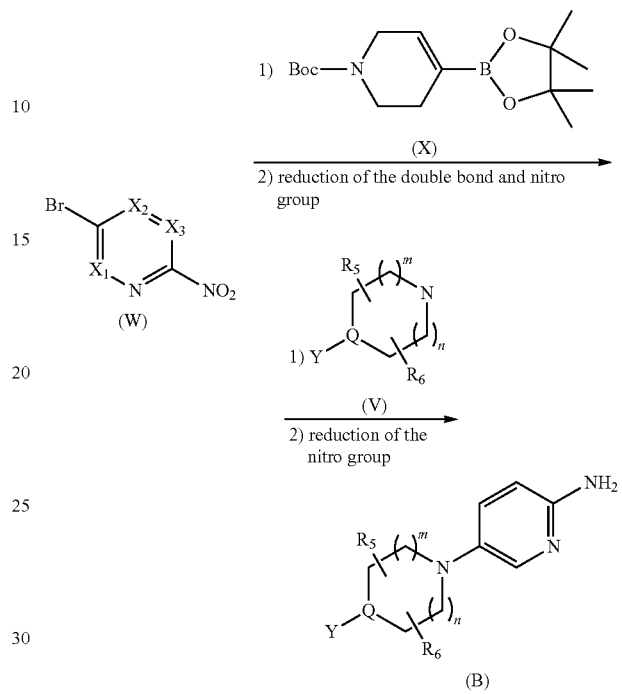

In the reaction shown in Reaction Scheme 5, when W is a directly linked single bond, 2-arylamine (B) can be prepared by the two processes below: (1) tert-butyl 4-(4,4,5,5-tetramethyl-1,3,2-dioxaborolan-2-yl)-5,6-dihydropyridine-1(2H)-carboxylate (X) and nitropyridine (W) first undergo a coupling reaction under palladium catalysis, followed by the reduction of the nitro group and the double bond; and (2) the bromine atom on nitropyridine (W) is substituted by the commercially available amine (V), followed by the reduction of the nitro group.

EMBODIMENTS

The following examples are provided to describe the present invention in more detail, but the scope of the present invention is not limited thereto.

Approach A

A general method for the preparation of Intermediate A, Intermediate B and Intermediate C is shown below.

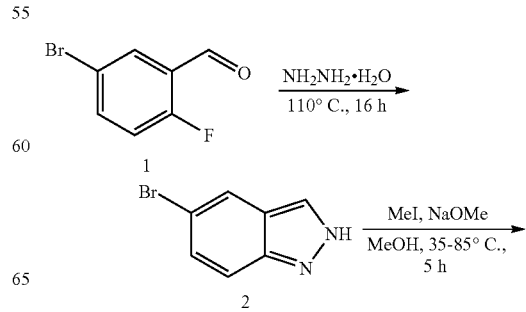

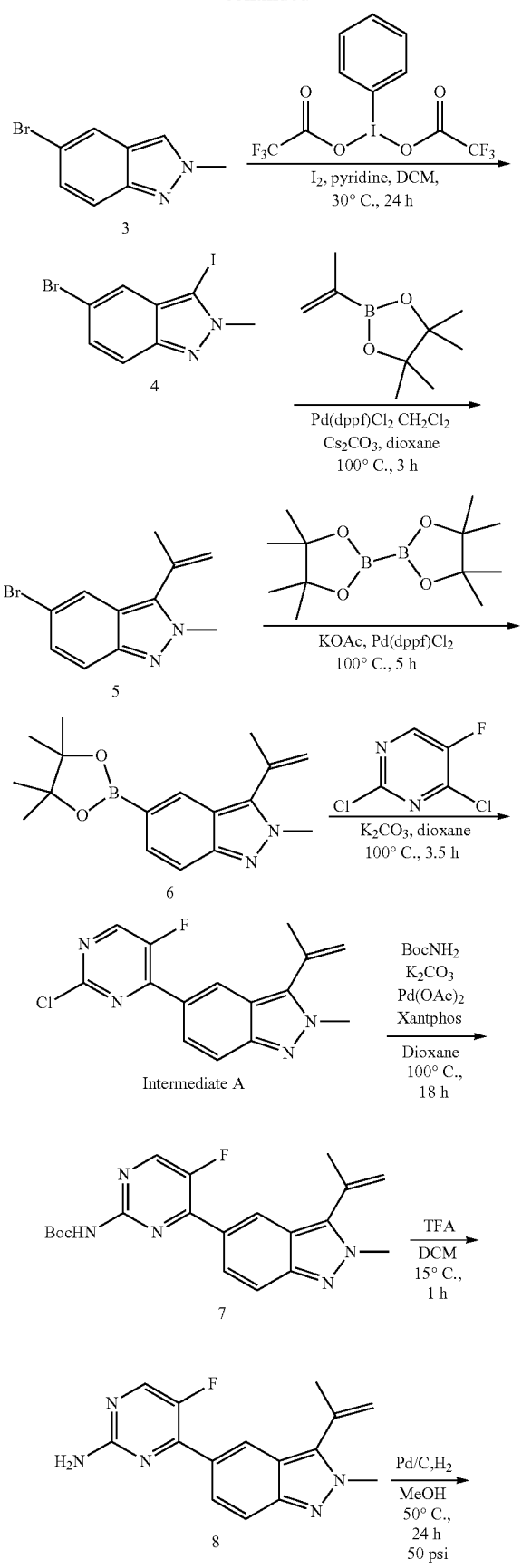

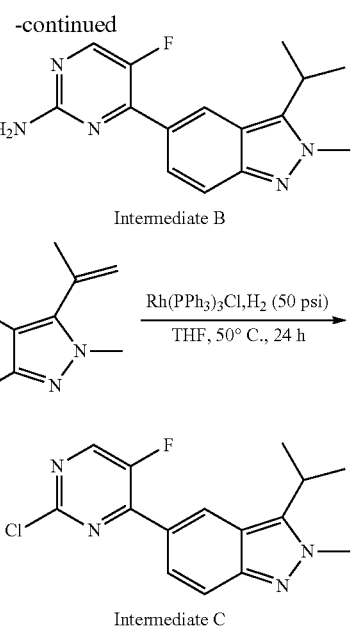

Step 1:

5-bromo-2(H)-indazole

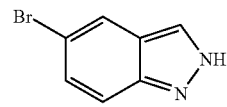

5-bromo-2-fluorobenzaldehyde (18.00 g, 88.67 mmol, 1.00 equivalent) was slowly added to a 85% aqueous solution of hydrazine hydrate (103.00 g, 2.06 mol, 23.20 equivalents), and a white solid slowly precipitated during the addition. The mixture was stirred at 110° C. for 16 hours. LC/MS showed that the majority was the target compound. The mixture was cooled to 16° C. and filtered. The filter cake was washed with water (100 mL) to give a crude product. The crude product was purified by column chromatography (petroleum ether: ethyl acetate=3:2) to give the title compound (6.50 g, 32.99 mmol, 37.21% yield) as a white solid. LC/MS (ESI) m/z: 197.1 (M+1).

Step 2:

5-bromo-2-methyl-2H-indazole

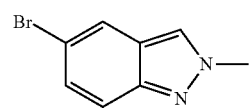

To a solution of 5-bromo-2H-indazole (20.00 g, 101.51 mmol, 1.00 equivalent) and sodium methoxide (5.48 g, 5.48 mmol, 5.48 equivalents) in methanol (150.00 mL) was added methyl iodide (57.00 g, 401.58 mmol, 3.96 equivalents) dropwise at 30° C. in a nitrogen atmosphere, and the dropping duration was controlled to be 1 hour. The mixture was then heated to 85° C. and stirred for 5 hours. LC/MS showed that the starting material was almost completely consumed, and detected the MS of the desired compound. The mixture was cooled to 16° C. and concentrated to give a crude product. The crude product was diluted with 3% aqueous solution of NaHCO$_3$ (30 mL), and subjected to extraction using ethyl acetate (80 mL×2). The organic phase was concentrated under reduced pressure. The residue was purified by column chromatography (petroleum ether: ethyl acetate=30:1 to 1:1) to give the title compound (8.40 g, 39.80 mmol, 39.21% yield) as a gray solid. $^1$H NMR (400 MHz, DMSO-d$_6$) δ 8.33 (s, 1H), 7.95 (s, 1H), 7.58 (d, J=8.0 Hz, 1H), 7.30 (dd, J=1.8 Hz, 8 Hz, 1H), 4.18 (s, 1H). LC/MS (ESI) m/z: 210.8 (M+1).

Step 3:

5-bromo-3-iodo-2-methyl-2H-indazole

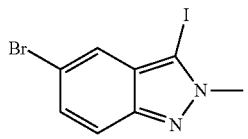

To a solution of 5-bromo-2-methyl-2H-indazole (8.40 g, 39.80 mmol, 1.00 equivalent) in dichloromethane (90 mL) were added pyridine (4.72 g, 59.70 mmol, 1.5 equivalents) and bis(trifluoroacetoxy)iodobenzene (20.54 g, 47.76 mmol, 1.20 equivalents) at 30° C. The mixture was stirred for 0.5 hours, and then iodine (12.12 g, 47.76 mmol, 1.20 equivalents) was added thereto and further stirred for 23.5 hours. LC/MS showed completion of the reaction. The mixture was filtered to give the title compound (8.20 g, crude product) as a yellow solid. LC/MS (ESI) m/z: 336.9 (M+1).

Step 4:

5-bromo-2-methyl-3-isopropenyl-2H-indazole

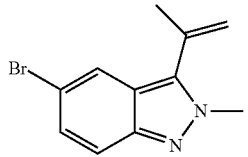

To a solution of 5-bromo-3-iodo-2-methyl-2H-indazole (7.68 g, 22.79 mmol, 1.00 equivalent) and isopropenyl borate (4.21 g, 25.07 mmol, 1.11 equivalents) in dioxane (90.00 mL) were added a saturated aqueous solution (30 mL) of K$_2$CO$_3$ (9.45 g, 68.38 mmol, 3.00 equivalents) and Pd(dppf)Cl$_2$.CHCl$_2$ (1.86 g, 2.28 mmol, 0.10 equivalent.). The mixture was stirred at 100° C. for 3 hours. TLC showed that the starting material reacted almost completely. The mixture was cooled to 30° C. and filtered, the filtrate was subjected to extraction using ethyl acetate (100 mL×3), washed with water (50 mL×3), washed with saturated brine (20 mL×3), dried over anhydrous Na$_2$SO$_4$, filtered and concentrated. The residue was purified by column chromatography (petroleum ether: ethyl acetate=1:1) to give the title compound (5.36 g, 21.34 mmol, 93.66% yield) as a yellow oil.

Step 5:

2-methyl-3-isopropenyl-5-borate-2H-indazole

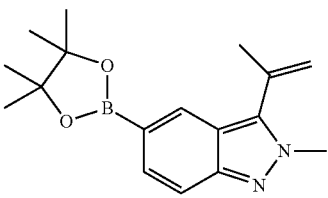

In a nitrogen atmosphere, to a solution of 5-bromo-2-methyl-3-isopropenyl-2H-indazole (2.80 g, 11.15 mmol, 1.00 equivalent) and bis(pinacolato)diboron (3.40 g, 13.38 mmol, 1.20 equivalents) in dioxane (56.00 mL) were added KOAc (3.28 g, 33.45 mmol, 3.00 equivalents) and Pd(dppf)Cl$_2$.CHCl$_2$ (1.82 g, 2.23 mmol, 0.20 equivalent). The mixture was stirred at 100° C. for 5 hours. LC/MS showed completion of the reaction, and detected the MS of the target product. The mixture was cooled to 16° C. The mixture was diluted with ethyl acetate (20 mL) and filtered to give the filtrate. The filtrate was purified by column chromatography (petroleum ether: ethyl acetate=1:1) to give the title product (3.30 g, 9.96 mmol, 89.33% yield, 90% purity) as a purple solid. LC/MS (ESI) m/z: 299.1 (M+1).

Step 6:

5-(2-chloro-5-fluoropyrimidin-4-yl)-2-methyl-3-isopropenyl-2H-indazole

Intermediate A

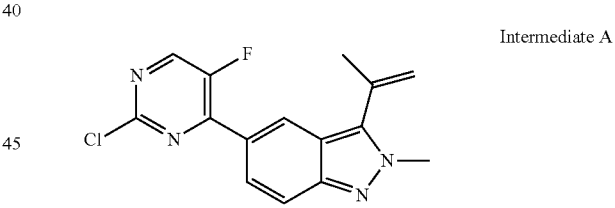

In a nitrogen atmosphere, to a solution of 2,4-dichloro-5-fluoro-pyrimidine (147.83 mg, 885.34 μmol, 1.20 equivalents) and 2-methyl-3-isopropenyl-5-borate-2H-indazole (220.00 mg, 737.78 μmol, 1.00 equivalent) in dioxane (4 mL) were added K$_2$CO$_3$ (305.91 mg, 2.21 mmol, 3.00 equivalents) and Pd(dppf)Cl$_2$.CH$_2$Cl$_2$ (120.50 mg, 147.56 μmol, 0.20 equivalent). The mixture was stirred at 100° C. for 3.5 hours. TLC showed that most of the starting material reacted completely, and LC/MS showed that the majority was the target product. The mixture was cooled to 30° C. and filtered. The filter cake was washed with ethyl acetate (5 mL) and the filtrate was concentrated. The residue was purified by column chromatography (petroleum ether: ethyl acetate=1:0 to 6:1) to give the title product (Intermediate A) (210.0 mg, 693.69 μmol, 94.02% yield) as a bright yellow solid. LC/MS (ESI) m/z: 303.0 (M+1).

Step 7:

tert-butyl 5-fluoro-4-(2-methyl-3-(prop-1-en-2-yl)-2H-indazol-5-yl) pyrimidin-2-yl-carbamate

To a solution of 5-(2-chloro-5-fluoropyrimidin-4-yl)-2-methyl-3-(prop-1-en-2-yl)-2H-indazole (Intermediate A) (1.00 g, 3.30 mmol, 1.00 equivalent) in dioxane (15.00 mL) were added tert-butyl carbamate (966.49 mg, 8.25 mmol, 2.50 equivalents), potassium carbonate (1.37 g, 9.90 mmol, 3.00 equivalents), palladium acetate (74.09 mg, 330.00 µmol, 0.10 equivalent) and Xantphos (381.89 mg, 660.00 µmol, 0.20 equivalent). The vessel was purged three times with nitrogen and stirred at 100° C. for 18 hours. LC/MS showed completion of the reaction and the product was detected. The solution was cooled to 20° C. and filtered. The filtrate was concentrated under reduced pressure to give the title compound (3.00 g, crude product) as a pale yellow solid. The crude product was used in the next step without purification. LC/MS (ESI) m/z: 384.1 (M+1).

Step 8:

5-fluoro-4-(2-methyl-3-(prop-1-en-2-yl)-2H-indazol-5-yl)pyrimidin-2-amine

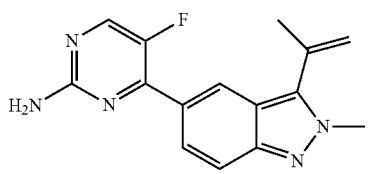 [SMILES: C=C(C)c1c2cc(-c3nc(N)ncc3F)ccc2nn1C]

To a solution of tert-butyl 5-fluoro-4-(2-methyl-3-(prop-1-en-2-yl)-2H-indazol-5-yl) pyrimidin-2-yl-carbamate (3.00 g, 3.31 mmol, 1.00 equivalent) in dichloromethane (30.00 mL) was added trifluoroacetic acid (10.00 mL) dropwise. The solution was stirred at 15° C. for 1 hour. TLC (petroleum ether: ethyl acetate=1:1) showed that the starting material reacted completely. The solution was dried using a rotary vacuum dryer under reduced pressure at 30° C. The crude product was diluted with dichloromethane (100 mL) and washed with saturated sodium bicarbonate (100 mL) and saturated brine (100 mL). The organic phase was dried over anhydrous sodium sulfate and concentrated. The crude product was purified by silica gel column (petroleum ether: ethyl acetate=5:1 to 3:1) to give the title compound (770.00 mg, 2.72 mmol, 82.11% yield) as a brown solid.

Step 9:

5-fluoro-4-(3-isopropyl-2-methyl-2H-indazol-5-yl) pyrimidine-2-amine

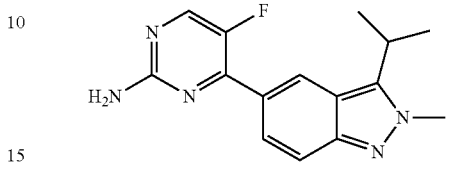

Intermediate B

To a solution of 5-fluoro-4-(2-methyl-3-(prop-1-en-2-yl)-2H-indazol-5-yl) pyrimidine-2-amine (770.00 mg, 2.72 mmol, 1.00 equivalent) in methanol (20.00 mL) was added palladium on carbon (250.00 mg). The solution was heated to 50° C. and stirred for 24 hours in a hydrogen (15 psi) atmosphere. LC/MS showed that the starting material reacted completely and the product was detected. The reaction solution was cooled to 20° C. and filtered. The filtrate was concentrated to give the title compound (Intermediate B) (600.00 mg, 2.10 mmol, 77.26% yield) as a yellow solid. $^1$H NMR (400 MHz, CDCl$_3$) δ 8.55 (s, 1H), 8.20 (d, J=3.9 Hz, 1H), 7.96 (d, J=9.2 Hz, 1H), 7.69 (d, J=9.7 Hz, 1H), 5.06 (br s, 2H), 4.17 (s, 3H), 3.54-3.45 (m, 1H), 1.57 (d, J=7.2 Hz, 6H).

Step 10:

5-(2-chloro-5-fluoropyrimidin-4-yl)-2-methyl-3-isopropyl-2H-indazole

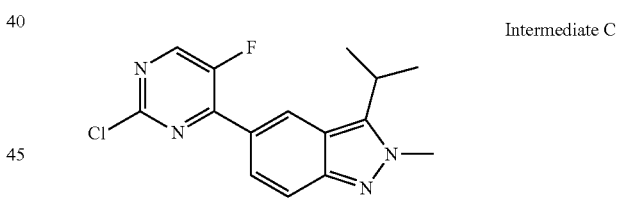

Intermediate C

To a solution of 5-(2-chloro-5-fluoropyrimidin-4-yl)-2-methyl-3-isopropenyl-2H-indazole (Intermediate A) (36.50 g, 120.57 mmol, 1.00 equivalent) in tetrahydrofuran (182.5 mL) was added Rh(PPh$_3$)$_3$Cl (11.16 g, 12.06 mmol, 0.10 equivalent). The reaction system was purged with hydrogen several times. The mixture was stirred at 50° C. in a hydrogen atmosphere of 50 psi for 24 hours. LC/MS showed completion of the reaction. The mixture was cooled to 25° C. and concentrated under reduced pressure. To the residue was added methanol (100 mL), and the mixture was beaten and stirred for 16 hours and then filtered. The filter cake was washed with methanol (15 mL×3) and dried under reduced pressure to give the title compound (Intermediate C) (28.00 g, 91.88 mmol, 76.20% yield) as a yellowish solid. $^1$H NMR (400 MHz, CDCl$_3$) 8.69 (s, 1H), 8.49 (d, J=3.5 Hz, 1H), 8.06 (d, J=9.3 Hz, 1H), 7.73 (d, J=9.3 Hz, 1H), 4.19 (s, 3H), 3.58-3.49 (m, 1H), 1.59 (d, J=7.2 Hz, 6H). LC/MS (ESI) m/z: 305.2 (M+1).

EXAMPLE 1

N-(5-fluoro-4-(3-isopropyl-2-methyl-2H-indazol-5-yl)pyrimidin-2-yl)-6-(4-methylpiperazin-1-yl)pyridazine-3-amine

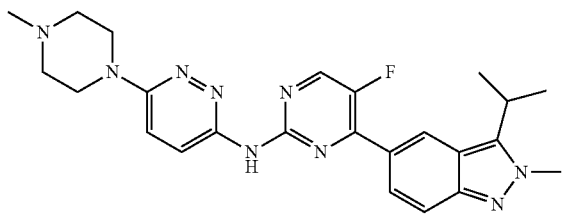

Step 1:

6-(4-methylpiperazin-1-yl)pyridazine-3-amine

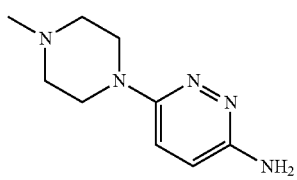

A mixture of 6-chloro-3-aminopyridazine (3.00 g, 23.16 mmol, 1.00 equivalent) and 1-methylpiperazine (8.10 g, 80.87 mmol, 3.49 equivalents) was added to a microwave tube, and the tube was sealed. The mixture was heated to 170° C. and stirred for 1.5 hours under microwave. LC/MS showed completion of the reaction. The mixture was cooled to 20° C. and concentrated under reduced pressure. The residue was purified by preparative HPLC (alkaline) to give the title compound (3.53 g, 18.27 mmol, 78.87% yield) as a white solid. $^1$H NMR (400 MHz, DMSO-$d_6$) δ 7.11 (d, J=9.6 Hz, 1H), 6.73 (d, J=9.6 Hz, 1H), 5.63 (s, 2H), 3.30-3.24 (m, 4H), 2.42-2.36 (m, 4H), 2.19 (s, 3H). LC/MS (ESI) m/z: 194.1 (M+1).

Step 2:

N-(5-fluoro-4-(2-methyl-3-isopropenyl-2H-indazol-5-yl)pyrimidin-2-yl)-6-(4-methylpiperazin-1-yl)pyridazine-3-amine

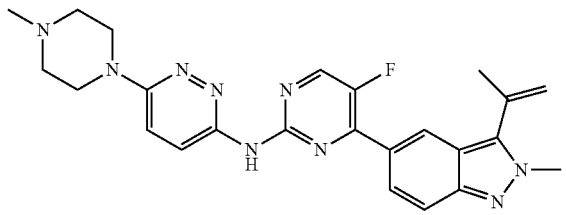

In a nitrogen atmosphere, to a solution of 5-(2-chloro-5-fluoropyrimidin-4-yl)-2-methyl-3-isopropenyl-2H-indazole (Intermediate A) (350.00 mg, 1.16 mmol, 1.00 equivalent) and 6-(4-methylpiperazin-1-yl)pyridazine-3-amine (228.65 mg, 1.18 mmol, 1.02 equivalents) in dioxane (8 mL) were added $Cs_2CO_3$ (753.39 mg, 2.31 μmol, 2.00 equivalents), Xantphos (267.59 mg, 462.46 μmol, 0.40 equivalent) and $Pd_2(dba)_3$ (211.74 mg, 231.21 μmol, 0.20 equivalent). The mixture was stirred at 100-110° C. for 16 hours. TLC and LC/MS showed that the starting material reacted completely. The mixture was cooled to 20° C., diluted with ethyl acetate (20 mL), and filtered. The filtrate was concentrated to give a crude product. The crude product was added to methanol (10 mL) and allowed to stand at 25° C. until yellow precipitate appeared, and filtered. The filter cake was washed with a small amount of methanol and dried to give the title compound (120.00 mg, 258.53 μmol, 22.29% yield, 99% purity) as a yellow solid. LC/MS (ESI) m/z: 460.3 (M+1).

Step 3:

N-(5-fluoro-4-(3-isopropyl-2-methyl-2H-indazol-5-yl)pyrimidin-2-yl)-6-(4-methylpiperazin-1-yl)pyridazine-3-amine

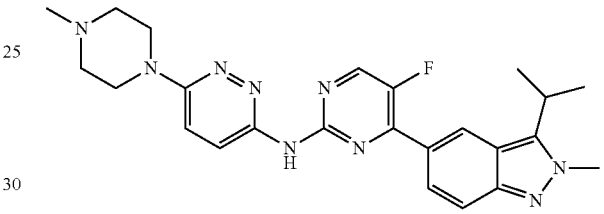

To a solution of Pd/C (50 mg) in methanol (10 mL) was added N-(5-fluoro-4-(2-methyl-3-isopropenyl-2H-indazol-5-yl)pyrimidin-2-yl)-6-(4-methylpiperazin-1-yl)pyridazine-3-amine (120.00 mg, 261.14 μmol, 1.00 equivalent). Hydrogen gas was introduced into the reaction system and maintained at a pressure of 15 psi. The mixture was stirred at 40-50° C. for 8 hours.

LC/MS showed completion of the reaction. After filtration, the filtrate was concentrated. The residue was purified by preparative HPLC (hydrochloric acid) to give the title compound (57.00 mg, 123.50 μmol, 47.29% yield). $^1$H NMR (400 MHz, methanol-$d_4$) δ 8.72 (s, 1H), 8.46 (d, J=4.0 Hz, 1H), 8.41 (d, J=9.6 Hz, 1H), 8.06 (d, J=9.2 Hz, 1H), 7.65 (d, J=9.2 Hz, 1H), 7.40 (d, J=9.2 Hz, 1H), 4.20 (s, 3H), 3.68-3.61 (m, 5H), 2.63 (t, J=4.8 Hz, 4H), 2.39 (s, 3H), 1.59 (d, J=7.2 Hz, 6H). LC/MS (ESI) m/z: 462.2 (M+1).

EXAMPLE 2

5-fluoro-4-(3-isopropyl-2-methyl-2H-indazol-5-yl)-N-(5-(piperazin-1-yl)pyrazin-2-yl) pyrimidine-2-amine

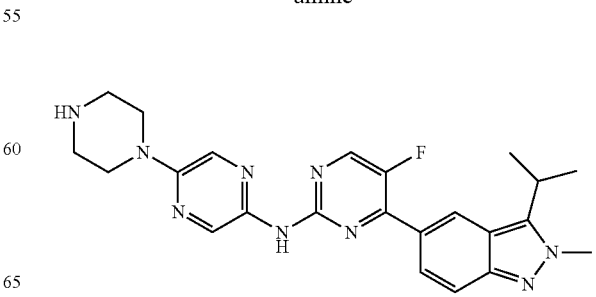

Step 1:

tert-butyl
4-(5-bromopyrazin-2-yl)piperazine-1-carboxylate

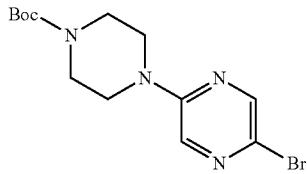 [SMILES: CC(C)(C)OC(=O)N1CCN(c2cnc(Br)cn2)CC1]

To a solution of 2,5-dibromopyrazine (10.00 g, 42.04 mmol, 1.00 equivalent) in N-methylpyrrolidone (100 mL) were added tert-butyl piperazine-1-carboxylate (7.83 g, 42.04 mmol, 1.00 equivalent) and K$_2$CO$_3$ (8.72 g, 63.06 mmol, 1.50 equivalents). The mixture was heated to 100° C. and stirred for 18 hours. TLC (petroleum ether: ethyl acetate=10:1) showed completion of the reaction. The mixture was cooled to 20° C., diluted with water (200 mL), subjected to extraction using ethyl acetate (200 mL×2), dried over anhydrous Na$_2$SO$_4$, filtered and concentrated. The residue was purified by column chromatography (petroleum ether: ethyl acetate=20:1 to 5:1) to give the title compound (11.00 g, 2.05 mmol, 76.24% yield) as a yellow solid. $^1$H NMR (400 MHz, CDCl$_3$) δ 8.15 (d, J=1.38 Hz, 1H) 7.87 (d, J=1.38 Hz, 1H) 3.56 (s, 8H) 1.49 (s, 9H).

Step 2:

tert-butyl
4-(5-aminopyrazin-2-yl)piperazine-1-carboxylate

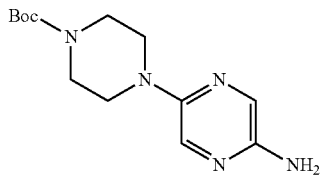 [SMILES: CC(C)(C)OC(=O)N1CCN(c2cnc(N)cn2)CC1]

In a nitrogen atmosphere, to a solution of tert-butyl 4-(5-bromopyrazin-2-yl)piperazine-1-carboxylate (10.00 g, 29.14 mmol, 1.00 equivalent) and tri-tertert-butylphosphine tetrafluoroborate (2.54 g, 8.74 mmol, 0.30 equivalent) in toluene (100 mL) were added LHMDS (1M, 60.00 mL, 2.06 equivalents) and Pd$_2$(dba)$_3$ (2.60 g, 2.84 mmol, 0.10 equivalent). The mixture was stirred at 65° C. for 16 hours. LC/MS showed completion of the reaction. The mixture was cooled to 20° C., quenched with water (50 mL), and subjected to extraction using ethyl acetate (100 mL×3). The organic phases were combined and concentrated. The residue was dissolved in ethyl acetate (100 mL) and purified by preparative HPLC (alkaline) to give the title compound (5.00 g, 17.90 mmol, 61.43% yield) as an orange solid. LC/MS (ESI) m/z: 280.1 (M+1).

Step 3:

tert-butyl 4-(5-((5-fluoro-4-(2-methyl-3-(isopropenyl)-2H-indazol-5-yl)pyrimidin-2-yl)amino)
pyrazin-2-yl)piperazine-1-carboxylate

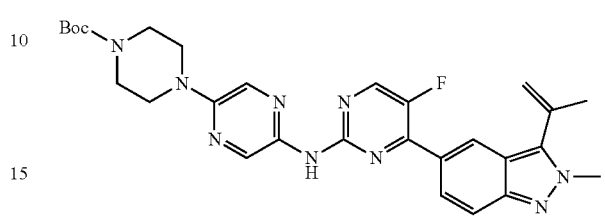

In a nitrogen atmosphere, to a solution of 5-(2-chloro-5-fluoropyrimidin-4-yl)-2-methyl-3-isopropenyl-2H-indazole (200.00 mg, 660.65 µmol, 1.00 equivalent) and tert-butyl 4-(5-aminopyrazin-2-yl) piperazin-1-carboxylate (246.06 mg, 792.78 µmol, 1.20 equivalents) in dioxane (10 mL) were added Cs$_2$CO$_3$ (430.51 mg, 1.32 mmol, 2.00 equivalents), Xantphos (152.91 mg, 264.26 µmol, 0.40 equivalent), and Pd$_2$(dba)$_3$ (120.99 mg, 132.13 µmol, 0.20 equivalent). The mixture was stirred at 110-120° C. for 16 hours. LC/MS showed completion of the reaction. The mixture was cooled to 25° C. and filtered. The filter cake was washed with ethyl acetate, and the filtrate was concentrated. The residue was purified by preparative TLC (dichloromethane:methanol=20:1) to give the title compound (150.00 mg, 247.43 µmol, 37.45% yield, 90% purity) as a green solid. LC/MS (ESI) m/z: 546.2 (M+1).

Step 4:

tert-butyl 4-(5-((5-fluoro-4-(3-isopropyl-2-methyl-2H-indazol-5-yl)pyrimidin-2-yl)amino) pyrazin-2-yl)piperazine-1-carboxylate

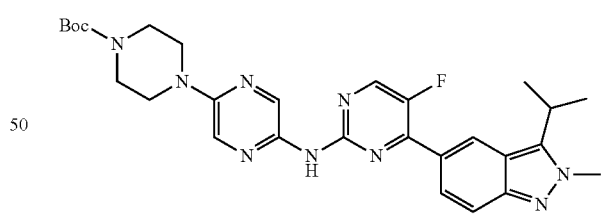

To a solution of tert-butyl 4-(5((5-fluoro-4-(2-methyl-3-(isopropenyl)-2H-indazol-5-yl)pyrimidin-2-yl)amino) pyrazin-2-yl)piperazine-1-carboxylate (90.00 mg, 164.95 µmol, 1.00 equivalent) in tetrahydrofuran (10 mL) were added Pd/C (100 mg) and a catalytic amount of acetic acid. Hydrogen gas was introduced into the reaction system and maintained at a pressure of 15 psi. The mixture was stirred at 50-60° C. for 16 hours. LC/MS showed completion of the reaction. The mixture was cooled to 20° C., and filtered. The filtrate was concentrated to give the title compound (90.00 mg, crude product), the crude product was used directly in the next step. LC/MS (ESI) m/z: 548.3 (M+1).

Step 5:

5-fluoro-4-(3-isopropyl-2-methyl-2H-indazol-5-yl)-N-(5-(piperazin-1-yl)pyrazin-2-yl) pyrimidine-2-amine

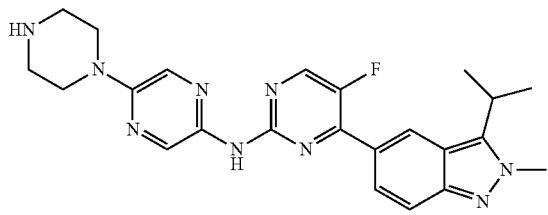 [SMILES: CC(C)c1c2cc(-c3nc(Nc4cnc(N5CCNCC5)cn4)ncc3F)ccc2nn1C]

To a solution of tert-butyl 4-(5-((5-fluoro-4-(3-isopropyl-2-methyl-2H-indazol-5-yl) pyrimidin-2-yl)amino)pyrazin-2-yl)piperazine-1-carboxylate (90.00 mg, 164.34 µmol, 1.00 equivalent) in methanol (5 mL) was added hydrochloric acid-methanol (4M, 1 mL, 20 mmol, 1.00 equivalent). The mixture was stirred at 30-40° C. for 3 hours. TLC (dichloromethane:methanol=30:1) showed complete consumption of the starting material. LC/MS showed that the product accounted for 49% and the by-product accounted for 44%. The mixture was cooled to 25° C. and concentrated. The residue was purified by preparative HPLC (hydrochloric acid) to give the title compound (6.00 mg, 13.41 µmol, 8.16% yield). $^1$H NMR (400 MHz, methanol-$d_4$) δ 8.96 (s, 1H), 8.68 (d, J=4.4 Hz, 1H), 8.31 (d, J=9.2 Hz, 1H), 8.12 (s, 1H), 7.79 (d, J=8.8 Hz, 1H), 4.29 (s, 3H), 3.91 (t, J=4.8 Hz, 4H), 3.74-3.69 (m, 1H), 3.43 (t, J=5.2 Hz, 4H), 1.65 (d, J=7.2 Hz, 6H). LC/MS (ESI) m/z: 448.1 (M+1).

EXAMPLE 3

5-fluoro-4-(3-isopropyl-2-methyl-2H-indazol-5-yl)-N-(5-(piperazin-1-yl)pyridin-2-yl) pyrimidine-2-amine

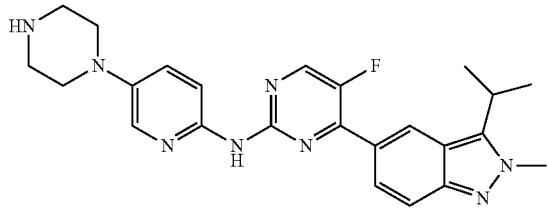 [SMILES: CC(C)c1c2cc(-c3nc(Nc4ccc(N5CCNCC5)cn4)ncc3F)ccc2nn1C]

Step 1:

tert-butyl 4-(6-nitropyridin-3-yl)piperazine-1-carboxylate

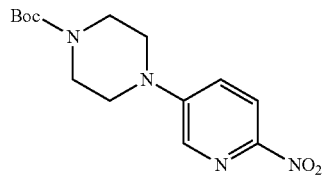 [SMILES: CC(C)(C)OC(=O)N1CCN(c2ccc([N+](=O)[O-])nc2)CC1]

To a solution of 5-bromo-2-nitropyridine (20.00 g, 98.53 mmol, 1.00 equivalent) in dimethylsulfoxide (52 mL) were added tert-butyl piperazine-1-carboxylate (24.00 g, 128.86 mmol, 1.31 equivalentalents) and triethylamine (20.00 g, 197.65 mmol, 2.01 equivalents). The solution was heated to 60° C. and stirred for 18 hours. TLC (petroleum ether: ethyl acetate=3:1) showed completion of the reaction. The solution was diluted with water (200 mL), stirred for 30 minutes, and then filtered. The filter cake was washed with water and dried in vacuo to give a crude product. The crude product was purified by silica gel column (petroleum ether: ethyl acetate=50:1 to 20:1) to give the title compound (27.00 g, 87.57 mmol, 88.87% yield) as a yellow solid. $^1$H NMR (400 MHz, CDCl$_3$) δ 8.18 (d, J=9.03 Hz, 1H), 8.13 (d, J=2.89 Hz, 1H), 7.21 (dd, J=9.10, 2.95 Hz, 1H), 3.69-3.59 (m, 4H), 3.51-3.40 (m, 4H), 1.49 (s, 9H).

Step 2:

tert-butyl 4-(6-aminopyridin-3-yl)piperazine-1-carboxylate

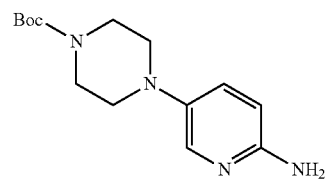 [SMILES: CC(C)(C)OC(=O)N1CCN(c2ccc(N)nc2)CC1]

In a nitrogen atmosphere, to a solution of tert-butyl 4-(6-nitropyridin-3-yl) piperazine-1-carboxylate (28.00 g, 90.81 mmol, 1.00 equivalent) in methanol (600 mL) was added palladium on carbon (6%, 1.7 g). The suspension was evacuated and filled with hydrogen several times. The solution was stirred at 50° C. in a hydrogen atmosphere (50 psi) for 18 hours. TLC (dichloromethane:methanol=10:1) showed that the starting material reacted completely. The suspension was filtered, and the filtrate was dried using a rotary vacuum dryer to give the title compound (24.13 g, 86.69 mmol, 95.46% yield) as a purple solid. $^1$H NMR (400 MHz, CDCl$_3$) δ 7.78 (d, J=2.64 Hz, 1H) 7.18 (dd, J=8.78, 2.89 Hz, 1H) 6.50 (d, J=8.78 Hz, 1H) 4.21 (br s, 2H) 3.60-3.54 (m, 4H) 3.00-2.92 (m, 4H) 1.48 (s, 9H).

Step 3:

tert-butyl 4-(6-((5-fluoro-4-(2-methyl-3-(prop-1-en-2-yl)-2H-indazol-5-yl)pyrimidin-2-yl)amino) pyridin-3-yl)piperazine-1-carboxylate

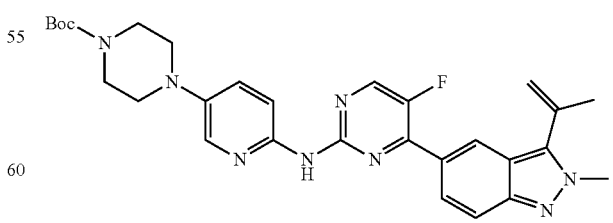

To a solution of 5-(2-chloro-5-fluoropyrimidin-4-yl)-2-methyl-3-(prop-1-en-2-yl)-2H-indazole (Intermediate A) (200.00 mg, 660.65 µmol, 1.00 equivalent) in dioxane (10.00 mL) were added tert-butyl 4-(6-aminopyridin-3-yl)

piperazine-1-carboxylate (220.67 mg, 792.79 μmol, 1.20 equivalents), Pd₂(dba)₃ (60.50 mg, 66.07 μmol, 0.10 equivalent), Xantphos (76.45 mg, 132.13 μmol, 0.20 equivalent), and cesium carbonate (430.51 mg, 1.32 mmol, 2.00 equivalents). The solution was heated to 110° C. in a nitrogen atmosphere and stirred for 16 hours. LC/MS showed completion of the reaction. The solution was cooled to 25° C., filtered, and concentrated to give a crude product. The crude product was purified by preparative TLC (ethyl acetate: petroleum ether=1:2) to give the title compound (320.00 mg, 587.57 μmol, 88.94% yield) as a pale yellow solid. LC/MS (ESI) m/z: 545.3 (M+1).

Step 4:

tert-butyl 4-(6-((5-fluoro-4-(3-isopropyl-2-methyl-2H-indazol-5-yl)pyrimidin-2-yl)amino)pyridin-3-yl)piperazine-1-carboxylate

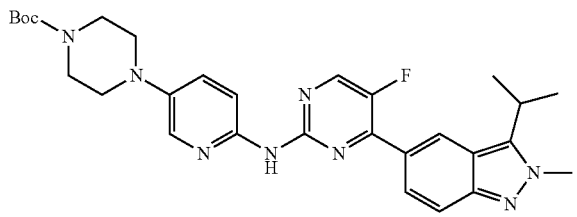 [SMILES: CC(C)c1c2cc(-c3nc(Nc4ccc(N5CCN(C(=O)OC(C)(C)C)CC5)cn4)ncc3F)ccc2nn1C]

In a nitrogen atmosphere, to a solution of tert-butyl 4-(6-((5-fluoro-4-(2-methyl-3-(prop-1-en-2-yl)-2H-indazol-5-yl)pyrimidin-2-yl)amino) pyridin-3-yl)piperazine-1-carboxylate in methanol (20.00 mL) were added palladium on carbon (200.00 mg) and acetic acid (2.10 g, 34.97 mmol, 59.52 equivalents). The suspension was evacuated and filled with hydrogen several times. The solution was stirred at 50° C. in a hydrogen atmosphere (32 psi) for 96 hours. LC/MS showed completion of the reaction. The suspension was cooled to 25° C., filtered, and concentrated to give the title compound (500.00 mg, crude product) as an off-white solid. LC/MS (ESI) m/z: 547.1 (M+1).

Step 5:

5-fluoro-4-(3-isopropyl-2-methyl-2H-indazol-5-yl)-N-(5-(piperazin-1-yl)pyridin-2-yl) pyrimidine-2-amine

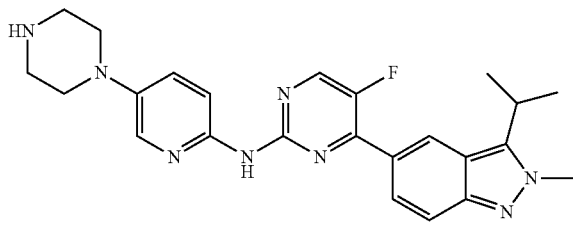 [SMILES: CC(C)c1c2cc(-c3nc(Nc4ccc(N5CCNCC5)cn4)ncc3F)ccc2nn1C]

At 25° C., to a solution of tert-butyl 4-(6-((5-fluoro-4-(3-isopropyl-2-methyl-2H-indazol-5-yl)pyrimidin-2-yl)amino) pyridin-3-yl) piperazine-1-carboxylate (500.00 mg, 914.68 μmol, 1.00 equivalent) in dichloromethane (5.00 mL) was added trifluoroacetic acid (2.09 g, 18.29 mmol, 20.00 equivalents) in one portion. The solution was stirred for 0.5 h. LC/MS showed completion of the reaction. The solution was concentrated under reduced pressure to give a crude product. The crude product was purified by preparative HPLC (hydrochloric acid) to give the title compound (99.69 mg, 223.26 μmol, 24.41% yield). ¹H NMR (400 MHz, Methanol-d₄) δ 8.98 (s, 1H), 8.85 (d, J=3.39 Hz, 1 H), 8.53 (d, J=9.03 Hz, 1H), 8.32 (dd, J=9.72, 2.20 Hz, 1H), 8.01-7.96 (m, 1H), 7.93 (d, J=9.03 Hz, 1H), 7.60 (d, J=9.66 Hz, 1H), 4.39 (s, 3H), 3.79 (dt, J=13.90, 6.92 Hz, 1H), 3.65-3.56 (m, 4H), 3.49 (d, J=5.02 Hz, 4H), 1.69 (d, J=7.03 Hz, 6H). LC/MS (ESI) m/z: 447.1 (M+1).

EXAMPLE 4

N-(5-(4-ethylpiperazin-1-yl)pyridin-2-yl)-5-fluoro-4-(3-isopropyl-2-methyl-2H-indazol-5-yl)pyrimidine-2-amine

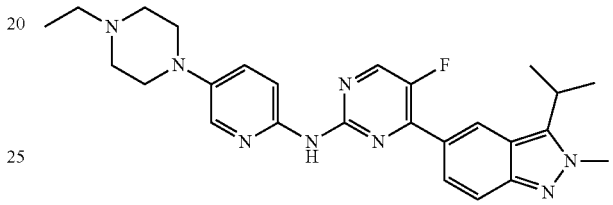

To a solution of 5-fluoro-4-(3-isopropyl-2-methyl-2H-indazol-5-yl)-N-(5-piperazin-1-yl-2-pyridyl)pyrimidine-2-amine (210.00 mg, 470.30 μmol, 1.00 equivalent) in methanol (5.00 mL) were added acetaldehyde (77.69 mg, 705.46 μmol, 1.50 equivalents), NaBH₃CN (59.11 mg, 940.61 μmol, 2.00 equivalents) and acetic acid (14.12 mg, 235.15 μmol, 0.50 equivalent). The solution was stirred at 20° C. for 2 hours. LC/MS showed completion of the reaction. The solution was filtered, and the filtrate was concentrated under reduced pressure to give a crude product. The crude product was purified by preparative HPLC (hydrochloric acid) to give the title compound (66.50 mg, 128.83 μmol, 27.39% yield, 99% purity, hydrochloride). ¹H NMR (400 MHz, Methanol-d₄) δ 8.97 (s, 1H), 8.84 (d, J=3.6 Hz, 1H), 8.52 (d, J=9.2 Hz, 1H), 8.32 (dd, J=9.7, 2.8 Hz, 1H), 7.98 (d, J=2.8 Hz, 1H), 7.92 (d, J=9.0 Hz, 1H), 7.59 (d, J=9.5 Hz, 1H), 4.38 (s, 3H), 4.02-3.93 (m, 2H), 3.82-3.74 (m, 3H), 3.38-3.34 (m, 4H), 3.32-3.28 (m, 2H), 1.69 (d, J=7.0 Hz, 6H), 1.46 (t, J=7.3 Hz, 3H). LC/MS (ESI) m/z: 475.2 (M+1).

EXAMPLE 5

N-(6-(1,4-diazepan-1-yl)pyridazin-3-yl)-5-fluoro-4-(3-isopropyl-2-methyl-2H-indazol-5-yl)pyrimidine-2-amine

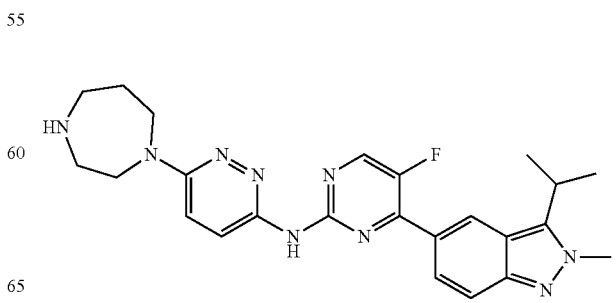

Step 1:

tert-butyl 4-(6-chloropyridazin-3-yl)-1,4-diazepane-1-carboxylate

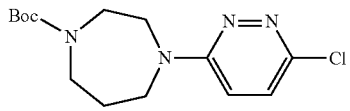 [SMILES: CC(C)(C)OC(=O)N1CCCN(c2ccc(Cl)nn2)CC1]

To a solution of 3,6-dichloropyridazine (2.00 g, 13.42 mmol, 1.05 equivalents), tert-butyl 1,4-diazepane-1-carboxylate (2.56 g, 12.78 mmol, 1.00 equivalent) in dimethyl sulfoxide (15.00 mL) was added triethylamine (3.88 g, 38.34 mmol, 3.00 equivalents) in one portion.

The solution was heated to 80° C. and stirred for 7 hours. LC/MS showed that the reaction was complete, and MS detected the product. The solution was cooled to 25° C. and concentrated to give a crude product. The crude product was purified by column chromatography (petroleum ether: ethyl acetate=30:1 to 20:1) to give the title compound (1.20 g, crude product). The crude product was a yellow solid. $^1$H NMR (400 MHz, CDCl$_3$) δ 7.18 (d, J=9.4 Hz, 1H), 6.79 (d, J=9.4 Hz, 1H), 3.87-3.57 (m, 6H), 3.39-3.23 (m, 2H), 1.99-1.93 (m, 2H), 1.40 (s, 9H). LC/MS (ESI) m/z: 313.1 (M+1).

Step 2:

tert-butyl 4-(6-(5-fluoro-4-(3-isopropyl-2-methyl-2H-indazol-5-yl)pyrimidin-2-yl-amino)pyridazin-3-yl)-1,4-diazepane-1-carboxylate

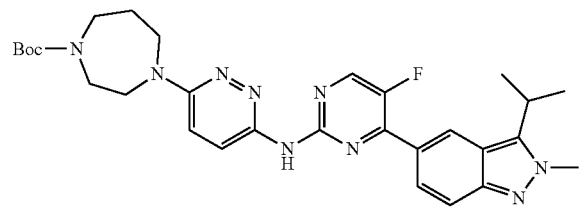 [SMILES: CC(C)c1c2cc(-c3nc(Nc4ccc(N5CCCN(C(=O)OC(C)(C)C)CC5)nn4)ncc3F)ccc2nn1C]

To a solution of 5-fluoro-4-(3-isopropyl-2-methyl-2H-indazol-5-yl)pyrimidine-2-amine (Intermediate B) (200.00 mg, 700.97 μmol, 1.00 equivalent) in dioxane (3.00 mL) were added tert-butyl 4-(6-chloropyridazin-3-yl)-1,4-diazepane-1-carboxylate, cesium carbonate (575.00 mg, 1.76 mmol, 2.52 equivalents), Pd$_2$(dba)$_3$ (65.00 mg, 70.98 μmol, 0.10 equivalent) and Xantphos (85.00 mg, 146.90 μmol, 0.21 equivalent). The air in the container was replaced with nitrogen three times. The mixture was heated to 100° C. and stirred for 18 hours. LC/MS showed that the starting material reacted completely and detected the product. The solution was cooled to 20° C. and concentrated to give a crude product. The crude product was purified by preparative TLC (ethyl acetate) to give the title compound (120.00 mg, 213.66 μmol, 30.48% yield) as a pale yellow solid. LC/MS (ESI) m/z: 562.2 (M+1).

Step 3:

N-(6-(1,4-diazepan-1-yl)pyridazin-3-yl)-5-fluoro-4-(3-isopropyl-2-methyl-2H-indazol-5-yl)pyrimidine-2-amine

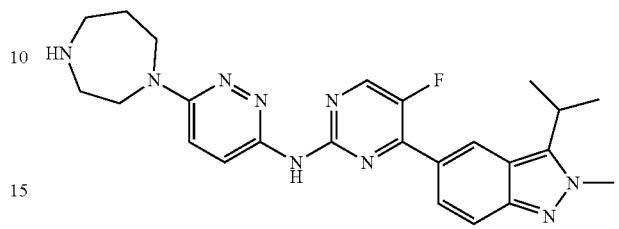

To a solution of tert-butyl 4-(6-(5-fluoro-4-(3-isopropyl-2-methyl-2H-indazol-5-yl) pyrimidin-2-yl-amino) pyridazin-3-yl)-1,4-diazepane-1-carboxylate (120.00 mg, 213.66 μmol, 1.00 equivalent) in dichloromethane (2.00 mL) was added trifluoroacetic acid (1.00 mL) dropwise. The solution was stirred at 25° C. for 1 hour. LC/MS showed that the starting material reacted completely and detected the product. The solution was concentrated under reduced pressure to give a crude product. The crude product was purified by preparative HPLC (hydrochloric acid) to give the title compound (45.38 mg, 98.32 μmol, 46.02% yield). $^1$H NMR (400 MHz, Methanol-d$_4$) δ 8.96 (s, 1H) 8.85 (d, J=3.4 Hz, 1H) 8.48 (d, J=9.2 Hz, 1H) 8.08 (d, J=10.0 Hz, 1H) 7.90 (d, J=9.2 Hz, 2H) 4.36 (s, 3H) 4.11 (t, J=5.0 Hz, 2H) 3.89 (t, J=5.9 Hz, 2H) 3.76 (quin, J=7.0 Hz, 1H) 3.52 (t, J=5.1 Hz, 2H) 3.48-3.36 (m, 2H) 2.28 (br s, 2H) 1.68 (d, J=7.0 Hz, 6H).

EXAMPLE 6

N-(6-(3-(dimethylamino)pyrrolidin-1-yl)pyridazin-3-yl)-5-fluoro-4-(3-isopropyl-2-methyl-2H-indazol-5-yl)pyrimidine-2-amine

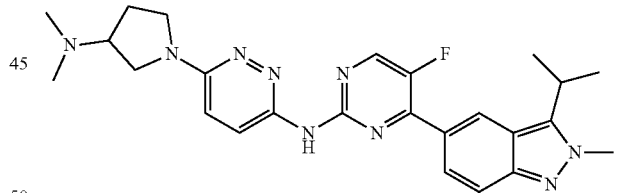

Step 1:

1-(6-chloropyridazin-3-yl)-N,N-dimethylpyrrolidine-3-amine

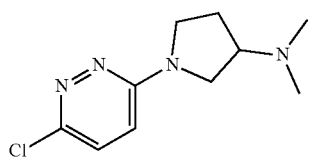

A solution of 3,6-dichloropyridazine (1.20 g, 8.05 mmol, 1.00 equivalent), N,N-dimethylpyrrolidine-3-amine (1.01 g, 8.86 mmol, 1.10 equivalents) and triethylamine (815.06 mg, 8.05 mmol, 1.00 equivalent) in N,N-dimethylformamide (15.00 mL) was heated to 80° C. and stirred for 16 hours. LC/MS showed completion of the reaction and MS detected the product. The solution was cooled to 25° C. The mixture was purified by preparative HPLC to give the title compound (1.40 g, 6.18 mmol, 76.71% yield) as a bright purple solid. LC/MS (ESI) m/z: 227.1 (M+1).

Step 2:

N-(6-(3-(dimethylamino)pyrrolidin-1-yl)pyridazin-3-yl)-5-fluoro-4-(3-isopropyl-2-methyl-2H-indazol-5-yl)pyrimidine-2-amine

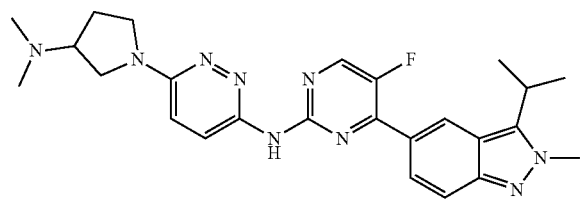

To a solution of 5-fluoro-4-(3-isopropyl-2-methyl-2H-indazol-5-yl)pyrimidine-2-amine (Intermediate B) (150.00 mg, 525.73 µmol, 1.00 equivalent) in dioxane (3.00 mL) were added 1-(6-chloropyridazin-3-yl)-N,N-dimethylpyrrolidin-3-amine (143.03 mg, 630.88 µmol, 1.20 equivalents), cesium carbonate (428.23 mg, 1.31 mmol, 2.50 equivalents), $Pd_2(dba)_3$ (48.14 mg, 52.57 µmol, 0.10 equivalent), and Xantphos (60.84 mg, 105.15 µmol, 0.20 equivalent). The container was replaced with nitrogen three times. The mixture was heated to 100° C. and stirred for 18 hours. LC/MS showed that some of the starting material did not react, while the product was detected. The solution was cooled to 20° C., diluted with dichloromethane (10 mL) and then filtered. The filtrate was concentrated to give a crude product. The crude product was purified by preparative HPLC (hydrochloric acid) to give the title compound (15.33 mg, 32.24 µmol, 6.13% yield). $^1$H NMR (400 MHz, Methanol-$d_4$) δ 8.94 (s, 1H), 8.81 (d, J=3.4 Hz, 1H), 8.46 (d, J=9.3 Hz, 1H), 7.99 (br s, 1H), 7.92-7.78 (m, 2H), 4.35 (s, 3H), 4.26-4.09 (m, 2H), 4.01-3.85 (m, 2H), 3.84-3.64 (m, 2H), 3.02 (s, 6H), 2.66 (br s, 1H), 2.46 (dd, J=7.9, 13.1 Hz, 1H), 1.67 (d, J=7.0 Hz, 6H).

EXAMPLE 7

3-[4-[6-[[5-fluoro-4-(3-isopropyl-2-methyl-2H-indazol-5-yl)pyrimidin-2-yl]amino]-3-pyridyl]piperazin-1-yl]propanenitrile

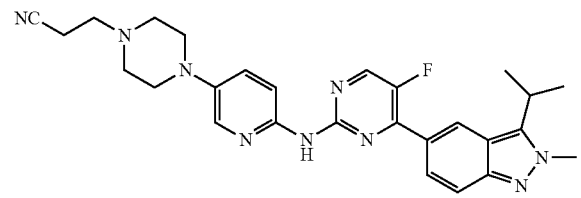 [SMILES: CC(C)c1c2cc(-c3nc(Nc4ccc(N5CCN(CCC#N)CC5)cn4)ncc3F)ccc2nn1C]

To a solution of 5-fluoro-4-(3-isopropyl-2-methyl-2H-indazol-5-yl)-N-(5-piperazin-1-yl-2-pyridyl)pyrimidine-2-amine (200.00 mg, 447.91 µmol, 1.00 equivalent) in dimethylsulfoxide (4 mL) were added potassium carbonate (123.81 mg, 895.82 µmol, 2.00 equivalents) and 3-bromopropionitrile (120.01 mg, 895.82 µmol, 73.63 µL, 2.00 equivalents). The mixture was stirred at 25° C. for 16 hours. LC/MS showed that about 50% of the starting material was present. The mixture was then heated to 50° C. and stirred at 50° C. for 2 hours. LC/MS showed that about 16% of the starting material was present. Methanol (3 mL) was then added to the mixture. The mixture was further stirred at 50° C. for 2 hours. LC/MS showed completion of the reaction. The mixture was cooled to 25° C. and concentrated to remove methanol to give a crude product. The resulting crude product was diluted with water (15 mL) and filtered. The resulting filter cake was beaten in methanol (5 mL) to give the title compound (146.40 mg, 276.05 µmol, 61.63% yield, 94.2% purity). $^1$H NMR (400 MHz, CDCl$_3$) δ 8.68 (s, 1H), 8.38-8.31 (m, 2H), 8.07-8.02 (m, 2H), 7.99 (s, 1H), 7.73 (d, J=9.16 Hz, 1H), 7.34 (dd, J=9.03, 3.01 Hz, 1H), 4.19 (s, 3H), 3.57-3.46 (m, 1H), 3.22-3.14 (m, 4H), 2.82-2.75 (m, 2H), 2.74-2.67 (m, 4H), 2.60-2.55 (m, 2H), 1.59 (d, J=7.03 Hz, 6H). LC/MS (ESI) m/z: 500.3 (M+1).

EXAMPLE 8

2-[4-[6-[[5-fluoro-4-(3-isopropyl-2-methyl-2H-indazol-5-yl)pyrimidin-2-yl]amino]-3-pyridyl]piperazin-1-yl]acetonitrile

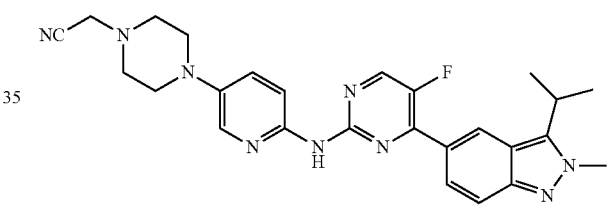

To a solution of 5-fluoro-4-(3-isopropyl-2-methyl-2H-indazol-5-yl)-N-(5-piperazin-1-yl-2-pyridyl)pyrimidine-2-amine (50.00 mg, 111.98 µmol, 1.00 equivalent) in dimethylsulfoxide (3 mL) was added potassium carbonate (30.95 mg, 223.96 µmol, 2.00 equivalents) and bromoacetonitrile (26.86 mg, 223.96 µmol, 2.00 equivalents). The mixture was stirred at 25° C. for 1 hour. LC/MS showed completion of reaction. The mixture was concentrated and then diluted with water (10 mL). The aqueous phase was subjected to extraction using ethyl acetate (10 mL×3). The combined organic phases was washed with saturated brine (15 mL), dried over anhydrous sodium sulfate, filtered and concentrated to give a crude product. The crude product was purified by being beaten in methanol (5 mL×2) to give the title compound (12.40 mg, 24.52 µmol), 21.89% yield, 96% purity). $^1$H NMR (300 MHz, DMSO-$d_6$) δ 9.70 (s, 1H), 8.67 (s, 1H), 8.58 (d, J=3.96 Hz, 1H), 8.14-8.00 (m, 2H), 7.92 (d, J=9.23 Hz, 1H), 7.66 (d, J=9.23 Hz, 1H), 7.43 (dd, J=9.04 Hz, 3.01 Hz, 1H), 4.14 (s, 3H), 3.81 (s, 2H), 3.60 (td, J=13.85, 6.83 Hz, 1H), 3.22-3.11 (m, 4H), 2.69-2.60 (m, 4H), 1.50 (d, J=6.97 Hz, 6H). LC/MS (ESI) m/z: 486.3 (M+1).

EXAMPLE 9

N-[5-[4-(2-aminoethyl)piperazin-1-yl]-2-pyridyl]-5-fluoro-4-(3-isopropyl-2-methyl-2H-indazol-5-yl)pyrimidine-2-amine

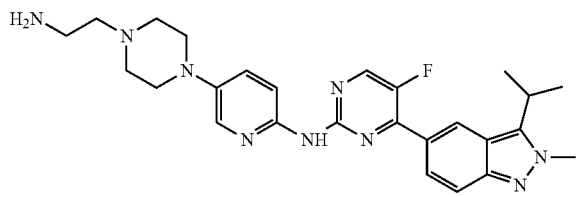 [SMILES: CC(C)c1c2cc(-c3nc(Nc4ccc(N5CCN(CCN)CC5)cn4)ncc3F)ccc2nn1C]

Step 1:

2-(4-(6-((5-fluoro-4-(3-isopropyl-2-methyl-2H-indazol-5-yl)pyrimidin-2-yl)amino)pyridin-3-yl)piperazin-1-yl)acetonitrile

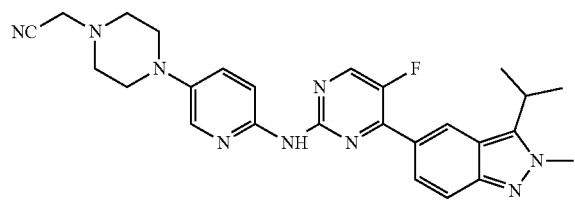 [SMILES: CC(C)c1c2cc(-c3nc(Nc4ccc(N5CCN(CC#N)CC5)cn4)ncc3F)ccc2nn1C]

To a solution of 5-fluoro-4-(3-isopropyl-2-methyl-2H-indazol-5-yl)-N-(5-piperazin-1-yl-2-pyridyl)pyrimidine-2-amine (17.60 g, 39.42 mmol, 1.00 equivalent) and potassium carbonate (10.90 g, 78.84 mmol, 2.00 equivalents) in dimethylsulfoxide (176.00 mL) was added 2-bromoacetonitrile (9.46 g, 78.84 mmol, 5.26 mL, 2.00 equivalents). The mixture was stirred at 30° C. for 1 hour. LC/MS showed completion of the reaction. The mixture was poured into water (30 mL) and filtered. The resulting filter cake was washed with water (5 mL×2) and dried in vacuo to give the title compound (16.00 g, 32.95 mmol, 83.59% yield) as a yellow solid. LC/MS (ESI) m/z: 486.3 (M+1).

Step 2:

N-[5-[4-(2-aminoethyl)piperazin-1-yl]-2-pyridyl]-5-fluoro-4-(3-isopropyl-2-methyl-2H-indazol-5-yl)pyrimidine-2-amine

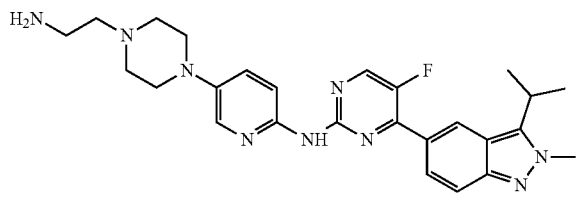 [SMILES: CC(C)c1c2cc(-c3nc(Nc4ccc(N5CCN(CCN)CC5)cn4)ncc3F)ccc2nn1C]

Under an atmosphere of hydrogen at 50 psi, 2-(4-(6-((5-fluoro-4-(3-isopropyl-2-methyl-2H-indazol-5-yl)pyrimidin-2-yl)amino)pyridin-3-yl)piperazin-1-yl)acetonitrile (6.00 g, 12.36 mmol, 1.00 equivalent) and raney nickel (8.47 g, 98.88 mmol, 8.00 equivalents) in a mixed solution of aqueous ammonia (10.00 mL) and tetrahydrofuran (100.00 mL) were stirred at 50° C. for 16 hours. LC/MS showed completion of the reaction. The mixture was filtered. The resulting filter cake was washed with ethanol (100 mL×3). The combined organic layers was concentrated in vacuo to give a crude product. The residue was purified by preparative HPLC (hydrochloric acid) to give the title compound (6.50 g, 10.85 mmol, 87.80% yield, 100% purity, hydrochloride). $^1$H NMR (400 MHz, Methanol-$d_4$) δ 8.90 (s, 1H), 8.79 (d, J=3.6 Hz, 1H), 8.39-8.22 (m, 2H), 7.95 (d, J=2.9 Hz, 1H), 7.82 (d, J=9.2 Hz, 1H), 7.58 (d, J=9.7 Hz, 1H), 4.30 (s, 3H), 3.73 (td, J=14.0, 7.1 Hz, 3H), 3.68-3.54 (m, 6H), 3.50 (br. s., 2H), 3.34 (br. s., 2H), 1.65 (d, J=7.0 Hz, 6H). LC/MS (ESI) m/z: 490.3 (M+1).

EXAMPLE 10

2-[4-[6-[[5-fluoro-4-(3-isopropyl-2-methyl-2H-indazol-5-yl)pyrimidin-2-yl]amino]-3-pyridyl]piperazin-1-yl]ethanol

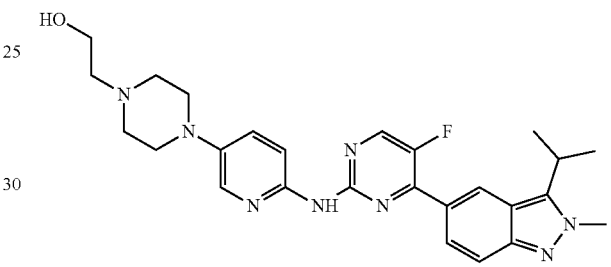

Step 1:

2-[4-[6-[[5-fluoro-4-(3-isopropyl-2-methyl-2H-indazol-5-yl)pyrimidin-2-yl]amino]-3-pyridyl]piperazin-1-yl]ethanol

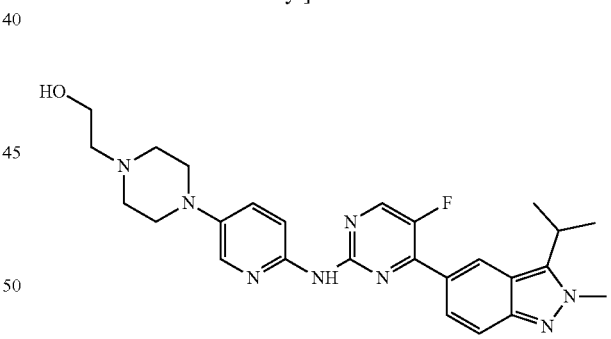

To a solution of 5-fluoro-4-(3-isopropyl-2-methyl-2H-indazol-5-yl)-N-(5-piperazin-1-yl-2-pyridyl)pyrimidine-2-amine (2.00 g, 4.48 mmol, 1.00 equivalent) and 2-bromoethanol (1.68 g, 13.44 mmol, 954.55 μL, 3.00 equivalents) in ethanol (30.00 mL) was added diisopropyl ethylamine (1.74 g, 13.44 mmol, 2.35 mL, 3.00 equivalents). The mixture was heated to 80° C. and stirred for 16 hours. LC/MS showed that the starting material was almost completely consumed, and MS detected the desired compound. The mixture was cooled to 25° C. and filtered. The filter cake was beaten in methanol (10 mL). The mixture was filtered, and the filter cake was dried to give the title compound (1.50 g, 2.97 mmol, 66.20% yield, 97% purity). $^1$H NMR (400 MHz, Methanol-$d_4$) δ 8.74 (s, 1H), 8.44 (d, J=3.9 Hz, 1H), 8.23 (d, J=9.0 Hz, 1H), 8.07 (d, J=8.9 Hz, 1H), 8.01 (d, J=2.6 Hz, 1H), 7.65 (d, J=9.2 Hz, 1H), 7.49 (dd, J=9.0, 2.9 Hz, 1H), 4.19 (s, 3H), 3.75 (t, J=6.0 Hz, 2H), 3.64 (td, J=14.1, 7.0 Hz, 1H), 3.26-3.18 (m, 4H), 2.80-2.70 (m, 4H), 2.62 (t, J=6.0 Hz, 2H), 1.60 (d, J=7.0 Hz, 6H). LC/MS (ESI) m/z: 491.3 (M+1).

EXAMPLE 11

(4-(6-((5-fluoro-4-(3-isopropyl-2-methyl-2H-indazol-5-yl)pyrimidin-2-yl)amino)pyridin-3-yl)piperazin-2-yl)methanol

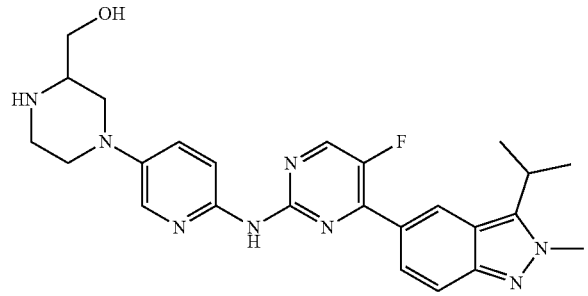 [SMILES: CC(C)c1c2cc(-c3nc(Nc4ccc(N5CCNC(CO)C5)cn4)ncc3F)ccc2nn1C]

Step 1:

(piperazin-2-yl)methanol

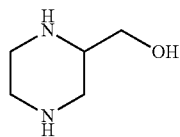

At 0° C., to a suspension of lithium aluminum tetrahydrate (5.61 g, 147.74 mmol, 1.5 equivalents) in tetrahydrofuran (300 mL) was added piperazine-2-carboxylic acid (20.00 g, 98.49 mmol, 1.00 equivalent, 2 hydrochloride) in separate portions. The mixture was heated to 70° C. and stirred for 18 hours. LC/MS showed complete conversion of the starting material and detected the target product. The reaction mixture was cooled to 0° C., and quenched with water (5 mL) and an aqueous solution of sodium hydroxide (15%, 5 mL). The mixture was filtered, and the filter cake was washed with dichloromethane (100 mL). The filtrate was dried over anhydrous sodium sulfate and concentrated to give the title compound (2.4 g, 20.66 mmol, 20.98% yield) as a pale yellow oil. $^1$H NMR (400 MHz, CDCl$_3$) δ 3.54 (dd, J=4.1, 10.7 Hz, 1H), 3.40 (d, J=7.2 Hz, 1H), 3.02-2.95 (m, 1H), 2.90 (dd, J=11.9, 2.6 Hz, 3H), 2.81-2.75 (m, 4H), 2.47 (dd, J=11.8, 10.3 Hz, 1H), 1.41 (s, 1H).
Step 2:

(4-(6-nitropyridin-3-yl)piperazin-2-yl)methanol

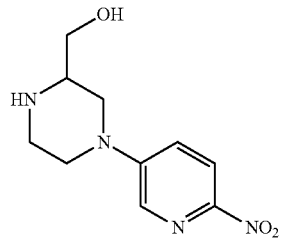 [SMILES: O=[N+]([O-])c1ccc(N2CCNC(CO)C2)cn1]

To a solution of (piperazin-2-yl)methanol (2.4 g, 20.66 mmol, 1.00 equivalent) in dimethylsulfoxide (20.00 mL) were added 5-bromo-2-nitropyridine (4.19 g, 20.66 mmol, 1.00 equivalent) and triethylamine (4.18 g, 41.32 mmol, 2.00 equivalents). The reaction mixture was heated to 50° C. and stirred for 18 hours. LC/MS showed complete conversion of the starting material and detected the target product. The reaction solution was used directly in the next step. LC/MS (ESI) m/z: 293.1 (M+1).
Step 3:

tert-butyl 2-(((t-butoxycarbonyl)oxy)methyl)-4-(6-nitropyridin-3-yl)piperazine-1-carboxylate

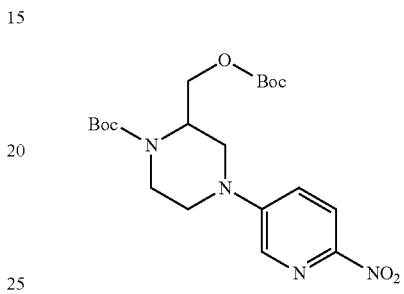

To a solution of (4-(6-nitropyridin-3-yl)piperazin-2-yl) methanol (4.92 g, 20.65 mmol, 1.00 equivalent) in dichloromethane (40.00 mL) were added triethylamine (6.27 g, 61.95 mmol, 3.00 equivalents) and di-tert-butyl dicarbonate (9.01 g, 41.3 mmol, 2.00 equivalents). The mixture was stirred at 15° C. for 18 hours. TLC (petroleum ether: ethyl acetate=1:1) showed complete conversion of the starting material. The reaction solution was diluted with water (100 mL), and dichloromethane was removed in vacuo. The aqueous phase was subjected to extraction using ethyl acetate (50 mL×3). The combined organic phases was washed successively with water (50 mL) and saturated brine (30 mL), dried over anhydrous sodium sulfate and concentrated to give a residue. The residue was purified by column chromatography (petroleum ether: ethyl acetate=10:1 to 3:1) to give the title compound (1.5 g, 3.42 mmol, 16.57% yield) as a yellow solid. $^1$H NMR (400 MHz, CDCl$_3$) δ 8.18 (d, J=9.03 Hz, 1H) 8.11 (d, J=3.01 Hz, 1H) 7.20 (dd, J=9.16, 3.14 Hz, 1H) 4.46 (br. s., 1H) 4.12-4.25 (m, 2H) 4.02 (br. s., 1H) 3.93 (d, J=13.30 Hz, 1H) 3.70-3.80 (m, 1H) 3.28-3.43 (m, 2H) 3.14-3.25 (m, 1H) 1.50 (s, 9H) 1.46 (s, 9H).
Step 4:

tert-butyl 4-(6-amino-3-pyridyl-2-(t-butoxycarbonyloxyethyl)piperazine-1-carboxylate

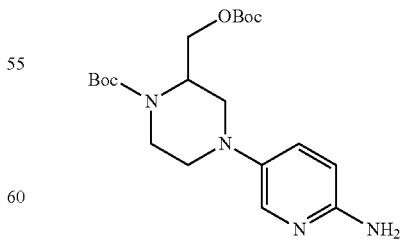

To a solution of tert-butyl 2-(((t-butoxycarbonyl)oxy) methyl)-4-(6-nitropyridin-3-yl) piperazine-1-carboxylate (500 mg, 1.14 mmol, 1.00 equivalent) in methanol (30.00 mL) was added wet palladium on carbon (200.00 mg). The reaction flask was purged with argon and hydrogen three times. The mixture was stirred at 15° C. for 18 hours under a hydrogen pressure (15 psi). TLC (petroleum ether: ethyl acetate=1:1) showed complete conversion of the starting material. The reaction mixture was filtered, and the filter cake was washed with methanol (10 mL). The residue obtained by concentrating the filtrate was purified by preparative TLC (ethyl acetate) to give the title compound (200.00 mg, 489.61 μmol, 42.95% yield) as a brown solid. LC/MS (ESI) m/z: 409.2 (M+1).

Step 5:

tert-butyl 2-(((t-butoxycarbonyl)oxy)methyl)-4-(6-((5-fluoro-4-(3-isopropyl-2-methyl-2H-indazol-5-yl)pyrimidin-2-yl)amino)pyridin-3-yl)piperazine-1-carboxylate

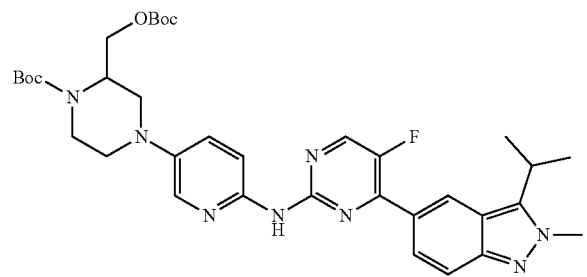

In a nitrogen atmosphere, to a solution of tert-butyl 4-(6-amino-3-pyridyl)-2-(t-butoxycarbonyloxymethyl)piperazine-1-carboxylate (200.00 mg, 489.61 μmol, 1.00 equivalent) in dioxane (5 mL) were added 5-(2-chloro-5-fluoro-pyrimidin-4-yl)-3-isopropyl-2-methyl-2H-indazole (Intermediate C) (150.70 mg, 494.51 μmol, 1.01 equivalents), cesium carbonate (319.05 mg, 979.22 μmol, 2.00 equivalents), Pd$_2$(dba)$_3$ (44.83 mg, 48.96 μmol, 0.10 equivalent) and Xantphos (56.66 mg, 97.92 μmol, 0.20 equivalent). The reaction flask was purged with nitrogen three times. The mixture was heated to 100° C. and stirred for 18 hours. LC/MS showed complete conversion of the starting material and detected the target product. The reaction solution was cooled to 15° C. and filtered. The filter cake was washed with ethyl acetate (5 mL). The residue obtained by concentrating the filtrate was purified by preparative TLC (petroleum ether: ethyl acetate=1:1) to give the title compound (104.00 mg, 153.67 μmol, 31.39% yield) as a brown solid. $^1$H NMR (300 MHz, CDCl$_3$) δ 8.69 (s, 1H), 8.37 (d, J=4.0 Hz, 1H), 8.07-7.98 (m, 2H), 7.73 (d, J=9.2 Hz, 1H), 7.35 (dd, J=2.9, 9.1 Hz, 1H), 4.49 (br. s., 1H), 4.46-4.25 (m, 2H), 4.19 (s, 3H), 4.03 (br. s., 1H), 3.57-3.50 (m, 2H), 3.39 (d, J=11.5 Hz, 1H), 3.23 (t, J=9.6 Hz, 1H), 2.94-2.69 (m, 2H), 1.60 (d, J=7.0 Hz, 6H), 1.50 (s, 9H), 1.50 (s, 9H).

Step 6:

(4-(6-((5-fluoro-4-(3-isopropyl-2-methyl-2H-indazol-5-yl)pyrimidin-2-yl)amino)pyridin-3-yl)piperazin-2-yl)methanol

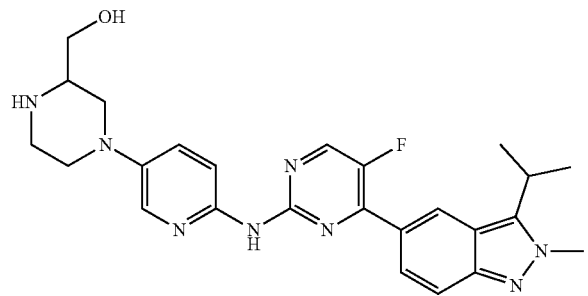 [SMILES: CC(C)c1c2cc(-c3nc(Nc4ccc(N5CCNC(CO)C5)cn4)ncc3F)ccc2nn1C]

To a solution of tert-butyl 2-((t-butoxycarbonyl)oxy)methyl)-4-(6-((5-fluoro-4-(3-isopropyl-2-methyl-2H-indazol-5-yl)pyrimidin-2-yl)amino)pyridin-3-yl)piperazine-1-carboxylate (100 mg, 147.76 μmol, 1.00 equivalent) in dichloromethane (2.00 mL) was added trifluoroacetic acid (1.00 mL). The mixture was stirred at 15° C. for 1 hour. LC/MS showed complete conversion of the starting material and detected the target product. The residue obtained by concentrating the reaction solution was purified by preparative HPLC (hydrochloric acid) to give the title compound (43.08 mg, 78.41 μmol, 53.07% yield, hydrochloride). $^1$H NMR (400 MHz, methanol-d$_4$) δ 8.92 (s, 1H), 8.80 (d, J=3.5 Hz, 1H), 8.41 (d, J=9.2 Hz, 1H), 8.30 (dd, J=2.5, 9.7 Hz, 1H), 7.96 (d, J=2.5 Hz, 1H), 7.85 (d, J=9.0 Hz, 1H), 7.57 (d, J=9.5 Hz, 1H), 4.33 (s, 3H), 3.96-3.84 (m, 3H), 3.84-3.69 (m, 2H), 3.57 (d, J=12.9 Hz, 2H), 3.39 (dt, J=3.0, 12.1 Hz, 1H), 3.28-3.09 (m, 2H), 1.65 (d, J=7.0 Hz, 6H). LC/MS (ESI) m/z: 477.2 (M+1).

EXAMPLE 12

N-[5-[3-(ethylamino)pyrrolidin-1-yl]-2-pyridyl]-5-fluoro-4-(3-isopropyl-2-methyl-2H-indazol-5-yl)pyrimidine-2-amine

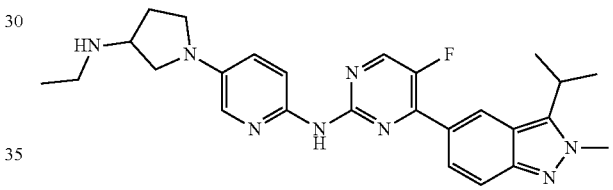

Step 1:

tert-butyl (3S)-3-hydroxypyrrolidine-1-carboxylate

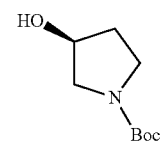

To a solution of (3S)-pyrrolidin-3-ol (3.50 g, 28.32 mmol, 1.00 equivalent, hydrochloride) in dichloromethane (30.00 mL) were added triethylamine (11.46 g, 113.28 mmol, 4.00 equivalents) and di-tert-butyl dicarbonate (8.04 g, 36.82 mmol, 1.30 equivalents). The mixture was stirred at 20° C. for 18 hours. TLC showed completion of the reaction. The mixture was diluted with water (10 mL) and then an aqueous solution of citric acid (10%, 20 mL) was added thereto. The aqueous phase was subjected to extraction using dichloromethane (10 mL×2). The combined organic phases was washed with saturated brine (20 mL×1), dried over anhydrous sodium sulfate, filtered, and concentrated to give the title compound (4.00 g, crude product) as a yellow oil. $^1$H NMR (400 MHz, Methanol-d$_4$) δ 4.42-4.32 (m, 1H), 3.49-3.35 (m, 3H), 3.31-3.19 (m, 1H), 2.08-1.82 (m, 2H), 1.51-1.42 (m, 9H).

Step 2:

tert-butyl 3-oxopyrrolidine-1-carboxylate

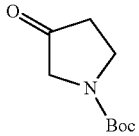 [SMILES: CC(C)(C)OC(=O)N1CCC(=O)C1]

At 0° C., to a solution of tertert-butyl (3S)-3-hydroxypyrrolidine-1-carboxylate (500.00 mg, 2.67 mmol, 1.00 equivalent) in dichloromethane (10.00 mL) was added Dess-Martin periodinane (1.70 g, 4.01 mmol, 1.50 equivalents) in separate portions. The mixture was heated to 20° C., and was stirred at 20° C. for 18 hours. TLC showed completion of the reaction. The reaction solution was quenched with 10 mL of a 30% sodium sulfite solution, and then a solution of sodium bicarbonate (5 mL) was added thereto. The aqueous phase was subjected to extraction using dichloromethane (5 mL×3). The combined organic phases was washed with saturated brine (15 mL×1), dried over anhydrous sodium sulfate, filtered, and concentrated to give the title compound (453.00 mg, crude product) as a yellow oil. $^1$H NMR (400 MHz, CDCl$_3$) δ 3.85-3.65 (m, 4H), 2.66-2.52 (m, 2H), 1.51-1.44 (m, 9H).

Step 3:

tert-butyl 3-[benzyl(ethyl)amino]pyrrolidine-1-carboxylate

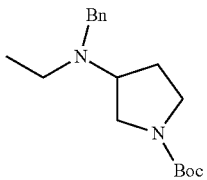 [SMILES: CCN(Cc1ccccc1)C1CCN(C(=O)OC(C)(C)C)C1]

At 0° C., to a solution of tert-butyl 3-oxopyrrolidine-1-carboxylate (353.00 mg, 1.91 mmol, 1.00 equivalent) in dichloromethane (8.00 mL) were added benzyl ethylamine (309.90 mg, 2.29 mmol, 1.20 equivalents) and acetic acid (1.15 mg, 19.10 μmol, 0.01 equivalent). The mixture was stirred at 0° C. for 0.5 h. Sodium cyanoborohydride (647.69 mg, 3.06 mmol, 1.60 equivalents) was then added. The mixture was stirred at 25° C. for 3 hours. LC/MS showed completion of the reaction. The mixture was quenched with water (10 mL). The aqueous phase was subjected to extraction using dichloromethane (10 mL×2). The combined organic phases were washed with saturated brine (10 mL×1), dried over anhydrous sodium sulfate, filtered, and concentrated to give a crude product. The crude product was purified by silica gel column chromatography (petroleum ether: ethyl acetate=20:1 to 10:1) to give the title compound (211.00 mg, 693.10 μmol, 36.29% yield) as a colorless oil. $^1$H NMR (400 MHz, CDCl$_3$) δ 7.38-7.28 (m, 4H), 7.25 (d, J=6.27 Hz, 1H), 3.71-3.06 (m, 7H), 2.59 (q, J=7.15 Hz, 2H), 2.06-1.98 (m, 1H), 1.90-1.77 (m, 1H), 1.46 (s, 9H), 1.04-0.97 (m, 3H). LC/MS (ESI) m/z: 305.3 (M+1).

Step 4:

N-benzyl-N-ethylpyrrolidine-3-amine

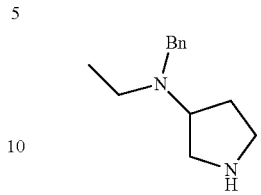

To a solution of tert-butyl 3-[benzyl(ethyl)amino]pyrrolidine-1-carboxylate (2.00 g, 6.57 mmol, 1.00 equivalent) in dichloromethane (12 mL) was added trifluoroacetic acid (4.59 g, 40.27 mmol, 6.13 equivalents). The mixture was stirred at 20° C. for 30 minutes. TLC showed completion of the reaction. The reaction solution was concentrated to give the title compound (2.00 g, crude product, trifluoroacetate) as a yellow oil. LC/MS (ESI) m/z: 205.3 (M+1).

Step 5:

N-benzyl-N-ethyl-1-(6-nitro-3-pyridyl)pyrrolidine-3-amine

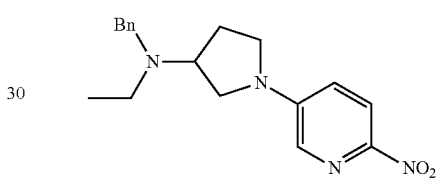

To a solution of N-benzyl-N-ethylpyrrolidine-3-amine (2.00 g, 4.63 mmol, 1.00 equivalent, trifluoroacetate) in dimethylsulfoxide (10.00 mL) were added triethylamine (2.74 g, 27.06 mmol, 5.85 equivalents) and 5-bromo-2-nitropyridine (1.13 g, 5.55 mmol, 1.20 equivalents). The mixture was stirred at 90° C. for 18 hours. LC/MS showed completion of the reaction. The mixture was diluted with water (20 mL), and the aqueous phase was subjected to extraction using ethyl acetate (15 mL×4). The combined organic phases was washed with saturated brine (20 mL×1), dried over anhydrous sodium sulfate, filtered, and concentrated to a crude product. The crude product was purified by silica gel column chromatography (petroleum ether: ethyl acetate=10:1 to 3:1) to give the title compound (700.00 mg, crude product) as a yellow solid. $^1$H NMR (400 MHz, CDCl$_3$) δ 8.16 (d, J=9.04 Hz, 1H), 7.77 (d, J=3.01 Hz, 1H), 7.41-7.28 (m, 4H), 6.81 (dd, J=9.14, 2.92 Hz, 1H), 3.85-3.25 (m, 8H), 2.68 (q, J=7.03 Hz, 2H), 2.36-1.97 (m, 2H), 1.09 (t, J=7.06 Hz, 3H). LC/MS (ESI) m/z: 327.2 (M+1).

Step 6:

5-[3-[benzyl(ethyl)amino]pyrrolidin-1-yl]pyridine-2-amine

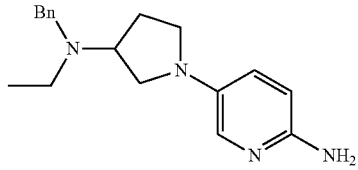 [SMILES: CCN(Cc1ccccc1)C1CCN(c2ccc(N)nc2)C1]

To a solution of N-benzyl-N-ethyl-1-(6-nitro-3-pyridyl)pyrrolidine-3-amine (450.00 mg, 1.38 mmol, 1.00 equivalent) in ethanol (10 mL) were added zinc dust (360.62 mg, 5.52 mmol, 4.00 equivalents) and ammonium chloride (737.48 mg, 13.80 mmol, 10.00 equivalents). The mixture was heated to 70° C. and stirred for 3 hours. LC/MS showed completion of the reaction. The mixture was filtered after it was cooled to 25° C. The filtrate was concentrated to give the title compound (216.00 mg, crude product) as a purple solid. LC/MS (ESI) m/z: 297.2 (M+1).

Step 7:

N-[5-[3-[benzyl(ethyl)amino]pyrrolidin-1-yl]-2-pyridyl]-5-fluoro-4-(3-isopropyl-2-methyl-2H-indazol-5-yl)pyrimidine-2-amine

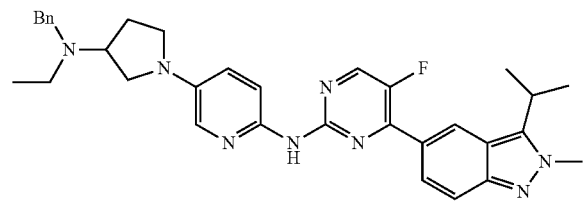 [SMILES: CCN(Cc1ccccc1)C1CCN(c2ccc(Nc3ncc(F)c(-c4ccc5nn(C)c(C(C)C)c5c4)n3)nc2)C1]

In a nitrogen atmosphere, to a solution of 5-[3-[benzyl(ethyl)amino]pyrrolidin-1-yl]pyridine-2-amine (129.00 mg, 435.21 μmol, 1.00 equivalent) in dioxane (4.00 mL) were added 5-(2-chloro-5-fluoro-pyrimidin-4-yl)-3-isopropyl-2-methyl-2H-indazole (Intermediate C) (159.16 mg, 522.25 μmol, 1.20 equivalents), Pd$_2$(dba)$_3$ (39.85 mg, 43.52 μmol, 0.10 equivalent), Xantphos (50.36 mg, 87.04 μmol, 0.20 equivalent), and cesium carbonate (354.50 mg, 1.09 mmol, 2.50 equivalents). The mixture was stirred at 110° C. for 18 hours. LC/MS showed completion of the reaction. The mixture was cooled to 25° C. and then concentrated to give a crude product. The crude product was purified by preparative TLC (ethyl acetate) to give the title compound (145.00 mg, crude product) as a yellow solid. LC/MS (ESI) m/z: 565.3 (M+1).

Step 8:

N-[5-[3-(ethylamino)pyrrolidin-1-yl]-2-pyridyl]-5-fluoro-4-(3-isopropyl-2-methyl-2H-indazol-5-yl)pyrimidine-2-amine

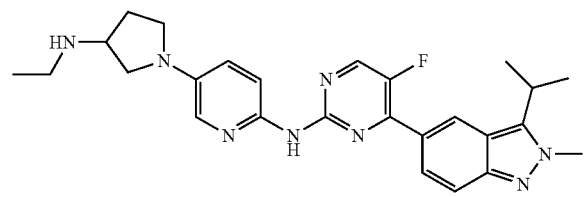 [SMILES: CCNC1CCN(c2ccc(Nc3ncc(F)c(-c4ccc5nn(C)c(C(C)C)c5c4)n3)nc2)C1]

To a solution of N-[5-[3-[benzyl(ethyl)amino]pyrrolidin-1-yl]-2-pyridyl]-5-fluoro-4-(3-isopropyl-2-methyl-2H-indazol-5-yl)pyrimidine-2-amine (181.00 mg, 320.52 μmol, 1.00 equivalent) in tetrahydrofuran (5 mL) were added wet palladium on carbon (400.00 mg) and formamide (2.02 g, 32.05 mmol, 100.00 equivalents). The mixture was stirred at 60° C. for 16 hours. LC/MS showed completion of the reaction. The mixture was cooled to 25° C. and then filtered. The filtrate was concentrated to give a crude product, and the crude product was purified by preparative HPLC (hydrochloric acid) to give the title compound (34.64 mg, 59.47 μmol, 18.56% yield, 94% purity, hydrochloride). $^1$H NMR (400 MHz, Methanol-d$_4$) δ 8.89 (s, 1H), 8.75 (d, J=3.64 Hz, 1H), 8.35 (d, J=9.29 Hz, 1H), 7.92 (dd, J=9.60, 2.95 Hz, 1H), 7.81 (d, J=9.16 Hz, 1H), 7.64 (d, J=2.89 Hz, 1H), 7.53 (d, J=9.54 Hz, 1H), 4.30 (s, 3H), 4.18-4.02 (m, 1H), 3.61-3.85 (m, 4H), 3.54-3.41 (m, 1H), 3.23 (q, J=7.24 Hz, 2H), 2.69-2.52 (m, 1H), 2.44-2.27 (m, 1H), 1.65 (d, J=7.03 Hz, 6H), 1.40 (t, J=7.28 Hz, 3H). LC/MS (ESI) m/z: 475.3 (M+1).

EXAMPLE 13

5-fluoro-4-(3-isopropyl-2-methyl-2H-indazol-5-yl)-N-[5-(piperidin-4-yl)-2-pyridyl]pyrimidine-2-amine

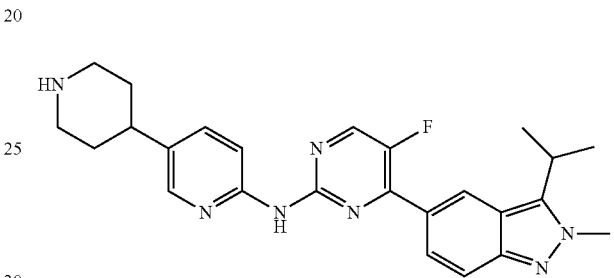

Step 1:

tert-butyl 4-[6-[[5-fluoro-4-(3-isopropyl-2-methyl-2H-indazol-5-yl)pyrimidin-2-yl]amino]-3-pyridyl]piperidine-1-carboxylate

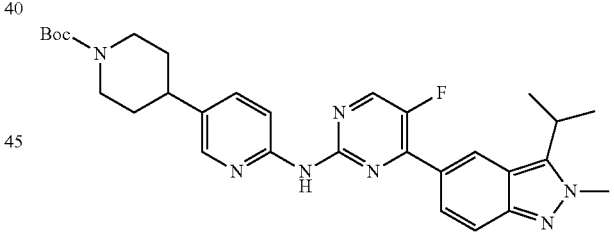

To a solution of 5-(2-chloro-5-fluoro-pyrimidin-4-yl)-3-isopropyl-2-methyl-2H-indazole (1.00 g, 3.28 mmol, 1.00 equivalent) in dioxane (10 mL) were added tert-butyl 4-(6-amino-3-pyridyl)piperidine-1-carboxylate (1.09 g, 3.94 mmol, 1.20 equivalents), Pd$_2$(dba)$_3$ (150.18 mg, 164.00 μmol, 0.05 equivalent), Xantphos (189.79 mg, 328.00 μmol, 0.10 equivalent) and cesium carbonate (2.14 g, 6.56 μmol, 2.00 equivalents) in a nitrogen atmosphere. The mixture was stirred at 110° C. for 16 hours. LC/MS showed completion of the reaction. The mixture was concentrated to give a crude product. The crude product was diluted with dichloromethane (10 mL) and filtered. The filtrate was concentrated to give a crude product. The crude product was purified by being beaten in methanol (10 mL) to give the title compound (1.11 g, crude product). LC/MS (ESI) m/z: 546.2 (M+1).

Step 2:

5-fluoro-4-(3-isopropyl-2-methyl-2H-indazol-5-yl)-N-[5-(piperidin-4-yl)-2-pyridyl]pyrimidine-2-amine

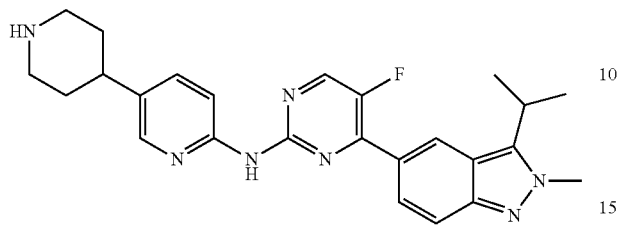

To a solution of tert-butyl 4-[6-[[5-fluoro-4-(3-isopropyl-2-methyl-2H-indazol-5-yl) pyrimidin-2-yl]amino]-3-pyridyl]piperidine-1-carboxylate (1.08 g, 1.98 mmol, 1.00 equivalent) in dichloromethane (12 mL) was added trifluoroacetic acid (5.36 g, 46.97 mmol, 3.48 mL, 23.72 equivalents). The mixture was stirred at 25° C. for 1 hour. LC/MS showed completion of the reaction. The mixture was concentrated to give a crude product. 0.7 g of the crude product was taken and purified by preparative HPLC (hydrochloric acid) to give the title compound (183.40 mg, 350.38 μmol, 17.70% yield, 99.05% purity) as a yellow solid. $^1$H NMR (400 MHz, Methanol-d$_4$) δ 8.93 (s, 1H), 8.83 (d, J=3.51 Hz, 1H), 8.32-8.45 (m, 3H), 7.85 (d, J=9.03 Hz, 1H), 7.62 (d, J=9.16 Hz, 1H), 4.33 (s, 3H), 3.74 (d, J=6.99 Hz, 1H), 3.57 (d, J=12.67 Hz, 2H), 3.10-3.27 (m, 3H), 2.20 (d, J=13.68 Hz, 2H), 1.96-2.10 (m, 2H), 1.66 (d, J=7.03 Hz, 6H). LC/MS (ESI) m/z: 446.2 (M+1).

EXAMPLE 14

3-[4-[6-[[5-fluoro-4-(3-isopropyl-2-methyl-2H-indazol-5-yl)pyrimidin-2-yl]amino]-3-pyridyl]1-piperidinyl]propanenitrile

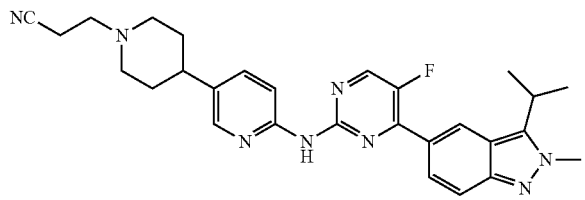 [SMILES: CC(C)c1c2cc(-c3nc(Nc4ccc(C5CCN(CCC#N)CC5)cn4)ncc3F)ccc2nn1C]

To a solution of 5-fluoro-4-(3-isopropyl-2-methyl-2H-indazol-5-yl)-N-[5-(4-piperidinyl)-2-pyridyl]pyrimidine-2-amine (1.25 g, 1.86 mmol, 1.00 equivalent, trifluoroacetate) in methanol (10 mL) was added triethylamine (1.10 g, 10.82 mmol, 1.50 mL, 5.82 equivalents). The mixture was stirred at 25° C. for 30 minutes, and then potassium carbonate (514.14 mg, 3.72 mmol, 2.00 equivalents) and 3-bromopropionitrile (498.37 mg, 3.72 mmol, 305.75 μl, 2.00 equivalents) were added thereto. The mixture was stirred at 25° C. for 16 hours. LC/MS showed completion of the reaction. The mixture was concentrated, diluted with water (15 mL) and then filtered to give a filter cake. The filter cake was beaten in methanol (8 mL) to give the title compound (217.00 mg, 412.59 μmol, 22.18% yield, 94.8% purity). $^1$H NMR (400 MHz, CDCl$_3$) δ 8.70 (s, 1H), 8.42-8.36 (m, 2H), 8.19 (d, J=2.13 Hz, 1H), 8.02-8.09 (m, 2H), 7.74 (d, J=9.16 Hz, 1H), 7.58 (dd, J=8.66 Hz, 2.38 Hz, 1H), 4.19 (s, 3H), 3.59-3.45 (m, 1H), 3.04 (d, J=11.29 Hz, 2H), 2.91-2.73 (m, 2H), 2.60-2.47 (m, 3H), 2.23 (dt, J=11.48 Hz, 2.51 Hz, 2H), 1.93-1.72 (m, 4H), 1.59 (s, 6H). LC/MS (ESI) m/z: 499.3 (M+1).

EXAMPLE 15

N-(5-((1S,4S)-2,5-diazabicyclo[2.2.1]heptan-2-yl)pyridin-2-yl)-5-fluoro-4-(3-isopropyl-2-methyl-2H-indazol-5-yl)pyrimidine-2-amine

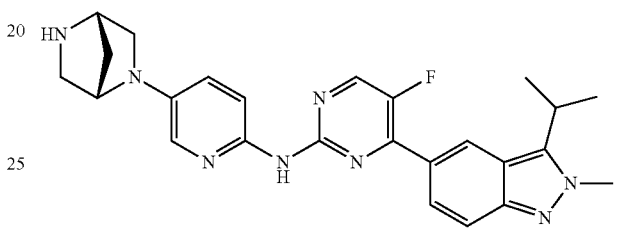

Step 1:

tert-butyl 5-(6-((5-fluoro-4-(3-isopropyl-2-methyl-2H-indazol-5-yl)pyrimidin-2-yl)amino)pyridin-3-yl)-(1S,4S)-2,5-diazabicyclo[2.2.1]heptane-2-carboxylate

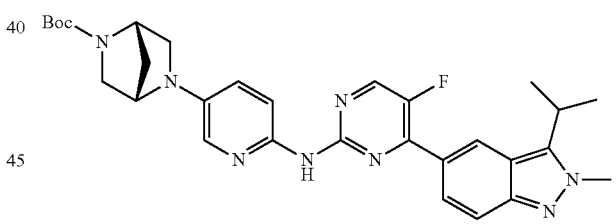

In a nitrogen atmosphere, a solution of 5-(2-chloro-5-fluoro-pyrimidin-4-yl)-3-isopropyl-2-methyl-2H-indazole (Intermediate C) (376.67 mg, 1.24 mmol, 1.20 equivalents), tert-butyl 5-(6-amino-3-pyridyl)-(1S,4S)-2,5-diazabicyclo[2.2.1]heptane-2-carboxylate (300.00 mg, 1.03 mmol, 1.00 equivalent), cesium carbonate (671.19 mg, 2.06 mmol, 2.00 equivalents), Pd(OAc)$_2$ (46.25 mg, 206.00 μmol, 0.20 equivalent) and XPhos (196.41 mg, 412.00 μmol, 0.40 equivalent) in dioxane (10.00 mL) was purged with nitrogen three times. The mixture was stirred at 100° C. for 16 hours. LC/MS showed completion of the reaction. The mixture was concentrated to a residue under reduced pressure, and the residue was purified by preparative TLC (petroleum ether: ethyl acetate=1:2) to give the title compound (350.00 mg, crude product) as a yellow solid. LC/MS (ESI) m/z: 559.3 (M+1).

Step 2:

N-(5-((1S,4S)-2,5-diazabicyclo[2.2.1]heptan-2-yl)pyridin-2-yl)-5-fluoro-4-(3-isopropyl-2-methyl-2H-indazol-5-yl)pyrimidine-2-amine

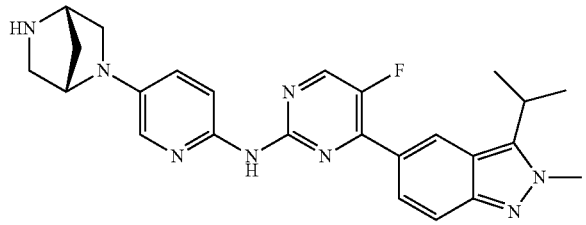 [SMILES: CC(C)c1c2cc(-c3nc(Nc4ccc(N5C[C@@H]6C[C@H]5CN6)cn4)ncc3F)ccc2nn1C]

To a solution of tert-butyl 5-(6-((5-fluoro-4-(3-isopropyl-2-methyl-2H-indazol-5-yl) pyrimidin-2-yl)amino)pyridin-3-yl)-(1S,4S)-2,5-diazabicyclo[2.2.1]heptane-2-carboxylate (365.00 mg, 653.36 μmol, 1.00 equivalent) in dichloromethane (8.00 mL) was added trifluoroacetic acid (4.00 mL) dropwise at 0° C. within 15 minutes. The reaction solution was allowed to react at 15° C. for 80 minutes. LC/MS showed completion of the reaction. The mixture was concentrated to a residue under reduced pressure, and the residue was purified by preparative HPLC (hydrochloric acid) to give the title compound (110.00 mg, 239.90 μmol, 36.72% yield, 100% purity). $^1$H NMR (400 MHz, Methanol-d$_4$) δ 8.92 (s, 1H), 8.78 (d, J=3.51 Hz, 1H), 8.43 (d, J=9.29 Hz, 1H), 7.98 (dd, J=9.66, 2.89 Hz, 1H), 7.88-7.83 (m, 1H), 7.72 (d, J=2.89 Hz, 1H), 7.54 (d, J=9.54 Hz, 1H), 4.83 (s, 1H), 4.62 (s, 1H), 4.34 (s, 3H), 3.80 (dd, J=10.60, 2.32 Hz, 1H), 3.77-3.70 (m, 1H), 3.55 (d, J=10.54 Hz, 1H), 3.50-3.41 (m, 2H), 2.36 (d, J=11.29 Hz, 1H), 2.17 (d, J=11.42 Hz, 1H), 1.66 (d, J=7.03 Hz, 6H). LC/MS (ESI) m/z: 459.3 (M+1).

EXAMPLE 16

N-(5-(1,7-diazaspiro[4.4]nonan-7-yl)pyridin-2-yl)-5-fluoro-4-(3-isopropyl-2-methyl-2H-indazol-5-yl)pyrimidine-2-amine

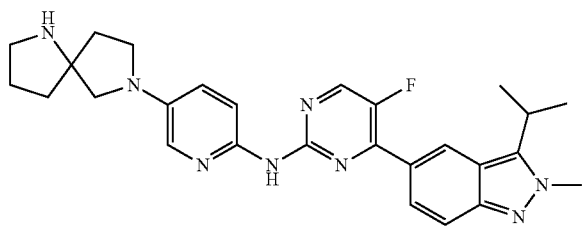 [SMILES: CC(C)c1c2cc(-c3nc(Nc4ccc(N5CCC6(CCCN6)C5)cn4)ncc3F)ccc2nn1C]

Step 1:

(S)-1-benzoylproline methyl ester

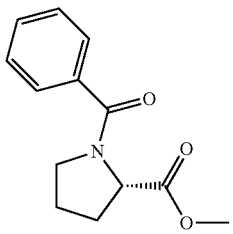 [SMILES: COC(=O)[C@@H]1CCCN1C(=O)c1ccccc1]

To a solution of L-proline methyl ester hydrochloride (20.00 g, 120.76 mmol, 1.00 equivalent) in dichloromethane (300.00 mL) were added triethylamine (36.66 g, 362.28 mmol, 3.00 equivalents) and benzoyl chloride (16.98 g, 120.76 mmol, 1.00 equivalent). The reaction mixture was stirred at 15° C. for 18 hours. LC/MS showed complete conversion of the starting material and detected the target product. The residue obtained by concentrating the reaction solution was diluted with ethyl acetate (200 mL) and washed successively with water (100 mL), an aqueous solution of citric acid (2.5%, 100 mL) and saturated sodium bicarbonate (100 mL). The organic phase was dried over anhydrous sodium sulfate and concentrated to give the title compound (24.00 g, 102.89 mmol, 85.20% yield) as a white solid. $^1$H NMR (400 MHz, CDCl$_3$) δ 7.63-7.52 (m, 2H), 7.45-7.38 (m, 3H), 4.68 (dd, J=5.2, 8.2 Hz, 1H), 3.82-3.75 (m, 3H), 3.66 (td, J=7.0, 10.2 Hz, 1H), 3.57-3.53 (m, 1H), 2.40-2.17 (m, 1H), 2.07-1.98 (m, 2H), 1.95-1.82 (m, 1H).

Step 2:

methyl 1-benzoyl-2-(nitrilomethyl)pyrrolidine-2-carboxylate

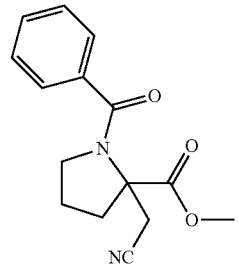 [SMILES: COC(=O)C1(CC#N)CCCN1C(=O)c1ccccc1]

At −78° C., to a solution of methyl (S)1-benzoylpyrrolidine-2-carboxylate (10.00 g, 42.87 mmol, 1.00 equivalent) in tetrahydrofuran (150.00 mL) was added a solution of lithium diisopropylamide in tetrahydrofuran (2 moles per liter, 25.72 mL, 1.20 equivalents) and the mixture was stirred for 1 hour. To this mixture was then added a solution of 2-bromoacetamide (6.17 g, 51.44 mmol, 1.20 equivalents) in tetrahydrofuran (30.00 mL) dropwise. The mixture was stirred at 15° C. for 18 hours. LC/MS showed complete conversion of the starting material and detected the target product. The reaction mixture was quenched with a saturated aqueous solution of ammonium chloride (100 mL) and subjected to phase separation, the aqueous phase was subjected to extraction using ethyl acetate (100 mL). The organic phases were combined, dried over anhydrous sodium sulfate and concentrated to give the title compound (12.00 g, crude product) as a brown oil. The crude product was used directly in the next step. $^1$H NMR (400 MHz, CDCl$_3$) δ 7.60-7.54 (m, 2H), 7.50-7.40 (m, 3H), 3.81 (s, 3H), 3.80-3.77 (m, 1H), 3.77-3.73 (m, 1H), 3.71-3.64 (m, 1H), 3.15 (d, J=17.2 Hz, 1H), 2.44-2.27 (m, 2H), 2.17-2.05 (m, 2H).

Step 3:

1-benzoyl-1,7-diazaspiro[4,4]nonane-6-one

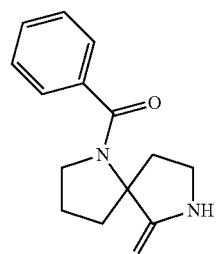

To a solution of methyl 1-benzoyl-2-(nitrilomethyl)pyrrolidine-2-carboxylate (5.00 g, 18.36 mmol, 1.00 equivalent) and aqueous ammonia (5.00 mL) in methanol (100.00 mL) was added raney nickel (5.00 g). The reaction flask was purged with argon and hydrogen three times. The mixture was heated to 70° C. under a hydrogen pressure of 55 psi and stirred for 18 hours. LC/MS showed complete conversion of the starting material and detected the target product. The reaction mixture was cooled to 25° C. and filtered. The residue obtained by concentrating the filtrate was purified by silica gel column (petroleum ether: ethyl acetate=3:1 to dichloromethane:methanol=30:1) to give the title compound (2.25 g, 50.17% yield) as a light brown solid. $^1$H NMR (400 MHz, CDCl$_3$) δ 7.62-7.50 (m, 2H), 7.45-7.35 (m, 3H), 5.84 (br. s., 1H), 3.71-3.53 (m, 3H), 3.42-3.34 (m, 1H), 2.95 (ddd, J=12.8, 9.7, 6.8 Hz, 1H), 2.34 (td, J=6.7, 12.5 Hz, 1H), 2.20-1.96 (m, 3H), 1.94-1.82 (m, 1H).

Step 4:

1-benzyl-1,7-diazaspiro[4,4]nonane

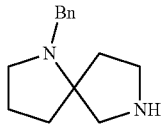

At 0° C., to a suspension of lithium aluminum hydride (7.13 g, 187.99 mmol, 5.60 equivalents) in tetrahydrofuran (300.00 mL) was added 1-benzoyl-1,7-diazaspiro[4,4]nonane-6-one (8.2 g, 33.57 mmol, 1.00 equivalent) in separate portions. After completion of the addition, the mixture was heated to 70° C. and stirred for 2 hours. LC/MS showed complete conversion of the starting material and detected the target product. The reaction mixture was cooled to 15° C. and quenched with water (7 mL), then an aqueous solution of sodium hydroxide (15%, 7 mL) and water (21 mL) were added. The mixture was filtered. The filtrate was dried over anhydrous sodium sulfate and the residue obtained by concentrating was purified by silica gel column (dichloromethane:methanol=30:1 to 10:1) to give the title compound (3.67 g, 16.97 mmol, 50.54% yield) as a pale yellow oil. $^1$H NMR (400 MHz, CDCl$_3$) δ 7.36-7.28 (m, 4H), 7.26-7.20 (m, 1H), 3.69 (d, J=13.2 Hz, 1H), 3.59 (d, J=13.2 Hz, 1H), 3.13-3.04 (m, 2H), 2.99 (td, J=10.8, 7.7 Hz, 1H), 2.77 (d, J=11.2 Hz, 1H), 2.70-2.62 (m, 1H), 2.59-2.51 (m, 1H), 2.01 (td, J=12.9, 8.1 Hz, 2H), 1.92-1.85 (m, 2H), 1.80-1.71 (m, 2H), 1.59 (ddd, J=12.6, 7.6, 4.6 Hz, 1H).

Step 5:

1-benzyl-7-(6-nitropyridin-3-yl)-1,7-diazaspiro[4,4]nonane

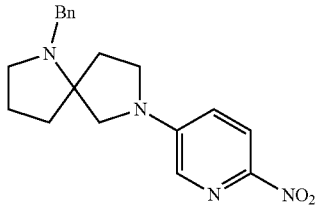 [SMILES: Nc1ccc(N2CCC3(CCCN3Cc3ccccc3)C2)cn1]

To a solution of 1-benzyl-1,7-diazaspiro[4,4]nonane (1.80 g, 8.32 mmol, 1.00 equivalent) and 5-bromo-2-nitropyridine (1.81 g, 8.90 mmol, 1.07 equivalents) in N,N-dimethylformamide (20.00 mL) was added triethylamine (1.80 g, 17.80 mmol, 2.14 equivalents). The mixture was heated to 100° C. and stirred for 18 hours. LC/MS showed complete conversion of the starting material and detected the target product. The reaction mixture was cooled to 15° C., diluted with ethyl acetate (40 mL), and then washed twice with water (50 mL×2). The aqueous phase was subjected to extraction using ethyl acetate (20 mL). The combined organic phases were dried over anhydrous sodium sulfate and the residue obtained by concentrating was purified by silica gel column (petroleum ether: ethyl acetate=10:1 to 1:1) to give the title compound (1.65 g, 4.88 mmol, 58.60% yield) as a yellow solid. $^1$H NMR (400 MHz, CDCl$_3$) δ 8.18 (d, J=9.0 Hz, 1H), 7.83 (d, J=2.9 Hz, 1H), 7.37-7.29 (m, 5H), 7.27-7.22 (m, 1H), 6.86 (dd, J=9.1, 2.9 Hz, 1H), 3.78-3.70 (m, 1H), 3.70-3.61 (m, 2H), 3.57-3.45 (m, 2H), 3.27 (d, J=10.3 Hz, 1H), 2.83-2.74 (m, 1H), 2.69 (td, J=7.4, 9.3 Hz, 1H), 2.35 (td, J=12.5, 9.0 Hz, 1H), 1.98-1.82 (m, 5H).

Step 6:

5-(1-benzyl-1,7-diazaspiro[4,4]nonan-7-yl)pyridine-2-amine

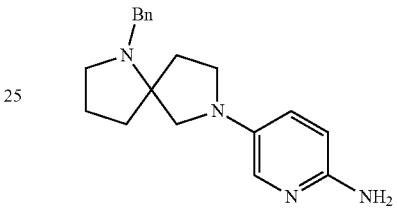

To a solution of 1-benzyl-7-(6-nitro-3-pyridyl)-1,7-diazaspiro[4,4]nonane (2.60 g, 7.68 mmol, 1.00 equivalent) in ethanol (40.00 mL) were added zinc dust (2.01 g, 30.73 mmol, 4.00 equivalents) and ammonium chloride (4.11 g, 76.83 mmol, 10.00 equivalents). The mixture was heated to 80° C. and stirred for 3 hours. LC/MS showed complete conversion of the starting material and detected the target product. The reaction mixture was cooled to 15° C., diluted with ethanol (30 mL), and then filtered. The filter cake was washed with ethanol (30 mL). The crude product obtained by concentrating the filtrate was purified by preparative HPLC (alkaline) to give the title compound (560.00 mg, 1.72 mmol, 22.34% yield, 94.5% purity) as a red oil. $^1$H NMR (400 MHz, CDCl$_3$) δ 7.52 (d, J=2.8 Hz, 1H), 7.36-7.28 (m, 4H), 7.21-7.14 (m, 1H), 6.86 (dd, J=8.8, 3.0 Hz, 1H), 6.51 (d, J=8.7 Hz, 1H), 3.98 (br. s., 2H), 3.74 (d, J=13.3 Hz, 1H), 3.63 (d, J=13.2 Hz, 1H), 3.47-3.38 (m, 2H), 3.24 (q, J=8.6 Hz, 1H), 3.04 (d, J=9.4 Hz, 1H), 2.77-2.59 (m, 2H), 2.37 (s, 1H), 2.27 (td, J=12.5, 8.6 Hz, 1H), 2.02-1.75 (m, 6H).

Step 7:

N-(5-(1-benzyl-1,7-diazaspiro[4,4]nonan-7-yl)pyridin-2-yl)-5-fluoro-4-(3-isopropyl-2-methyl-2H-indazol-5-yl)pyrimidine-2-amine

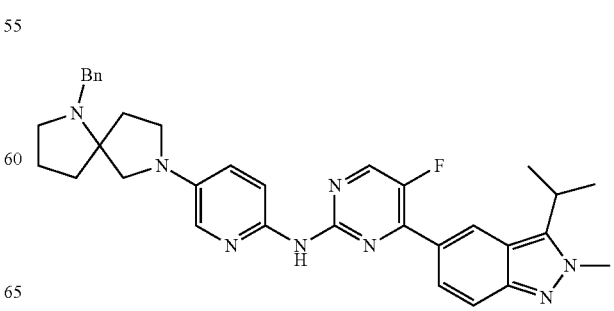

In a nitrogen atmosphere, to a solution of 5-(1-benzyl-1,7-diazaspiro[4,4]nonan-7-yl)pyridine-2-amine (370 mg, 1.20 mmol, 1.00 equivalent) and 5-(2-chloro-5-fluoro-pyrimidin-4-yl)-3-isopropyl-2-methyl-2H-indazole (438.84 mg, 1.44 mmol, 1.20 equivalents) in tetrahydrofuran (20.00 mL) were added potassium tert-butoxide (403.84 mg, 3.60 mmol, 3.00 equivalents) and chloro[2-(dicyclohexylphosphino)-2',4',6'-triisopropyl-1,1'-biphenyl][2-(2-aminoethyl)phenyl]palladium(II) (88.63 mg, 120.00 mmol, 0.10 equivalent). The mixture was heated to 80° C. and stirred for 18 hours. LC/MS showed that there remained 9.9% of the starting material, and detected 33.6% of the target product. The reaction mixture was cooled to 15° C., diluted with water (20 mL) and ethyl acetate (20 mL), and filtered. After the filtrate was subjected to phase separation, the aqueous phase was subjected to extraction twice using ethyl acetate (20 mL×2). The combined organic phases were washed with saturated brine (10 mL) and then concentrated. The resulting residue was purified by preparative TLC (ethyl acetate: methanol=10:1) to give the title compound (220.00 mg, 381.47 μmol, 31.79% yield) as a brown solid. $^1$H NMR (400 MHz, CDCl$_3$) δ 8.69 (s, 1H), 8.34 (d, J=4.0 Hz, 1H), 8.22 (br. s., 1H), 8.06 (d, J=9.3 Hz, 1H), 7.89 (br. s., 1H), 7.78-7.69 (m, 2H), 7.40-7.29 (m, 4H), 7.27-7.22 (m, 1H), 7.00 (dd, J=2.9, 9.0 Hz, 1H), 4.17 (s, 3H), 3.74 (br. s., 1H), 3.70-3.59 (m, 1H), 3.56-3.49 (m, 3H), 3.33 (q, J=8.4 Hz, 1H), 3.13 (d, J=9.2 Hz, 1H), 2.75 (br. s., 1H), 2.69 (br. s., 1H), 2.31 (br. s., 1H), 1.95-1.84 (m, 5H), 1.60 (d, J=7.0 Hz, 6H).

Step 8:

N-(5-(1,7-diazaspiro[4,4]nonan-7-yl)pyridin-2-yl)-5-fluoro-4-(3-isopropyl-2-methyl-2H-indazol-5-yl)pyrimidine-2-amine

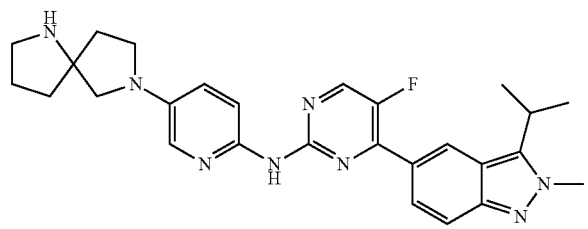 [SMILES: CC(C)c1c2cc(-c3nc(Nc4ccc(N5CCC6(CCCN6)C5)cn4)ncc3F)ccc2nn1C]

At 80° C., N-(5-(1-benzyl-1,7-diazaspiro[4,4]nonan-7-yl)-2-pyridyl)-5-fluoro-4-(3-isopropyl-2-methyl-2H-indazol-5-yl)pyrimidine-2-amine (220.00 mg, 381.47 μmol, 1.00 equivalent), ammonium formate (481.12 mg, 7.63 mmol, 20.00 equivalents) and wet Pd/C (220.00 mg) were stirred in a mixture of tetrahydrofuran (22.00 mL) and methanol (22.00 mL) for 16 hours. LC/MS showed completion of the reaction. The mixture was filtered, and the filtrate was concentrated in vacuo to give a crude product. The crude product was purified by preparative HPLC (hydrochloric acid) to give the title compound (30.00 mg, 80.56 μmol, 21.12% yield, 98% purity). $^1$H NMR (400 MHz, Methanol-d$_4$) δ 8.92 (s, 1H), 8.78 (d, J=3.5 Hz, 1H), 8.41 (d, J=9.2 Hz, 1H), 8.00-7.81 (m, 2H), 7.66 (d, J=2.5 Hz, 1H), 7.55 (d, J=9.5 Hz, 1H), 4.34 (s, 3H), 3.93 (d, J=10.9 Hz, 1H), 3.80-3.67 (m, 2H), 3.65-3.47 (m, 4H), 2.64-2.54 (m, 1H), 2.53-2.43 (m, 1H), 2.35-2.18 (m, 4H), 1.67 (d, J=7.0 Hz, 6H). LC/MS (ESI) m/z: 487.4 (M+1).

EXAMPLE 17

5-fluoro-N-(5-(hexahydropyrrolo[3,4-b][1,4]oxazin-6(2H)-yl)pyridin-2-yl)-4-(3-isopropyl-2-methyl-2H-indazol-5-yl)pyrimidine-2-amine

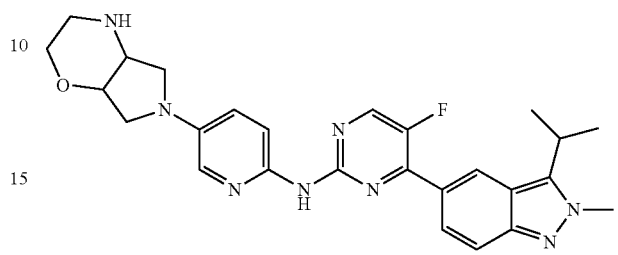

Step 1:

tert-butyl 3-bromo-4-(2-hydroxyethoxy)pyrrolidine-1-carboxylate

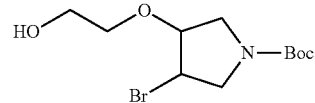 [SMILES: CC(C)(C)OC(=O)N1CC(Br)C(OCCO)C1]

To a solution of tert-butyl 2,5-dihydropyrrole-1-carboxylate (8.00 g, 47.28 mmol, 1.00 equivalent) in ethylene glycol (30.00 mL) was added N-bromosuccinimide (9.26 g, 52.01 mmol, 1.10 equivalents) in separate portions. The mixture was stirred at 15° C. for 16 hours. LC/MS and TLC showed completion of the reaction. Water (100 mL) was added to the mixture. The resulting mixture was stirred at 15° C. for 0.5 h and subjected to extraction using ethyl acetate (100 mL×3). The combined organic layers was dried over sodium sulfate and concentrated in vacuo to give the title compound (14.00 g, crude product) as a white oil. $^1$H NMR (400 MHz, CDCl$_3$) δ 4.31 (br. s., 1H), 4.17 (d, J=5.5 Hz, 1H), 3.98-3.92 (m, 1H), 3.87-3.82 (m, 1H), 3.77-3.72 (m, 2H), 3.71-3.58 (m, 2H), 3.57-3.39 (m, 1H), 2.06-2.01 (m, 1H), 1.49 (d, J=6.7 Hz, 9H). LC/MS (ESI) m/z: 264.0 (M+1-56).

Step 2:

tert-butyl 3-bromo-4-(2-(tosyloxy)ethoxy)pyrrolidine-1-carboxylate

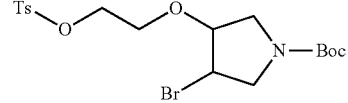 [SMILES: Cc1ccc(S(=O)(=O)OCCOC2CN(C(=O)OC(C)(C)C)CC2Br)cc1]

At 0° C., to a solution of tert-butyl 3-bromo-4-(2-hydroxyethoxy)pyrrolidine-1-carboxylate (14.00 g, 45.14 mmol, 1.00 equivalent), triethylamine (6.85 g, 67.71 mmol, 1.50 equivalents) and 4-dimethylaminopyridine (551.48 mg, 4.51 mmol, 0.10 equivalent) in toluene (100.00 mL) was added p-toluenesulfonyl chloride (11.19 g, 58.68 mmol, 1.30 equivalents). The mixture was stirred at 10° C. for 16 hours. LC/MS and TLC showed completion of the reaction. The mixture was diluted with water (100 mL), and the aqueous layer was subjected to extraction using ethyl acetate (100 mL). The combined organic layers was washed with a saturated aqueous solution of sodium chloride (30 mL×2), dried over sodium sulfate and concentrated in vacuo to give a crude product, which was then purified by column chromatography (petroleum ether: ethyl acetate=4:1) to give the title compound (11.10 g, 23.90 mmol, 52.95% yield) as a white oil. $^1$H NMR (400 MHz, CDCl$_3$) δ 7.81 (d, J=8.3 Hz, 2H), 7.38 (d, J=8.0 Hz, 2H), 4.19-4.11 (m, 3H), 4.10-4.02 (m, 1H), 3.90-3.66 (m, 5H), 3.45-3.29 (m, 1H), 2.48 (s, 3H), 1.49 (s, 9H). LC/MS (ESI) m/z: 408.0 (M+1-56).

Step 3:

tert-butyl 4-benzylhexahydropyrrolo[3,4-b][1,4]oxazin-6(2H)-carboxylate

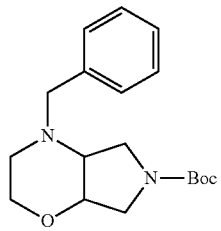 [SMILES: CC(C)(C)OC(=O)N1CC2OCCN(Cc3ccccc3)C2C1]

At 140° C., tert-butyl 3-bromo-4-(2-(tosyloxy)ethoxy)pyrrolidine-1-carboxylate (11.10 g, 23.90 mmol, 1.00 equivalent) and benzylamine (7.68 g, 71.70 mmol, 3.00 equivalents) in xylene (150.00 mL) were stirred for 16 hours. TLC and LC/MS showed completion of the reaction. The mixture was concentrated in vacuo to give a residue. The residue was diluted with ethyl acetate (100 mL) and water (100 mL). The aqueous layer was subjected to extraction using ethyl acetate (100 mL×2). The combined organic layers was dried over sodium sulfate and concentrated in vacuo to give a crude product, which was then purified by column chromatography (PE:EA=20:1 to 4:1) to give the title compound (5.80 g, 14.21 mmol, 59.45% yield, 78% purity) as a yellow oil. $^1$H NMR (400 MHz, CDCl$_3$) δ 7.81 (d, J=8.3 Hz, 2H), 7.38 (d, J=8.0 Hz, 2H), 4.19-4.11 (m, 3H), 4.10-4.02 (m, 1H), 3.90-3.66 (m, 5H), 3.45-3.29 (m, 1H), 2.48 (s, 3H), 1.49 (s, 9H). LC/MS (ESI) m/z: 319.1 (M+1).

Step 4:

4-benzylhexahydropyrrolo[3,4-b][1,4]oxazine

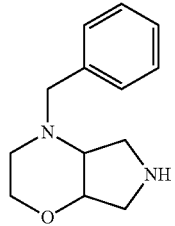 [SMILES: c1ccc(CN2CCOC3CNCC32)cc1]

At 0° C., to a solution of tert-butyl 4-benzylhexahydropyrrolo[3,4-b][1,4]oxazin-6(2H)-carboxylate (2.90 g, 9.11 mmol, 1.00 equivalent) in ethyl acetate (30.00 mL) was added hydrochloric acid/ethyl acetate (30.00 mL). The mixture was stirred at 10° C. for 16 hours. LC/MS showed completion of the reaction. The mixture was concentrated in vacuo to give the title compound (2.60 g, 8.93 mmol, 98.00% yield, hydrochloride) as a white solid. LC/MS (ESI) m/z: 219.3 (M+1).

Step 5:

4-benzyl-6-(6-nitropyridin-3-yl)octahydropyrrolo[3,4-b][1,4]oxazine

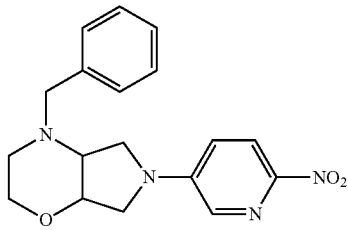

At 80° C., a mixture of 4-benzylhexahydropyrrolo[3,4-b][1,4]oxazine (2.60 g, 8.93 mmol, 1.00 equivalent, 2HCl), 5-bromo-2-nitro-pyridine (1.81 g, 8.93 mmol, 1.00 equivalent) and triethylamine (3.61 g, 35.72 mmol, 4.00 equivalents) in N,N-dimethylformamide (30.00 mL) was stirred for 16 hours. LC/MS showed completion of the reaction. The mixture was diluted with ethyl acetate (40 mL) and water (120 mL) and subjected to extraction using ethyl acetate (40 mL×3). The combined organic layers was dried over sodium sulfate and concentrated in vacuo to give a crude product, which was then purified by column chromatography (petroleum ether: ethyl acetate 3:1 to 1:1) to give the title compound (2.00 g, 5.88 mmol, 65.80% yield) as a yellow solid. LC/MS (ESI) m/z: 341.1 (M+1).

Step 6:

5-(4-benzylhexahydropyrrolo[3,4-b][1,4]oxazin-6(2H)-yl)pyridine-2-amine

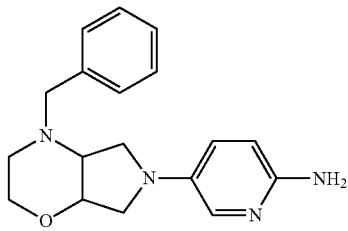 [SMILES: O=[N+]([O-])c1ccc(N2CC3OCCN(Cc4ccccc4)C3C2)cn1]

At 80° C., a mixture of 4-benzyl-6-(6-nitropyridin-3-yl)octahydropyrrolo[3,4-b][1,4]oxazine (2.00 g, 5.88 mmol, 1.00 equivalent), iron powder (1.64 g, 29.40 mmol, 5.00 equivalents) and ammonium chloride (3.15 g, 58.80 mmol, 10.00 equivalents) in ethanol (50.00 mL) and water (10.00 mL) was stirred for 16 hours. LC/MS showed completion of the reaction. The mixture was filtered, and the filtrate was concentrated in vacuo to give a crude product, which was then purified by preparative HPLC (trifluoroacetic acid) to give the title compound (1.00 g, 3.13 mmol, 53.15% yield, 97% purity) as a brown oil. LC/MS (ESI) m/z: 311.2 (M+1).

Step 7:

N-(5-(4-benzylhexahydropyrrolo[3,4-b][1,4]oxazin-6(2H)-yl)pyridin-2-yl)-5-fluoro-4-(3-isopropyl-2-methyl-2H-indazol-5-yl)pyrimidine-2-amine

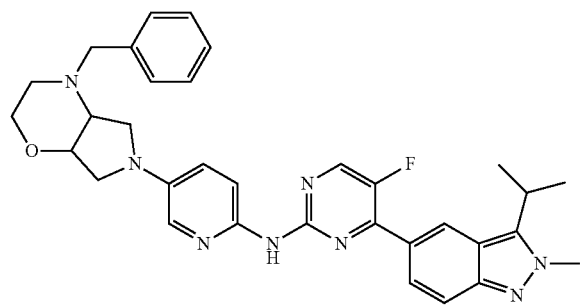 [SMILES: CC(C)c1c2cc(-c3nc(Nc4ccc(N5CC6OCCN(Cc7ccccc7)C6C5)cn4)ncc3F)ccc2nn1C]

In a nitrogen atmosphere, a solution of 5-(4-benzyl hexahydropyrrolo[3,4-b][1,4]oxazin-6(2H)-yl)pyridine-2-amine (300.00 mg, 966.53 μmol, 1.00 equivalent), 5-(2-chloro-5-fluoro-pyrimidin-4-yl)-3-isopropyl-2-methylindazole (Intermediate C) (294.55 mg, 966.53 μmol, 1.00 equivalent), chloro[2-(dicyclohexylphosphino)-2'-4'-6'-triisopropyl-1,1'-biphenyl][2-(2-aminoethyl)phenyl]palladium(II) (71.40 mg, 96.65 μmol, 0.10 equivalent) and potassium tert-butoxide (325.36 mg, 2.90 mmol, 3.00 equivalents) in tetrahydrofuran (30.00 mL) was stirred at 80° C. for 16 hours. LC/MS showed completion of the reaction. To the mixture were added successively water (30 ml) and ethyl acetate (30 mL). The resulting mixture was stirred at 20° C. for 15 minutes, filtered and subjected to phase separation. The aqueous layer was subjected to extraction using ethyl acetate (20 mL×2). The combined organic layers was dried over anhydrous sodium sulfate and concentrated in vacuo to give a crude product, which was then purified by preparative TLC plate (dichloromethane:methanol=10:1) to give the title compound (190.00 mg, 265.95 μmol, 27.52% yield, 81% purity) as a yellow solid. LC/MS (ESI) m/z: 579.4 (M+1).

Step 8:

5-fluoro-N-(5-(hexahydropyrrolo[3,4-b][1,4]oxazin-6(2H)-yl)pyridin-2-yl)-4-(3-isopropyl-2-methyl-2H-indazol-5-yl)pyrimidine-2-amine

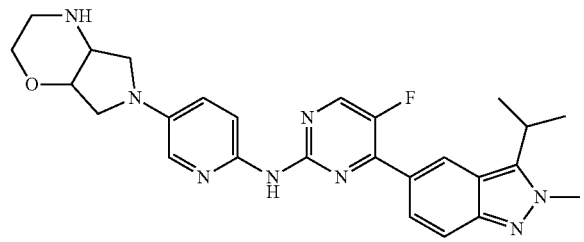 [SMILES: CC(C)c1c2cc(-c3nc(Nc4ccc(N5CC6NCCOC6C5)cn4)ncc3F)ccc2nn1C]

A mixed solution of N-(5-(4-benzylhexahydropyrrolo[3,4-b][1,4]oxazin-6(2H)-yl) pyridin-2-yl)-5-fluoro-4-(3-isopropyl-2-methyl-2H-indazol-5-yl)pyrimidine-2-amine (160.00 mg, 276.49 μmol, 1.00 equivalent), ammonium formate (348.38 mg, 5.53 mmol, 20.00 equivalents) and wet Pd/C (15.00 mg) in tetrahydrofuran (16.00 mL) and methanol (16.00 mL) was stirred at 80° C. for 16 hours. LC/MS showed that the desired product was produced. The mixture was filtered, and the filtrate was concentrated in vacuo to give a crude product, which was then purified by preparative HPLC (hydrochloric acid) to give the title compound (20.00 mg, 40.94 μmol, 14.81% yield, 100% purity). $^1$H NMR (400 MHz, Methanol-d$_4$) δ 8.89 (s, 1H), 8.75 (d, J=3.6 Hz, 1H), 8.33 (d, J=9.0 Hz, 1H), 7.90 (d, J=7.7 Hz, 1H), 7.81 (d, J=9.0 Hz, 1H), 7.62 (s, 1H), 7.54 (d, J=9.4 Hz, 1H), 4.59 (br. s., 1H), 4.30 (s, 3H), 4.19 (br. s., 1H), 4.11 (d, J=11.9 Hz, 1H), 3.97-3.79 (m, 3H), 3.79-3.67 (m, 2H), 3.58 (d, J=11.0 Hz, 1H), 3.51 (br. s., 1H), 3.28 (d, J=13.1 Hz, 1H), 1.65 (d, J=6.9 Hz, 6H). LC/MS (ESI) m/z: 489.4 (M+1).

EXAMPLE 18

1-(6-((5-fluoro-4-(3-isopropyl-2-methyl-2H-indazol-5-yl)pyrimidin-2-yl)amino)pyridin-3-yl)piperazine-2-one

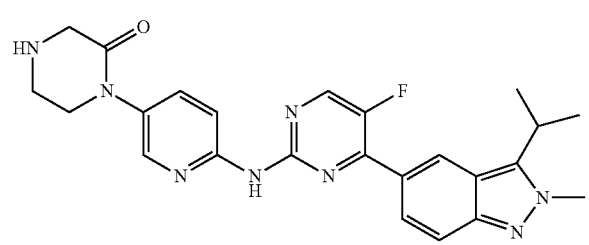 [SMILES: CC(C)c1c2cc(-c3nc(Nc4ccc(N5CCNCC5=O)cn4)ncc3F)ccc2nn1C]

Step 1:

tert-butyl N-(5-bromo-2-pyridyl)-N-tert-butoxycarbonylcarbamate

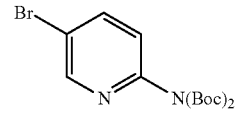

At 0° C., to a solution of 5-bromopyridine-2-amine (2.00 g, 11.56 mmol, 1.00 equivalent), N,N-diisopropylethylamine (4.48 g, 34.68 mmol, 6.05 mL, 3.00 equivalents) and dimethylaminopyridine (282.46 mg, 2.31 mmol, 0.20 equivalent) in dichloromethane (30.00 mL) was added di-tert-butyl carbonate (7.57 g, 34.68 mmol, 7.97 mL, 3.00 equivalents). The reaction mixture was stirred at 30° C. for 16 hours. LC/MS and TLC showed completion of the reaction. The mixture was concentrated in vacuo to give a crude product. The crude product was purified by column chromatography (ethyl acetate: petroleum ether=50:1) to give the title compound (2.00 g, 5.36 mmol, 46.35% yield) as a white solid. $^1$H NMR (400 MHz, CDCl$_3$) δ 8.55 (d, J=2.3 Hz, 1H), 7.86 (dd, J=2.5, 8.4 Hz, 1H), 7.20 (d, J=8.5 Hz, 1H), 1.47 (s, 18H). LC/MS (ESI) m/z: 373.1 (M+1).

Step 2:

benzyl 3-oxopiperazine-1-carboxylate

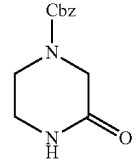

At 0° C., to a mixture solution of sodium carbonate (24.77 g, 233.73 mmol, 3.00 equivalents) and piperazine-2-one (7.80 g, 77.91 mmol, 1.00 equivalent) in ethyl acetate (70.00 mL) and water (70.00 mL) was added benzyl chloroformate (16.79 g, 93.49 mmol, 13.99 mL, 95% purity, 1.20 equivalents). The reaction mixture was stirred at 30° C. for 16 hours. TLC showed completion of the reaction. The mixture was subjected to extraction using ethyl acetate (80 mL×3). The combined organic layers was washed with a saturated aqueous solution of sodium chloride (80 mL×3), dried over sodium sulfate and concentrated in vacuo to give a crude product. The crude product was beaten in (petroleum ether: ethyl acetate=20:1, 80 mL). The resulting mixture was stirred at 30° C. for 15 minutes and filtered. The solid was dried in vacuo to give the title compound (15.50 g, 66.17 mmol, 84.93% yield) as a white solid.

Step 3:

benzyl 4-[6-[bis(tert-butoxycarbonyl)amino]-3-pyridyl]-3-oxo-piperazine-1-carboxylate

In a nitrogen atmosphere, a mixture of benzyl 3-oxopiperazine-1-carboxylate (4.00 g, 17.08 mmol, 1.00 equivalent), tert-butyl N-(5-bromo-2-pyridyl)-N-tert-butoxycarbonylcarbamate (6.37 g, 17.08 mmol, 1.00 equivalent), N,N-dimethylethane-1,2-diamine (602.09 mg, 6.83 mmol, 734.26 μl, 0.40 equivalent), potassium carbonate (7.08 g, 51.24 mmol, 3.00 equivalents) and CuI (650.42 mg, 3.42 mmol, 0.20 equivalent) in dioxane (80.00 mL) was stirred at 100° C. for 16 hours. LC/MS showed completion of the reaction. The mixture was filtered, and the filtrate was concentrated in vacuo to give a crude product, which was then purified by preparative TLC (petroleum ether: ethyl acetate=1:1) to give a mixture of the title compound and mono-Boc product (3.20 g, crude product). LC/MS (ESI) m/z: 527.2 (M+1).

Step 4:

benzyl 4-(6-aminopyridin-3-yl)-3-oxo-piperazine-1-carboxylate

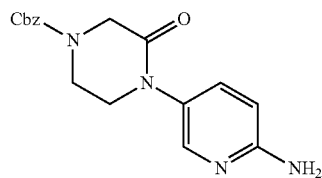 [SMILES: Nc1ccc(N2CCN(C(=O)OCc3ccccc3)CC2=O)cn1]

To a solution of benzyl 4-[6-[bis(tert-butoxycarbonyl)amino]-3-pyridyl]-3-oxo-piperazine-1-carboxylate (3.20 g, 6.08 mmol, 1.00 equivalent) in dichloromethane (20.00 mL) was added trifluoroacetic acid (10.00 mL) at 0° C. The reaction mixture was stirred at 30° C. for 2 hours. LC/MS showed completion of the reaction. The reaction mixture was concentrated in vacuo to give a crude product, which was diluted with dichloromethane. Potassium carbonate (10 g) was added to the mixture. The resulting mixture was stirred at 30° C. for 15 minutes and filtered. The filtrate was concentrated in vacuo to give the title compound (2.00 g, crude product) as a brown oil. $^1$H NMR (400 MHz, Methanol-$d_4$) δ 7.87 (d, J=2.5 Hz, 1H), 7.42-7.36 (m, 4H), 7.25-7.13 (m, 2H), 6.63 (d, J=8.8 Hz, 1H), 5.21 (s, 2H), 4.28 (br. s., 2H), 3.88 (br. s., 2H), 3.73 (t, J=5.3 Hz, 2H). LC/MS (ESI) m/z: 327.1 (M+1).

Step 5:

benzyl 4-(6-((5-fluoro-4-(3-isopropyl-2-methyl-2H-indazol-5-yl)pyrimidin-2-yl)amino)pyridin-3-yl)-3-oxopiperazine-1-carboxylate

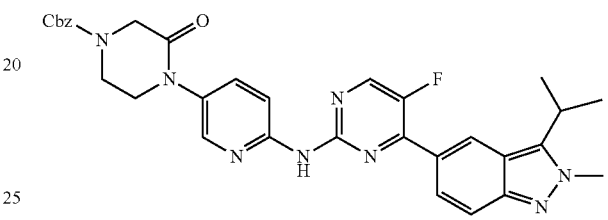

In a nitrogen atmosphere, a mixture of 5-(2-chloro-5-fluoro-pyrimidin-4-yl)-3-isopropyl-2-methylindazole (Intermediate C) (1.60 g, 5.25 mmol, 1.00 equivalent), benzyl 4-(6-aminopyridin-3-yl)-3-oxo-piperazine-1-carboxylate (2.06 g, 6.30 mmol, 1.20 equivalents), cesium carbonate (5.13 g, 15.75 mmol, 3.00 equivalents), XPhos (500.58 mg, 1.05 mmol, 0.20 equivalent) and Pd(OAc)$_2$ (117.87 mg, 525.00 μmol, 0.10 equivalent) in dioxane (50.00 mL) was stirred at 110° C. for 16 hours. LC/MS showed completion of the reaction. The mixture was filtered, and the filtrate was concentrated in vacuo to give a crude product. The crude product was purified by column chromatography (dichloromethane:methanol=20:1) to give the title compound (2.40 g, 3.59 mmol, 68.42% yield, 89% purity) as a yellow solid. $^1$H NMR (400 MHz, CDCl$_3$) δ 8.65 (s, 1H), 8.70 (s, 1H), 8.57 (d, J=9.0 Hz, 1H), 8.45 (d, J=3.8 Hz, 1H), 8.33 (d, J=2.5 Hz, 1H), 8.05 (d, J=9.2 Hz, 1H), 7.75 (d, J=9.2 Hz, 1H), 7.67 (dd, J=8.9, 2.6 Hz, 1H), 7.47-7.31 (m, 5H), 5.22 (s, 2H), 4.37 (s, 2H), 4.20 (s, 3H), 3.93-3.86 (m, 2H), 3.82-3.72 (m, 2H), 3.58-3.46 (m, 1H), 1.61 (d, J=7.0 Hz, 6H). LC/MS (ESI) m/z: 595.2 (M+1).

Step 6:

1-(6-((5-fluoro-4-(3-isopropyl-2-methyl-2H-indazol-5-yl)pyrimidin-2-yl)amino)pyridin-3-yl)piperazine-2-one

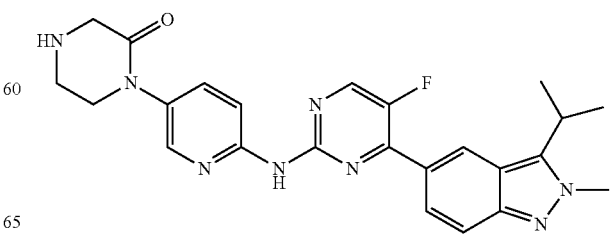

Under an atmosphere of hydrogen, a mixture of benzyl 4-(6-((5-fluoro-4-(3-isopropyl-2-methyl-2H-indazol-5-yl)pyrimidin-2-yl)amino)pyridin-3-yl)-3-oxopiperazine-1-carboxylate (2.40 g, 3.59 mmol, 1.00 equivalent) and wet Pd/C (400.00 mg, 10% purity) in methanol (20.00 mL) and tetrahydrofuran (20.00 mL) was stirred at 30° C. for 16 hours. LC/MS showed completion of the reaction. The mixture was filtered, and the filtrate was concentrated in vacuo to give a crude product, which was diluted with dichloromethane (20 mL). To the mixture was added hydrochloric acid/ethyl acetate (5 mL, 4M) dropwise. The resulting mixture was then concentrated in vacuo to give a crude product, which was then purified by preparative HPLC (hydrochloric acid) to give the title compound (1.25 g, 2.32 mmol, 64.62% yield, 99% purity, hydrochloride). $^1$H NMR (400 MHz, Methanol-d$_4$) δ 8.92 (s, 1H), 8.83 (d, J=3.6 Hz, 1H), 8.63 (d, J=2.1 Hz, 1H), 8.45 (dd, J=2.5, 9.4 Hz, 1H), 8.36 (d, J=9.3 Hz, 1H), 7.86-7.78 (m, 1H), 7.67 (d, J=9.5 Hz, 1H), 4.31 (s, 3H), 4.20-4.10 (m, 4H), 3.83-3.68 (m, 3H), 1.66 (d, J=7.0 Hz, 6H). LC/MS (ESI) m/z: 461.2 (M+1).

EXAMPLE 19

N-[5-(3,8-diazabicyclo[3.2.1]octan-3-yl)-2-pyridyl]-5-fluoro-4-(3-isopropyl-2-methyl-2H-indazol-5-yl)pyrimidine-2-amine

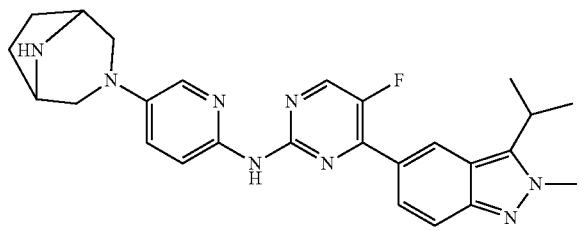 [SMILES: CC(C)c1c2cc(-c3nc(Nc4ccc(N5CC6CCC(C5)N6)cn4)ncc3F)ccc2nn1C]

Step 1:

tert-butyl 3-(6-nitro-3-pyridyl)-3,8-diazabicyclo[3.2.1]octane-8-carboxylate

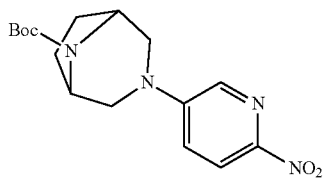

To a solution of tert-butyl 3,8-diazabicyclo[3.2.1]octane-8-carboxylate (1.00 g, 4.71 mmol, 1.00 equivalent) in dimethylsulfoxide (20.00 mL) were added triethylamine (1.43 g, 14.13 mmol, 3.00 equivalents) and 5-bromo-2-nitro-pyridine (1.15 g, 5.65 mmol, 1.20 equivalents). The mixture was stirred at 100° C. for 16 hours. LC/MS showed completion of the reaction. 40 mL of water was added to the mixture until the mixture was cooled to 20° C. The aqueous phase was subjected to extraction using dichloromethane (50 mL×2), washed with saturated brine (50 mL×1), dried over anhydrous sodium sulfate, filtered and concentrated. The crude product was purified by being beaten in methanol (2 mL×3) to give the title compound (639.00 mg, crude product) as a yellow solid. $^1$H NMR (400 MHz, CDCl$_3$) δ 8.18 (d, J=9.2 Hz, 1H), 8.09 (d, J=3.0 Hz, 1H), 7.15 (dd, J=9.2 Hz, 3.0 Hz, 1H), 4.47 (br. s., 2H), 3.58 (d, J=10.0 Hz, 2H), 3.27 (br. s., 2H), 2.12-1.99 (m, 2H), 1.86-1.76 (m, 2H), 1.49 (s, 9H). LC/MS (ESI) m/z: 335.2 (M+1).

Step 2:

tert-butyl 3-(6-amino-3-pyridyl)-3,8-diazabicyclo[3.2.1]octane-8-carboxylate

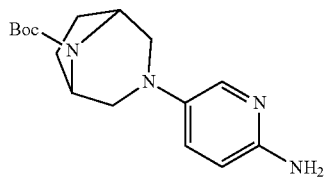 [SMILES: CC(C)(C)OC(=O)N1C2CCC1CN(c1ccc([N+](=O)[O-])nc1)C2]

To a solution of tert-butyl 3-(6-nitro-3-pyridyl)-3,8-diazabicyclo[3.2.1]octane-8-carboxylate (339.00 mg, 1.01 mmol, 1.00 equivalent) in methanol (11.00 mL) was added palladium on carbon (50.00 mg) in a hydrogen atmosphere (15 psi). The reaction mixture was stirred at 20° C. for 18 hours. LC/MS showed completion of the reaction. The mixture was filtered and concentrated to give the title compound (287.00 mg, crude product) as a purple solid. LC/MS (ESI) m/z: 305.2 (M+1).

Step 3:

tert-butyl 3-[6-[[5-fluoro-4-(3-isopropyl-2-methyl-2H-indazol-5-yl)pyrimidin-2-yl]amino]-3-pyridyl]-3,8 diazabicyclo[3.2.1]octane-8-carboxylate

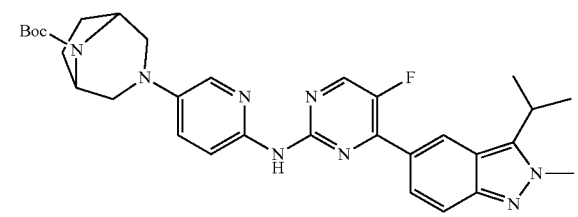 [SMILES: CC(C)c1c2cc(-c3nc(Nc4ccc(N5CC6CCC(C5)N6C(=O)OC(C)(C)C)cn4)ncc3F)ccc2nn1C]

To a solution of tert-butyl 3-(6-amino-3-pyridyl)-3,8-diazabicyclo[3.2.1]octane-8-carboxylate (140.00 mg, 459.94 μmol, 1.00 equivalent) in dioxane were added 5-(2-chloro-5-fluoro-pyrimidin-4-yl)-3-isopropyl-2-methyl-2H-indazole (Intermediate C) (249.50 mg, 818.69 μmol, 1.78 equivalents), Xantphos (79.84 mg, 137.98 μmol, 0.30 equivalent), cesium carbonate (446.58 mg, 1.37 mmol, 2.98 equivalents) and Pd$_2$(dba)$_3$ (63.18 mg, 68.99 μmol, 0.15 equivalent) in a nitrogen atmosphere. The mixture was stirred at 110° C. for 18 hours. LC/MS showed that the starting material reacted completely and detected no product. TLC showed that the starting material reacted completely and two new points were produced. The reaction mixture was filtered, and the filter cake was dissolved in 10 mL of water. The aqueous phase was subjected to extraction using dichloromethane (10 mL×2). The combined organic phases was washed with saturated brine (10 mL), dried over anhydrous sodium sulfate, filtered, and concentrated to give the title compound (25.00 mg, crude product) as a yellow solid. LC/MS (ESI) m/z: 573.3 (M+1).

Step 4:

N-[5-(3,8-diazabicyclo[3.2.1]octan-3-yl)-2-pyridyl]-5-fluoro-4-(3-isopropyl-2-methyl-2H-indazol-5-yl) pyrimidine-2-amine

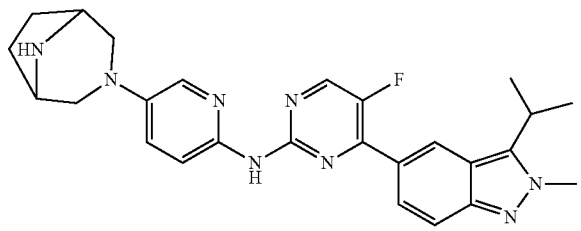 [SMILES: CC(C)c1c2cc(-c3nc(Nc4ccc(N5CC6CCC(C5)N6)cn4)ncc3F)ccc2nn1C]

To a solution of tert-butyl 3-[6-[[5-fluoro-4-(3-isopropyl-2-methyl-2H-indazol-5-yl)pyrimidin-2-yl]amino]-3-pyridyl]-3,8-diazabicyclo[3.2.1]octane-8-carboxylate (25.00 mg, 43.66 μmol, 1.00 equivalent) in dichloromethane (2 mL) was added trifluoroacetic acid (765.00 mg, 6.71 mmol, 153.67 equivalents). The mixture was stirred at 20° C. for 0.5 hour. LC/MS showed completion of the reaction. The reaction mixture was concentrated to give a crude product. The crude product was purified by preparative HPLC (hydrochloric acid) to give the title compound (11.80 mg, 22.82 μmol, 52.27% yield, 91.39% purity). $^1$H NMR (400 MHz, Methanol-$d_4$) δ 8.89 (s, 1H), 8.77 (d, J=3.5 Hz, 1H), 8.35 (d, J=9.2 Hz, 1H), 8.25 (dd, J=9.5, 2.1 Hz, 1H), 7.87 (d, J=1.9 Hz, 1H), 7.81 (d, J=9.0 Hz, 1H), 7.55 (d, J=9.5 Hz, 1H), 4.30 (s, 5H), 3.84-3.67 (m, 3H), 3.36-3.32 (m, 2H), 2.20 (s, 4H), 1.64 (d, J=6.9 Hz, 6H). LC/MS (ESI) m/z: 473.3 (M+1).

EXAMPLE 20

5-fluoro-4-(3-isopropyl-2-methyl-2H-indazol-5-yl)-N-(4-methyl-5-piperazin-1-yl-2-pyridyl) pyrimidine-2-amine

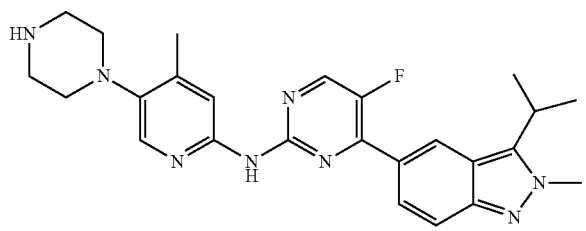 [SMILES: Cc1cc(Nc2ncc(F)c(-c3ccc4nn(C)c(C(C)C)c4c3)n2)ncc1N1CCNCC1]

Step 1:

tert-butyl 4-[6-[[5-fluoro-4-(3-isopropyl-2-methyl-2H-indazol-5-yl)pyrimidin-2-yl]amino]-4-methyl-3-pyridyl]piperazine-1-carboxylate

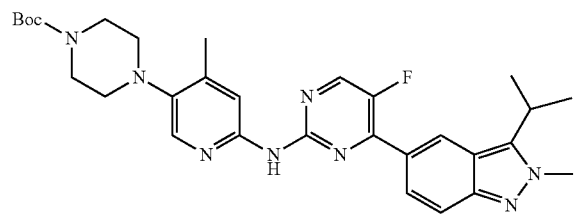 [SMILES: Cc1cc(Nc2ncc(F)c(-c3ccc4nn(C)c(C(C)C)c4c3)n2)ncc1N1CCN(C(=O)OC(C)(C)C)CC1]

To a solution of tert-butyl 4-(6-amino-4-methyl-3-pyridyl)piperazine-1-carboxylate (200.00 mg, 684.04 μmol, 1.00 equivalent) in dioxane (5.00 mL) were added 5-(2-chloro-5-fluoro-pyrimidin-4-yl)-3-isopropyl-2-methyl-2H-indazole (Intermediate C) (250.15 mg, 820.85 μmol, 1.20 equivalents), Pd$_2$(dba)$_3$ (62.64 mg, 68.40 μmol, 0.10 equivalent), Xantphos (79.16 mg, 136.81 μmol, 0.20 equivalent) and cesium carbonate (445.75 mg, 1.37 mmol, 2.00 equivalents) in a nitrogen atmosphere. The mixture was stirred at 110° C. for 16 hours. LC/MS showed completion of the reaction. The mixture was concentrated, the crude product was purified by preparative TLC (ethyl acetate: petroleum ether=2:1) to give the title compound (150.00 mg, crude product) as a yellow solid. LC/MS (ESI) m/z: 561.4 (M+1).

Step 2:

5-fluoro-4-(3-isopropyl-2-methyl-2H-indazol-5-yl)-N-(4-methyl-5-piperazin-1-yl-2-pyridyl) pyrimidine-2-amine

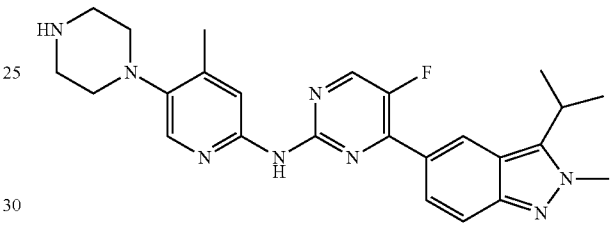

To a solution of tert-butyl 4-[6-[[5-fluoro-4-(3-isopropyl-2-methyl-2H-indazol-5-yl)pyrimidin-2-yl]amino]-4-methyl-3-pyridyl]piperazine-1-carboxylate (150.00 mg, 267.54 μmol, 1.00 equivalent) in dichloromethane (4 mL) was added trifluoroacetic acid (1.53 g, 13.42 mmol, 50.16 equivalents) at 20° C. The reaction mixture was stirred for 0.5 hour. LC/MS showed completion of the reaction. The mixture was concentrated to give a crude product, which was then purified by preparative HPLC (hydrochloric acid) to give the title compound (111.60 mg, 224.54 μmol, 83.93% yield, 100% purity, hydrochloride). $^1$H NMR (400 MHz, Methanol-$d_4$) δ 8.93 (s, 1H), 8.83 (d, J=3.51 Hz, 1H), 8.32-8.45 (m, 3H), 7.85 (d, J=9.03 Hz, 1H), 7.62 (d, J=9.16 Hz, 1H), 4.33 (s, 3H), 3.74 (d, J=6.99 Hz, 1H), 3.57 (d, J=12.67 Hz, 2H), 3.10-3.27 (m, 3H), 2.20 (d, J=13.68 Hz, 2H), 1.96-2.10 (m, 2H), 1.66 (d, J=7.03 Hz, 6H). LC/MS (ESI) m/z: 446.2 (M+1).

Approach B

Preparation of 5-fluoro-4-(3-isopropyl-2-methyl-2H-indazol-5-yl)-N-(5-(piperazin-1-yl)pyridin-2-yl)pyridine-2-amine

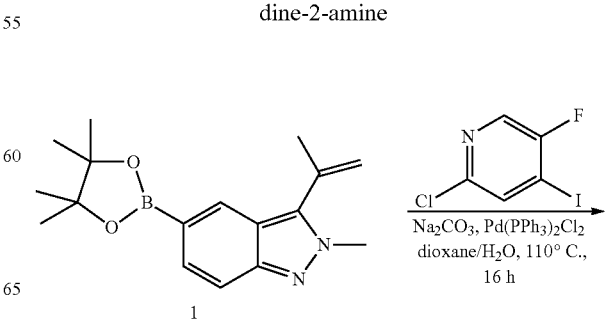

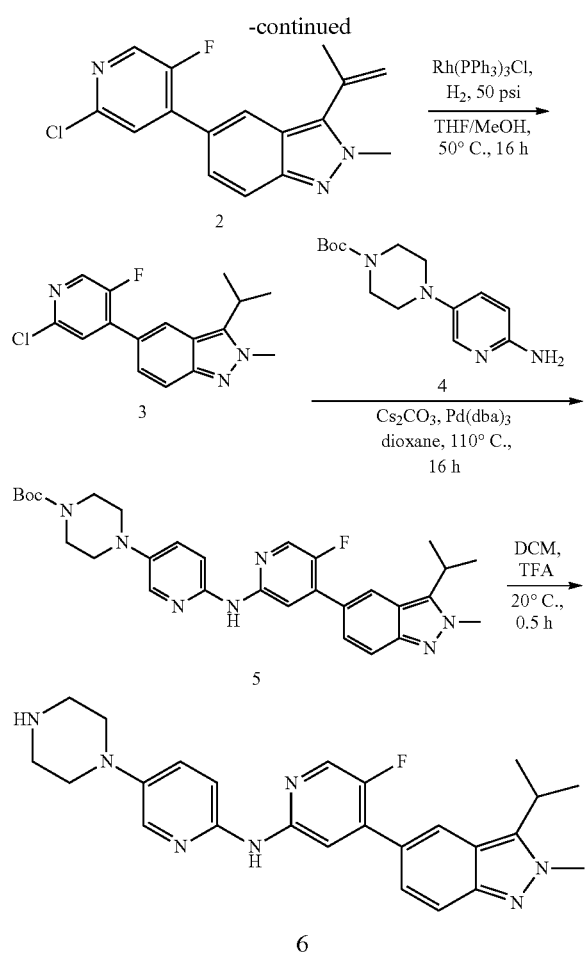

EXAMPLE 21

5-fluoro-4-(3-isopropyl-2-methyl-2H-indazol-5-yl)-N-(5-(piperazin-1-yl)pyridin-2-yl)pyridine-2-amine

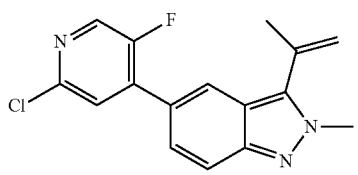

Step 1:

5-(2-chloro-5-fluoropyridin-4-yl)-2-methyl-3-isopropenyl-2H-indazole

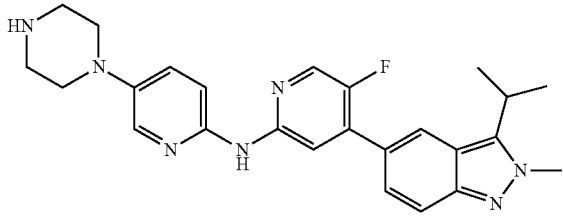 [SMILES: CC(C)c1c2cc(-c3cc(Nc4ccc(N5CCNCC5)cn4)ncc3F)ccc2nn1C]

In a nitrogen atmosphere, to a mixed solution of 2-methyl-3-isopropenyl-5-borate-2H-indazole (500.00 mg, 1.68 mmol, 1.00 equivalent) in dioxane (10 mL) and water (2 mL) were added 2-chloro-5-fluoro-4-iodo-pyridine (518.98 mg, 2.02 mmol, 1.20 equivalents), K₂CO₃ (696.58 mg, 5.04 mmol, 3.00 equivalents) and Pd(dppf)Cl₂ (122.93 mg, 168.00 μmol, 0.10 equivalent). The mixture was stirred at 110° C. for 3 hours. LC/MS showed completion of the reaction. The mixture was cooled to 20° C., and then water (10 mL) was added thereto. Extraction with ethyl acetate (15 mL×3) was performed. The organic phases were combined and washed with brine (15 mL×2), dried over anhydrous sodium sulfate, and filtered. The residue obtained by concentrating the filtrate was purified by silica gel column (petroleum ether: ethyl acetate=30:1 to 5:1) to give the title product (500 mg, 1.66 mmol, 98.63% yield) as a yellow oil. ¹H NMR (400 MHz, CDCl₃) δ 8.32 (d, J=2.1 Hz, 1H), 7.89 (s, 1H), 7.77 (dd, J=9.0, 0.8 Hz, 1H), 7.52-7.47 (m, 2H), 5.69 (t, J=1.5 Hz, 1H), 5.35 (s, 1H), 4.22 (s, 3H), 2.30 (d, J=1.0 Hz, 3H). LC/MS (ESI) m/z: 302.0 (M+1).

Step 2:

5-(2-chloro-5-fluoropyridin-4-yl)-3-isopropyl-2-methyl-2H-indazole

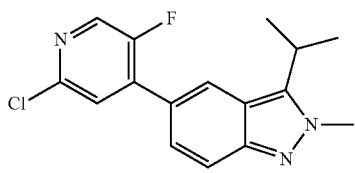 [SMILES: CC(C)c1c2cc(-c3cc(Cl)ncc3F)ccc2nn1C]

To a mixed solution of 5-(2-chloro-5-fluoropyridin-4-yl)-2-methyl-3-isopropenyl-2H-indazole (500 mg, 1.66 mmol, 1.00 equivalent) in methanol (5 mL) and tetrahydrofuran (5 mL) was added Rh(PPh₃)₃Cl (153.59 mg, 166.00 μmol, 0.1 equivalent). Hydrogen gas was introduced into the system and the pressure was maintained at 50 psi. The mixture was stirred at 50° C. for 16 hours. LC/MS showed completion of the reaction. The mixture was cooled to 20° C. and concentrated to give a residue. The residue was purified by silica gel column chromatography (petroleum ether: ethyl acetate=20:1 to 5:1) to give the title compound (460.00 mg, 1.51 mmol, 91.23% yield) as a white oil. ¹H NMR (400 MHz, CDCl₃) δ 8.33 (d, J=2.3 Hz, 1H), 8.05 (s, 1H), 7.75 (dd, J=9.0, 0.8 Hz, 1H), 7.50 (d, J=5.6 Hz, 1H), 7.45 (td, J=9.0, 1.7 Hz, 1H), 4.20 (s, 3H), 3.55-3.48 (m, 1H), 1.58 (d, J=7.0 Hz, 6H). LC/MS (ESI) m/z: 304.0 (M+1).

Step 3:

tert-butyl 4-(5-(((5-fluoro-4-(3-isopropyl-2-methyl-2H-indazol-5-yl)pyridin-2-yl)amino)pyridin-2-yl)piperazine-1-carboxylate

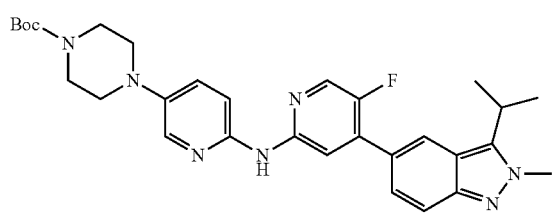 [SMILES: CC(C)c1c2cc(-c3cc(Nc4ccc(N5CCN(C(=O)OC(C)(C)C)CC5)cn4)ncc3F)ccc2nn1C]

In a nitrogen atmosphere, to a solution of 5-(2-chloro-5-fluoropyridin-4-yl)-3-isopropyl-2-methyl-2H-indazole (200.00 mg, 658.41 μmol, 1.00 equivalent) and tert-butyl 4-(6-amino-3-pyridin)piperazine-1-carboxylate (274.90 mg, 987.62 μmol, 1.50 equivalents) in dioxane (8 mL) were added Cs$_2$CO$_3$ (643.57 mg, 1.98 mmol, 3.00 equivalents), Xantphos (76.19 mg, 131.68 μmol, 0.20 equivalent), and Pd$_2$(dba)$_3$ (60.29 mg, 65.84 μmol, 0.10 equivalent). The mixture was stirred at 110° C. for 16 hours. LC/MS showed completion of the reaction. The mixture was cooled to 20° C. and filtered. The filter cake was washed with ethyl acetate and the filtrate was concentrated to give the title compound (350.00 mg, crude product) as a black oil, which was used directly in the next step without purification. LC/MS (ESI) m/z: 546.4 (M+1).

Step 4:

5-fluoro-4-(3-isopropyl-2-methyl-2H-indazol-5-yl)-N-(5-(piperazin-1-yl)pyridin-2-yl)pyridine-2-amine

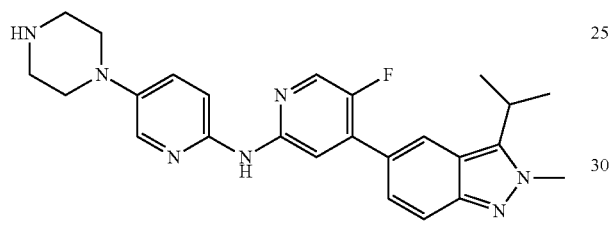

To a solution of tert-butyl 4-(5-((5-fluoro-4-(3-isopropyl-2-methyl-2H-indazol-5-yl) pyridin-2-yl)amino)pyridin-2-yl) piperazine-1-carboxylate (350.00 mg, 641.44 μmol, 1.00 equivalent) in dichloromethane (5 mL) was added trifluoroacetic acid (2.0 mL). The mixture was stirred at 20° C. for 0.5 h. LC/MS showed completion of the reaction. The mixture was concentrated under reduced pressure to remove dichloromethane and trifluoroacetic acid to give a residue. The residue was purified by preparative HPLC (hydrochloric acid) to give the title compound (250.00 mg, 558.27 μmol, 87.03% yield, 99.49% purity). $^1$H NMR (400 MHz, Methanol-d$_4$) δ 8.47 (d, J=2.6 Hz, 1H), 8.39 (s, 1H), 8.21 (dd, J=9.7, 2.9 Hz, 1H), 7.89 (d, J=2.8 Hz, 1H), 7.87-7.80 (m, 2H), 7.44 (d, J=9.5 Hz, 1H), 7.40 (d, J=5.5 Hz, 1H), 4.31 (s, 3H), 3.76-3.69 (m, 1H), 3.56-3.51 (m, 4H), 3.50-3.45 (m, 4H), 1.64 (d, J=7.0 Hz, 6H). LC/MS (ESI) m/z: 304.0 (M+1).

Approach C

A general method for the preparation of Intermediate D is shown below.

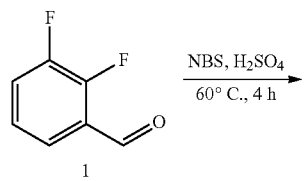

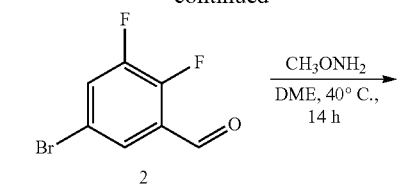

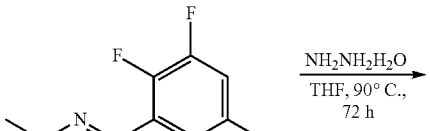

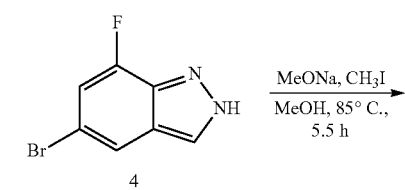

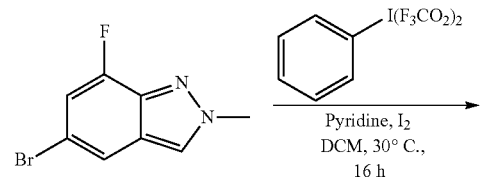

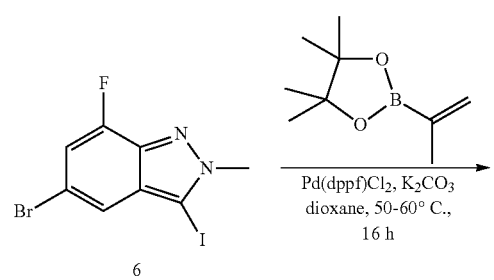

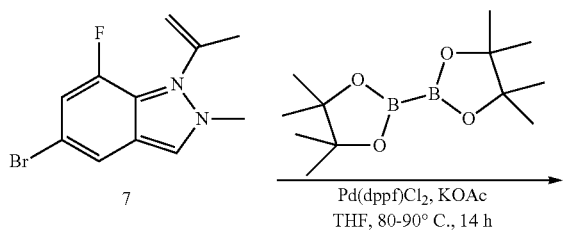

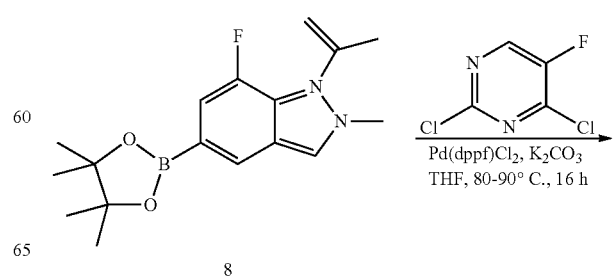

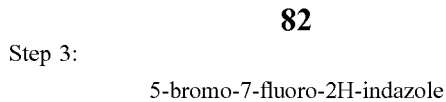

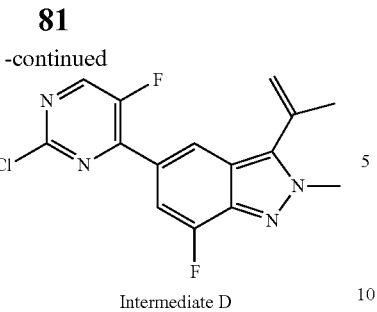

Intermediate D

Step 1:

5-bromo-2,3-difluorobenzaldehyde

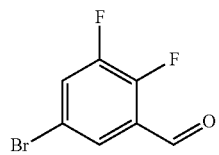

2,3-difluorobenzaldehyde (3.00 g, 21.22 mmol, 1.00 equivalent) was dissolved in sulfuric acid (18.4 mol/L, 10.20 mL, 8.89 equivalents) and was heated to 60° C. within 40 minutes. At this time, 1-bromopyrrolidine-2,5-dione (4.51 g, 25.33 mmol, 1.20 equivalents) was added in three portions within 20 minutes. The mixture was heated for 3 hours in a nitrogen atmosphere. TLC and HPLC showed completion of the reaction. The reaction mixture was poured into ice water, subjected to extraction twice using petroleum ether (30 mL×2, washed with water (30 mL×2) and saturated brine (30 mL×2), and then concentrated under reduced pressure. The concentrated residue was purified by column chromatography (petroleum ether) to give the title compound (2.10 g, 9.50 mmol, 45.00% yield) as a yellow liquid. $^1$H NMR (400 MHz, CDCl$_3$) δ 10.29 (s, 1H), 7.77 (br s, 1H), 7.65-7.54 (m, 1H).

Step 2:

(trans)-5-bromo-2,3-difluorobenzaldehyde-oxo-methyloxime

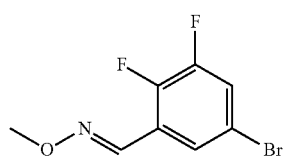

A mixture of 5-bromo-2,3-difluoro-benzaldehyde (1.50 g, 6.79 mmol, 1.00 equivalent), O-methylhydroxylamine (680.52 mg, 8.15 mmol, 1.20 equivalents) and potassium carbonate (1.13 g, 8.15 mmol, 1.2 equivalents) in dimethyl ether (20.00 mL) was heated to 40° C. and stirred for 14 hours. TLC showed that about 1% of the starting material was not consumed. The reaction mixture was filtered, and the filtrate was concentrated under reduced pressure to give the title compound (1.00 g, crude product), which was used directly in the next step without further purification. $^1$H NMR (400 MHz, CDCl$_3$) δ 8.22 (s, 1H), 7.77-7.75 (m, 1H), 7.35-7.27 (m, 1H), 4.04 (s, 3H).

Step 3:

5-bromo-7-fluoro-2H-indazole

A solution of (trans)-5-bromo-2,3-difluorobenzaldehyde-oxo-methyloxime (4.90 g, 19.60 mmol, 1.00 equivalent) in tetrahydrofuran (35.00 mL) and hydrazine hydrate (20.60 g, 411.51 mmol, 21.00 equivalents, 85% strength) was heated to 90° C. and stirred for 72 h. LC/MS showed that 20% of the starting material was not consumed. The organic solvent was concentrated, and the resulting mixture was diluted with ethyl acetate (20 mL), washed with water (20 mL×2) and then concentrated under reduced pressure to give a residue. The residue was purified by column chromatography (petroleum ether: ethyl acetate=60:1 to 40:1) to give the title compound (3.25 g, 12.09 mmol, 61.69% yield, 80% purity) as a white solid. LC/MS (ESI) m/z: 215.0 (M+1).

Step 4:

5-bromo-7-fluoro-2-methyl-2H-indazole

In a nitrogen atmosphere, to a solution of 5-bromo-7-fluoro-2H-indazole (1.10 g, 5.12 mmol, 1.00 equivalent) and sodium methoxide (552.71 mg, 10.23 mmol, 2.00 equivalents) in methanol (20.00 mL) was added methyl iodide (1.09 g, 7.67 mmol, 1.50 equivalents) dropwise at 30° C. within 30 minutes. The mixture was heated to 85° C. within 30 minutes and stirred for 5 hours. LC/MS showed that about 3% of the starting material was not consumed. The reaction mixture was cooled to 30° C., concentrated under reduced pressure, diluted with a 3% aqueous solution of sodium bicarbonate and then subjected to extraction using ethyl acetate (20 mL×2). The organic phase was concentrated under reduced pressure to give a residue, and the residue was purified by column chromatography (petroleum ether: ethyl acetate=20:1 to 5:1) to give the title compound (360.00 mg, 1.57 mmol, 30.66% yield) as yellow solid. LC/MS (ESI) m/z: 229.0 (M+1).

Step 5:

5-bromo-7-fluoro-3-iodo-2-methyl-2H-indazole

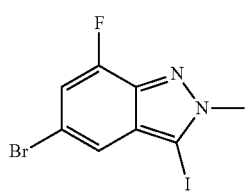

At 30° C., to a solution of 5-bromo-7-fluoro-2-methyl-2H-indazole (500.00 mg, 2.18 mmol, 1.00 equivalent) in dichloromethane (5.00 mL) were added pyridine (259.00 mL, 3.27 mmol, 1.50 equivalents) and bis(trifluoroacetoxy)iodobenzene (1.13 g, 2.62 mmol, 1.20 equivalents), and the mixture was stirred for 30 minutes. Iodine (664.86 mg, 2.62 mmol, 1.20 equivalents) was added at 30° C. and stirred for 23.5 hours. LC/MS showed complete conversion of the starting material. The reaction solution was filtered to give a filter cake. The filter cake was washed with a solvent (petroleum ether:dichloromethane=2:1, 10 mL) to give the title compound (300.00 mg, 828.31 µmol, 38.00% yield, 98% purity) as a white solid. LC/MS (ESI) m/z: 354.8 (M+1).

Step 6:

6-bromo-4-fluoro-2-methyl-3-(propen-2-yl)-2H-indazole

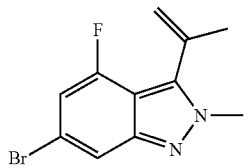

In a nitrogen atmosphere, to a solution of 5-bromo-7-fluoro-3-iodo-2-methyl-2H-indazole (320.00 mg, 901.56 µmol, 1.00 equivalent) and 2-isopropenyl-4,4,5,5-tetramethyl-1,3,2-dioxaborolane (181.80 mg, 1.08 mmol, 1.20 equivalents) in tetrahydrofuran (8.00 mL) and water (5.00 µL-) were added potassium carbonate (373.81 mg, 2.70 mmol, 3.00 equivalents) and Pd(dppf)Cl$_2$ (131.93 mg, 180.31 µmol, 0.20 equivalent). The reaction mixture was stirred at 50-60° C. for 16 hours. LC/MS showed 55% of the target product. TLC showed complete conversion of the starting material. The mixture was filtered, and the filtrate was concentrated to dryness. The concentrated residue was purified by column chromatography (petroleum ether: ethyl acetate=10:1) to give the title compound (210.00 mg, 780.35 µmol, 86.56% yield) as a light brown liquid. LC/MS (ESI) m/z: 268.9 (M+1).

Step 7:

4-fluoro-2-methyl-6-(4,4,5,5-tetramethyl-1,3,2-dioxaborolan-2-yl)-3-(propen-2-yl)-2H-indazole

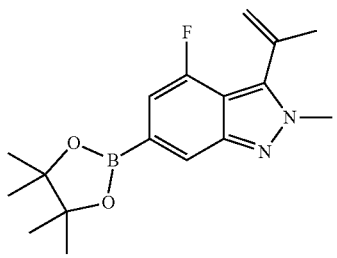

In a nitrogen atmosphere, to a solution of 5-bromo-7-fluoro-3-isopropenyl-2-methyl-2H-indazole (302.00 mg, 1.12 mmol, 1.00 equivalent) and bis(pinacolato)diboron (341.30 mg, 1.34 mmol, 1.20 equivalents) in tetrahydrofuran (10.00 mL) were added 3 drops of water, Pd(dppf)Cl$_2$ (163.90 mg, 224.00 µmol, 0.20 equivalent) and potassium acetate (329.75 mg, 3.36 mmol, 3.00 equivalents). The mixture was stirred at 80-90° C. for 14 hours. TLC (petroleum ether: ethyl acetate=5:1) showed completion of the reaction of most of the starting material. The mixture was cooled to 25° C. and filtered. The filtrate was concentrated to dryness. The concentrated residue was purified by column chromatography (petroleum ether: ethyl acetate=8:1) to give the title compound (306.00 mg, 967.80 µmol, 86.41% yield) as a white solid. LC/MS (ESI) m/z: 317.2 (M+1).

Step 8:

5-(2-chloro-5-fluoropyrimidin-4-yl)-7-fluoro-2-methyl-3-(propen-2-yl)-2H-indazole

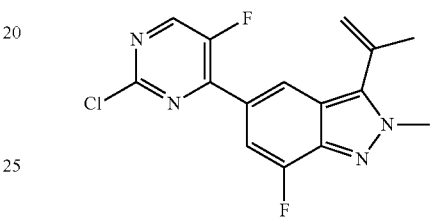

In a nitrogen atmosphere, to a solution of 2,4-dichloro-5-fluoro-pyrimidine (177.44 mg, 1.06 mmol, 1.20 equivalents) and 7-fluoro-3-isopropenyl-2-methyl-5-(4,4,5,5-tetramethyl-1,3,2-dioxaborolan-2-yl)indazole (280.00 mg, 885.57 µmol, 1.00 equivalent) in tetrahydrofuran were added potassium carbonate (367.18 mg, 2.66 mmol, 3.00 equivalents), Pd(dppf)Cl$_2$ (129.59 mg, 177.11 µmol, 0.20 equivalent) and 3 drops of water. The mixture was stirred at 80-90° C. for 16 hours. TLC (petroleum ether: ethyl acetate=5:1) showed conversion of most of the starting material. The mixture was cooled to 25° C. and filtered. The filter cake was washed with ethyl acetate (3 mL×2), and the filtrate was concentrated to dryness. The residue obtained by concentrating was purified by column chromatography (petroleum ether: ethyl acetate=7:1) to give the title compound (Intermediate D) (260.00 mg, 802.57 µmol, 90.63% yield, 99% purity). LC/MS (ESI) m/z: 320.9 (M+1).

EXAMPLE 22

5-fluoro-4-(7-fluoro-3-isopropyl-2-methyl-2H-indazol-5-yl)-N-(5-(piperazin-1-yl)pyridin-2-yl)pyrimidine-2-amine

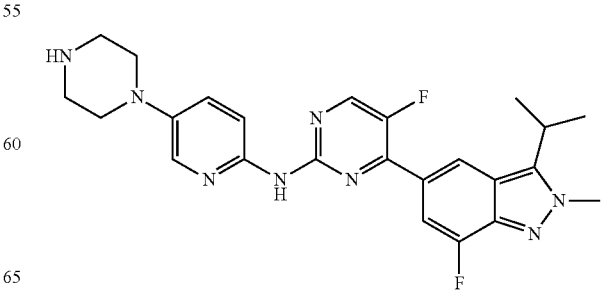

Step 1:

tert-butyl 4-(6-((5-fluoro-4-(7-fluoro-2-methyl-3-(isopropen-2-yl)-2H-indazol-5-yl)pyrimidin-2-yl)amino)pyridin-3-yl)piperazine-1-carboxylate

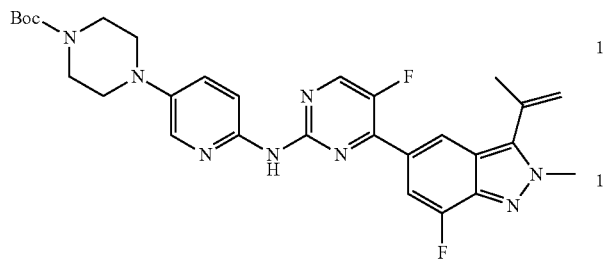

In a nitrogen atmosphere, to a solution of 5-(2-chloro-5-fluoropyrimidin-4-yl)-7-fluoro-2-methyl-3-(isopropen-2-yl)-2H-indazole (Intermediate D) (100 mg, 311.80 mmol, 1.00 equivalent) in dioxane (3 mL) were added tert-butyl 4-(6-amino-3-pyridyl)piperazine-1-carboxylate (99.81 mg, 358.57 mmol, 1.15 equivalents), cesium carbonate (203.18 mg, 623.6 mmol, 2.00 equivalents), $Pd_2(dba)_3$ (57.1 mg, 62.36 μmol, 0.2 equivalent) and Xantphos (72.17 mg, 124.72 μmol, 0.40 equivalent). The mixture was purged with nitrogen three times and heated to 100° C. and stirred for 18 hours. LC/MS showed complete conversion of the starting material and detected the target product. The reaction solution was cooled to 25° C., diluted with dichloromethane (5 mL) and filtered. The residue obtained by concentrating the filtrate was purified by preparative TLC (ethyl acetate) to give the title compound (100.00 mg, 177.74 μmol, 57.01% yield) as a yellow solid. $^1$H NMR (400 MHz, $CDCl_3$) δ 8.38 (d, J=3.9 Hz, 1H), 8.30 (s, 1H), 8.03 (d, J=2.8 Hz, 1H), 7.80 (d, J=12.7 Hz, 1H), 7.38 (dd, J=9.0, 2.9 Hz, 1H), 5.75-5.69 (m, 1H), 5.37 (s, 1H), 4.23 (s, 3H), 3.67-3.56 (m, 4H), 3.17-3.04 (m, 4H), 2.31 (s, 3H), 1.50 (s, 9H).

Step 2:

tert-butyl 4-(6-((5-fluoro-4-(7-fluoro-3-isopropyl-2-methyl-2H-indazol-5-yl)pyrimidin-2-yl)amino) pyridin-3-yl)piperazine-1-carboxylate

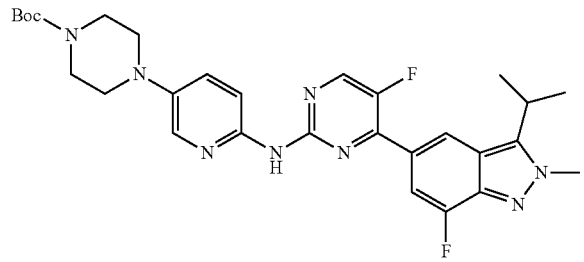 [SMILES: CC(C)c1c2cc(-c3nc(Nc4ccc(N5CCN(C(=O)OC(C)(C)C)CC5)cn4)ncc3F)cc(F)c2nn1C]

To a mixed solution of tert-butyl 4-(6-((5-fluoro-4-(7-fluoro-2-methyl-3-(isopropen-2-yl)-2H-indazol-5-yl)pyrimidin-2-yl)amino)pyridin-3-yl)piperazine-1-carboxylate (100.00 mg, 177.74 μmol, 1.00 equivalent) in methanol (10.00 mL) and acetic acid (500 μL) was added tris(triphenylphosphine)rhodium chloride (49.33 mg, 53.32 μmol, 0.3 equivalent). The reaction flask was purged with argon and hydrogen three times. Under a hydrogen pressure (50 psi), the mixture was heated to 50° C. and stirred for 18 hours. LC/MS showed complete conversion of the starting material and detected the target product. The reaction solution was cooled to 25° C. and filtered. The residue obtained by concentrating the filtrate was purified by preparative TLC (ethyl acetate) to give the title compound (15 mg, crude product) as a yellow solid. LC/MS (ESI) m/z: 565.3 (M+1).

Step 3:

5-fluoro-4-(7-fluoro-3-isopropyl-2-methyl-2H-indazol-5-yl)-N-(5-(piperazin-1-yl)pyridin-2-yl)pyrimidine-2-amine

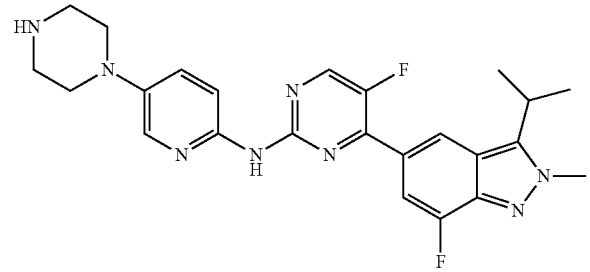 [SMILES: CC(C)c1c2cc(-c3nc(Nc4ccc(N5CCNCC5)cn4)ncc3F)cc(F)c2nn1C]

To a solution of tert-butyl 4-(6-((5-fluoro-4-(7-fluoro-3-isopropyl-2-methyl-2H-indazol-5-yl)pyrimidin-2-yl)amino)pyridin-3-yl)piperazine-1-carboxylate (15 mg, 26.57 μmol, 1.00 equivalent) in dichloromethane (1 mL) was added trifluoroacetic acid (500 μL). The mixture was stirred at 25° C. for 1 hour. LC/MS showed complete conversion of the starting material and detected the target product. The residue obtained by concentrating the reaction solution was purified by preparative HPLC (hydrochloric acid) to give the title compound (3.88 mg, 8.27 μmol), 31.12% yield, 99% purity). $^1$H NMR (400 MHz, Methanol-$d_4$) δ 8.73 (d, J=3.9 Hz, 1H), 8.63 (s, 1H), 8.27 (dd, J=2.6, 9.7 Hz, 1H), 7.91 (d, J=2.4 Hz, 1H), 7.84 (d, J=13.2 Hz, 1H), 7.55 (d, J=9.7 Hz, 1H), 4.22 (s, 3H), 3.71-3.61 (m, 1H), 3.60-3.51 (m, 4H), 3.49-3.41 (m, 4H), 1.59 (d, J=7.0 Hz, 6H) LC/MS (ESI) m/z: 465.2 (M+1).

EXAMPLE 23

2-[4-[6-[[5-fluoro-4-(7-fluoro-3-isopropyl-2-methyl-2H-indazol-5-yl)pyrimidin-2-yl]amino]-3-pyridinyl]piperazin-1-yl]ethanol

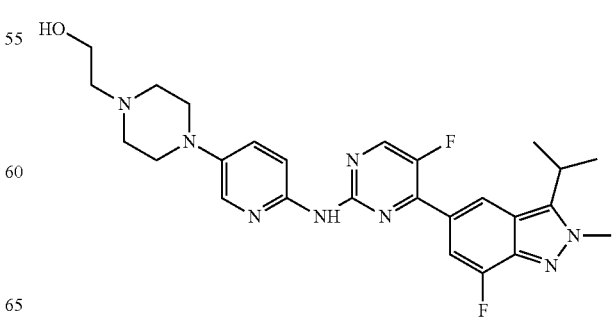

Step 1:

2-[4-[6-[[5-fluoro-4-(7-fluoro-3-isopropyl-2-methyl-2H-indazol-5-yl)pyrimidin-2-yl]amino]-3-pyridinyl]piperazin-1-yl]ethanol

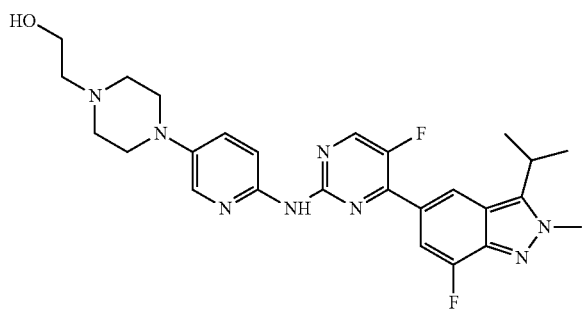 [SMILES: CC(C)c1c2cc(-c3nc(Nc4ccc(N5CCN(CCO)CC5)cn4)ncc3F)cc(F)c2nn1C]

To a solution of 5-fluoro-4-(7-fluoro-3-isopropyl-2-methyl-2H-indazol-5-yl)-N-(5-piperazin-1-yl-2-pyridyl)pyrimidine-2-amine (80.00 mg, 172.22 μmol, 1.00 equivalent) and 2-bromoethanol (64.56 mg, 516.66 μmol, 3.00 equivalents) in acetonitrile (5.00 mL) was added diisopropylethylamine (66.77 mg, 516.66 μmol, 3.00 equivalents). The mixture was heated to 70° C. and stirred for 16 hours. LC/MS showed almost complete consumption of the starting material and MS detected the desired compound. The reaction mixture was concentrated under reduced pressure to give a residue. The residue was diluted with ethyl acetate (10 mL) and washed successively with water (5×3 mL) and brine (3×5 mL). The organic phase was dried over sodium sulfate and filtered. The filtrate was concentrated to give a residue. This residue was purified by preparative HPLC (alkaline conditions) to give the title compound (20.31 mg, 39.14 μmol, 22.72% yield, 98% purity). $^1$H NMR (400 MHz, Methanol-d$_4$) δ 8.59 (s, 1H), 8.48 (d, J=3.5 Hz, 1H), 8.18 (d, J=8.8 Hz, 1H), 8.01 (br. s, 1H), 7.80 (d, J=12.5 Hz, 1H), 7.73-7.63 (m, 1H), 4.22 (s, 3H), 3.76 (t, J=5.8 Hz, 2H), 3.71-3.60 (m, 1H), 3.24 (br s, 5H), 2.76 (br. s, 4H), 2.64 (t, J=5.5 Hz, 2H), 1.60 (d, J=7.0 Hz, 6H). LC/MS (ESI) m/z: 509.3 (M+1).

Approach D

A general method for the preparation of Intermediate E is shown below.

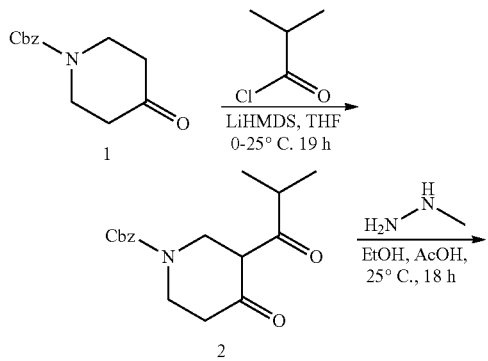

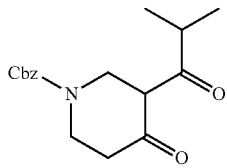 [SMILES: CC(C)C(=O)C1CN(C(=O)OCc2ccccc2)CCC1=O]

Step 1:

benzyl 3-isobutyryl-4-oxopiperidine-1-carboxylate

At 0° C., to a solution of benzyl 4-oxopiperidine-1-carboxylate (128.07 g, 549.04 mmol, 1.95 equivalents) in toluene (600.00 mL) was slowly added LiHMDS (550 mL, 550.00 mmol, 1.95 equivalents) dropwise. The mixture was stirred at 0° C. for 1 hour. Then, 2-methylpropionyl chloride (30.00 g, 281.56 mmol, 1.00 equivalent) was slowly added dropwise to the reaction mixture at 0° C. After completion of the addition, the mixture was heated to 25° C. and stirred for 18 hours. TLC (petroleum ether: ethyl acetate=5:1) showed completion of the reaction of the starting material. The reaction was quenched by adding a 10% aqueous solution of acetic acid (100 mL) to the reaction mixture. The resulting mixture was subjected to phase separation. The organic layer was washed successively with water (500 mL) and saturated brine (500 mL). The resulting organic layer was dried over anhydrous sodium sulfate and filtered. The filtrate was concentrated to give a residue, which was then purified by silica gel column chromatography (petroleum ether: ethyl acetate=50:1 to 20:1) to give the title compound (57.00 g, crude product) as a pale yellow oil. $^1$H NMR (400 MHz, CDCl$_3$) δ 16.10 (s, 1H), 7.38-7.36 (m, 5H), 5.18 (s, 2H), 4.33 (s, 2H), 3.69-3.66 (m, 2H), 2.68-2.57 (m, 1H), 2.48 (br s, 2H), 1.14 (d, J=6.4 Hz, 6H).

Step 2:

benzyl 6,7-dihydro-3-isopropyl-2-methyl-2H-pyrazolo[4,3-c]pyridine-5(4H)-carboxylate

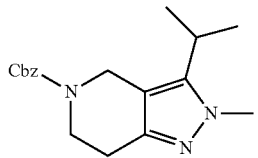 [SMILES: CC(C)c1c2c(nn1C)CCN(C(=O)OCc1ccccc1)C2]

At 25° C., to a solution of benzyl 3-isobutyryl-4-oxopiperidine-1-carboxylate (57.00 g, 187.90 mmol, 1.00 equivalent) in ethanol (600.00 mL) was added a 40% aqueous solution of methylhydrazine (110.00 g, 954.53 mmol, 5.08 equivalents). The mixture was stirred for 1 hour.

LC/MS showed completion of the reaction of the starting material. The reaction solution was concentrated to give a crude product. The crude product was purified by preparative HPLC (trifluoroacetic acid) to give an integral solution. Acetonitrile in the integral solution was removed by concentrating the solution. The pH of the aqueous phase was adjusted to 8 with sodium bicarbonate, and then the aqueous phase was subjected to extraction twice using dichloromethane (500 mL×2). The combined organic layers was dried over sodium sulfate and filtered. The filtrate was concentrated to give the title compound (6.50 g, 20.74 mmol, 11.4% yield) as a colorless oil. $^1$H NMR (400 MHz, CDCl$_3$) δ 7.43-7.29 (m, 5H), 5.18 (s, 2H), 4.58 (s, 2H), 3.82-3.71 (m, 5H), 3.03 (quin, J=7.0 Hz, 1H), 2.82-2.67 (m, 2H), 1.28 (d, J=6.4 Hz, 6H).

Step 3:

3-isopropyl-2-methyl-4,5,6-tetrahydro-2H-pyrazolo[4,3-c]pyridine

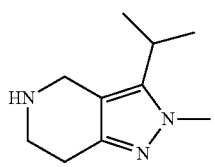

At 25° C., to a solution of benzyl 6,7-dihydro-3-isopropyl-2-methyl-2H-pyrazolo[4,3-c]pyridine-5(4H)-carboxylate (6.50 g, 20.74 mmol, 1.00 equivalent) in methanol (100.00 mL) were added Pd/C (1.00 g) and a solution of hydrochloric acid (1.00 mL) with a concentration of 12 mol/L. The mixture was purged successively with nitrogen and hydrogen three times. Hydrogen was introduced into the reaction solution, and the mixture was stirred at a pressure of 50 psi for 2 hours. TLC (petroleum ether: ethyl acetate=1:1) showed completion of the reaction of the starting material. The reaction mixture was filtered, and the filtrate was concentrated to give the title compound (5.25 g, crude product) as an off-white solid. $^1$H NMR (400 MHz, CDCl$_3$) δ 9.93 (br s, 2H), 4.31 (br s, 2H), 3.76 (s, 3H), 3.09-2.98 (m, 3H), 2.10 (br s, 2H), 1.26 (d, J=7.0 Hz, 6H).

Step 4:

5-(2-chloro-5-fluoropyrimidin-4-yl)-3-isopropyl-2-methyl-4,5,6,7-tetrahydro-2H-pyrazolo[4,3-c]pyridine

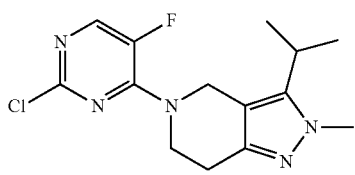

Intermediate E

At 25° C., to a solution of 3-isopropyl-2-methyl-4,5,6,7-tetrahydro-2H-pyrazolo[4,3-c]pyridine (5.25 g, 20.75 mmol, 1.00 equivalent) in tetrahydrofuran (60.00 mL) were added 2,4-dichloro-5-fluoropyrimidine (3.50 g, 20.96 mmol, 1.01 equivalents) and triethylamine (9.51 g, 94.01 mmol, 4.53 equivalents). The reaction mixture was stirred for 18 hours. TLC (petroleum ether: ethyl acetate=3:1) showed completion of the reaction of the starting material. The reaction solution was diluted with water (200 mL) and subjected to extraction using ethyl acetate (200 mL×2). The combined organic layers was dried over anhydrous sodium sulfate, filtered, and concentrated to give a crude product. The crude product was purified by column chromatography (petroleum ether: ethyl acetate=5:1 to 2:1) to give the title compound (Intermediate E) (5.60 g, 18.08 mmol, 87.12% yield) as an off-white solid. $^1$H NMR (300 MHz, CDCl$_3$) δ 7.94 (d, J=6.0 Hz, 1H), 4.84 (s, 2H), 4.03 (t, J=5.8 Hz, 2H), 3.79 (s, 3H), 3.07 (spt, J=7.1 Hz, 1H), 2.88 (t, J=5.7 Hz, 2H), 1.32 (d, J=7.2 Hz, 6H).

EXAMPLE 24

5-fluoro-4-(6,7-dihydro-3-isopropyl-2-methyl-2H-pyrazolo[4,3-c]pyridin-5(4H)-yl)-N-(5-(1-methylpiperidin-4-yl)pyridin-2-yl)pyridine-2-amine Step 1:

tert-butyl 6-nitro-5',6'-dihydro-[3,4'-bipyridyl]-1' (2'H)carboxylate

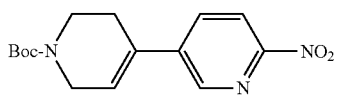

In a nitrogen atmosphere, to a mixed solution of 5-bromo-2-nitropyridine (10.00 g, 49.26 mmol, 1.02 equivalents) in dioxane (120 mL) and water (10 mL) were added tert-butyl 4-(4,4,5,5-tetramethyl-1,3,2-dioxaborolan-2-yl)-3,6-dihydro-2H-pyridine-1-carboxylate (15.00 g, 48.51 mmol, 1.00 equivalent), potassium carbonate (5.9 g, 72.77 mmol, 1.50 equivalents) and Pd(dppf)Cl$_2$ (1.77 g, 2.43 mmol, 0.05 equivalent). The reaction mixture was heated to 80° C. and stirred for 18 hours. TLC (petroleum ether: ethyl acetate=3:1) showed completion of the reaction of the starting material. The reaction solution was filtered, dried over anhydrous sodium sulfate, filtered, and concentrated to give a crude product. The crude product was purified by column chromatography (petroleum ether: ethyl acetate=3:1) to give the title compound (18.70 g, crude product) as a light yellow solid. $^1$H NMR (400 MHz, CDCl$_3$) δ 8.64 (d, J=2.0 Hz, 1H) 8.24 (d, J=8.4 Hz, 1H) 7.95 (dd, J=8.5, 2.3 Hz, 1H) 6.33 (br s, 1H) 4.16 (d, J=2.6 Hz, 2H) 3.69 (t, J=5.6 Hz, 2H) 2.57 (br s, 2H) 1.50 (s, 9H).

Step 2:

tert-butyl 4-(6-aminopyridin-3-yl)piperidine-1-carboxylate

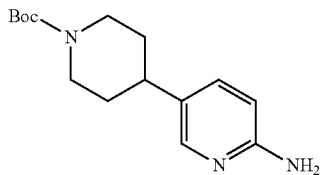 [SMILES: CC(C)(C)OC(=O)N1CCC(c2ccc(N)nc2)CC1]

To a solution of tert-butyl 4-(6-nitro-3-pyridyl)-3,6-dihydro-2H-pyridine-1-carboxylate (18.70 g, 48.51 mmol, 1.00 equivalent) in methanol (500 mL) was added Pd/C (2.00 g). The reaction system was successively purged with nitrogen and hydrogen three times. Hydrogen was introduced into the reaction solution to keep the reaction system under a pressure of 50 psi. The reaction mixture was heated to 50° C. and stirred for 18 hours. LC/MS showed completion of the reaction of the starting material. The mixture was filtered, and the filtrate was concentrated to give the title compound (10.40 g, 37.50 mmol, 77.31% yield) as an off-white solid. $^1$H NMR (400 MHz, CDCl$_3$) δ 7.92 (d, J=2.4 Hz, 1H) 7.31-7.27 (m, 1H) 6.48 (d, J=8.5 Hz, 1H) 4.35 (br s, 2H) 4.23 (br s, 2H) 2.78 (t, J=12.1 Hz, 2H) 2.60-2.48 (m, 1H) 1.78 (br s, 2H) 1.61-1.52 (m, 2H) 1.48 (s, 9H).

Step 3:

5-(1-methylpiperidin-4-yl)pyridine-2-amine

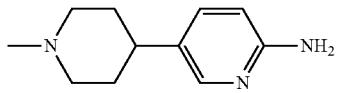

At 0° C., to a solution of lithium aluminum hydride (2.05 g, 54.09 mmol, 3.00 equivalents) in tetrahydrofuran (100 mL) was slowly added a solution of tert-butyl 4-(6-amino-3-pyridinyl)piperidine-1-carboxylate (5.00 g, 3.18 mmol, 1.00 equivalent) in tetrahydrofuran (50 mL) dropwise. After completion of the addition, the mixture was heated to 70° C. and stirred for 2 hours. LC/MS showed completion of the reaction of the starting material. At 0° C., the reaction was quenched by adding a 20% aqueous solution of potassium hydroxide (4 mL) to the reaction mixture to yield a large amount of solid. The reaction mixture was filtered, and the filtrate was concentrated to give the title compound (4.00 g, crude product) as a white solid. $^1$H NMR (400 MHz, CDCl$_3$) δ 7.93 (d, J=2.3 Hz, 1H) 7.31 (dd, J=8.4, 2.4 Hz, 1H) 6.46 (d, J=8.4 Hz, 1H) 4.33 (br s, 2H) 2.95 (d, J=11.7 Hz, 2H) 2.41-2.32 (m, 1H) 2.31 (s, 3H) 2.04-1.98 (m, 2H) 1.80-1.67 (m, 4H).

Step 4:

5-fluoro-4-(3-isopropyl-2-methyl-6,7-dihydro-2H-pyrazolo[4,3-c]pyridin-5(4H)-yl)-N-(5-(1-methylpiperidin-4-yl)pyridin-2-yl)pyrimidine-2-amine

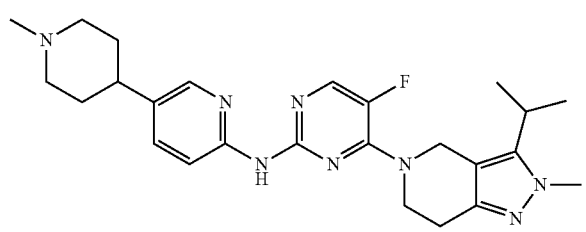

In a nitrogen atmosphere, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (2.00 g, 6.46 mmol, 1.00 equivalent) in toluene (20.00 mL) were added 5-(1-methyl-4-piperidinyl)pyridine-2-amine (1.36 g, 7.10 mmol, 1.10 equivalents), cesium carbonate (4.21 g, 12.91 mmol, 2.00 equivalents), Pd$_2$(dba)$_3$ (400.00 mg, 436.81 μmol, 0.07 equivalent) and Xantphos (520.00 mg, 898.69 μmol, 0.14 equivalent). The mixture was heated to 110° C. and stirred for 18 hours. LC/MS showed completion of the reaction of the starting material. The reaction mixture was cooled to 20° C. and concentrated to give a residue. The residue was purified by column chromatography (ethyl acetate to dichloromethane:methanol=10:1) to give a crude product. The crude product was purified by preparative HPLC (alkaline) to give the title compound (2.48 g, 4.61 mmol, 71.42% yield). $^1$H NMR (400 MHz, Methanol-d$_4$) δ 8.27 (d, J=1.9 Hz, 1H), 8.13 (d, J=7.2 Hz, 1H), 8.01 (d, J=8.5 Hz, 1H), 7.45 (d, J=8.8 Hz, 1H), 5.01 (s, 2H), 4.16 (t, J=5.8 Hz, 2H), 3.77 (s, 3H), 3.65 (d, J=12.3 Hz, 2H), 3.26-3.12 (m, 3H), 3.09-2.98 (m, 1H), 2.93 (s, 3H), 2.86 (t, J=5.8 Hz, 2H), 2.22-1.98 (m, 4H), 1.34 (d, J=7.0 Hz, 6H).

EXAMPLE 25

N-(5-fluoro-4-(3-isopropyl-2-methyl-6,7-dihydro-2H-pyrazolo[4,3-c]pyridin-5 (4H)-yl) pyrimidin-2-yl)-6-(4-methylpiperazin-1-yl)pyridazin-3-amine

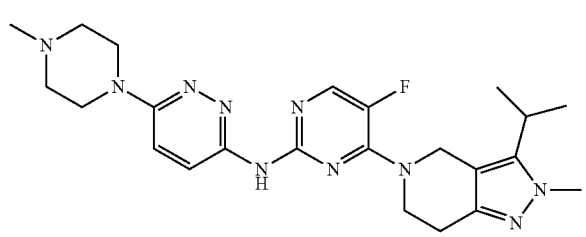

In a nitrogen atmosphere, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (200.00 mg, 645.64 μmol, 1.00 equivalent) and 6-(4-methylpiperazin-1-yl)pyridazin-3-amine (124.77 mg, 645.64 μmol, 1.00 equivalent) in dioxane (5.00 mL) were added cesium carbonate (420.72 mg, 1.29 mmol, 2.00 equivalents), Pd$_2$(dba)$_3$ (59.12 mg, 64.56 μmol, 0.10 equivalent) and Xantphos (74.72 mg, 129.13 μmol, 0.20 equivalent). The reaction mixture was then heated to 110° C. and stirred for 16 hours. LC/MS showed completion of the reaction of the starting material. The reaction mixture was cooled to 25° C., filtered and concentrated under reduced pressure to give a crude product. The crude product was purified by preparative HPLC (alkaline) to give the title compound (132.29 mg, 283.54 μmol, 43.92% yield). $^1$H NMR (400 MHz, Methanol-d$_4$) δ 8.23 (d, J=9.91 Hz, 1H), 7.93 (d, J=6.90 Hz, 1H), 7.34 (d, J=9.91 Hz, 1H), 4.85 (s, 2H), 4.02 (t, J=5.84 Hz, 2H), 3.77 (s, 3H), 3.63-3.57 (m, 4H), 3.17 (q, J=7.00 Hz, 1H), 2.81 (t, J=5.77 Hz, 2H), 2.65-2.59 (m, 4H), 2.38 (s, 3H), 1.32 (d, J=7.03 Hz, 6H). LC/MS (ESI) m/z: 467.2 (M+1).

EXAMPLE 26

5-fluoro-4-(6,7-dihydro-3-isopropyl-2-methyl-2H-pyrazolo[4,3c]pyridin-5(4H)-yl)-N-(5-(4-methyl-1,4-diazepan-1-yl)pyridin-2-yl)pyrimidine-2-amine

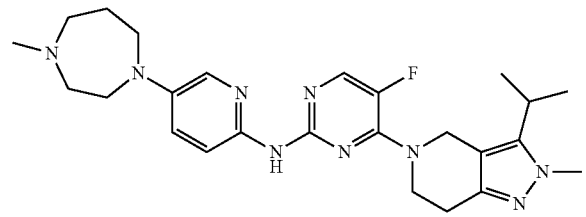

Step 1:

1-methyl-4-(6-nitropyridin-3-yl)-1,4-diazepane

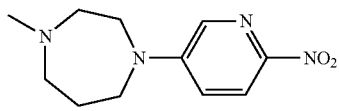

To a solution of 5-bromo-2-nitro-pyridine (2.00 g, 9.85 mmol, 1.00 equivalent) and 1-methyl-1,4-diazepane (1.69 g, 14.78 mmol, 1.50 equivalents) in dimethyl sulfoxide (20.00 mL) was added potassium carbonate (2.72 g, 19.70 mmol, 200 equivalents). The mixture was heated to 80° C. and stirred for 16 hours. LC/MS showed completion of the reaction of the starting material. The reaction mixture was cooled to 25° C., and water (50 mL) was added. The mixture was then subjected to extraction using ethyl acetate (100 mL×3). The combined organic phases was washed with saturated brine (100 mL×3), dried over anhydrous sodium sulfate, filtered and concentrated to give a crude product. The crude product was purified by column chromatography (petroleum ether: ethyl acetate=30:1 to 1:3) to give the title compound (2.00 g, 8.46 mmol, 85.94% yield) as a white solid. LC/MS (ESI) m/z: 237.1 (M+1).

Step 2:

5-(4-methyl-1,4-diazepan-1-yl)pyridine-2-amine

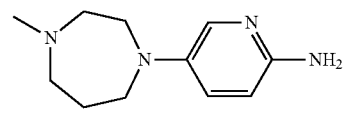

At 25° C., to a solution of 1-methyl-4-(6-nitropyridin-3-yl)-1,4-diazepane (2.00 g, 8.46 mmol, 1.00 equivalent) in methanol (20.00 mL) was added Pd/C (10%, 500 mg). The reaction system was successively purged with nitrogen and hydrogen three times. Hydrogen was introduced into the reaction solution to keep the reaction system under a pressure of 15 psi. The reaction solution was stirred for 2 hours. TLC showed completion of the reaction of the starting material. The reaction mixture was filtered and concentrated under reduced pressure to give the title compound (1.70 g, 8.24 mmol, 97.41% yield) as a white solid. LC/MS (ESI) m/z: 207.1 (M+1).

Step 3:

5-fluoro-4-(6,7-dihydro-3-isopropyl-2-methyl-2H-pyrazolo[4,3-c]pyridin-5(4H)-yl)-N-(5-(4-methyl-1,4-diazepan-1-yl)pyridin-2-yl)pyrimidine-2-amine

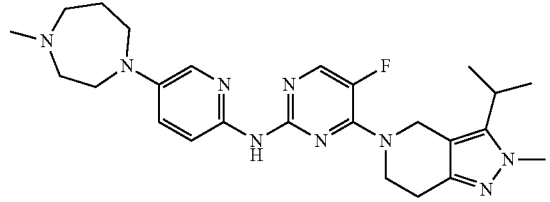

In a nitrogen atmosphere, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (200.00 mg, 645.64 μmol, 1.00 equivalent) and 5-(4-methyl-1,4-diazepan-1-yl)pyridine-2-amine (159.83 mg, 774.77 μmol, 1.20 equivalents) in dioxane (5.00 mL) were added cesium carbonate (420.72 mg, 1.29 mmol, 2.00 equivalents), Pd$_2$(dba)$_3$ (59.12 mg, 64.56 μmol, 0.10 equivalent) and Xantphos (74.72 mg, 129.13 μmol, 0.20 equivalent). The reaction mixture was then heated to 110° C. and stirred for 16 hours. LC/MS showed completion of the reaction of the starting material. The reaction mixture was cooled to 25° C., filtered and concentrated under reduced pressure to give a crude product. The crude product was purified by preparative HPLC (alkaline) to give the title compound (93.10 mg, 194.12 μmol, 30.07% yield). $^1$H NMR (400 MHz, Methanol-d$_4$) δ 7.91-7.84 (m, 2H), 7.77 (d, J=3.01 Hz, 1H), 7.22 (dd, J=9.16, 3.14 Hz, 1H), 4.85 (s, 2H), 4.01 (t, J=5.83 Hz, 2H), 3.77 (s, 3H), 3.62-3.57 (m, 2H), 3.52 (t, J=6.27 Hz, 2H), 3.17 (q, J=7.03 Hz, 1H), 2.83-2.75 (m, 4H), 2.67-2.61 (m, 2H), 2.40 (s, 3H), 2.06 (dt, J=11.51, 5.98 Hz, 2H), 1.36-1.29 (m, 6H). LC/MS (ESI) m/z: 480.2 (M+1).

EXAMPLE 27

N-(5-(4-(dimethylamino)piperidin-1-yl)pyridin-2-yl)-5-fluoro-4-(6,7-dihydro-3-isopropyl-2-methyl-2H-pyrazolo[4,3-c]pyridin-5(4H)-yl)pyrimidine-2-amine

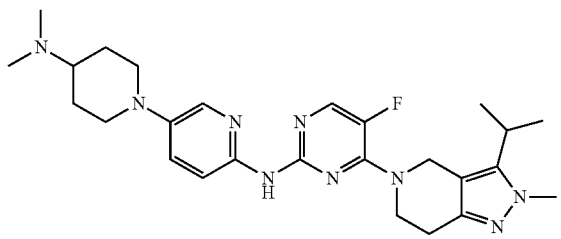

Step 1:

N,N-dimethyl-1-(6-nitropyridin-3-yl)piperidine-4-amine

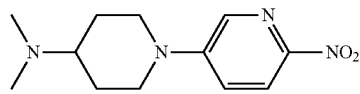 [SMILES: CN(C)C1CCN(c2ccc([N+](=O)[O-])nc2)CC1]

In a nitrogen atmosphere, to a solution of N,N-dimethyl-piperidine-4-amine (100.00 mg, 779.97 μmol, 1.00 equivalent) and 5-bromo-2-nitropyridine (158.33 mg, 779.97 μmol, 1.00 equivalent) in dioxane (5 mL) were added BINAP (48.57 mg, 78.00 μmol, 0.10 equivalent), cesium carbonate (508.26 mg, 1.56 mmol, 2.00 equivalents) and Pd(OAc)$_2$ (17.51 mg, 78.00 μmol, 0.10 equivalent). The reaction mixture was then heated to 90° C. and stirred for 16 hours. TLC showed completion of the reaction of the starting material. The reaction mixture was filtered and concentrated to give a crude product. The crude product was purified by preparative TLC (dichloromethane:methanol=10:1) to give the title compound (125.00 mg, 499.40 μmol, 64.03% yield) as a yellow solid. $^1$H NMR (400 MHz, CDCl$_3$) δ 8.20-8.14 (m, 2H), 7.21 (dd, J=9.2, 3.2 Hz, 1H), 3.99 (d, J=13.2 Hz, 2H), 3.12-3.02 (m, 2H), 2.47-2.39 (m, 1H), 2.33 (s, 6H), 2.01 (d, J=12.4 Hz, 2H), 1.70-1.64 (m, 2H). LC/MS (ESI) m/z: 251.1 (M+1).

Step 2:

5-(4-(dimethylamino)piperidin-1-yl)pyridine-2-amine

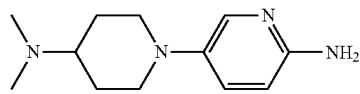 [SMILES: CN(C)C1CCN(c2ccc(N)nc2)CC1]

To a solution of N,N-dimethyl-1-(6-nitropyridin-3-yl)piperidine-4-amine (525.00 mg, 2.10 mmol, 1.00 equivalent) in methanol (10 mL) was added Pd—C (10%, 100 mg). The reaction system was successively purged with nitrogen and hydrogen three times. Hydrogen was introduced into the reaction solution to keep the reaction system under a pressure of 15 psi. The reaction solution was stirred for 4 hours. TLC showed completion of the reaction of the starting material. The reaction mixture was filtered, and the filtrate was concentrated to give the title compound (450.00 mg, 2.04 mmol, 97.27% yield) as a yellow solid. $^1$H NMR (400 MHz, Methanol-d$_4$) δ 7.65-7.61 (m, 1H), 7.34 (dd, J=9.2, 2.4 Hz, 1H), 6.59 (dd, J=8.8, 0.8 Hz, 1H), 3.52-3.44 (m, 2H), 2.65 (dt, J=12.4, 2.4 Hz, 2H), 2.42-2.38 (m, 6H), 2.05-1.98 (m, 2H), 1.67 (dq, J=12.4, 4.4 Hz, 2H). LC/MS (ESI) m/z: 221.0 (M+1).

Step 3:

N-(5-(4-(dimethylamino)piperidin-1-yl)pyridin-2-yl)-5-fluoro-4-(6,7-dihydro-3-isopropyl-2-methyl-2H-pyrazolo[4,3-c]pyridin-5(4H)-yl)pyrimidine-2-amine

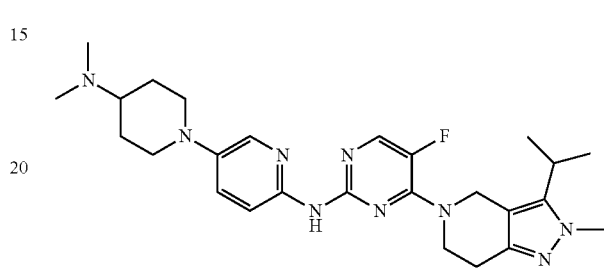

In a nitrogen atmosphere, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (150.00 mg, 484.23 μmol, 1.00 equivalent) and 5-[4-(dimethylamino)-1-piperidinyl]pyridine-2-amine (128.02 mg, 581.08 μmol, 1.20 equivalents) in dioxane (5.00 mL) were added Pd$_2$(dba)$_3$ (44.34 mg, 48.42 μmol, 0.10 equivalent), cesium carbonate (315.54 mg, 968.46 μmol, 2.00 equivalents) and Xantphos (56.04 mg, 96.85 μmol, 0.20 equivalent). The reaction mixture was then heated to 110° C. and stirred for 16 hours. LC/MS showed completion of the reaction of the starting material. The reaction mixture was cooled to 25° C., filtered and concentrated to give a crude product. The crude product was purified by preparative HPLC (formic acid) to give the title mixture (81.64 mg, 165.39 μmol, 34.16% yield). $^1$H NMR (400 MHz, Methanol-d$_4$) δ 8.01-7.86 (m, 3H), 7.51 (dd, J=9.16, 2.76 Hz, 1H), 4.85 (s, 2H), 4.06-3.96 (m, 2H), 3.84-3.72 (m, 5H), 3.38-3.33 (m, 1H), 3.17 (dt, J=14.02, 6.98 Hz, 2H), 2.90 (s, 6H), 2.85-2.77 (m, 4H), 2.22 (d, J=12.05 Hz, 2H), 1.90 (qd, J=12.03, 3.70 Hz, 2H), 1.32 (d, J=7.03 Hz, 6H). LC/MS (ESI) m/z: 494.2 (M+1).

EXAMPLE 28

N$^5$-(2-(dimethylamino)ethyl)-N$^2$-(5-fluoro-4-(6,7-dihydro-3-isopropyl-2-methyl-2H-pyrazolo[4,3-c]pyridin-5 (4H)-yl)pyrimidin-2-yl)-N$^5$-methylpyridine-2,5-diamine

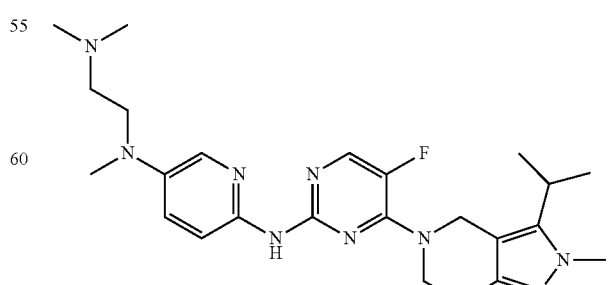

Step 1:

N-(2-(dimethylamino)ethyl)-N-methyl-6-nitropyridine-3-amine

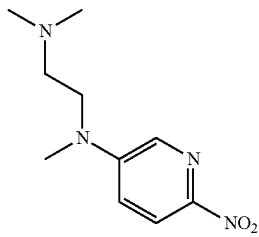

To a solution of 5-bromo-2-nitro-pyridine (2.00 g, 9.85 mmol, 1.00 equivalent) and N,N,N-trimethylethane-1,2-diamine (1.51 g, 14.78 mmol, 1.50 equivalents) in dimethylformamide (20.00 mL) was added potassium carbonate (2.72 g, 19.70 mmol, 2.00 equivalents) in one portion. The reaction mixture was heated to 90° C. and stirred for 16 hours. LC/MS showed completion of the reaction. After the reaction solution was cooled to 25° C., water (50 mL) was added to thereto. The reaction mixture was subjected to extraction using ethyl acetate (100 mL×3). The organic phases were combined and washed with saturated brine (100 mL×3), then dried over anhydrous sodium sulfate, filtered and concentrated to give a crude product. The crude product was purified by column chromatography (petroleum ether: ethyl acetate=30:1 to 1:3) to give the title compound (1.50 g, 6.69 mmol, 67.91% yield) as a white solid. $^1$H NMR (400 MHz, CDCl$_3$): δ, 8.19-8.15 (m, 1H), 7.99 (d, J=3.14 Hz, 1H), 7.02 (dd, J=9.29, 3.14 Hz, 1H), 3.63-3.57 (m, 2H), 3.16 (s, 3H), 2.57-2.51 (m, 2H), 2.31 (s, 6H). LC/MS (ESI) m/z: 225.1 (M+1).

Step 2:

N$^3$-(2-(dimethylamino)ethyl)-N$^3$-methylpyridine-3,6-diamine

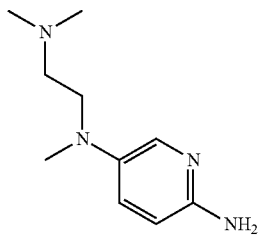 [SMILES: CN(C)CCN(C)c1ccc([N+](=O)[O-])nc1]

In a nitrogen atmosphere, to a solution of N,N,N'-trimethyl-N'-(6-nitro-3-pyridyl)ethane-1,2-diamine (1.50 g, 6.69 mmol, 1.00 equivalent) in methanol (15.00 mL) was added Pd/C (300 mg). The suspension was purged with H$_2$ several times and then stirred at 25° C. in a H$_2$ atmosphere (one atmosphere) for 2 hours. TLC showed completion of the reaction. The reaction solution was filtered and concentrated to give the title compound (1.20 g, 6.18 mmol, 92.33% yield) as a white solid which did not require further purification. LC/MS (ESI) m/z: 195.1 (M+1).

Step 3:

N$^5$-(2-(dimethylamino)ethyl)-N$^2$-(5-fluoro-4-(6,7-dihydro-3-isopropyl-2-methyl-2H-pyrazolo[4,3-c]pyridin-5 (4H)-yl)pyrimidin-2-yl)-N$^5$-methylpyridine-2,5-diamine

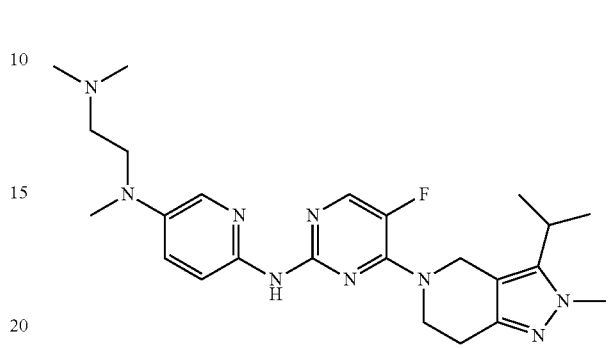

To a microwave tube was added a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (150.00 mg, 484.23 µmol, 1.00 equivalent), N$^3$-(2-(dimethylamino)ethyl)-N$^3$-methylpyridine-3,6-diamine (112.89 mg, 581.08 µmol, 1.20 equivalents), cesium carbonate (315.54 mg, 968.46 µmol, 2.00 equivalents), Pd$_2$(dba)$_3$ (88.68 mg, 96.85 µmol, 0.20 equivalent) and Xantphos (56.04 mg, 96.85 µmol, 0.20 equivalent) in dioxane (5.00 mL). The reaction solution was purged with nitrogen several times, heated to 130° C. and stirred for 2.5 hours. LC/MS showed incomplete reaction of the reactant and the product accounted for about 14%. The reaction solution was cooled to 25° C., filtered and concentrated to give a crude product. The crude product was purified by preparative HPLC (hydrochloric acid) to give the title compound (91.63 mg, 7 µmol, 47% yield). $^1$H NMR (400 MHz, Methanol-d$_4$): δ, 8.25 (d, J=7.03 Hz, 1H), 8.03 (dd, J=9.54, 3.01 Hz, 1H), 7.95 (d, J=2.89 Hz, 1H), 7.46 (d, J=9.54 Hz, 1H), 5.08 (s, 2H), 4.25 (t, J=5.58 Hz, 2H), 4.06 (s, 3H), 3.88 (t, J=7.22 Hz, 2H), 3.45 (t, J=7.22 Hz, 2H), 3.40-3.35 (m, 1H), 3.15-3.07 (m, 5H), 3.0-22.97 (m, 6H), 1.43 (d, J=7.03 Hz, 6H). LC/MS (ESI) m/z: 468.3 (M+1).

EXAMPLE 29

4-(6-((5-fluoro-4-(6,7-dihydro-3-isopropyl-2-methyl-2H-pyrazolo[4,3-c]pyridin-5 (4H)-yl)pyrimidin-2-yl)amino)pyridin-3-yl)piperidin-4-ol

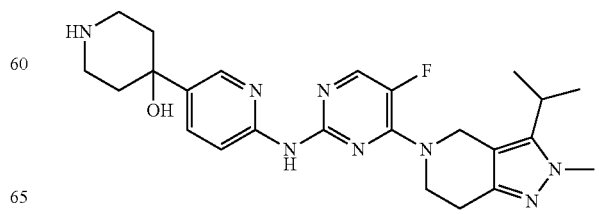

Step 1:

tert-butyl 4-(6-aminopyridin-3-yl)-4-hydroxypiperidine-carboxylate

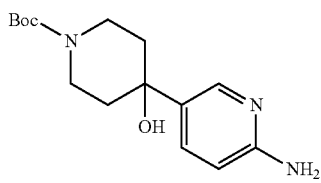 [SMILES: CC(C)(C)OC(=O)N1CCC(O)(c2ccc(N)nc2)CC1]

At −70° C., to a solution of 5-bromopyridine-2-amine (1.00 g, 5.78 mmol, 1.00 equivalent) in tetrahydrofuran (13.00 mL) was slowly added n-butyllithium (2.5 M, 7.07 mL, 3.06 equivalents) dropwise. After stirring the mixture at −70° C. for 1.5 hours, the reaction solution was warmed to 25° C. and then stirred for 2 hours. LC/MS showed that there were still about 19% of the reactant. LC/MS showed several new points and that the product accounted for about 8%. The reaction solution was quenched with water and a saturated solution of ammonium chloride at −70° C. and then warmed to 25° C. The mixture was subjected to extraction using ethyl acetate (50 mL×3), and the combined organic phases was washed with saturated brine (20 mL×3), dried over anhydrous sodium sulfate, filtered and concentrated to give a crude product. The crude product was purified by preparative HPLC (alkaline) to give the title compound (300.00 mg, 1.02 mmol, 17.69% yield) as a yellow oil. $^1$H NMR (300 MHz, DMSO-d$_6$): δ, 7.98 (d, J=2.07 Hz, 1H), 7.43 (dd, J=8.67, 2.45 Hz, 1H), 6.38 (d, J=8.67 Hz, 1H), 5.75 (s, 2H), 4.89 (s, 1H), 3.79 (d, J=9.80 Hz, 2H), 3.11 (br s, 2H), 1.77-1.63 (m, 2H), 1.62-1.52 (m, 2H), 1.41 (s, 9H). LC/MS (ESI) m/z: 294.0 (M+1).

Step 2:

tert-butyl 4-(6-(5-fluoro-4-(6,7-dihydro-3-isopropyl-2-methyl-2H-pyrazolo[4,3-c]pyridin-5 (4H)-yl) pyrimidin-2-yl-aminopyridin-3-yl)-4-hydroxypiperidine-carboxylate

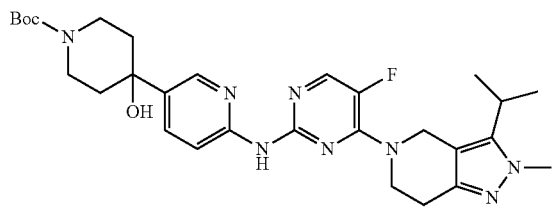 [SMILES: CC(C)c1c2c(nn1C)CCN(c1nc(Nc3ccc(C4(O)CCN(C(=O)OC(C)(C)C)CC4)cn3)ncc1F)C2]

In a nitrogen atmosphere, to a solution of tert-butyl 4-(6-amino-3-pyridyl)-4-hydroxy-piperidine-1-carboxylate (130.00 mg, 443.14 μmol, 1.00 equivalent) in dioxane (5.00 mL) were added 5-(2-chloro-5-fluoropyrimidin-4-yl)-3-isopropyl-2-methyl-4,5,6,7-tetrahydro-2H-pyrazolo[4,3-c]pyridine (Intermediate E) (164.73 mg, 531.77 μmol, 1.20 equivalents), Pd$_2$(dba)$_3$ (40.58 mg, 44.31 μmol, 0.10 equivalent), xantphos (51.28 mg, 88.62 μmol, 0.20 equivalent) and cesium carbonate (288.77 mg, 886.28 μmol, 2.00 equivalents). The reaction mixture was stirred at 110° C. for 16 hours. LC/MS showed completion of the reaction and detected the product. When the reaction solution was cooled to 25° C., it was subjected to suction filtration. The filtrate was concentrated to give a crude product. The crude product was purified by preparative TLC (dichloromethane:methanol=10:1) to give the title compound (220.00 mg, crude product) as a yellow solid. LC/MS (ESI) m/z: 567.2 (M+1).

Step 3:

4-(6-(5-fluoro-4-(6,7-dihydro-3-isopropyl-2-methyl-2H-pyrazolo[4,3-c]pyridin-5 (4H)-yl) pyrimidin-2-yl-aminopyridin-3-yl)piperidin-4-ol

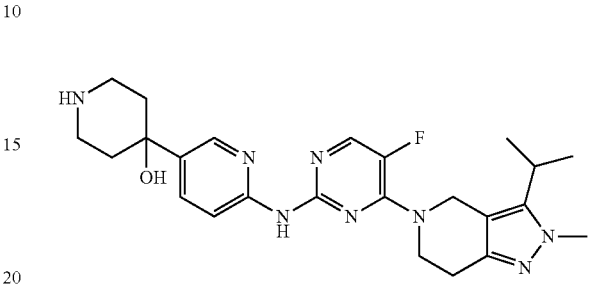

At 0° C., to a solution of tert-butyl 4-(6-(5-fluoro-4-(6,7-dihydro-3-isopropyl-2-methyl-2H-pyrazolo[4,3-c]pyridin-5(4H)-yl)pyrimidin-2-yl-aminopyridin-3-yl)-4-hydroxypiperidine-carboxylate (220.00 mg, 388.23 μmol, 1.00 equivalent) in dichloromethane (4.00 mL) was added trifluoroacetic acid (2.00 mL). The reaction mixture was heated to 25° C. and stirred for 1 hour. LC/MS showed completion of the reaction and detected the product. The reaction solution was concentrated to give a crude product. The crude product was purified by preparative HPLC (hydrochloric acid) to give the title compound (115.01 mg, 246.51 μmol, 63.50% yield). $^1$H NMR (300 MHz, Methanol-d$_4$) δ 8.53 (d, J=1.9 Hz, 1H), 8.35 (dd, J=9.0, 2.3 Hz, 1H), 8.29 (d, J=6.6 Hz, 1H), 7.50 (d, J=9.0 Hz, 1H), 4.26 (t, J=5 Hz, 2H), 4.07 (s, 3H), 3.60-3.32 (m, 7H), 3.16-3.06 (m, 2H), 2.47-2.30 (m, 2H), 2.02 (d, J=13.8 Hz, 2H), 1.49-1.40 (m, 6H). LC/MS (ESI) m/z: 467.2 (M+1).

EXAMPLE 30

N-(5-(1,4-diazepan-1-yl)pyridin-2-yl)-5-fluoro-4-(6,7-dihydro-3-isopropyl-2-methyl-2H-pyrazolo[4,3-c]pyridin-5(4H)-yl)pyrimidine-2-amine

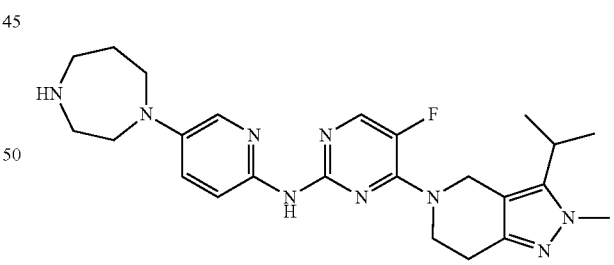

Step 1:

tert-butyl 4-(6-nitropyridin-3-yl)-1,4-diazepane-1-carboxylate

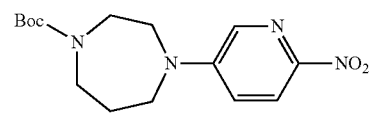 [SMILES: CC(C)(C)OC(=O)N1CCCN(c2ccc([N+](=O)[O-])nc2)CC1]

To a solution of 5-bromo-2-nitro-pyridine (2.00 g, 9.85 mmol, 1.00 equivalent) and tert-butyl 1,4-diazepane-1-carboxylate (2.37 g, 11.82 mmol, 1.20 equivalents) in dimethyl sulfoxide (20.00 mL) was added potassium carbonate (2.72 g, 19.70 mmol, 2.00 equivalents) in one portion. The reaction mixture was heated to 80° C. and stirred for 16 hours. LC/MS showed completion of the reaction and detected the product. The reaction solution was cooled to 25° C., and then water (50 mL) was added to the reaction mixture. The resulting mixture was subjected to extraction using ethyl acetate (100 mL×3). The combined organic phases was washed with saturated brine (100 mL×3), dried over anhydrous sodium sulfate, filtered and concentrated to give a crude product. The crude product was purified by column chromatography (petroleum ether: ethyl acetate=30:1 to 1:3) to give the title compound (2.00 g, 6.20 mmol, 62.99% yield) as a white solid. LC/MS (ESI) m/z: 323.1 (M+1).

Step 2:

tert-butyl 4-(6-aminopyridin-3-yl)-1,4-diazepane-1-carboxylate

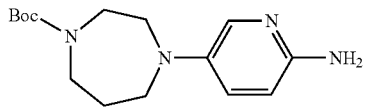 [SMILES: CC(C)(C)OC(=O)N1CCCN(c2ccc(N)nc2)CC1]

In a nitrogen atmosphere, to a solution of tert-butyl 4-(6-nitropyridin-3-yl)-1,4-diazepane-1-carboxylate (1.80 g, 5.58 mmol, 1.00 equivalent) in methanol (20.00 mL) was added Pd/C (300 mg). The suspension was purged with H$_2$ several times and then stirred at 25° C. in a H$_2$ atmosphere (one atmosphere) for 2 hours. TLC showed completion of the reaction and a new point was produced. The reaction was filtered, and the filtrate was concentrated to give a crude product (1.70 g, crude product) as a white solid. The crude product was not purified and used directly in the next step. LC/MS (ESI) m/z: 293.2 (M+1).

Step 3:

tert-butyl 4-(6-(5-fluoro-4-(6,7-dihydro-3-isopropyl-2-methyl-2H-pyrazolo[4,3-c]pyridin-5 (4H)-yl) pyrimidin-2-yl-amino)pyridin-3-yl)-1,4-diazepane-carboxylate

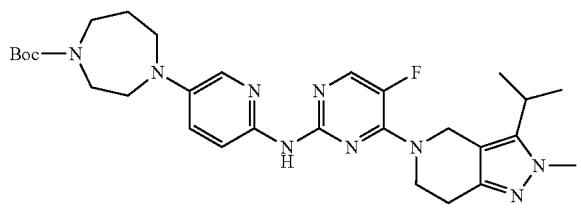 [SMILES: CC(C)c1c2c(nn1C)CCN(c1nc(Nc3ccc(N4CCCN(C(=O)OC(C)(C)C)CC4)cn3)ncc1F)C2]

In a nitrogen atmosphere, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (200.00 mg, 645.64 μmol, 1.00 equivalent) in dioxane (5.00 mL) was added tert-butyl 4-(6-aminopyridin-3-yl)-1,4-diazepane-1-carboxylate (226.53 mg, 774.77 μmol, 1.20 equivalents), Pd$_2$(dba)$_3$ (59.12 mg, 164.56 μmol, 0.01 equivalent), cesium carbonate (420.72 mg, 1.29 mmol, 2.00 equivalents) and Xantphos (74.72 mg, 129.13 μmol, 0.20 equivalent). The reaction mixture was stirred at 110° C. for 16 hours. LC/MS showed completion of the reaction and detected the desired product. The reaction solution was cooled to 25° C., it was subjected to suction filtration. The filtrate was concentrated to give a crude product. The crude product was purified by preparative TLC (ethyl acetate) to give the title compound (250.00 mg, crude product) as a white solid. LC/MS (ESI) m/z: 566.2 (M+1).

Step 4:

N-(5-(1,4-diazepan-1-yl)pyridin-2-yl)-5-fluoro-4-(6,7-dihydro-3-isopropyl-2-methyl-2H-pyrazolo[4,3-c]pyridin-5(4H)-yl)pyrimidine-2-amine

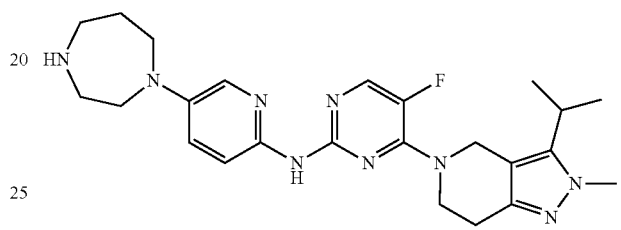

In a nitrogen atmosphere, to a solution of tert-butyl 4-(6-(5-fluoro-4-(6,7-dihydro-3-isopropyl-2-methyl-2H-pyrazolo[4,3-c]pyridin-5(4H)-yl)pyrimidin-2-yl-amino)pyridin-3-yl)-1, 4-diazepane-1-carboxylate (250.00 mg, 441.95 μmol, 1.00 equivalent) in dichloromethane (5.00 mL) was added trifluoroacetic acid (3 mL) at 25° C. The reaction mixture was stirred at 25° C. for half an hour. LC/MS showed completion of the reaction and detected the desired product. The reaction solution was concentrated to give a crude product. The crude product was purified by preparative HPLC (hydrochloric acid) to give the title compound (127.94 mg, 274.80 μmol, 62.18% yield). $^1$H NMR (400 MHz, Methanol-d$_4$) δ 8.23 (d, J=6.78 Hz, 1 H), 7.94 (dd, J=9.47, 2.70 Hz, 1 H), 7.86 (d, J=2.64 Hz, 1 H), 7.41 (d, J=9.41 Hz, 1 H), 5.04-5.14 (m, 2 H), 4.24 (t, J=5.21 Hz, 2 H), 4.06 (s, 3 H), 3.83-3.94 (m, 2 H), 3.65 (t, J=6.02 Hz, 2 H), 3.45-3.53 (m, 2 H), 3.34-3.42 (m, 3 H), 3.06-3.13 (m, 2 H), 2.24-2.33 (m, 2 H), 1.44 (d, J=7.03 Hz, 6 H). LC/MS (ESI) m/z: 466.2 (M+1).

EXAMPLE 31

N-(5-fluoro-4-(6,7-dihydro-3-isopropyl-2-methyl-2H-pyrazolo[4,3-c]pyridin-5 (4H)-yl) pyrimidin-2-yl)-5-(piperazin-1-yl)pyrazine-2-amine

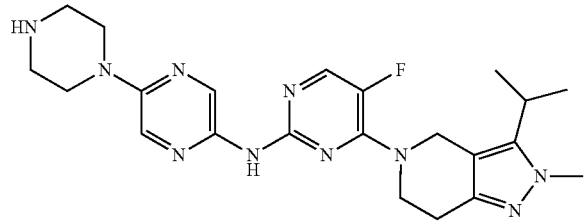 [SMILES: CC(C)c1c2c(nn1C)CCN(c1nc(Nc3cnc(N4CCNCC4)cn3)ncc1F)C2]

Step 1:

tert-butyl 4-(5-aminopyrazin-2-yl)piperazine-1-carboxylate

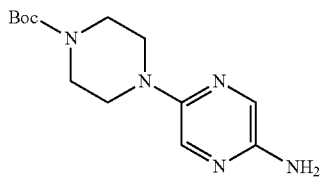

In a nitrogen atmosphere, to a solution of tert-buty 4-(5-bromopyrazin-2-yl)piperazine-1-carboxylate (10.00 g, 29.14 mmol, 1.00 equivalent) and tri-tert-butylphosphonium tetrafluoroborate (2.54 g, 8.74 mmol, 0.30 equivalent) in toluene (100.00 mL) were added LiHMDS (1 M, 60.00 mL, 2.06 equivalents) and $Pd_2(dba)_3$ (2.60 g, 2.84 mmol, 0.10 equivalent). The reaction solution was stirred at 65° C. for 16 hours. LC/MS showed completion of the reaction and detected the desired product. The reaction mixture was cooled to 25° C., and the reaction was quenched by adding water (50 mL) to the reaction solution. The resulting mixture was subjected to extraction using ethyl acetate (100 mL×3). The combined organic phases was concentrated to dryness to give a crude product. The crude product was purified by preparative HPLC (alkaline) to give the title compound (5.00 g, 17.90 mmol, 61.43% yield) as an orange solid. LC/MS (ESI) m/z: 280.1 (M+1).

Step 2:

tert-butyl 4-(5-(5-fluoro-4-(6,7-dihydro-3-isopropyl-2-methyl-2H-pyrazolo[4,3-c]pyridin-5 (4H)-yl) pyrimidin-2-yl-amino)pyrazin-2-yl)piperazine-1-carboxylate

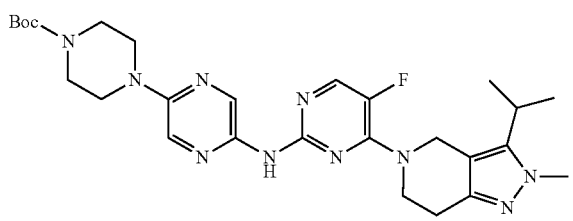 [SMILES: CC(C)c1c2c(nn1C)CCN(c1nc(Nc3cnc(N4CCN(C(=O)OC(C)(C)C)CC4)cn3)ncc1F)C2]

In a microwave tube, to a solution of 5-(2-chloro-5-fluoropyrimidin-4-yl)-3-isopropyl-2-methyl-4,5,6,7-tetrahydro-2H-pyrazolo[4,3-c]pyridine (Intermediate E) (500.00 mg, 1.61 mmol, 1.00 equivalent) and tert-butyl 4-(5-aminopyrazin-2-yl)piperazine-1-carboxylate (495.97 mg, 1.78 mmol, 1.10 equivalents) in dioxane (16.00 mL) were added $Pd_2(dba)_3$ (147.81 mg, 161.41 µmol, 0.10 equivalent), BINAP (201.01 mg, 322.82 µmol, 0.20 equivalent), sodium t-butoxide (232.67 mg, 2.42 mmol, 1.50 equivalents) and water (400.00 µL). Nitrogen was introduced into the reaction system for 2 minutes, and then the tube was sealed, heated to 140° C. and stirred for 4 hours. LC/MS showed completion of the reaction and detected the desired product. The reaction solution was filtered through diatomite (washed with ethyl acetate), and the filtrate was washed with water (20 mL). The organic phase was concentrated to dryness to give a crude product. The crude product was purified by preparative TLC (petroleum ether: ethyl acetate=2:1) to give the title compound (800.00 mg, crude product) as a yellow solid. LC/MS (ESI) m/z: 553.3 (M+1).

Step 3:

N-(5-fluoro-4-(6,7-dihydro-3-isopropyl-2-methyl-2H-pyrazolo[4,3-c]pyridin-5 (4H)-yl) pyrimidin-2-yl)-5-(piperazin-1-yl)pyrazine-2-amine

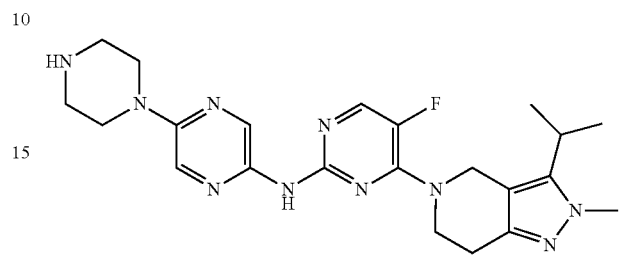

To a solution of tert-butyl 4-(5-((5-fluoro-4-(3-isopropyl-2-methyl-6,7-dihydro-2H-pyrazolo[4,3-c]pyridin-5(4H)-yl)pyrimidin-2-yl)-amino)pyrazin-2-yl)piperazine-1-carboxylate (800.00 mg, 1.45 mmol, 1.00 equivalent) in dichloromethane (15.00 mL) was added trifluoroacetic acid (23.03 g, 201.95 mmol, 139.28 equivalents). The reaction mixture was stirred at 30° C. for 7 hours. LC/MS showed completion of the reaction and detected the desired product. The reaction solution was concentrated to dryness to give a crude product. The crude product was purified by preparative HPLC (hydrochloric acid) to give the title compound (213.05 mg, 435.69 µmol, 30.05% yield). $^1$H NMR (400 MHz, methanol-$d_4$): δ 8.26 (s, 1H), 8.16-8.24 (m, 2H), 5.20 (s, 2H), 4.36 (br s, 2H), 4.07 (s, 3H), 3.84-3.98 (m, 4H), 3.35-3.44 (m, 5H), 3.15 (br s., 2H), 1.33-1.53 (m, 6H). LC/MS (ESI) m/z: 453.2 (M+1).

EXAMPLE 32

N-(5-fluoro-4-(6,7-dihydro-3-isopropyl-2-methyl-2H-pyrazolo[4,3-c]pyridin-5(4H)-yl) pyrimidin-2-yl)-5-(4-methylpiperazin-1-yl)pyrazine-2-amine

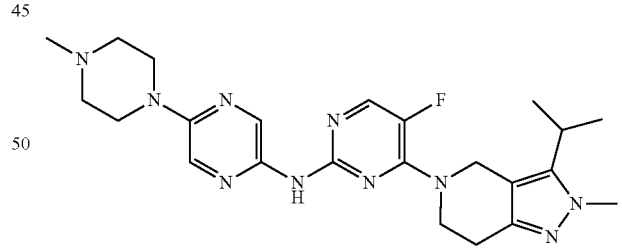

At 30° C., to a solution of 5-fluoro-4-(3-isopropyl-2-methyl-6,7-dihydro-2H-pyrazolo[4,3-c]pyridin-5(4H)-yl)-N-(5-(piperazin-1-yl)pyrazin-2-yl)pyrimidine-2-amine (250.00 mg, 552.45 µmol, 1.00 equivalent) in methanol (25.00 mL) were added $NaBH_3CN$ (69.43 mg, 1.10 mmol, 2.00 equivalents), HCHO (24.89 mg, 828.68 µmol, 1.50 equivalents) and trifluoroacetic acid (62.99 mg, 552.45 µmol, 1.00 equivalent). The reaction mixture was stirred at 30° C. for 4 hours. LC/MS showed completion of the reaction. The reaction mixture was concentrated and dried. The obtained crude product was first purified by preparative HPLC (hydrochloric acid) and then purified by silica gel column chromatography (petroleum ether: ethyl acetate=1: 1) to give the title compound (35.03 mg, 75.08 μmol, 13.59% yield). $^1$H NMR (400 MHz, methanol-d$_4$) δ 8.88 (s, 1H), 7.97 (d, J=1.13 Hz, 1H), 7.93 (d, J=6.90 Hz, 1H), 4.04 (t, J=5.84 Hz, 2H), 3.75-3.79 (m, 3H), 3.57-3.67 (m, 4H), 3.12-3.22 (m, 1H), 2.77-2.85 (m, 6H), 2.52 (s, 3H), 2.03 (s, 1H), 1.33 (d, J=7.03 Hz, 6H), 1.28-1.32 (m, 1H). LC/MS (ESI) m/z: 467.2 (M+1).

EXAMPLE 33

5-fluoro-4-(6,7-dihydro-3-isopropyl-2-methyl-2H-pyrazolo[4,3-c]pyridin-5 (4H)-yl)-N-(4-methyl-5-(piperazin-1-yl)pyridin-2-yl)pyrimidine-2-amine

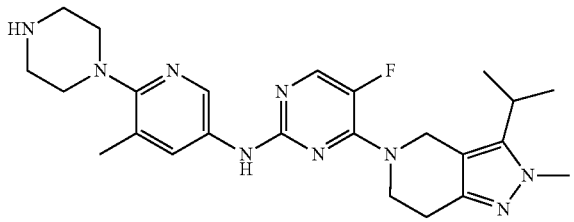 [SMILES: Cc1cc(Nc2ncc(F)c(N3CCc4nn(C)c(C(C)C)c4C3)n2)cnc1N1CCNCC1]

Step 1:

5-bromo-4-methyl-2-nitropyridine

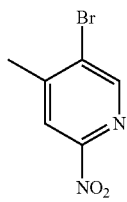

H$_2$O$_2$ (58.06 g, 1.71 mol, 21.28 equivalents) was slowly added dropwise to H$_2$SO$_4$ (184.00 g, 1.88 mol, 23.39 equivalents) which was cooled to 0° C., and the temperature was maintained below −20° C. during the dropwise addition. A mixture of 5-bromo-4-methylpyridine-2-amine (15.00 g, 80.20 mmol, 1.00 equivalent) in H$_2$SO$_4$ (100.00 mL) was then added thereto. The reaction mixture was first stirred for 45 minutes in an ice bath and then warmed to 30° C. After three hours, the color of the reaction solution changed gradually from grass green to bright yellow. Ice (500 mL) was added to the reaction mixture. The precipitated solid was filtered, washed with water and then dried in vacuo to give the title compound (12.00 g, 55.29 mmol, 68.95% yield) as a bright orange solid without further purification. LC/MS (ESI) m/z: 216.9 (M+1), 218.9 (M+3).

Step 2:

tert-butyl 4-(4-methyl-6-nitropyridin-3-yl)piperazine-1-carboxylate

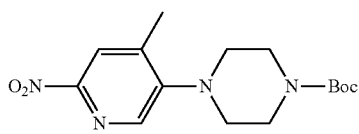

In a nitrogen atmosphere, to a mixed solution of 5-bromo-4-methyl-2-nitropyridine (500.00 mg, 2.30 mmol, 1.00 equivalent), tert-butyl piperazine-1-carboxylate (514.05 mg, 2.76 mmol, 1.20 equivalents), BINAP (286.43 mg, 460.00 μmol, 0.20 equivalent) and Cs$_2$CO$_3$ (1.05 g, 3.22 mmol, 1.40 equivalents) in dioxane (20.00 mL) was added Pd$_2$(dba)$_3$ (210.62 mg, 230.00 μmol, 0.10 equivalent). The reaction mixture was stirred at 110° C. for 16 hours in a nitrogen atmosphere. LC/MS showed completion of the reaction. The reaction mixture was cooled to 20° C. and then filtered. The filtrate was concentrated, dried and then purified by TLC plate (petroleum ether: ethyl acetate=4:1) to give the title compound (420.00 mg, 1.30 mmol, 56.65% yield) as a yellow solid. LC/MS (ESI) m/z: 323.0 (M+1).

Step 3:

tert-butyl 4-(6-amino-4-methylpyridin-3-yl)piperazine-1-carboxylate

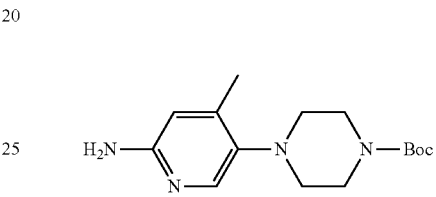

In a nitrogen atmosphere, to a solution of tert-butyl 4-(4-methyl-6-nitropyridin-3-yl) piperazine-1-carboxylate (350.00 mg, 651.45 μmol, 1.00 equivalent) in methanol (15.00 mL) was added 10% Pd—C (200 mg). The suspension was evacuated and charged with hydrogen, followed by being stirred at 30° C. in a H$_2$ atmosphere (15 psi) for 1.5 hours. LC/MS showed completion of the reaction. The mixture was filtered, concentrated and dried. The obtained crude product was purified by silica gel column chromatography (petroleum ether: ethyl acetate=1:1) to give the title compound (125.00 mg, 427.53 μmol, 65.63% yield) as a yellow solid. LC/MS (ESI) m/z: 293.2 (M+1).

Step 4:

tert-butyl 4-(6-(5-fluoro-4-(6,7-dihydro-3-isopropyl-2-methyl-2H-pyrazolo[4,3-c]pyridin-5 (4H)-yl) pyrimidin-2-yl-amino)-4-methylpyridin-3-yl)piperazine-1-carboxylate

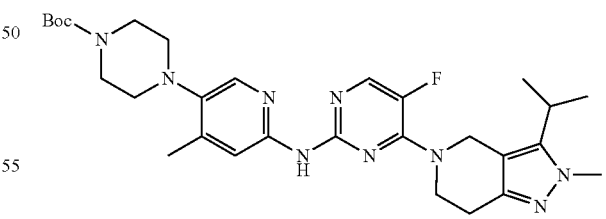

The mixture of tert-butyl 4-(6-amino-4-methylpyridin-3-yl)piperazine-1-carboxylate (124.59 mg, 426.12 μmol, 1.10 equivalents), 5-(2-chloro-5-fluoropyrimidin-4-yl)-3-isopropyl-2-methyl-4,5,6,7-tetrahydro-2H-pyrazolo[4,3-c]pyridine (Intermediate E) (120.00 mg, 387.38 μmol, 1.00 equivalent), Pd$_2$(dba)$_3$ (35.47 mg, 38.74 μmol, 0.10 equivalent), Xantphos (44.83 mg, 77.48 μmol, 0.20 equivalent) and Cs$_2$CO$_3$ (252.43 mg, 774.76 μmol, 2.00 equivalents) in dioxane (20.00 mL) was charged with N$_2$. The reaction mixture was then stirred at 110° C. for 16 hours. LC/MS showed completion of the reaction. The reaction mixture was filtered, concentrated and dried. The obtained crude product was diluted with ethyl acetate (50 mL) and washed with water (20 mL). The organic phase was dried using a rotary vacuum dryer and purified by preparative TLC plate (petroleum ether: ethyl acetate=1:1) to give the title compound (150.00 mg, 265.17 µmol, 68.45% yield) as a yellow solid. LC/MS (ESI) m/z: 566.3 (M+1).

Step 5:

5-fluoro-4-(6,7-dihydro-3-isopropyl-2-methyl-2H-pyrazolo[4,3-c]pyridin-5 (4H)-yl)-N-(4-methyl-5-(piperazin-1-yl)pyridin-2-yl)pyrimidine-2-amine

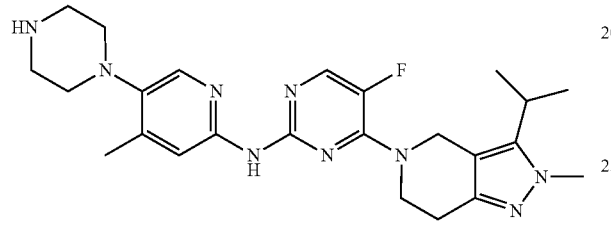

To a solution of tert-butyl 4-(6-(5-fluoro-4-(6,7-dihydro-3-isopropyl-2-methyl-2H-pyrazolo[4,3-c]pyridin-5(4H)-yl)pyrimidin-2-yl-amino)-4-methylpyridin-3-yl)piperazine-1-carboxylate (150.00 mg, 265.17 µmol, 1.00 equivalent) in dichloromethane (7.50 mL) was added trifluoroacetic acid (11.52 g, 101.00 mmol, 380.87 equivalents). The reaction mixture was stirred at 30° C. for 2 hours. LC/MS showed completion of the reaction. The mixture was concentrated and dried. The obtained crude product was purified by preparative HPLC (formic acid) to give the title compound (121.00 mg, 236.52 µmol, 89.19% yield) as a yellow oil. $^1$H NMR (400 MHz, Methanol-$d_4$) δ 8.15 (d, J=7.2 Hz, 1H), 8.05 (s, 1H), 7.24 (s, 1H), 5.00 (s, 2H), 4.16 (t, J=5.8 Hz, 2H), 3.81 (s, 3H), 3.51-3.39 (m, 4H), 3.31-3.24 (m, 4H), 3.24-3.16 (m, 1H), 2.89 (t, J=5.8 Hz, 2H), 2.55-2.45 (m, 3H), 1.36 (d, J=7.2 Hz, 6H). LC/MS (ESI) m/z: 466.2 (M+1).

Approach E

Synthesis of 5-fluoro-4-(6,7-dihydro-3-isopropyl-2,7,7-trimethyl-2H-pyrazolo[4,3-c]pyridin-5(4H)-yl)-N-(5-(1-methylpiperidin-4-yl)pyridin-2-yl)pyrimidine-2-amine

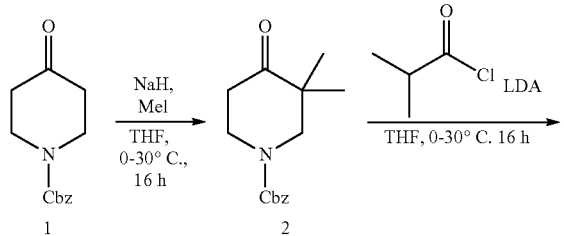

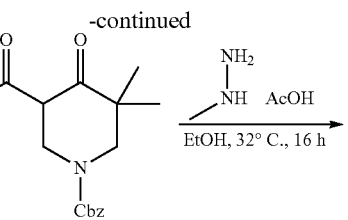

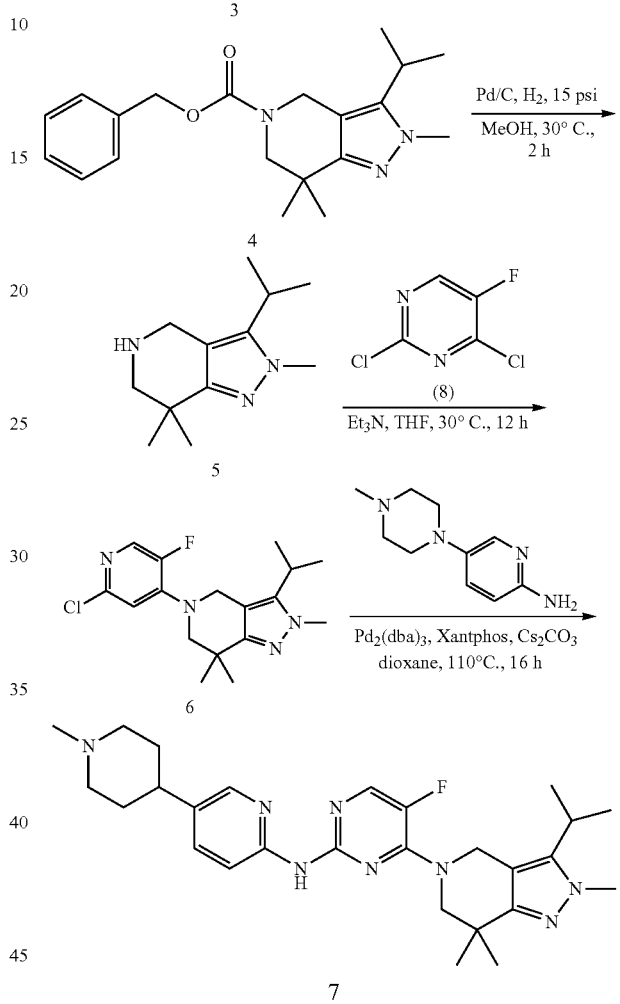

EXAMPLE 34

5-fluoro-4-(6,7-dihydro-3-isopropyl-2,7,7-trimethyl-2H-pyrazolo[4,3-c]pyridin-5 (4H)-yl)-N-(5-(1-methylpiperidin-4-yl)pyridin-2-yl)pyrimidine-2-amine

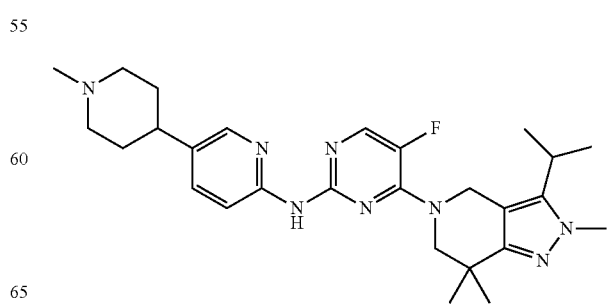

Step 1:

benzyl 3,3-dimethyl-4-oxopiperidine-1-carboxylate

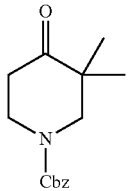

At 0° C., to a solution of benzyl 4-oxopiperidine-1-carboxylate (2.00 g, 8.57 mmol, 1.00 equivalent) in tetrahydrofuran (25 mL) were added sodium hydride (719.88 mg, 18.00 mmol, 2.10 equivalents) and potassium iodide (3.80 g, 26.74 mmol, 3.12 equivalents) in one portion. The mixture was stirred at 30° C. for 16 hours. LC/MS showed completion of the reaction. The reaction mixture was added a solution of ammonium chloride (50 mL) thereto and then subjected to extraction using ethyl acetate (50 mL×2). The organic phase was concentrated and dried. The obtained residue was purified by preparative TLC plate (petroleum ether: ethyl acetate=6:1) to give the title compound (870.00 mg, 3.33 mmol, 38.86% yield) as a transparent oil. $^1$H NMR (400 MHz, Methanol-$d_4$) δ 7.38-7.33 (m, 5H), 5.19 (s, 2H), 3.81-3.77 (t, J=6.4 Hz, 2H), 3.50-3.46 (m, 2H), 2.50 (s, 2H), 1.11-1.04 (m, 6H). LC/MS (ESI) m/z: 284.1 (M+1).

Step 2:

benzyl 5-(isobutyryl)-3,3-dimethyl-4-oxopiperidine-1-carboxylate

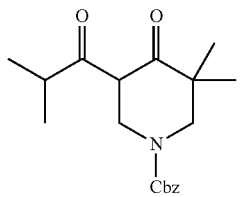 [SMILES: CC(C)C(=O)C1CN(C(=O)OCc2ccccc2)CC(C)(C)C1=O]

At 0° C., to a solution of benzyl 3,3-dimethyl 4-oxopiperidine-1-carboxylate (6.00 g, 22.96 mmol, 1.00 equivalent) in toluene (150.00 mL) was added LDA (2M, 22.96 mL, 2.00 equivalents) in one portion. After the reaction mixture was stirred at this temperature for 30 minutes, isobutyryl chloride (3.67 g, 34.44 mmol, 1.50 equivalents) was added, and then the resulting mixture was slowly warmed to 30° C. and stirred for 16 hours. TLC (petroleum ether: ethyl acetate=6:1) showed completion of the reaction. The reaction mixture was quenched with a solution of ammonium chloride (80 mL) and then subjected to extraction using ethyl acetate (100 mL×2). The organic phases were combined, concentrated and dried. The obtained crude product was purified by silica gel column chromatography (petroleum ether: ethyl acetate=50:1) to give the title compound (5.60 g, 16.90 mmol, 73.60% yield) as a yellow oil.

Step 3:

benzyl 6,7-dihydro-3-isopropyl-2,7,7-trimethyl-2H-pyrazolo[4,3-c]pyridine-5 (4H)-carboxylate

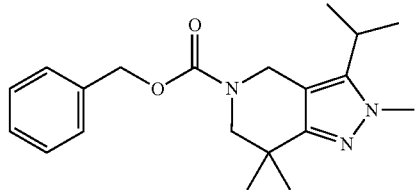 [SMILES: CC(C)c1c2c(nn1C)C(C)(C)CN(C(=O)OCc1ccccc1)C2]

To a solution of benzyl 5-(isobutyryl)-3,3-dimethyl-4-oxopiperidine-1-carboxylate (3.90 g, 11.77 mmol, 1.00 equivalent) and a 40% aqueous solution of methylhydrazine (13.99 g, 121.47 mmol, 10.32 equivalents) in ethanol (35.00 mL) was added acetic acid (706.66 mg, 11.77 mmol, 1.00 equivalent) in one portion. The reaction mixture was stirred at 32° C. for 16 hours. LC/MS showed completion of the reaction. The reaction mixture was concentrated and dried. The obtained crude product was purified by preparative TLC plate (petroleum ether: ethyl acetate=5:1) to give the title compound (600.00 mg, 1.76 mmol, 14.93% yield) as a transparent oil. LC/MS (ESI) m/z: 342.2 (M+1).

Step 4:

3-isopropyl-2,7,7-trimethyl-4,5,6,7-tetrahydro-2H-pyrazolo[4,3-c]pyridine

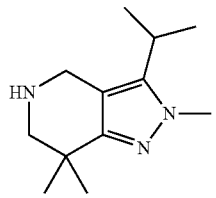

In a nitrogen atmosphere, to a solution of benzyl 6,7-dihydro-3-isopropyl-2,7,7-trimethyl-2H-pyrazolo[4,3-c]pyridine-5(4H)-carboxylate (600.00 mg, 1.76 mmol, 1.00 equivalent) in methanol (20.00 mL) was added 10% Pd/C (0.4 g). The suspension was evacuated, charged with hydrogen, and then stirred at 30° C. in a H$_2$ atmosphere (15 psi) for 2 hours. LC/MS showed completion of the reaction. The mixture was filtered, concentrated and dried to give the title compound (323.00 mg, 1.56 mmol, 88.53% yield) as a yellow oil. LC/MS (ESI) m/z: 208.2 (M+1).

Step 5:

5-(2-chloro-5-fluoropyrimidin-4-yl)-4,5,6,7-tetrahydro-3-isopropyl-2,7,7-trimethyl-2H-pyrazolo[4,3-c]pyridine

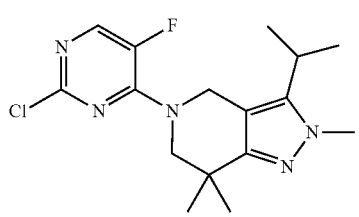 [SMILES: CC(C)c1c2c(nn1C)C(C)(C)CN(c1nc(Cl)ncc1F)C2]

At 30° C., to a solution of 3-isopropyl-2,7,7-trimethyl-4,5,6,7-tetrahydro-2H-pyrazolo[4,3-c]pyridine (323.00 mg, 1.56 mmol, 1.00 equivalent) and 2,4-dichloro-5-fluoropyrimidine (338.62 mg, 2.03 mmol, 1.30 equivalents) in tetrahydrofuran (25.00 mL) was added triethylamine (1.58 g, 15.58 mmol, 10.00 equivalents). The reaction mixture was stirred at 30° C. for 12 hours. LC/MS showed completion of the reaction. The reaction mixture was diluted with saturated brine (20 mL) and then subjected to extraction using ethyl acetate (50 mL×2). The organic phases were combined and then dried. The obtained residue was purified by preparative TLC plate (petroleum ether: ethyl acetate=4:1) to give the title compound (380.00 mg, 1.12 mmol, 72.11% yield) as a yellow oil. LC/MS (ESI) m/z: 338.1 (M+1).

Step 6:

5-fluoro-4-(6,7-dihydro-3-isopropyl-2,7,7-trimethyl-2H-pyrazolo[4,3-c]pyridin-5 (4H)-yl)-N-(5-(1-methylpiperidin-4-yl)pyridin-2-yl)pyrimidine-2-amine

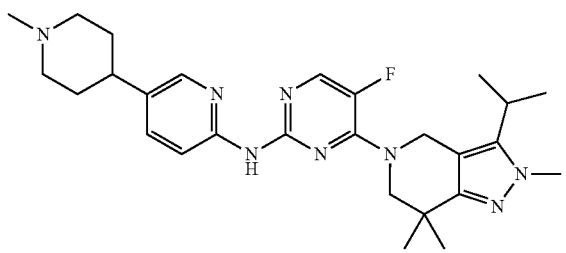

In a nitrogen atmosphere, to a mixture of 5-(2-chloro-5-fluoropyrimidin-4-yl)-4,5,6,7-tetrahydro-3-isopropyl-2,7,7-trimethyl-2H-pyrazolo[4,3-c]pyridine (380.00 mg, 1.12 mmol, 1.00 equivalent), 5-(1-methylpiperidin-4-yl)pyridine-2-amine (257.07 mg, 1.34 mmol, 1.20 equivalents) and Cs$_2$CO$_3$ (729.84 mg, 2.24 mmol, 2.00 equivalents) in dioxane (25.00 mL) were added Pd$_2$(dba)$_3$ (102.56 mg, 112.00 mmol, 0.10 equivalent) and Xantphos (129.61 mg, 224.00 μmol, 0.20 equivalent) in one portion. The reaction mixture was charged with N$_2$ and then stirred at 110° C. for 16 hours. LC/MS showed completion of the reaction. The reaction-mixture was diluted with water (10 mL) and then subjected to extraction using ethyl acetate (50 mL×2). The organic phases were combined and then dried. The obtained residue was purified by preparative HPLC (hydrochloric acid), followed by being purified by SFC (AD-3S_5_40_3 ML, Column: Chiralpak AD-3100×4.6 mm ID 3 um, Mobile phase: 40% ethanol (0.05% DEA) in CO$_2$, Flow rate: 3 mL/min, Wavelength: 220 nm) to give the title compound (60.00 mg, 121.80 μmol, 10.87% yield). $^1$H NMR (400 MHz, Methanol-d$_4$) δ 8.36 (s, 1H), 8.30 (d, J=6.8 Hz, 1H), 8.27-8.19 (m, 1H), 7.56-7.48 (m, 1H), 5.09 (s, 2H), 4.12 (s, 3H), 4.05 (s, 2H), 3.73-3.60 (m, 2H), 3.44-3.35 (m, 1H), 3.31-3.25 (m, 1H), 3.21-3.09 (m, 1H), 2.96 (s, 3H), 2.35 (s, 1H), 2.26-2.08 (m, 4H), 1.51-1.44 (m, 12H). LC/MS (ESI) m/z: 493.3 (M+1).

Approach F

Synthesis of N-(5-(1,4-diazepan-1-yl)pyridin-2-yl)-5-fluoro-4-(6,7-dihydro-3-isopropyl-2-phenyl-2H-pyrazolo[4,3-c]pyridin-5(4H)-yl)pyrimidine-2-amine

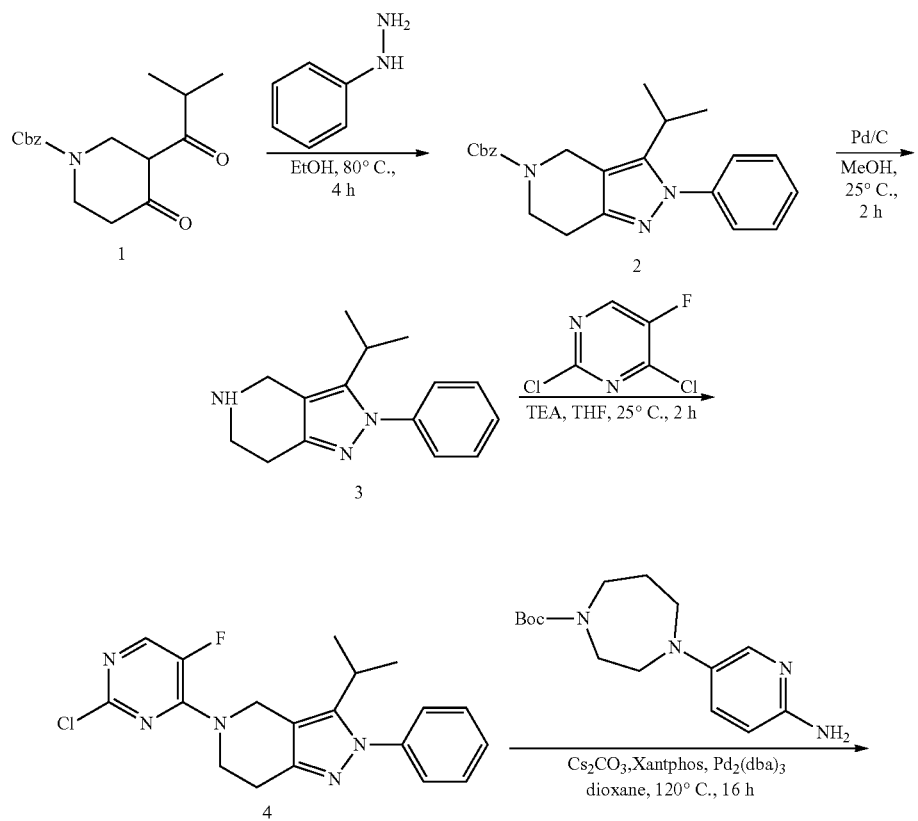

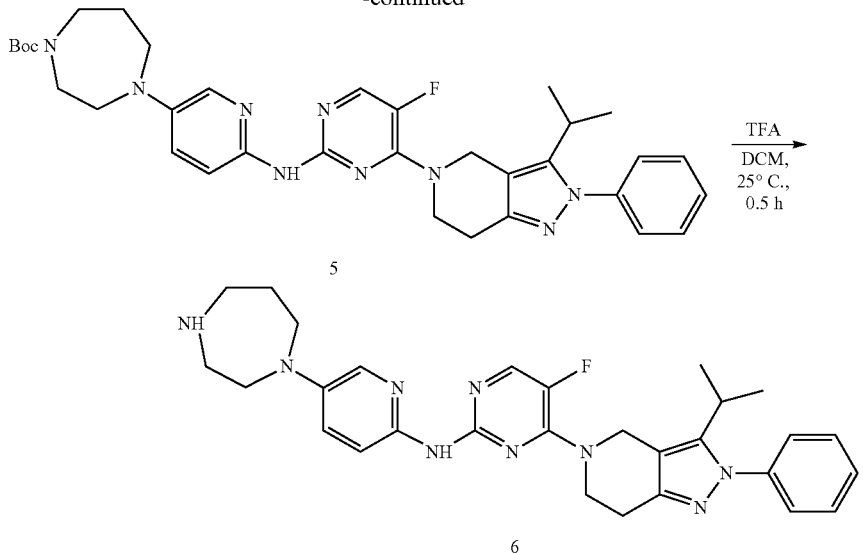

EXAMPLE 35

N-(5-(1,4-diazepan-1-yl)pyridin-2-yl)-5-fluoro-4-(6,7-dihydro-3-isopropyl-2-phenyl-2H-pyrazolo[4,3-c]pyridin-5(4H)-yl)pyrimidine-2-amine

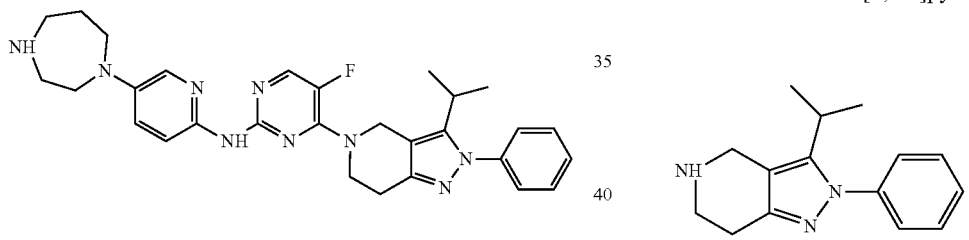

Step 1:

benzyl 6,7-dihydro-3-isopropyl-2-phenyl-2H-pyrazolo[4,3-c]pyridine-5(4H)-carboxylate To a solution of benzyl 3-(2-methylpropionyl)-4-oxo-piperidine-1-carboxylate (500.00 mg, 1.65 mmol, 1.00 equivalent) in ethanol (5.00 mL) was added phenylhydrazine (178.24 mg, 1.65 mmol, 1.00 equivalent). The reaction mixture was heated to 80° C. and stirred at this temperature for 4 hours. TLC (petroleum ether: ethyl acetate=2:1) and LC/MS showed completion of the reaction. The reaction mixture was cooled to 25° C. and then concentrated under reduced pressure to remove the solvent. The resulting residue was purified by silica gel column chromatography (petroleum ether: ethyl acetate=5:1) to give the title compound (330.00 mg, 878.92 μmol, 53.27% yield) as a red oil. $^1$H NMR (400 MHz, CDCl$_3$) δ 7.50-7.36 (m, 10H), 5.23 (s, 2H), 4.70 (s, 2H), 3.83 (br s, 2H), 3.07 (q, J=7.0 Hz, 1H), 2.86 (br s, 2H), 1.28-1.20 (m, 6H). LC/MS (ESI) m/z: 376.1 (M+1).

Step 2:

4,5,6,7-tetrahydro-3-isopropyl-2-phenyl-2H-pyrazolo[4,3-c]pyridine

To a solution of benzyl 6,7-dihydro-3-isopropyl-2-phenyl-2H-pyrazolo[4,3-c]pyridine-5(4H)-carboxylate (330.0 mg, 878.92 μmol, 1.00 equivalent) in methanol (5.00 mL) was added 10% palladium on carbon (50 mg). The reaction mixture was stirred at 25° C. for 2 hours in a H$_2$ atmosphere (15 psi). TLC (dichloromethane:methanol=10:1) showed completion of the reaction. The reaction mixture was filtered, and the filtrate was concentrated to give the title compound (200.00 mg, crude product) as a yellow oil.

Step 3:

5-(2-chloro-5-fluoropyrimidin-4-yl)-4,5,6,7-tetrahydro-3-isopropyl-2-phenyl-2H-pyrazolo[4,3-c]pyridine

To a solution of 4,5,6,7-tetrahydro-3-isopropyl-2-phenyl-2H-pyrazolo[4,3-c]pyridine (200.00 mg, 828.74 μmol, 1.00 equivalent) in tetrahydrofuran (5.00 mL) were added triethylamine (167.72 mg, 1.66 mmol, 2.00 equivalents) and 2,4-dichloro-5-fluoro-pyrimidine (166.05 mg, 994.49 μmol, 1.20 equivalents). The reaction mixture was stirred at 25° C. for 2 hours. LC/MS showed completion of the reaction. The reaction mixture was concentrated and dried. The obtained residue was purified by preparative TLC plate (petroleum ether: ethyl acetate=2:1) to give the title compound (190.00 mg, 510.97 μmol, 61.66% yield) as a white solid. $^1$H NMR (400 MHz, CDCl$_3$) δ 7.99 (d, J=6.0 Hz, 1H), 7.52-7.43 (m, 3H), 7.40-7.36 (m, 2H), 4.97 (s, 2H), 4.12 (t, J=5.9 Hz, 2H), 3.10 (q, J=7.1 Hz, 1H), 2.99 (t, J=5.9 Hz, 2H), 1.30 (d, J=7.0 Hz, 6H). LC/MS (ESI) m/z: 372.0 (M+1).

Step: 4 tert-butyl 4-(6-(5-fluoro-4-(6,7-dihydro-3-isopropyl-2-phenyl-2H-pyrazolo[4,3-c]pyridin-5 (4H)-yl) pyrimidine-2-aminopyridin-3-yl)-1,4-diazepane-1-carboxylate

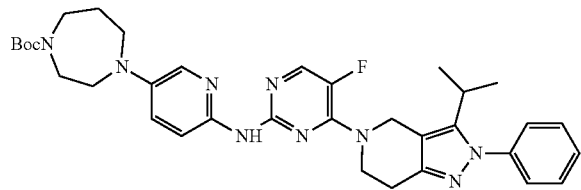 [SMILES: CC(C)c1c2c(nn1-c1ccccc1)CCN(c1nc(Nc3ccc(N4CCCN(C(=O)OC(C)(C)C)CC4)cn3)ncc1F)C2]

In a nitrogen atmosphere, to a mixed solution of 5-(2-chloro-5-fluoropyrimidin-4-yl)-4,5,6,7-tetrahydro-3-isopropyl-2-phenyl-2H-pyrazolo[4,3-c]pyridine (190.00 mg, 510.97 μmol, 1.00 equivalent), and tert-butyl 4-(6-amino-3-pyridyl)-1,4-diazepane-1-carboxylate (224.10 mg, 766.46 μmol, 1.50 equivalents) in dioxane (5.00 mL) were added Cs$_2$CO$_3$ (499.45 mg, 1.53 mmol, 3.00 equivalents), Xantphos (59.13 mg, 102.19 μmol, 0.20 equivalent), and Pd$_2$(dba)$_3$ (46.79 mg, 51.10 μmol, 0.10 equivalent). The reaction mixture was heated to 120° C. and stirred at this temperature for 16 hours. LC/MS showed completion of the reaction. The reaction mixture was filtered, and the filtrate was concentrated. The obtained residue was purified by preparative TLC plate (pure ethyl acetate) to give the title compound (100.00 mg, crude product) as a yellow solid. LC/MS (ESI) m/z: 628.3 (M+1).

Step 5:

N-(5-(1,4-diazepan-1-yl)pyridin-2-yl)-5-fluoro-4-(6,7-dihydro-3-isopropyl-2-phenyl-2H-pyrazolo[4,3-c]pyridin-5(4H)-yl)pyrimidine-2-amine

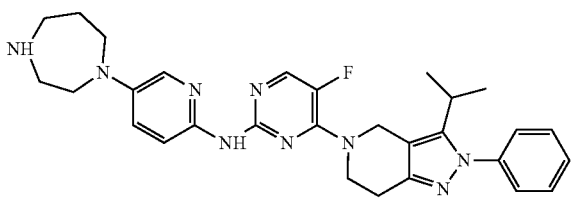 [SMILES: CC(C)c1c2c(nn1-c1ccccc1)CCN(c1nc(Nc3ccc(N4CCCNCC4)cn3)ncc1F)C2]

To a solution of tert-butyl 4-(6-(5-fluoro-4-(6,7-dihydro-3-isopropyl-2-phenyl-2H-pyrazolo[4,3-c]pyridin-5(4H)-yl) pyrimidine-2-aminopyridin-3-yl)-1,4-diazepane-1-carboxylate (100.00 mg, 159.30 μmol, 1.00 equivalent) in dichloromethane (3.00 mL) was added trifluoroacetic acid (1 mL). The reaction mixture was stirred at 25° C. for 0.5 h. LC/MS showed completion of the reaction. The reaction mixture was concentrated under reduced pressure to remove the solvent. The resulting residue was purified by preparative HPLC (hydrochloric acid) to give the title compound (50.00 mg, 94.76 μmol, 59.49% yield). $^1$H NMR (400 MHz, Methanol-d$_4$) δ 8.24 (d, J=6.8 Hz, 1H), 7.92 (dd, J=9.4, 2.8 Hz, 1H), 7.86 (d, J=2.6 Hz, 1H), 7.73-7.68 (m, 3H), 7.65-7.57 (m, 2H), 7.39 (d, J=9.5 Hz, 1H), 5.17 (s, 2H), 4.31 (t, J=5.0 Hz, 2H), 3.92-3.84 (m, 2H), 3.65 (t, J=6.0 Hz, 2H), 3.52-3.45 (m, 2H), 3.41-3.36 (m, 2H), 3.14 (t, J=5.1 Hz, 2H), 3.06 (td, J=14.0, 6.9 Hz, 1H), 2.33-2.24 (m, 2H), 1.37 (d, J=7.0 Hz, 6H). LC/MS (ESI) m/z: 528.2 (M+1).

Pharmacological Experiments

The compounds of the present invention are selective CDK4/6 inhibitors, for example, their activities against CDK2 were lower than that against CDK4/6 (by comparing their IC$_{50}$ values). The following experimental results confirmed that the compounds listed in the present invention were specific CDK4/6 inhibitors indeed and could be used as potential anticancer drugs. The IC$_{50}$ used herein refers to the corresponding concentration of an agent when the agent produces 50% of the maximum inhibition. The compounds of the present invention also have unpredictable biological activities. For instance, the compound of Example 13 was not a substrate of an efflux transporter, whereas palbociclib and LY2835219 was proved to be substrates of efflux transporters. Further, the exposure of the compound of Example 13 in the brain tissue was much higher than that of palbociclib or LY2835219 at the same time. It can be speculated that the compound of Example 13, in comparison with palbociclib and LY2835219, is more promising in treating cases of breast cancer with brain metastase, which account for about 15% of the breast cancer cases. The biological activities shown herein are only the representative biological activities of some individual examples.

Biochemical Experiments

Experimental Materials:

The experimental materials included CDK2/cyclin A, CDK4/cyclin D1, CDK6/cyclin D1 (Life Technologies); ULight-labeled polypeptide substrates, i.e., ULight-4E-BP1 and ULight-MBP (PerkinElmer); the europium-labeled antibody against anti-myelin basic protein and europium-labeled rabbit antibody (PerkinElmer); and Envision® Multilabel Plate Reader (PerkinElmer) used for signal detection.

Experimental Method:

The compounds to be tested were diluted three times so as to be at ten gradually varied concentrations. The final concentrations ranged from 5 μM to 0.25 nM.

The Enzyme Reaction System of CDK2/Cyclin A

The standard Lance Ultra method was carried out in a 10 μL of enzyme reaction system containing 0.5 nM CDK2/cyclin A protein, 100 nM ULight-MBP polypeptide, and 25 μM ATP. The gradient dilutions of the compounds were dissolved in enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction started, the OptiPlate 384-well plate was sealed with top heat-sealing film TopSeal-A and incubated at room temperature for 60 minutes.

The Enzyme Reaction System of CDK4/Cyclin D1

The standard Lance Ultra method was carried out in a 10 μL enzyme reaction system containing 0.3 nM CDK4/cyclin D1 protein, 50 nM ULight-4E-BP1 polypeptide, and 350 μM ATP. The dilutions of the compounds were dissolved in enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction started, the OptiPlate 384-well plate was sealed with top heat-sealing film TopSeal-A and incubated at room temperature for 180 minutes.

The Enzyme Reaction System of CDK6/Cyclin D1

The standard Lance Ultra method was carried out in a 10 μL enzyme reaction system containing 0.8 nM CDK6/cyclin D1 protein, 50 nM ULight-4E-BP1 polypeptide, and 250 μM ATP. The dilutions of the compounds were dissolved in enzyme buffer, respectively. The components of the buffer included 50 mM hydroxyethylpiperazine ethanesulfonic acid solution (pH 7.5), 1 mM ethylenediaminetetraacetic acid, 10 mM magnesium chloride, 0.01% Brij-35, and 2 mM dithiothreitol. After the reaction started, the OptiPlate 384-well plate was sealed with top heat-sealing film TopSeal-A and incubated at room temperature for 180 minutes.

The stop buffer of the enzyme reaction was prepared by dissolving EDTA in a one-fold dilution of the assay buffer. The reaction was terminated at room temperature for 5 minutes. To each of the reaction systems of CDK2/cyclin A, CDK4/cyclin D1 and CDK6/cyclin D1 was added 5 μL assay mixture (provided with antibody the europium-labeled against anti-myelin basic protein and the europium-labeled rabbit antibody, respectively). They were incubated at room temperature for 60 minutes. The reaction signals were detected by the EnVision instrument according to the principle of time-resolved fluorescence resonance energy transfer.

Data Analysis:

The original data was converted into the inhibition rate using the equation (Max-Ratio)/(Max-Min)*100%. The $IC_{50}$ values were obtained by curve fitting using four parameters (obtained from the 205 mode in XLFIT5, iDBS). Table 1 provides the inhibitory activities of the compounds of the invention against the kinases CDK2, CDK4 and CDK6.

MCF-7 cells) to each of the wells. The plate was incubated overnight in a carbon dioxide incubator.

The compounds to be tested were diluted three times using Bravo to the tenth concentration, i.e., diluted from 10 μM to 0.508 nM. A duplicate well test was performed. The medium was added to the middle plate in an amount of 49 μL per well. The gradient dilutions of the compounds were transferred in an amount of 1 μL per well to the middle plate at the corresponding positions, and the mixture was mixed and transferred to the cell plate in an amount of 5 μL per well. The cell plate was incubated in a carbon dioxide incubator for 6 days. Promega CellTiter-Glo reagent was added to the cell plate in an amount of 25 μL per well. The cell plate was incubated at room temperature for 10 minutes to stabilize the luminescence signal. EnVision® Multilabel Plate Reader (PerkinElmer) was used for signal detection.

Data Analysis:

The original data was converted into the inhibition rate using the equation (Max-Ratio)/(Max-Min)*100%. The $IC_{50}$ values were obtained by curve fitting using four parameters (obtained from the 205 mode in XLFIT5, iDBS). Table 1 provides the inhibitory activities of the compounds of the invention against the proliferation of MCF-7 cells and MDA-MB-436 cells.

Experimental Conclusion:

The compounds of the present invention had significant inhibitory activities against CDK4 and CDK6 and had high selectivity against CDK2. Besides, the compounds of the present invention had significant inhibitory activities against the proliferation of estrogen receptor positive MCF-7 breast cancer cells and poor inhibitory activities against the proliferation of estrogen receptor negative MDA-MB-436 cells. Compounds of Examples 3, 9, 10, and 15 had higher inhibitory activities against CDK4 and CDK6 than the reference compounds Palbociclib and LY2835219. The compounds of Examples 3, 7, 9, 10 and 15 had higher inhibitory activities against the proliferation of MCF-7 cells than the reference compounds Palbociclib and LY2835219. The compound of Example 7 had higher selectivity in inhibiting the proliferation of estrogen receptor positive breast cancer cells than the reference compound LY2835219 (MCF-7/MDA-MB-436).

TABLE 1

| Test compounds | CDK4 $IC_{50}$ (nM) | CDK6 $IC_{50}$ (nM) | CDK2 $IC_{50}$ (nM) | MCF-7 $IC_{50}$ (nM) | MDA-MB-436 $IC_{50}$ (nM) | MCF-7/ MDA-MB-436 |
|---|---|---|---|---|---|---|
| Palbociclib | 5.49 | 1.31 | 1594 | 87 | 9845 | 113 |
| LY2835219 | 1.02 | 1.01 | 14.4 | 60 | 1033 | 17.3 |
| Example 3 | <0.30 | <0.80 | 2.40 | 32.1 | 328 | 10.2 |
| Example 7 | 1.82 | 4.52 | 12.0 | 37.2 | 1157 | 31.1 |
| Example 9 | 0.31 | <0.80 | 5.95 | 45.0 | 667 | 14.8 |
| Example 10 | 0.88 | 0.97 | 6.62 | 28.9 | 496 | 17.2 |
| Example 15 | <0.30 | <0.80 | 2.82 | 56.0 | 522 | 9.3 |
| Example 24 | 1.38 | 5.79 | 32.8 | 265 | 3280 | 12.4 |

Cell Experiments

Experimental Materials:

RPMI 1640 medium, fetal bovine serum, penicillin/streptomycin were purchased from Promega (Madison, Wis.). The MCF-7 cell line and the MDA-MB-436 cell line were purchased from the European Collection of Authenticated Cell Cultures (ECACC). EnVision® Multilabel Plate Reader (PerkinElmer) was used.

Experimental Method:

MCF-7 cells were inoculated in a black 384-well plate by adding 45 μL of the cell suspension (containing 200 of Caco-2 Cell Bi-Directional Permeability Assessment Experiment Experimental Purpose:

Caco-2 cells, human colon cancer cells, are in vitro model widely used to study the absorption of small intestine. The monolayer Caco-2 cell model has been widely used to assess the passive and active transport processes in the absorption process of small intestine. GF120918A is a strong inhibitor of efflux transporters, these efflux transporters contain P-glycoprotein (P-gp), breast cancer resistance protein (BCRP) and the like. This experiment was used to determine the bi-directional permeability of the compound of Example 7 and the reference compounds Palbociclib and LY2835219 through the Caco-2 cell model and to evaluate the efflux transportation of the test compounds by adding GF120918A.
Experimental Procedures:
The standard experimental conditions were as follows:
Test concentration: 2 μM (DMSO≤1%);
Number of replication: n=2;
Direction: bi-directional transportation, including two directions, i.e., A→B and B→A;
Incubation time: single time point, 2 hours;
Transport buffer: HBSS, pH 7.4;
Incubation conditions: 37° C., 5% $CO_2$.
After the incubation, sample solutions taken from the dosing wells and the receiving wells were immediately mixed with a cold acetonitrile solution containing the internal standard. Concentrations of the test compounds in all samples (including the initial dosing solutions, the supernatants of the dosing wells and the receiving solutions) were determined by a LC/MS/MS method. The apparent permeability coefficients, the efflux ratios and other parameters were calculated.
Experimental Conclusion:
Table 2 lists the permeability coefficients of the compound of Example 7 and the reference compounds Palbociclib and LY2835219 in Caco-2 monolayer cells. Compared to the reference compounds Palbociclib and LY2835219, the compound of Example 7 had higher permeability, and its in vivo absorption and transportation were less likely to be affected by the efflux transporters. The higher permeability might enable the compound of Example 7 to be distributed more in the body tissues (such as breast and lung), thereby bringing about better antitumor efficacy in vivo. The higher permeability also enabled the compound of Example 7 to have the possibility to penetrate the blood-brain barrier, thereby achieving the purpose of treating brain metastases from breast cancer or lung cancer.

collected. The plasma was prepared by centrifuging the whole blood (3000 g, 15 minutes, 4° C.). The samples of brain homogenate were prepared by mixing the brain tissues with a mixture of methanol and a phosphate buffer (methanol:phosphate buffer=1:2) as homogenate at a ratio of 5:1. The drug concentration of each sample was determined by LC/MS/MS, and AUC was calculated to evaluate the exposure.
Experimental Conclusion:
Table 3 shows the data of the exposure of the compound of Example 7 and the reference compounds Palbociclib and LY2835219 in brain tissue when the oral dose is 10 mg/kg. The results showed that the compound of Example 7 had higher exposure in rat brain tissue than the reference compounds Palbociclib and LY2835219 at the two time points of 0.5 hour and 2 hour, indicating that the compound of Example 7 was advantageous in being developed to a medication for the treatment of brain metastases from cancer. Meanwhile, the exposure of the compound of Example 7 of the present invention in brain significantly decreased after 8 hours, which fell between the exposure of the reference compounds Palbociclib and LY2835219, indicating that the compound of Example 7 of the present invention would not accumulate in brain for a long period of time, and had better safety.

TABLE 3

| | Test compounds (10 mg/kg) | | | | | | | | |
|---|---|---|---|---|---|---|---|---|---|
| | Palbociclib | | | LY2835219 | | | Example 7 | | |
| | Time point (h) | | | | | | | | |
| | 0.5 | 2 | 8 | 0.5 | 2 | 8 | 0.5 | 2 | 8 |
| Exposure in brain (nmol/kg) | 80 | 329 | 184 | 62 | 525 | 774 | 1564 | 2922 | 307 |

TABLE 2

| Test compounds | Inhibitors of efflux transporters | Average apparent permeability coefficient ($10^{-6}$ cm/s) | | Efflux ratio | Classification | |
|---|---|---|---|---|---|---|
| | | A to B | B to A | | Permeability | Substrates of efflux transporters |
| Palbociclib | / | 0.85 | 16.46 | 19.39 | Medium | Probable |
| | GF-120918A | 9.18 | 7.51 | 0.82 | | |
| LY2835219 | / | 2.69 | 6.34 | 2.36 | High | Probable |
| | GF-120918A | 6.82 | 3.91 | 0.57 | | |
| Example 7 | / | 6.55 | 3.38 | 0.52 | High | Unlikely |
| | GF-120918A | 11.28 | 3.88 | 0.34 | | |

The Study of Brain Permeability
Experimental Purpose:
SD rats were used as the test animals. The drug concentrations in brain and plasma at different time points were determined by LC/MS/MS after oral administration of the compounds of Example 7 and the reference compounds Palbociclib and LY2835219 to evaluate their distribution characteristics in brain tissue.
Experimental Procedures:
Twelve healthy 7- to 9-week-old adult male SD rats were purchased from Shanghai Slack Laboratory Animal Co., Ltd. A proper amount of the test compound was weighed to prepare a 0.5% methylcellulose suspension at 1 mg/mL. The rats received a single oral dose of 10 mg/kg. 0.5 h, 2 h, 8 h, and 24 hours after the administration, 3 rats were respectively killed, and their whole blood and brain tissues were In Vivo Pharmacodynamic Study
The in vivo pharmacodynamic study was carried out in human-based tumor cell line-derived xenografted (CDX) BALB/c nude mice, in which were subcutaneously implanted human breast cancer cell line MCF-7.
Experimental Procedures:
Female 6- to 8-week old BALB/c nude mice which weighed about 18-22 g were kept in separate ventilated cages (10 mice per cage) in a special pathogen-free environment. All the cages, matts and water were disinfected before use. All the animals had free access to a standard certified commercial laboratory diet. A total of 100 mice were purchased from Shanghai BK Laboratory Animal Co., LTD for study. An estrogen tablet (0.36 g, sustained release within 60 days) was subcutaneously implanted in the left next abdomen of each mice. After 3 days, the tumor cells ($10 \times 10^6$ in 0.2 mL of phosphate buffer) were subcutaneously implanted in the right next abdomen of each mice for the tumor growth. The administration started when the average tumor volume reached about 150-200 mm³. The test compounds were orally administered daily, the doses were shown as Table 5. The tumor volumes were measured with a two-dimensional caliper every three days, the volumes were expressed in cubic millimeters and calculated by the formula $V=0.5a \times b^2$, wherein a and b were the major diameter and minor diameter of the tumor, respectively. Antitumor efficacy was determined by dividing an average increase of the tumor volumes of the animals treated with the compounds by an increase of the tumor volumes of the untreated animals.

Experimental Conclusion:

The compounds of Examples 3 and Example 7 of the present invention exhibited significant antitumor activities in the human-based cell line-derived xenograft (CDX) model of MCF-7 breast cancer. As shown in Table 4, 21 days after the start of the experiment, the tumor volumes of the untreated animal group increased rapidly from the initial 187 mm³ to 1443 mm³, whereas the tumor volumes of the animal group to which the compound of Example 3 was administered increased slowly from the initial 187 mm³ to 432 mm³, and the tumor growth rate of the group to which the compound of Example 3 was administered was significantly slower than that of the groups to which the reference compounds Palbociclib and LY2835219 were administered. Considering the fact that the administered dose of the compound of Example 3 (25 mg/kg) was only half of the reference compound LY2835219 (50 mg/kg) or almost half of the reference compound Palbociclib (45 mg/kg) (high doses of Palbociclib were proved to be intolerable to the animals), we considered that the compound of Example 3 was significantly superior to the two reference compounds in antitumor activity. Meanwhile, 21 days after the administration, the tumor volumes of the animal group to which the compound of Example 7 was administered increased slowly from the initial 187 mm³ to 350 mm³, and the growth rate was significantly slower than that of the group to which the same dose of the reference compound LY2835219 was administered, indicating that the compound of Example 7 had more significant antitumor activity than the reference compound LY2835219 of the same dose.

TABLE 4

| Test compounds | Administered doses (mg/kg) | Tumor volumes (mm³) | | | |
|---|---|---|---|---|---|
| | | 0 day | 7th day | 14th day | 21st day |
| Vehicle | 0 | 188 | 395 | 809 | 1443 |
| Palbociclib | 45.0 | 187 | 264 | 387 | 633 |
| LY2835219 | 50.0 | 187 | 261 | 315 | 443 |
| Example 3 | 25.0 | 187 | 249 | 288 | 432 |
| Example 7 | 50.0 | 187 | 271 | 318 | 350 |

What is claimed is:
1. A compound of formula (I) or a pharmaceutically acceptable salt thereof

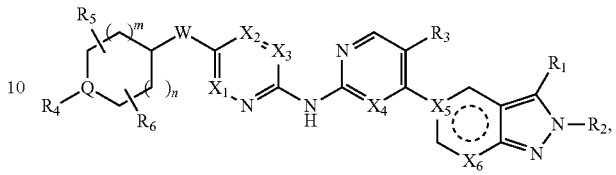

wherein

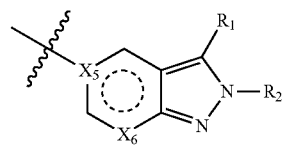

is selected from the group consisting of

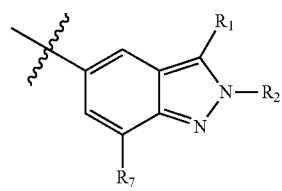

and

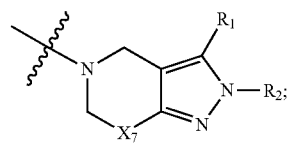

$R_1$ is selected from the group consisting of H, halogen, OH, $NH_2$, $C_{1-8}$ alkyl, $C_{2-8}$ alkenyl, $C_{2-8}$ alkenylalkyl and $C_{3-7}$ cycloalkyl;

$R_2$ is selected from the group consisting of H, halogen, $C_{1-8}$ alkyl, $C_{3-7}$ cycloalkyl, aryl group and heteroaryl group;

$R_3$ is selected from the group consisting of H, halogen, —$OR_8$, —$SR_8$, —$N(R_8)(R_9)$ and $C_{1-3}$ alkyl;

$R_4$, $R_5$ and $R_6$ are each independently selected from the group consisting of H, halogen, OH, $NH_2$, CN, $NO_2$ and =O, or selected from the group consisting of $C_{1-8}$ alkyl, $C_{1-8}$ alkylamino, N,N-di($C_{1-8}$ alkyl)amino, $C_{1-8}$ alkoxyl-$C_{1-8}$ alkyl-, $C_{1-8}$ hydroxyalkyl, $C_{2-8}$ alkenyl, $C_{2-8}$ alkynyl, $C_{3-7}$ cycloalkyl and a 3- to 7-membered heterocycloalkyl group, each of which is optionally substituted with 1, 2 or 3 Rs;

optionally, any two of $R_4$, $R_5$ and $R_6$ form a 3- to 7-membered ring together;

$R_7$ is selected from the group consisting of H, halogen, —$OR_8$, —$SR_8$, —$N(R_8)(R_9)$ and $C_{3-7}$ cycloalkyl;

$X_1$, $X_2$, $X_3$ and $X_4$ are each independently selected from the group consisting of N and $C(R_{10})$;

X₇ is selected from the group consisting of carbonyl and C(R₁₁)(R₁₂);
W is selected from the group consisting of O, S and a single bond;
T is selected from the group consisting of N and C(R₁₀), and T is not N when W is O or S;
Q is selected from the group consisting of N and C(R₁₀);
m and n are each independently selected from the group consisting of 0, 1 and 2;
R₈ and R₉ are each independently selected from the group consisting of H, C₁₋₈ alkyl and C₃₋₇ cycloalkyl;
R is selected from the group consisting of F, Cl, Br, I, NH₂, CN, OH, CF₃, CHF₂, CH₂F, NHCH₃ and N(CH₃)₂;
optionally, R₈ and R₉ are linked to the same one atom and form a 3- to 7-membered ring with 1-4 heteroatoms;
the term "hetero" or "heteroatom" represents O, S, S(=O), S(=O)₂, or N;
R₁₀ is selected from the group consisting of H, halogen, OH, NH₂, CN, C₁₋₆ alkyl, C₁₋₆ alkoxyl, C₃₋₅ cycloalkyl, CN, —OR₈, —SR₈, —N(R₈)(R₉), —C(=O)R₈, —C(=O)OR₈, —C(=O)N(R₈)(R₉), —S(=O)R₈, —S(=O)₂R₈, —S(=O)N(R₈)(R₉) and —S(=O)₂N(R₈)(R₉);
R₁₁ and R₁₂ are each independently selected from the group consisting of H, OH, halogen, C₁₋₈ alkyl and C₃₋₇ cycloalkyl;
optionally, R₄ and R₁₀ are linked to the same one atom and form a 3- to 7-membered ring.

2. The compound or a pharmaceutically acceptable salt thereof according to claim 1, wherein R₁ is selected from the group consisting of isopropyl, 2-propenyl and allyl.

3. The compound or a pharmaceutically acceptable salt thereof according to claim 1, wherein R₂ is selected from the group consisting of methyl and phenyl.

4. The compound or a pharmaceutically acceptable salt thereof according to claim 1, wherein R₃ is F.

5. The compound or a pharmaceutically acceptable salt thereof according to claim 1, wherein R₄, R₅ and R₆ are each independently selected from the group consisting of H, halogen, OH, NH₂,

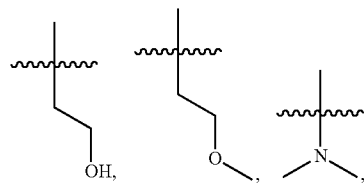

Me, Et, CN, NO₂,

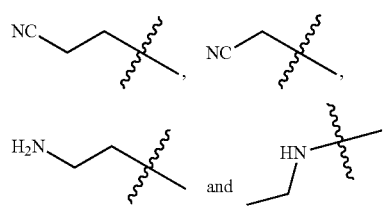

6. The compound or a pharmaceutically acceptable salt thereof according to claim 1, wherein R₇ is selected from the group consisting of H, F and Cl.

7. The compound or a pharmaceutically acceptable salt thereof according to claim 1, wherein the structural unit

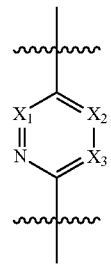

is selected from the group consisting of

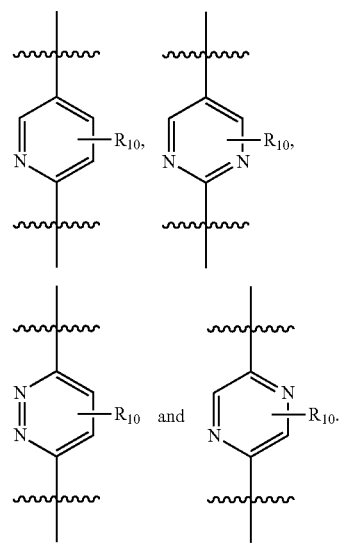

8. The compound or a pharmaceutically acceptable salt thereof according to claim 1, wherein R₁₀ is selected from the group consisting of H, OH, NH₂, F, Cl, CN,

and Me.

9. The compound or a pharmaceutically acceptable salt thereof according to claim 1, wherein X₄ is selected from the group consisting of N and CH.

10. The compound or a pharmaceutically acceptable salt thereof according to claim 1, wherein the structural unit

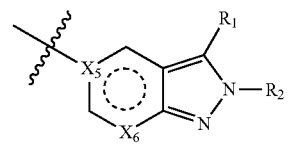

125
is selected from the group consisting of
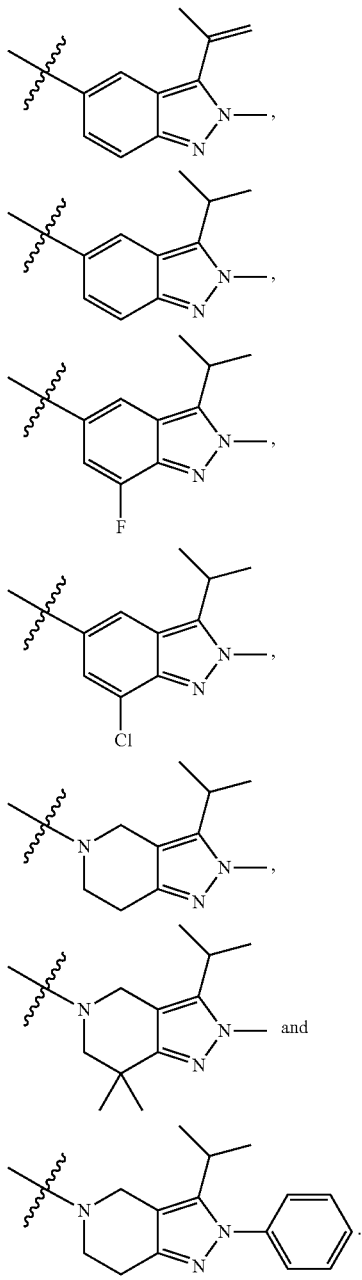
11. The compound or a pharmaceutically acceptable salt thereof according to claim 1, wherein the structural unit
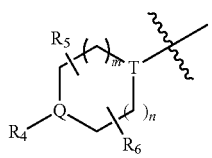
126
is selected from the group consisting of
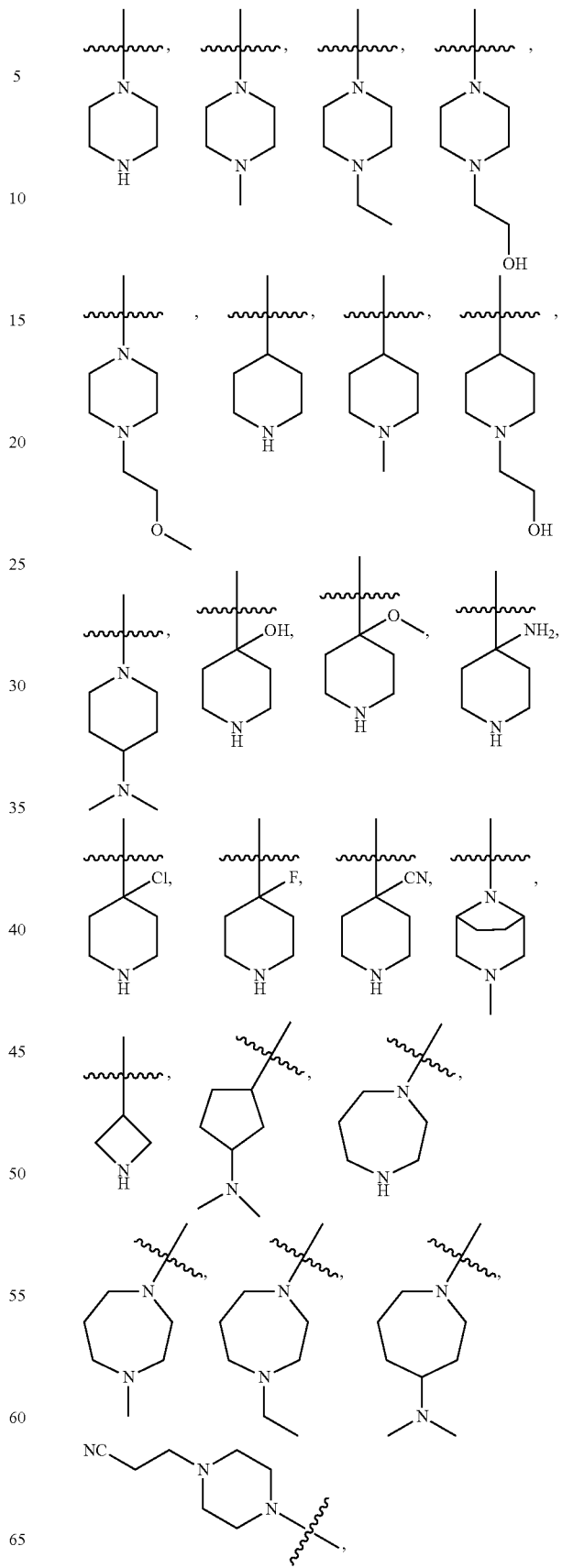

127
-continued
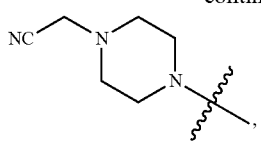
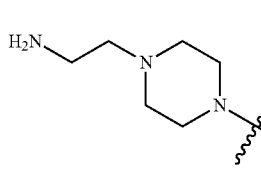
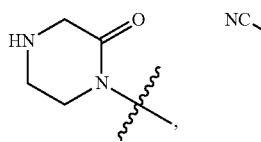 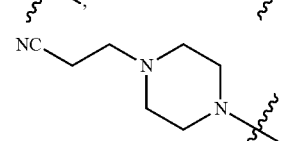
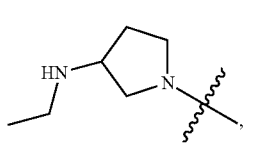 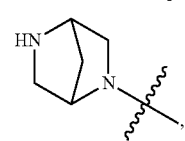
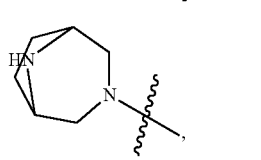 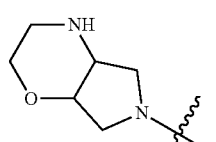
and
12. A compound selected from the group consisting of
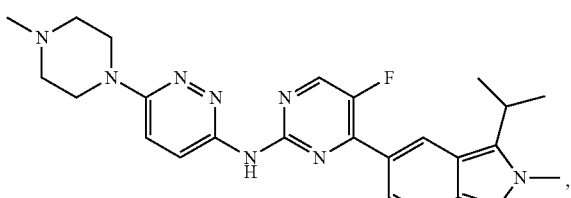
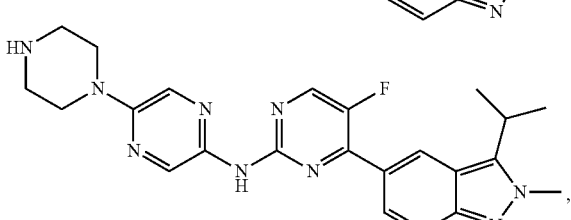
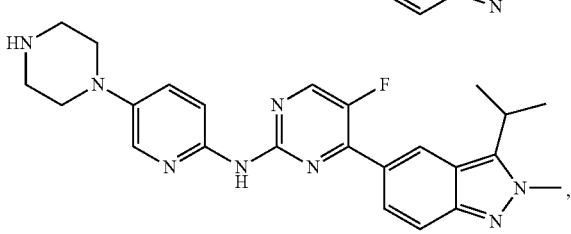
128
-continued
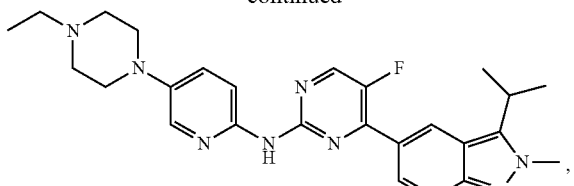
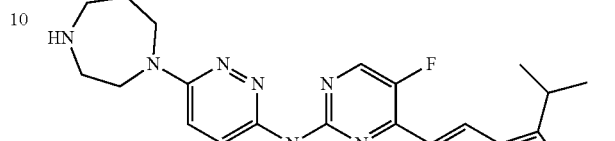
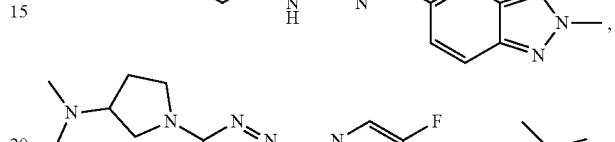
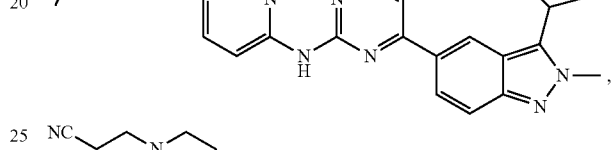
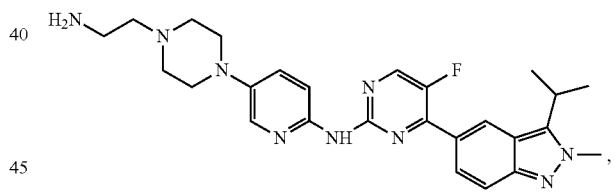
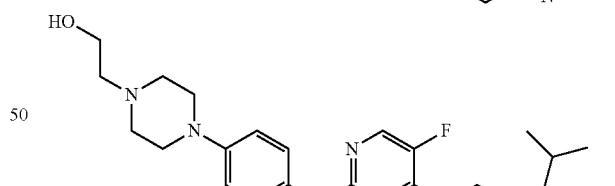
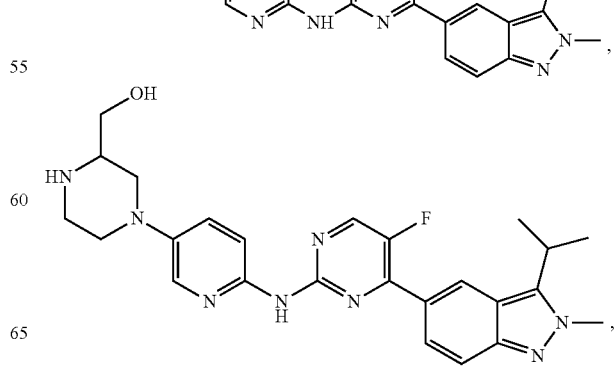

129
-continued
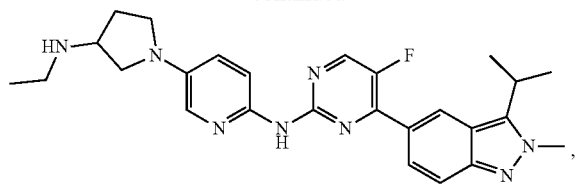,
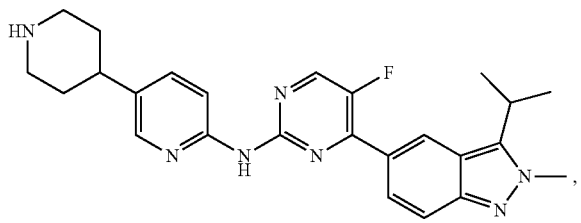,
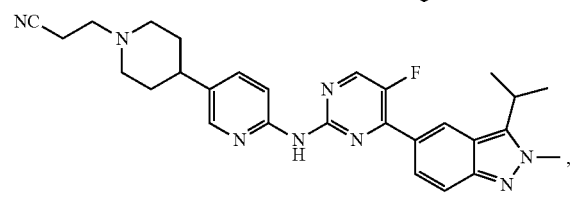,
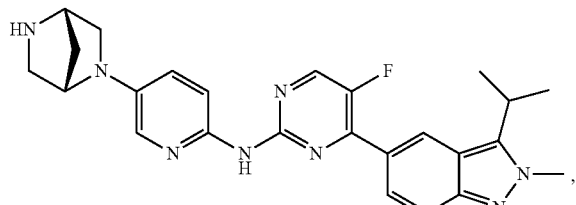,
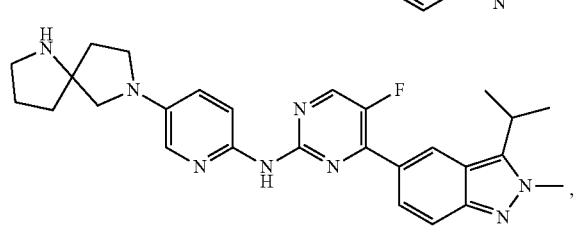,
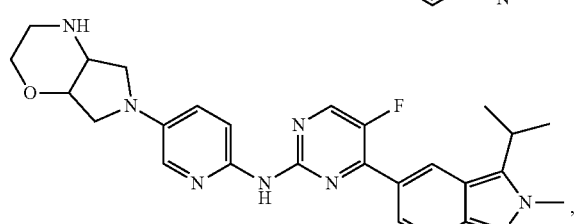,
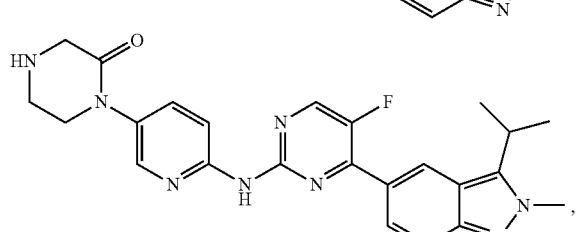,
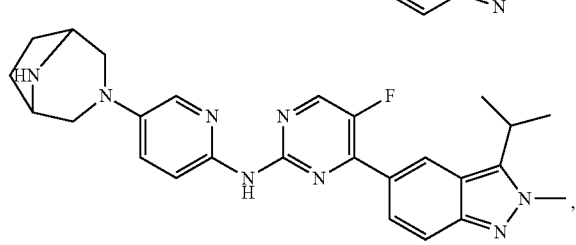,
130
-continued
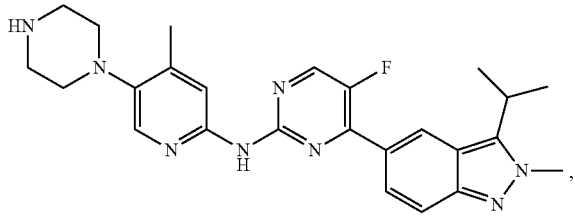,
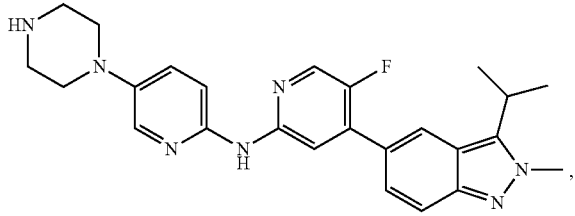,
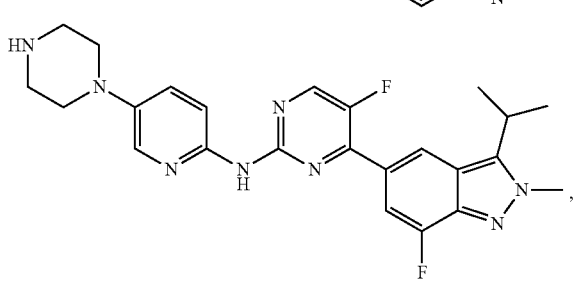,
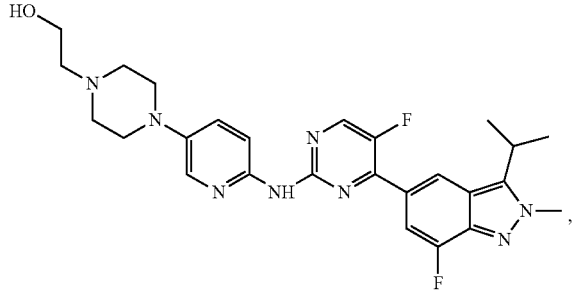,
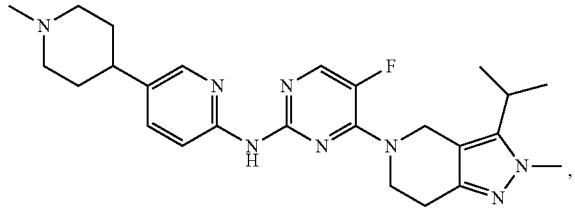,
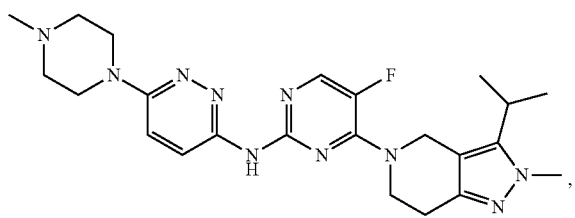,
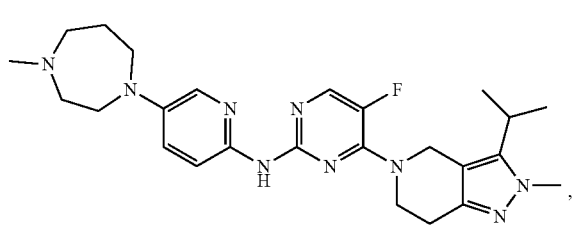, 131
-continued
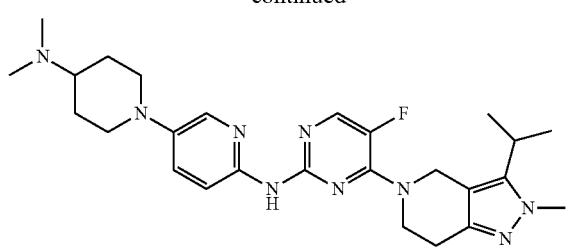
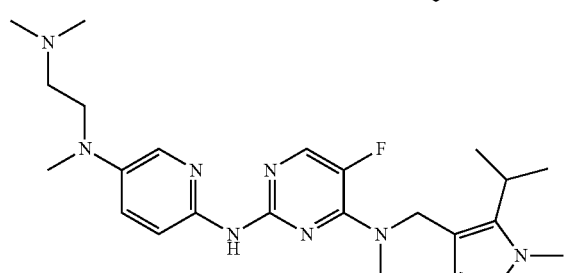
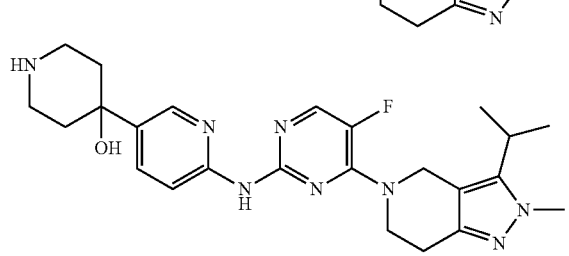
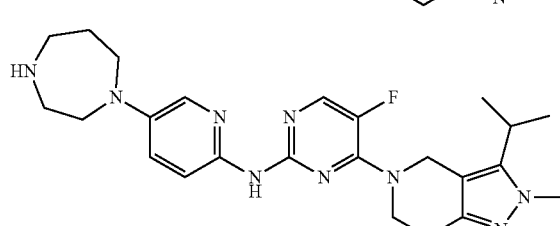
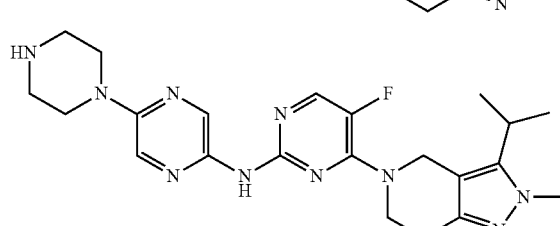
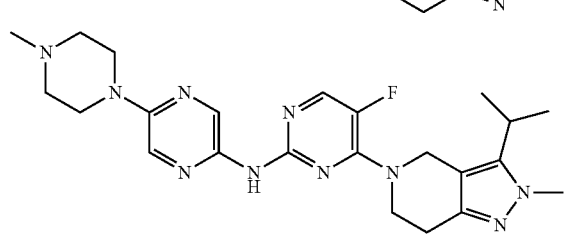
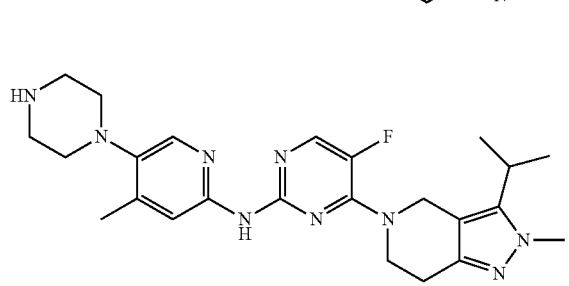
132
-continued
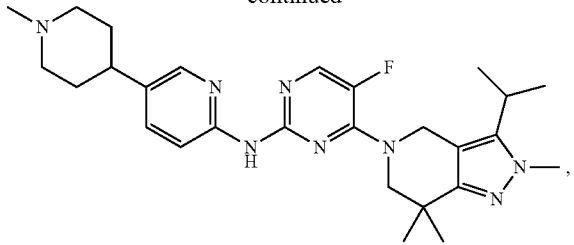
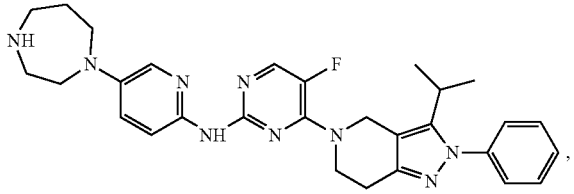
and pharmaceutically acceptable salts thereof.
13. A compound of formula (I) or a pharmaceutically acceptable salt thereof
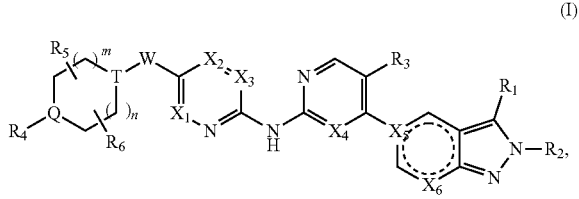
(I)
wherein
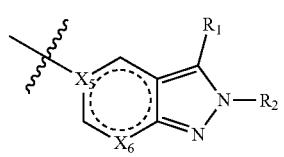
is selected from the group consisting of
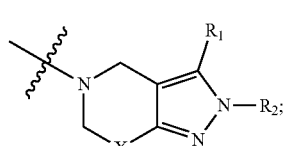
and
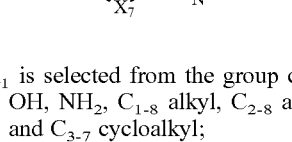
$R_1$ is selected from the group consisting of H, halogen, OH, $NH_2$, $C_{1-8}$ alkyl, $C_{2-8}$ alkenyl, $C_{2-8}$ alkenylalkyl and $C_{3-7}$ cycloalkyl;

R$_2$ is selected from the group consisting of H, halogen, C$_{1-8}$ alkyl, C$_{3-7}$ cycloalkyl, aryl group and heteroaryl group;

R$_3$ is selected from the group consisting of H, halogen, —OR$_8$, —SR$_8$, —N(R$_8$)(R$_9$) and C$_{1-3}$ alkyl;

R$_4$, R$_5$ and R$_6$ are each independently selected from the group consisting of H, halogen, OH, NH$_2$, CN, NO$_2$ and =O, or selected from the group consisting of C$_{1-8}$ alkyl, C$_{1-8}$ alkylamino, N,N-di(C$_{1-8}$ alkyl)amino, C$_{1-8}$ alkoxyl-C$_{1-8}$ alkyl-, C$_{1-8}$ hydroxyalkyl, C$_{2-8\ alkenyl}$, C2-8 alkenyl, C$_{3-7}$ cycloalkyl and a 3- to 7-membered heterocycloalkyl group, each of which is optionally substituted with 1, 2 or 3 Rs;

optionally, any two of R$_4$, R$_5$ and R$_6$ form a 3- to 7-membered ring together;

R$_7$ is selected from the group consisting of H, halogen, —OR$_8$, —SR8, —N(R$_8$)(R$_9$) and C$_{3-7}$ cycloalkyl;

X$_1$, X$_{2\ 1}$, $_{X3}$ and X$_4$ are each independently selected from the group consisting of N and C(R$_{10}$);

X$_7$ is selected from the group consisting of carbonyl and C(R$_{11}$)(R$_{12}$);

W is selected from the group consisting of O, S and a single bond;

T is selected from the group consisting of N and C(R$_{10}$), and T is not N when W is O or S;

Q is selected from the group consisting of N and C(R$_{10}$);

m and n are each independently selected from the group consisting of 0, 1 and 2;

R$_8$ and R$_9$ are each independently selected from the group consisting of H, C$_{1-8}$ alkyl and C$_{3-7}$ cycloalkyl;

R is selected from the group consisting of F, Cl, Br, I, NH$_2$, CN, OH, CF$_3$, CHF$_2$, CH$_2$F, NHCH$_3$ and N(CH$_3$)$_2$;

optionally, R$_8$ and R$_9$ are linked to the same one atom and form a 3- to 7-membered ring with 1-4 heteroatoms;

the term "hetero" or "heteroatom" represents O, S, S(=O), S(=O)$_2$, or N;

R$_{10}$ is selected from the group consisting of H, halogen, OH, NH$_2$, CN, C$_{1-6}$ alkyl, C$_{1-6}$ alkoxyl, C$_{3-5}$ cycloalkyl, CN,—OR$_8$,—SR$_8$, —N(R$_8$)(R$_9$), —C(=O)R$_8$, —C(=O)OR$_8$, —C(=O)N(R$_8$)(R$_9$), —S(=O)R$_8$, —S(=O)$_2$R$_8$, —S(=O)N(R$_8$)(R$_9$) and —S(=)$_2$N(R$_8$)(R$_9$);

R$_{11}$ and R$_{12}$ are each independently selected from the group consisting of H, OH, halogen, C$_{1-8}$ alkyl and C$_{3-7}$ cycloalkyl;

optionally, R$_4$ and R$_{10}$ are linked to the same one atom and form a 3- to 7-membered ring, wherein the structural unit

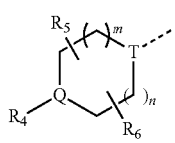

is substituted by

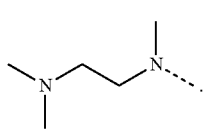

14. The compound or a pharmaceutically acceptable salt thereof according to claim 13, wherein R$_3$ is F, the structural unit

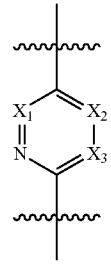

is selected from the group consisting of

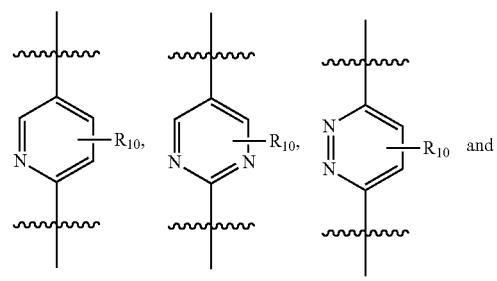

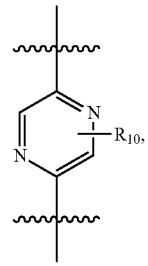

X$_4$ is selected from the group consisting of N and CH.

15. The compound or a pharmaceutically acceptable salt thereof according to claim 13, wherein the structural unit

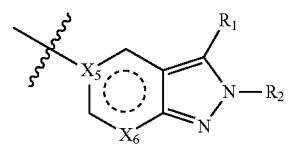

is selected from the group consisting of

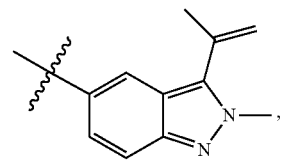

-continued
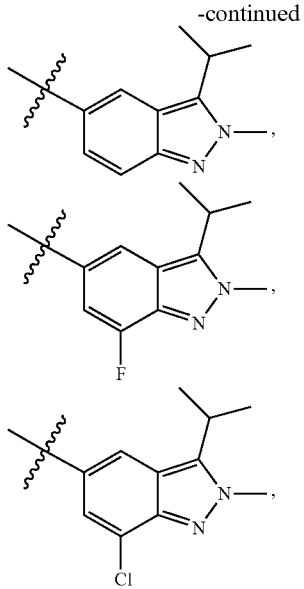
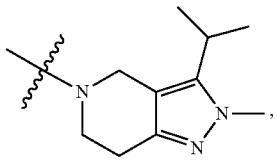
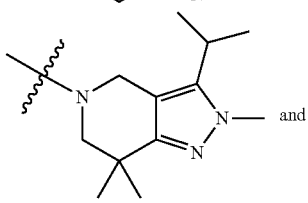
and
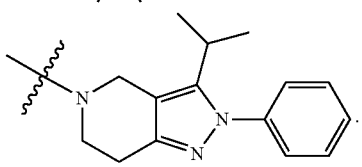
* * * * *

UNITED STATES PATENT AND TRADEMARK OFFICE
CERTIFICATE OF CORRECTION

| | | |
|---|---|---|
| PATENT NO. | : 9,969,719 B2 | Page 1 of 2 |
| APPLICATION NO. | : 15/557210 | |
| DATED | : May 15, 2018 | |
| INVENTOR(S) | : Charles Z. Ding et al. | |

It is certified that error appears in the above-identified patent and that said Letters Patent is hereby corrected as shown below:

On the Title Page

Column 1, Inventors, Line 2, delete "Shenghai" and insert -- Shanghai --.

Column 1, Notice, Line 3, after "0 days." delete "days.".

In the Claims

Column 122, Lines 5-12, Claim 1, delete " " and insert -- --.

Column 122, Line 53, Claim 1, delete "—$SR_8$,—$N(R_8)(R_9)$" and insert -- —$SR_8$, —$N(R_8)(R_9)$ --.

Column 123, Line 22, Claim 1, delete "—$N(R_8)(R_9)$,—$C(=O)R_8$," and insert -- —$N(R_8)(R_9)$, —$C(=O)R_8$, --.

Signed and Sealed this
Fourteenth Day of August, 2018

Andrei Iancu
*Director of the United States Patent and Trademark Office*

CERTIFICATE OF CORRECTION (continued)
U.S. Pat. No. 9,969,719 B2

Column 126, Lines 43-52, Claim 11, delete " 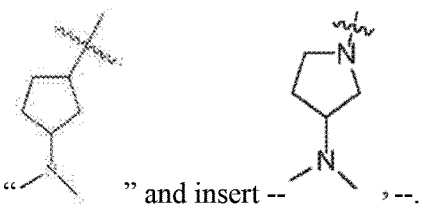 " and insert -- --.

Column 127, Lines 15-19, Claim 11, delete "  " and insert

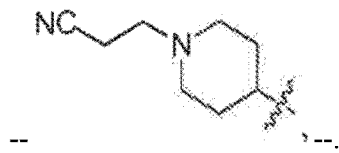

-- --.

Column 133, Lines 10-11, Claim 13, delete "$C_{1-8}$ hydroxyalkyl ,$C_{2-8\ alkenyl,\ C2-8}$ alkenyl," and insert -- $C_{1-8}$ hydroxyalkyl, $C_{2-8}$ alkenyl, $C_{2-8}$ alkynyl, --.

Column 133, Line 18, Claim 13, delete "$X_{21,\ x3}$" and insert -- $X_2$, $X_3$ --.

Column 133, Line 40, Claim 13, delete "CN,—$OR_8$,—$SR_8$," and insert -- CN, —$OR_8$, —$SR_8$, --.

Column 133, Lines 42-43, Claim 13, delete "—S(=)$_2$N($R_8$)($R_9$);" and insert -- —S(=O)$_2$N($R_8$)($R_9$); --.